United States Patent
Lin et al.

(10) Patent No.: US 10,806,694 B2
(45) Date of Patent: Oct. 20, 2020

(54) NANOPARTICLES FOR PHOTODYNAMIC THERAPY, X-RAY INDUCED PHOTODYNAMIC THERAPY, RADIOTHERAPY, RADIODYNAMIC THERAPY, CHEMOTHERAPY, IMMUNOTHERAPY, AND ANY COMBINATION THEREOF

(71) Applicant: The University of Chicago, Chicago, IL (US)

(72) Inventors: Wenbin Lin, Chicago, IL (US);
Chunbai He, Chicago, IL (US);
Kuangda Lu, Chicago, IL (US);
Kaiyuan Ni, Chicago, IL (US);
Guangxu Lan, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 15/884,036

(22) Filed: Jan. 30, 2018

(65) Prior Publication Data

US 2018/0153796 A1 Jun. 7, 2018

Related U.S. Application Data

(63) Continuation-in-part of application No. 15/518,665, filed as application No. PCT/US2015/055574 on Oct. 14, 2015, now Pat. No. 10,206,871.

(60) Provisional application No. 62/173,103, filed on Jun. 9, 2015, provisional application No. 62/063,770, filed on Oct. 14, 2014.

(51) Int. Cl.
*A61K 9/00* (2006.01)
*A61K 31/282* (2006.01)
*A61K 31/337* (2006.01)
*A61K 31/405* (2006.01)
*A61K 31/4745* (2006.01)
*A61K 31/704* (2006.01)
*A61K 31/409* (2006.01)
*A61K 9/19* (2006.01)
*B82Y 5/00* (2011.01)
*A61K 41/00* (2020.01)

(52) U.S. Cl.
CPC .......... *A61K 9/0009* (2013.01); *A61K 9/0019* (2013.01); *A61K 9/19* (2013.01); *A61K 31/282* (2013.01); *A61K 31/337* (2013.01); *A61K 31/405* (2013.01); *A61K 31/409* (2013.01); *A61K 31/4745* (2013.01); *A61K 31/704* (2013.01); *A61K 41/0038* (2013.01); *A61K 41/0071* (2013.01); *B82Y 5/00* (2013.01)

(58) Field of Classification Search
CPC ...... A61K 9/0009; A61K 9/0019; A61K 9/19; A61K 31/405; A61K 31/337; A61K 31/409; A61K 31/704; A61K 41/0071; A61K 41/0038; A61K 31/4745; A61K 31/282; B82Y 5/00
See application file for complete search history.

(56) References Cited

U.S. PATENT DOCUMENTS

| | | | |
|---|---|---|---|
| 4,405,771 | A | 9/1983 | Jagur |
| 5,147,806 | A | 9/1992 | Kamin et al. |
| 5,213,788 | A | 5/1993 | Ranney |
| 5,641,623 | A | 6/1997 | Martin |
| 5,648,508 | A | 7/1997 | Yaghi |
| 5,827,925 | A | 10/1998 | Tremont et al. |
| 5,858,784 | A | 1/1999 | Debs et al. |
| 5,871,710 | A | 2/1999 | Bogdanov et al. |
| 6,013,638 | A | 1/2000 | Crystal et al. |
| 6,022,737 | A | 2/2000 | Niven et al. |
| 6,136,295 | A | 10/2000 | Edwards et al. |
| 6,180,082 | B1 | 1/2001 | Woltering et al. |
| 6,818,227 | B1 | 11/2004 | Uster et al. |
| 7,196,210 | B2 | 3/2007 | Yaghi et al. |
| 7,263,170 | B2 | 8/2007 | Pellegrino |

(Continued)

FOREIGN PATENT DOCUMENTS

| | | |
|---|---|---|
| CA | 2896797 A1 | 7/2014 |
| CN | 163258 | 9/2005 |

(Continued)

OTHER PUBLICATIONS

Cai, W., "Metal—organic framework-based nanomedicine platforms for drug delivery and molecular imaging." Small 11.37 (2015): 4806-4822.*

(Continued)

*Primary Examiner* — John M Mauro
(74) *Attorney, Agent, or Firm* — Jenkins, Wilson, Taylor & Hunt, P.A.

(57) ABSTRACT

Metal-organic frameworks (MOFs) comprising photosensitizers are described. The MOFs can also include moieties capable of absorbing X-rays or other ionizing irradiation energy and/or scintillation. Optionally, the photosensitizer or a derivative thereof can form a bridging ligand of the MOF. Further optionally, the MOF can comprise inorganic nanoparticles in the cavities or channels of the MOF or can be used in combination with an inorganic nanoparticle. Also described are methods of using MOFs and/or inorganic nanoparticles in photodynamic therapy, X-ray induced photodynamic therapy, radiotherapy, radiodynamic therapy, or in radiotherapy-radiodynamic therapy, either with or without the co-administration of one or more immunotherapeutic agent and/or one or more chemotherapeutic agent.

18 Claims, 60 Drawing Sheets

(56) References Cited

U.S. PATENT DOCUMENTS

| | | |
|---|---|---|
| 7,430,282 B2 | 9/2008 | Mori et al. |
| 7,985,868 B1 | 7/2011 | Bauer |
| 8,623,837 B2 | 1/2014 | Fewell |
| 8,668,764 B2 | 3/2014 | Brown et al. |
| 9,162,079 B2 | 10/2015 | Levy et al. |
| 10,206,871 B2 | 2/2019 | Lin et al. |
| 2001/0018187 A1 | 8/2001 | Sun et al. |
| 2002/0103517 A1 | 8/2002 | West et al. |
| 2002/0115747 A1 | 8/2002 | Feldheim et al. |
| 2002/0127224 A1 | 9/2002 | Chen |
| 2005/0112131 A1 | 5/2005 | Pogue et al. |
| 2005/0147963 A1 | 7/2005 | Su et al. |
| 2005/0227929 A1 | 10/2005 | Masferrer |
| 2006/0204754 A1 | 9/2006 | Kang |
| 2006/0228554 A1 | 10/2006 | Tan et al. |
| 2006/0233883 A1 | 10/2006 | Ishihara et al. |
| 2007/0076851 A1 | 4/2007 | Pellegrino |
| 2007/0128049 A1 | 9/2007 | Chen et al. |
| 2007/0218049 A1 | 9/2007 | Chen et al. |
| 2007/0259966 A1 | 11/2007 | Cagnoni et al. |
| 2008/0063714 A1 | 3/2008 | Sahouani et al. |
| 2008/0124281 A1 | 5/2008 | Gao et al. |
| 2010/0189222 A1 | 7/2010 | Eaton et al. |
| 2010/0286022 A1 | 11/2010 | Yaghi et al. |
| 2011/0135571 A1 | 6/2011 | Lin et al. |
| 2011/0238001 A1 | 9/2011 | Chen et al. |
| 2012/0093918 A1 | 4/2012 | Sanche et al. |
| 2012/0130146 A1 | 5/2012 | Picard et al. |
| 2012/0226217 A1 | 9/2012 | Klaveness et al. |
| 2014/0107333 A1 | 4/2014 | Ma et al. |
| 2014/0220143 A1 | 8/2014 | Dhar et al. |
| 2014/0234210 A1 | 8/2014 | Lin et al. |
| 2014/0335015 A1* | 11/2014 | Pottier .................. A61K 33/24 424/1.29 |
| 2015/0086541 A1 | 3/2015 | Aguilar-Cordova |
| 2016/0346204 A1 | 12/2016 | Lin et al. |
| 2017/0231903 A1 | 8/2017 | Lin et al. |

FOREIGN PATENT DOCUMENTS

| | | |
|---|---|---|
| CN | 102448497 | 5/2012 |
| CN | 102648004 | 8/2012 |
| CN | 107001031 B | 11/2019 |
| EP | 3206987 B1 | 7/2020 |
| JP | 6731404 B2 | 7/2020 |
| WO | WO2004/101575 A2 | 11/2004 |
| WO | WO2007/090295 | 8/2007 |
| WO | WO2007/108618 | 9/2007 |
| WO | WO 2008/102632 A1 | 8/2008 |
| WO | WO2009/139939 | 11/2009 |
| WO | WO 2011/049743 A1 | 4/2011 |
| WO | WO 2013/009701 A2 | 1/2013 |
| WO | WO 2013/188763 A1 | 12/2013 |
| WO | WO 2015/069926 A1 | 5/2015 |
| WO | WO 2015/149068 A1 | 10/2015 |
| WO | WO 2015/149072 A1 | 10/2015 |
| WO | WO 2016/06256 A1 | 4/2016 |

OTHER PUBLICATIONS

Káčáková S., "X-ray-induced radiophotodynamic therapy (RPDT) using lanthanide micelles: Beyond depth limitations." Nano Research 8.7 (2015): 2373-2379.*

Freitas, F. F. G., "Biological basis for analysis of lasers' action in infectious processes. Biofilm, Interaction of light with matter, pathophysiological aspects." (2013) in Microbial pathogens and strategies for combating them: science, technology and education (A. Méndez-Vilas, Ed.)*

Jerjes, W., "Photodynamic therapy vs. photochemical internalization: the surgical margin." Head & neck oncology 3.1 (2011): 53.*

Granados-Oliveros, G.,"Visible light production of superoxide anion with MCarboxyphenylporphyrins (M=H, Fe, Co, Ni, Cu, and Zn) free and anchored on TiO2: EPR characterization." Journal of Molecular Catalysis A: Chemical 339.1-2 (2011): 79-85.*

Allison et al., "Oncologic photodynamic therapy photosensitizers: A clinical review," Photodiagnosis and Photodynamic Therapy, vol. 7, No. 2, pp. 61-75 (Jun. 2010).

Ash et al., "New drugs and future developments in photodynamic therapy," Eur. J. Cancer, vol. 29A, No. 12, pp. 1781-1783 (1993).

Bechet et al., "Nanoparticles as vehicles for delivery of photodynamic therapy agents," Trends in biotechnology, vol. 26, No. 11, pp. 612-621 (2008).

Biel, "Photodynamic Therapy of Head and Neck Cancers," Photodynamic Therapy, Methods in Molecular Biology, Springer+ Business Media, LLC, vol. 635 (25 pages), pp. 281-296 (2010).

Bonvalot et al. First human study testing a new radio enhancer using nanoparticles (NBTXR3) activated by radiation therapy in patients with locally advanced soft tissue sarcomas. Clinical Cancer Research, vol. 23, No. 4, 1297, pp. 908-917(2016).

Bowden et al., "Hydrothermal syntheses and crystal structures of three zinc succinates: Zn(C4H4O4)-α, Zn(C4H4O4)-β and K2Zn(C4H4O4)2," Dalton Transactions, pp. 936-969 (2003).

Brannon-Peppas et al., "Nanoparticle and targeted systems for cancer therapy," Advanced Drug Delivery Reviews, vol. 56, pp. 1649-1659 (2004).

Carter et al., "Porphyrin-phospholipid liposomes permeabilized by near-infrared light," Nature communications, vol. 5, No. 3546 (25 pages), pp. 1-11 (Apr. 3, 2014).

Catala et al., "Cyanide-Bridged CrIII-NiII Super paramagnetic Nanoparticles," Advanced Materials, vol. 15, No. 10, pp. 826-829 (2003).

Cavka et al., "A New Zirconium Inorganic Building Brick Forming Metal Organic Frameworks with Exceptional Stability," J. Am. Chem. Soc., vol. 130, No. 42, pp. 13850-13851 (2008).

Chen et al., "Immuno gold nanocages with tailored optical properties for targeted photothermal destruction of cancer cells," Nano Lett., vol. 7, No. 5, pp. 1318-1322 (11 pages) (Apr. 2007).

Chen et al., "Nanoscintillator-mediated X-ray inducible photodynamic therapy for in vivo cancer treatment," Nano letters, vol. 15, pp. 2249-2256 (2015).

Chen et al., "Using nanoparticles to enable simultaneous radiation and photodynamic therapies for cancer treatment," Journal of nanoscience and nanotechnology, vol. 6, pp. 1159-1166 (2006).

Cheng et al., "Near Infrared Light-Triggered Drug Generation and Release From Gold Nanoparticle Carriers for Photodynamic Therapy," Small, vol. 10, No. 9, pp. 1799-1804 (13 pages) (Feb. 2014).

Cobley et al., "Gold nanostructures: a class of multifunctional materials for biomedical applications," Chem. Soc. Rev., vol. 40, pp. 44-56 (2011).

Communication of European publication number and information on the application of Atricle 67(3) EPC corresponding to Application No. PCT/US2015055574 dated Jul. 26, 2017.

Communication of Extended European Search Report corresponding to Application No. 15851357.2 dated Feb. 28, 2018.

Dai et al. Electron Crystallography Reveals Atomic Structures of Metal-Organic Nanoplates with M12 (μ3-O) 8 (μ3-OH) 8 (μ2-OH) 6 (M=Zr, Hf) Secondary Building Units. Inorganic Chemistry 56, 8128-8134 (2017).

deKrafft et al., "Iodinated Nanoscale Coordination Polymers as Potential Contrast Agents for Computed Tomography,"Angewandte Chemie, vol. 48, pp. 9901-9904 (2009).

Della Rocca et al., "Nanoscale Metal-Organic Frameworks for Biomedical Imaging and Drug Delivery," Acc. Chem. Res., vol. 44, No. 10, pp. 957-968 (2011).

Deng et al., "Irradiation and anti-PD-L1 treatment synergistically promote antitumor immunity in mice," The Journal of clinical investigation, 124, 687 (2014).

Dolmans et al., "Photodynamic therapy for cancer." Nature Reviews Cancer, vol. 3, pp. 380-387 (May 2003).

Dougherty, "Photodynamic Therapy," Photochem. and Photobiol., vol. 58, No. 6, pp. 895-900 (Dec. 1993).

Fang et al., "The EPR effect: Unique features of tumor blood vessels for drug delivery, factors involved, and limitations and augmentation of the effect," Adv. Drug Deliv. Rev., vol. 63, No. 3, pp. 136-151 (Mar. 2011).

(56) References Cited

OTHER PUBLICATIONS

Feng et al., "Zirconium-metalloporphyrin PCN-222: mesoporous metal-organic frameworks with ultrahigh stability as biomimetic catalysts," Angew. Chem. Int. Ed., vol. 51, No. 41, pp. 10307-10310 (2012).
Feng et al., "Zirconium-Metalloporphyrin PCN-222: Mesoporous Metal-Organic Frameworks with Ultrahigh Stability as Biomimetic Catalysts," Angew. Chem., vol. 124, pp. 10453-10456 (2012).
Gao et al., "Metal-metalloporphyrin frameworks: a resurging class of functional materials," Chemical Society Reviews, vol. 43, pp. 5841-5866 (2014).
Giustini et al., "Microstructure and Dynamics of the Water-in-Oil CTAB/n-Pentanol/n-Hexane/Water Microemulsion: A Spectroscopic and Conductivity Study," Journal of Physical Chemistry, vol. 100, No. 8, pp. 3190-3198 (1996).
Graf et al., "A General Method for the Controlled Embedding of Nanoparticles in Silica Colloids," Langmuir, vol. 22, No. 13, pp. 5604-5610 (2006).
Graf et al., "A General Method to Coat Colloidal Particles with Silica," Langmuir, vol. 19, No. 17 pp. 6693-6700 (2003).
Hajri et al., "In vitro and in vivo efficacy of photofrin and pheophorbide a, a bacteriochlorin, in photodynamic therapy of colonic cancer cells," Photochem Photobiol, vol. 75, No. 2, pp. 140-148 (2002).
Hauptvogel et al., "Flexible and Hydrophobic Zn-Based Metal-Organic Framework," Inorg. Chem., vol. 50, pp. 8367-8374 (2011).
He et al., "Nanoscale Metal-Organic Frameworks for Real-Time Intracellular pH Sensing in Live Cells," J. Am. Chem. Soc., vol. 136, No. 35, pp. 12253-12256 (2014).
He et al., "Nanoscale Metal-Organic Frameworks for the Co-Delivery of Cisplatin and Pooled siRNAs to Enhance Therapeutic Efficacy in Drug-Resistant Ovarian Cancer Cells," J. Am. Chem. Soc., vol. 136, No. 14, pp. 5181-5184 (2014).
Henderson et al., "Interaction of Photodynamic Therapy and Hyperthermia: Tumor Response and Cell Survival Studies after Treatment of Mice in Vivo," Cancer research, vol. 45, pp. 6071-6077 (1985).
Horcajada et al., "Porous metal-organic-framework nanoscale carriers as a potential platform for drug delivery and imaging," Nat Mater., vol. 9, pp. 172-178 (Feb. 2010).
Ji et al., "Size Control of Gold Nanocrystals in Citrate Reduction: The Third Role of Citrate," J. Am. Chem. Soc., vol. 129, pp. 13939-13948 (2007).
Jin et al., "Targeting-Triggered Porphysome Nanostructure Disruption for Activatable Photodynamic Therapy," Advanced Healthcare Materials, vol. 3, pp. 1240-1249 (2014).
Kalayda et al., "Synthesis, Structure, and Biological Activity of New Azine-Bridged Dnuclear Platinum(II) Complexes," Eur. J. Inorg. Chem., pp. 4347-4355 (2003).
Kanofsky, "Measurement of singlet-oxygen In Vivo: Progress and Pitfalls," Photochem Photobiol., vol. 87, No. 1, pp. 14-17 (2011).
Kroemer et al., "Immunogenic Cell Death in Cancer Therapy," Annu. Rev. Immunol., vol. 31, pp. 51-72 (Mar. 2013).
Kumar et al., "In vivo biodistribution and clearance studies using multimodal organically modified silica nanoparticles.," ACS nano, vol. 4, No. 2, pp. 699-708 (19 pages) (Feb. 23, 2010).
Lee et al., "Light-Harvesting Metal-Organic Frameworks (MOFs): Efficient Strut-to-Strut Energy Transfer in Bodipy and Porphyrin-Based MOFs," Journal of the American Chemical Society, vol. 133, pp. 15858-15861 (2011).
Lee et al., "Porphyrins & Phthalocyanines web themed issue," Chemical Communications, vol. 48, pp. 5512-5514 (2012).
Leigh, "Comprehensive Coordination Chemistry II From Biology to Nanotechnology," Journal of Organometallic Chemistry. vol. 689, No. 16, pp. 2733-2742 (2004).
Levine, D., et al. "Olsalazine-Based Metal-Organic Frameworks as Biocompatible Platforms for H2 Adsorption and Drug Delivery." Journal of the American Chemical Society 138, 10143-10150 (2016).
Liu et al., "Phosphorescent Nanoscale Coordination Polymers as Contrast Agents for Optical Imaging," Angewandte Chemie International Edition, vol. 50, pp. 3696-3700 (2011).

Loo et al., "Immunotargeted Nanoshells for Integrated Cancer Imaging and Therapy," Nano letters, vol. 5, No. 4, pp. 709-711 (2005).
Lovell et al., "Porphysome nanovesicles generated by porphyrin bilayers for use as multimodal biophotonic contrast agents," Nat. Mater., vol. 10, pp. 324-332 (2011).
Lu et al., "A Chlorin-Based Nanoscale Metal-Organic Framework for Photodynamic Therapy of Colon Cancer," J. Am. Chem. Soc., vol. 137, No. 24 (11 pages), pp. 7600-7603 (2015).
Lu et al., "Low Dose X-ray Radiotherapy-Radiodynamic Therapy via Nanoscale Metal-organic Frameworks Enhances Checkpoint Blockade Immunotherapy" Nature Biomedical Engineering (Mar. 28, 2018) DOI: 10.1038/541551-018-0203-4.
Lu et al.. "Nanoscale Metal-Organic Framework for Highly Effective Photodynamic Therapy of Resistant Head and Neck Cancer," J. Am. Chem. Soc., vol. 136, pp. 16712-16715 (Nov. 19, 2014).
Mack et al., "The effects of terbium on the cellular accumulation of cisplatin in MDA-MB-231 human breast tumor cells," Cancer Chemotherapy and Pharmacology. vol. 39, pp. 217-222 (1997).
Maeda et al., "Mechanism of tumor-targeted delivery of macromolecular drugs, including the EPR effect in solid tumor and clinical overview of the prototype polymeric drug SMANCS," J. Controlled Release, vol. 74, pp. 47-61 (2001).
Maggiorella et al., "Nanoscale radiotherapy with hafnium oxide nanoparticles," Future oncology 8, 1167-1181 (2012).
Manna et al., "Metal-Organic Framework Nodes Support Single-Site Magnesium-Alkyl Catalysts for Hydroboration and Hydroamination Reactions," Journal of the American Chemical Society, vol. 138, pp. 7488-7491 (2016).
Matsumura et al., "A New Concept for Macromolecular Therapeutics in Cancer Chemotherapy: Mechanism of Tumoritropic Accumulation of Proteins and the Antitumor Agent Smancs," Cancer Research, vol. 46, pp. 6387-6392 (1986).
Mellman et al., "Cancer immunotherapy comes of age," Nature, vol. 480, pp. 480-489 (2011).
Merkel et al., "Radiationless decay of singlet molecular oxygen in solution. Experimental and therorectical study of electronic-to-vibrational energy transfer," J. Am. Chem. Soc., vol. 94, No. 21, pp. 7244-7253 (1972).
Min, Y., et al. Antigen-capturing nanoparticles improve the abscopal effect and cancer immunotherapy. Nature nanotechnology 12, 877 (2017).
Moan et al., "The photodegradation of porphyrins in cells can be used to estimate the lifetime of singlet oxygen," Photochem Photobiol., vol. 53, No. 4, pp. 549-553 (1991).
Morris et al., "Nucleic Acid—Metal Organic Framework (MOF) Nanoparticle Conjugates," J. Am. Chem. Soc., vol. 136, No. 20, pp. 7261-7264 (2014).
Mukhopadhyay et al., "Conjugated Platinum (IV)—Peptide Complexes for Targeting Angiogenic Tumor Vasculature," Bioconjugate Chemistry, vol. 19, No. 1, pp. 39-49 (2008).
Notice of Allowance corresponding to U.S. Appl. No. 15/518,665 dated Sep. 26, 2018.
Notification Concerning Transmittal of International Preliminary Report on Patentability and the Written Opinion of the International Searching Authority corresponding to International Application No. PCT/US2015/055574 dated Apr. 27, 2017.
Notification Concerning Transmittal of International Preliminary Report on Patentability (Chapter I of the Patent CooperationTreaty) corresponding to International Patent Application No. PCT/US2009/034867 dated Sep. 2, 2010.
Notification of Transmittal of the International Search Authority and the Written Opinion of the International Searching Authority, or the Declaration corresponding to PCT/US2015/055574 dated Feb. 18, 2016.
Notification of Transmittal of the International Search Report and the Written Opinion of the International Searching Authority, or the Declaration corresponding to the International Application No. PCT/US2009/034867 dated Feb. 3, 2010.
Office Action (Restriction Requirement) corresponding to U.S. Appl. No. 15/518,665 dated Dec. 12, 2017.
Office Action corresponding to U.S. Appl. No. 15/518,665 dated May 16, 2018.

(56) References Cited

OTHER PUBLICATIONS

Official Action (Restriction Requirement) corresponding to U.S. Appl. No. 12/918,748 dated Oct. 18, 2012.

Official Action corresponding to U.S. Appl. No. 12/918,748 dated Mar. 28, 2013.

Office Action corresponding to Chinese Patent Application Serial No. 201580068173X dated Oct. 31, 2018.

Pass, "Photodynamic Therapy in Oncology: Mechanisms and Clinical Use," Journal of the National Cancer Institute, vol. 85, No. 6, pp. 443-456 (1993).

Pinna et al., "Non-Aqueous Synthesis of High-Purity Metal Oxide Nanopowders Using an Ether Elimination Process," Advanced Materials, vol. 16 (23-24), pp. 2196-2200 (2004).

Retif et al. "Nanoparticles for radiation therapy enhancement: the key parameters,"Theranostics, vol. 5, pp. 1030-1045 (2015).

Rieter et al., "Nanoscale Coordination Polymers for Platinum-Based Anticancer Drug Delivery," Jounal of the American Chemical Society, vol. 130, No. 35, pp. 11584-11585 (2008).

Rieter et al., "Nanoscale Metal-Organic Frameworks as Potential Multimodal Contrast Enhancing Agents," J Am Chem Soc., vol. 128, No. 28, pp. 9024-9025 (Jul. 2006).

Rodgers et al., "Lifetime of 02(IΔ) in Liquid Water as Determined by Time-Resolved Infrared Luminescence Measurements," J. Am. Chem. Soc., vol. 104, pp. 5541-5543 (1982).

Samia et al., "Semiconductor Quantum Dots for Photodynamic Therapy," J. Am. Chem. Soc., vol. 125, No. 51, pp. 15736-15737 (2003).

Scandola et al., "Photophysical properties of metal-mediated assemblies of porphyrins," Coord. Chem. Rev., vol. 250, pp. 1471-1496 (2006).

Schöder, "Head and Neck Cancer," Nuclear Oncology; Pathophysiology and Clinical Applications Sprinter Science=Businessd Media New York, pp. 269-295 (2013).

Senge et al., "Temoporfin (Foscan®, 5, 10, 15, 10-Tetra(m-Hydroxyphenyl)chlorin)-13 A Second-Generation Photosensitizer," Photochem. Photobiol., vol. 87, No. 6, pp. 1240-1296 (Sep. 2011).

Sheats, "History of Organometallic Polymers," Journal of Macromolecular Science: Part A—Chemistry, vol. 15, No. 6, pp. 1173-1199 (1981).

Snyder et al., "Subcellular, Time-Resolved Studies of Singlet Oxygen in Single Cells," J. Am. Chem. Soc., vol. 127, pp. 14558-14559 (2005).

Spokoyny et al., "Infinite coordination polymer nano- and microparticle structures," Chem. Soc. Rev., vol. 38, pp. 1218-1227 (2009).

St-Denis et al., "Diffusivity of oxygen in water," Can J Chem Eng., vol. 49, No. 6, pp. 885 (Dec. 1971).

Taylor-Pashow et al., "Postsynthetic Modifications of Iron-Carboxylate Nanoscale Metal-Organic Frameworks for Imaging and Drug Delivery," J Am Chem Soc., vol. 131, No. 40, pp. 14261-14263 (2009).

Tranchemontagne et al., "Secondary building units, nets and bonding in the chemistry of metal-organic frameworks," Chem. Soc. Rev., vol. 38, pp. 1257-1283 (2009).

Uemura et al., "Prussian Blue Nanoparticles Protected by Poly(vinylpyrrolidone)," Journal of the American Chemical Society, vol. 125, No. 26, pp. 7814-7815 (2003).

Vaucher et al., "Molecule-Based Magnetic Nanoparticles: Synthesis of Cobalt Hexacyanoferrate, Cobalt Pentacyanonitrosylferrate, and Chromium Hexacyanochromate Coordination Polymers in Water-in-Oil Microemulsions," Nano Letters. vol. 2, No. 3, pp. 225-229 (2002).

Vaucher et al., "Synthesis of Prussian Blue Nanoparticles and Nanocrystal Superlattices in Reverse Microemulsions," Angew. Chem. Int. Ed. vol. 39, No. 10, pp. 1793-1796 (2000).

Vesper et al., "Photodynamic therapy (PDT): An evolving therapeutic technique in head and neck cancer treatment," Head & Neck Cancer: Current Perspectives, Advances, and Challenges, Springer Netherlands, vol. 9789400758278, pp. 649-676 (2013).

Wang et al., "Comparison Study of Gold Nanohexapods, Nanorods, and Nanocages for Photothermal Cancer Treatment," ACS Nano, vol. 7, No. 3, pp. 2068-2077 (Feb. 2013).

Wang et al., "Nanoparticle delivery of cancer drugs," Annual Review of Medicine, vol. 63, pp. 185-198 (2012).

Wang et al., "One-Step Sythesis of β meso-Unsubstituted Dipyrromethane," Synlett, pp. 1267-1268 (1995).

Wang et al., "Synergistic Assembly of Heavy Metal Clusters and Luminescent Organic Bridging Ligands in Metal-Organic Frameworks for Highly Efficient X-ray Scintillation," Journal of the American Chemical Society, vol. 136, pp. 6171-6174 (2014).

White et al., "Photooxidation of Diglycine in Confined Media. Application of the Microreactor Model for Spin-Correlated Radical Pairs in Reverse Micelles and Water-in-Oil Microemulsions," Langmuir, vol. 21, No. 7, pp. 2721-2727 (2005).

Wong et al., "Fluorescence Probing of Inverted Micelles. The State of Solublized Water Clusters in Alkane/Diisooctyl Sulfosuccinate (Aerosol OT) Solution," Journal of the American Chemical Society, vol. 98, No. 9, pp. 2391-2397 (1976).

Xu et al., "Nanoscale Metal-Organic Frameworks for Ratiometric Oxygen Sensing in Live Cells," Journal of the American Chemical Society, 138, 2158-2161 (2016).

Xu et al., "Reverse micellar synthesis of CdS nanoparticles and self-assembly into a superlattice," Materials Letters, vol. 58, pp. 2623-2626 (2004).

Yamada et al., "Synthesis and Isolation of Cobalt Hexacyanoferrate/Chromate Metal Coordination Nanopolymers Stabilized by Alkylamino Ligand with Metal Elemental Control," Journal of the American Chemical Society, vol. 126, pp. 9482-9483 (2004).

Yu et al., "Immobilization of polymer-stabilized metal colloids by a modified coordination capture: preparation of supported metal colloids with singular catalytic properties," Journal of Molecular Catalysis A: Chemical, vol. 142, pp. 201-211 (1999).

Zhang et al., "Biomimicry in metal-organic material," Coordination Chemistry Reviews, vol. 293-294, pp. 327-356 (2015).

Zhang et al., "Three-Dimensional Lanthanoid-Containing Coordination Frameworks: Structure, Magnetic and Fluorescent Properties," European Journal of Inorganic Chemistry, pp. 766-772 (2005).

Lan et al., "Nanoscale metal-organic frameworks for phototherapy of cancer," Coordination Chemistry Reviews, vol. 379, No. 15, pp. 65-81 (2019).

Chen et al., "Biomimetic Catalysis of a Porous Iron-Based Metal-Metalloporphyrin Framework," Inorganic Chemistry, vol. 51, No. 23, pp. 12600-12602 (2012).

Feng et al., "Metal-Organic Frameworks Based on Previously Unknown Zr8/Hf8 Cubic Clusters," Inorganic Chemistry, vol. 52, No. 21, pp. 12661-12667 (2013).

Jin et al., "Energy Transfer from Quantum Dots to Metal-Organic Frameworks for Enhanced Light Harvesting," Journal of the American Chemical Society vol. 135, pp. 955-958, (2013).

Office Action corresponding to Japanese Application No. 2017-520324 dated Jul. 9, 2019.

Office Action (Restriction Requirement) corresponding to U.S. Appl. No. 16/235,752 dated Jul. 10, 2019.

Wang et al., "Elucidating Molecular Iridium Water Oxidation Catalysts Using Metal-Organic Frameworks: A Comprehensive Structural, Catalytic, Spectroscopic, and Kinetic Study," Journal of the American Chemical Society, vol. 134, pp. 19895-19908 (2012).

Wang et al., "Pt Nanoparticles@Photoactive Metal-Organic Frameworks: Efficient Hydrogen Evolution via Synergistic Photoexcitation and Electron Injection," Journal of the American Chemical Society, vol. 134, pp. 7211-7214 (2012).

Nyman: "Polyoxometalates and Other Metal-Oxo Clusters in Nature," In: Encyclopedia of Geochemistry, Springer International Publishing, pp. 1-5 (2016).

Office Action corresponding to Chinese Patent Application Serial No. 201580068173X dated Apr. 10, 2019.

Office Action corresponding to European Application No. 15851357.2 dated Jun. 7, 2019.

Kudinov et al., "On the Possibility of Combining Radiotherapy and Photodynamic Therapy." CLEO: Science and Innovations. Optical Society of America, pp. 1-2 (2014).

(56) References Cited

OTHER PUBLICATIONS

Notice of Allowance corresponding to Chinese Patent Application Serial No. 201580068173X dated Aug. 12, 2019.
Office Action corresponding to U.S. Appl. No. 16/235,752 dated Oct. 24, 2019.
Intention to Grant corresponding to European Application No. 15851357.2 dated Jan. 30, 2020.
Office Action corresponding to Japanese Patent Application No. 2017520324 dated Feb. 12, 2020.
Office Action corresponding to U.S. Appl. No. 16/235,752 dated Feb. 20, 2020.
Notice of Allowance corresponding to U.S. Appl. No. 16/235,752 dated May 6, 2020.
Decision to Grant corresponding to Japanese Patent Application No. 2017520324 dated Jun. 8, 2020.
Decision to Grant corresponding to European Patent Application No. 15851357.2 dated Jun. 5, 2020.

* cited by examiner

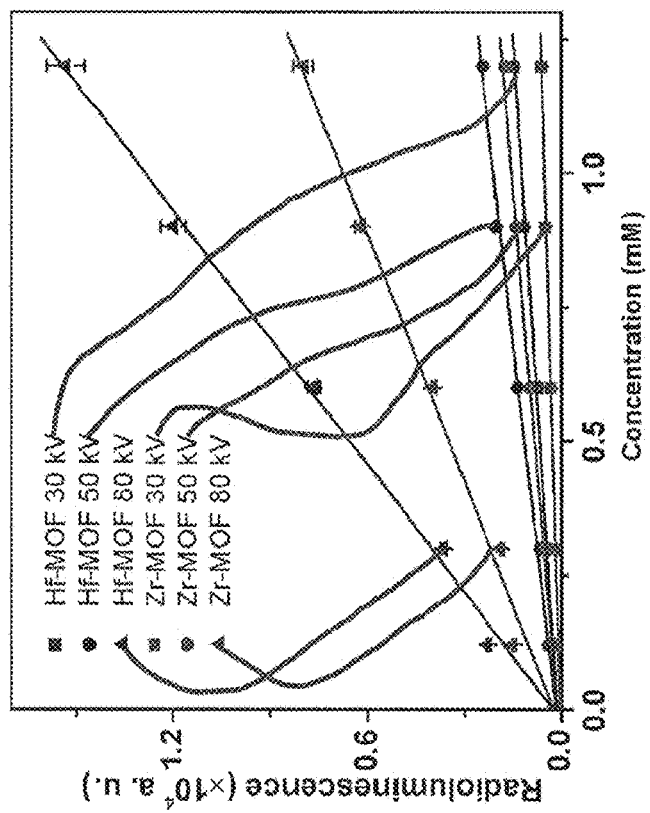
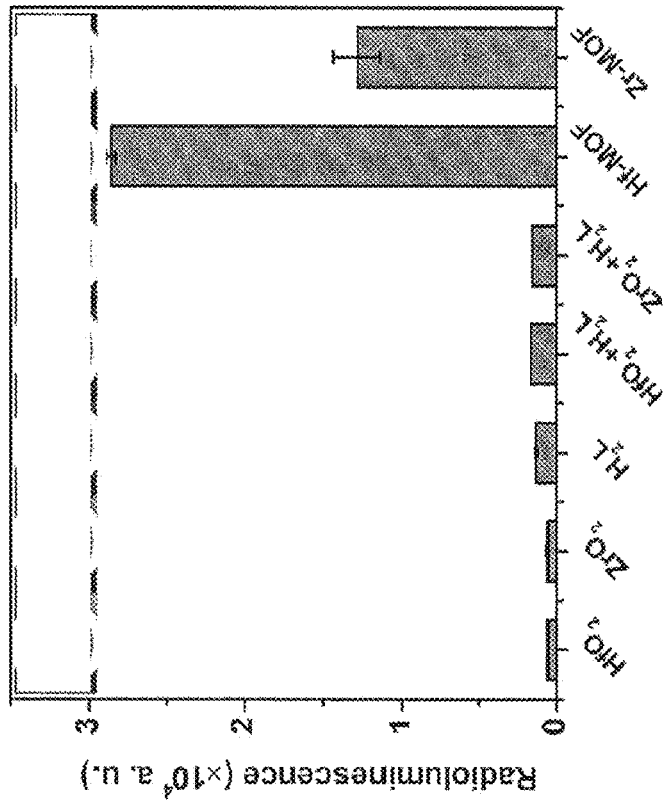
FIG. 7B
FIG. 7A

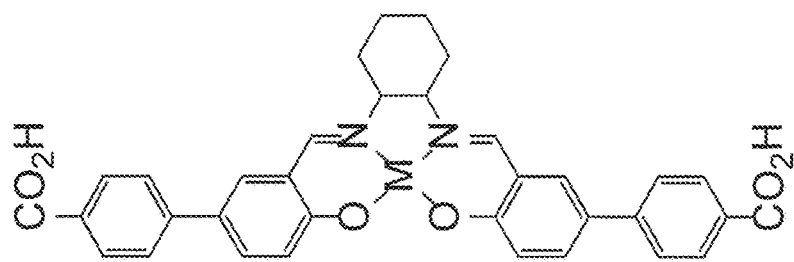
disalycylidene-1,2-cyclohexylidenediamine complex
FIG. 31
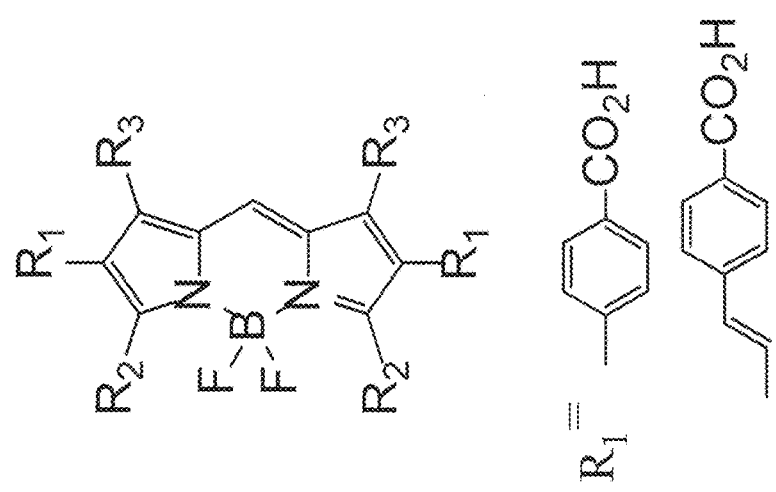
BODIPY derivatives

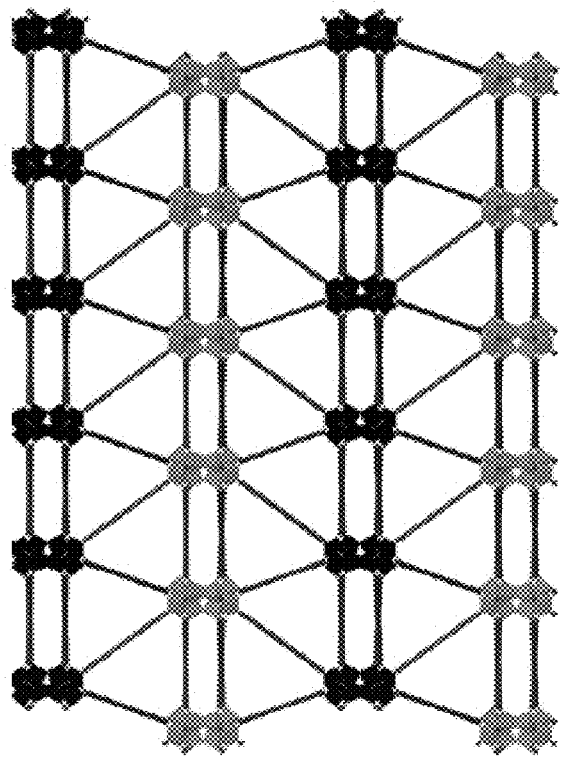
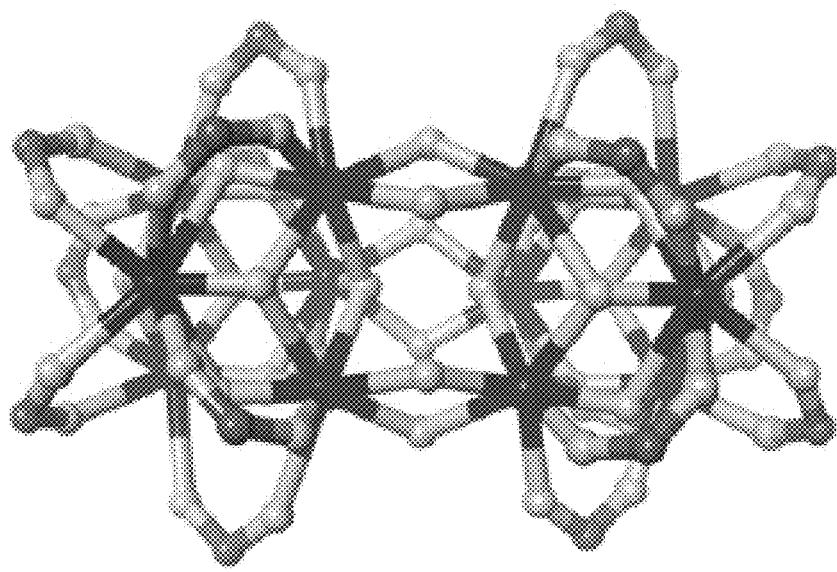
FIG. 34B
FIG. 34A

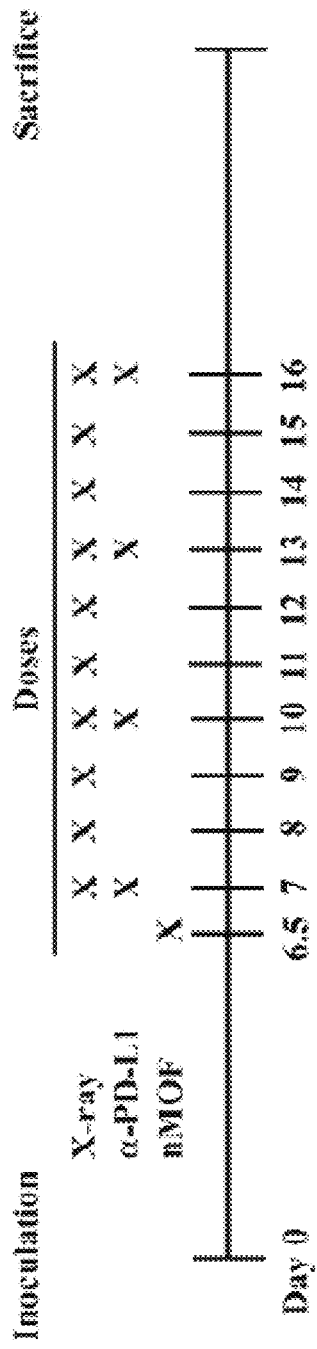
FIG. 35A
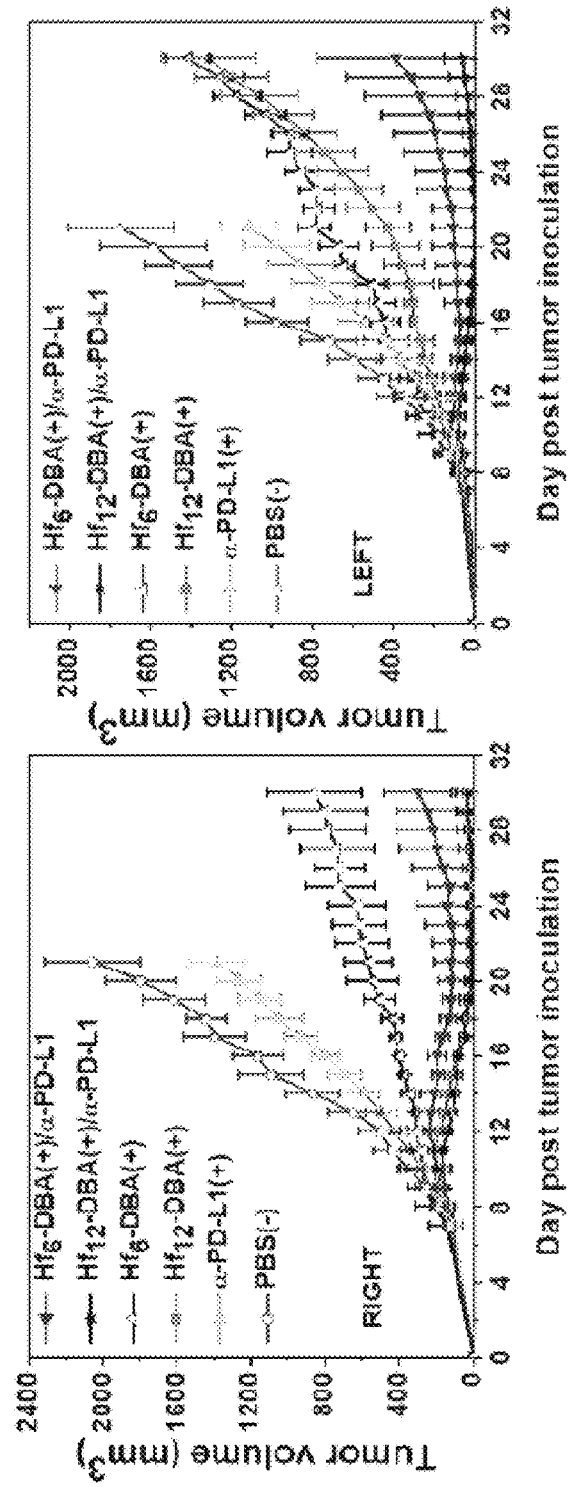
FIG. 35B
FIG. 35C

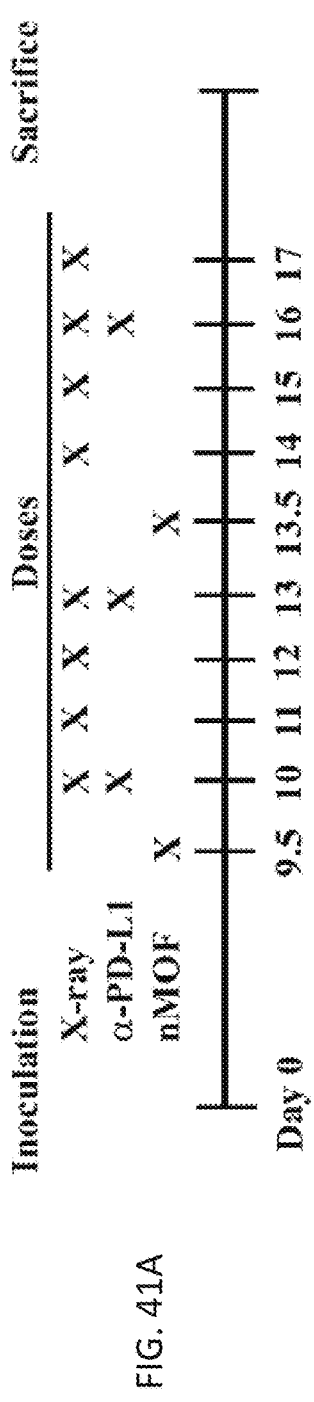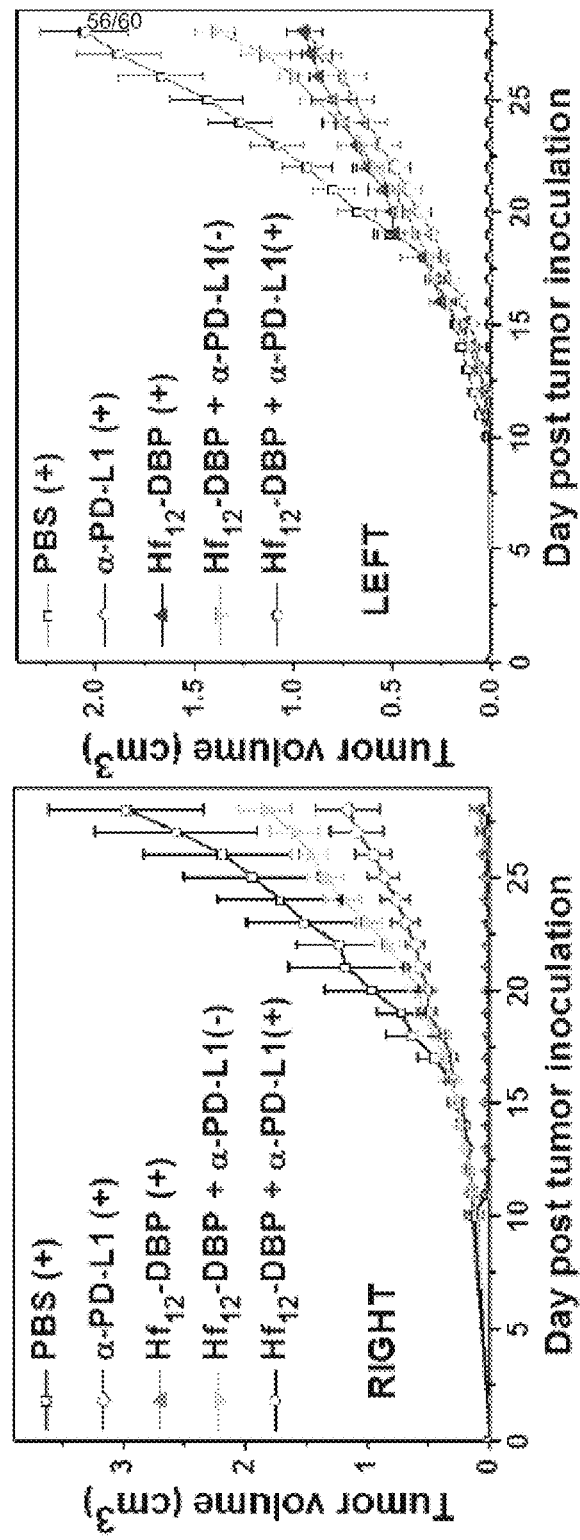
FIG. 41A
FIG. 41B
FIG. 41C

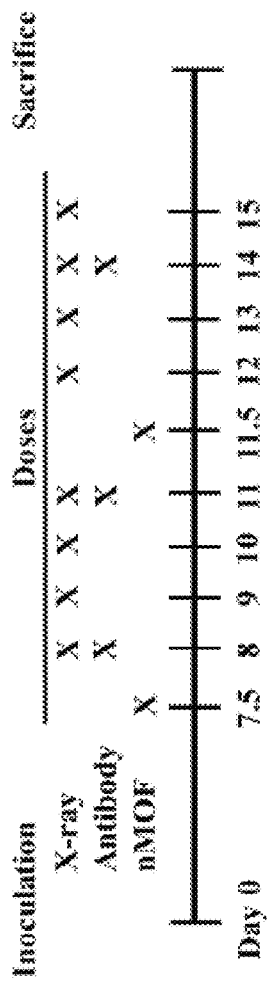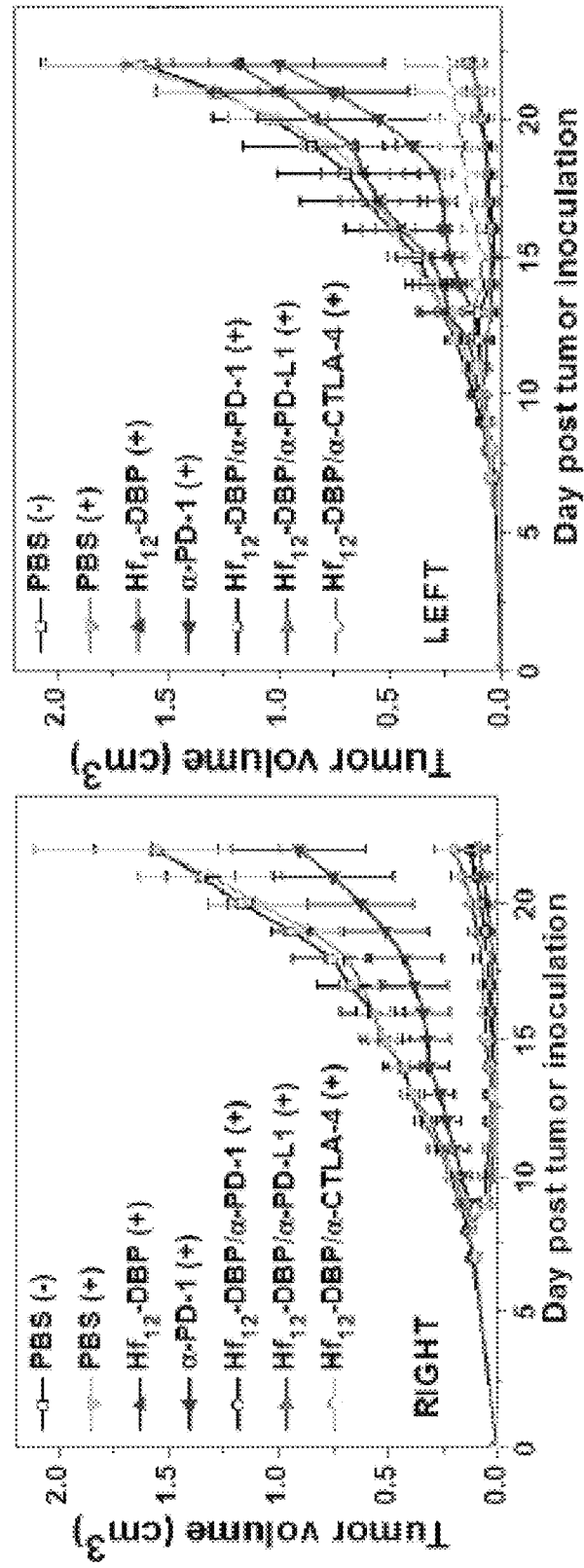
FIG. 43A
FIG. 43B
FIG. 43C

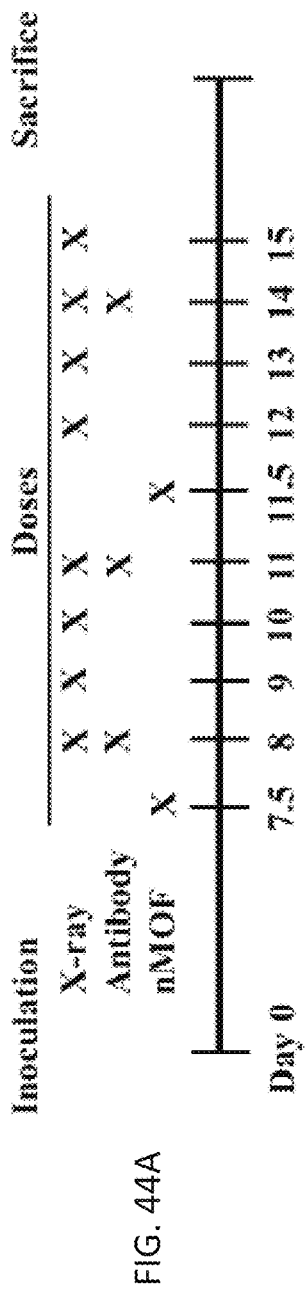
FIG. 44A
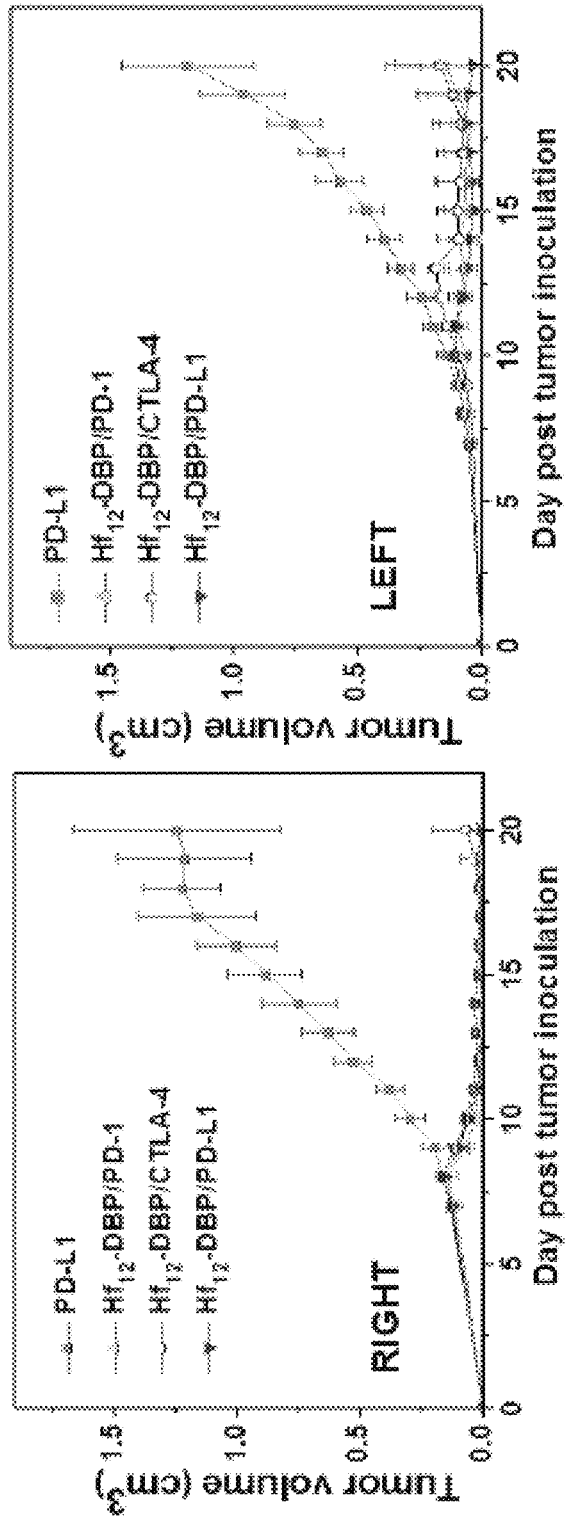
FIG. 44C
FIG. 44B

NANOPARTICLES FOR PHOTODYNAMIC THERAPY, X-RAY INDUCED PHOTODYNAMIC THERAPY, RADIOTHERAPY, RADIODYNAMIC THERAPY, CHEMOTHERAPY, IMMUNOTHERAPY, AND ANY COMBINATION THEREOF

RELATED APPLICATIONS

This application is a Continuation-in-Part of U.S. patent application Ser. No. 15/518,665, filed on Apr. 12, 2017, which is a national stage application of PCT/US2015/055574, filed on Oct. 14, 2015, which claims the benefit of U.S. Provisional Patent Application Ser. No. 62/063,770, filed Oct. 14, 2014; and of U.S. Provisional Patent Application Ser. No. 62/173,103, filed Jun. 9, 2015, the disclosures of each of which are incorporated herein by reference in their entireties.

GOVERNMENT INTEREST

This invention was made with government support under Grant Nos. U01-CA151455, U01-CA198989, and 1S10RR026988-01 awarded by the National Institutes of Health. The government has certain rights in the invention.

TECHNICAL FIELD

The presently disclosed subject matter provides a nanocarrier platform based on metal-organic frameworks (MOF) materials (including nanoscale metal-organic frameworks (NMOFs)), for photodynamic therapy (PDT), X-ray induced photodynamic therapy (X-PDT), radiotherapy (RT), radiodynamic therapy (RDT), radiotherapy-radiodynamic therapy (RT-RDT), chemotherapy, immunotherapy, or any combination thereof. In some embodiments, the platform is for PDT. In some embodiments, the platform is for X-PDT. In some embodiments, the platform is used for RT, RDT, or RT-RDT. In some embodiments, the platform is used for the combination of X-PDT and RT. In some embodiments, the platform is used for combined PDT, RT, RDT, RT-RDT, or X-PDT and immunotherapy. In some embodiments, the platform is for combined chemotherapy, PDT, and immunotherapy. In some embodiments, the platform is used for combined chemotherapy and immunotherapy. In some embodiments, the platform is used for combined RT or RT-RDT, chemotherapy, and immunotherapy.

ABBREVIATIONS

° C.=degrees Celsius
%=percentage
μl=microliter
μM=micromolar
BODIPY=boron-dipyrromethene
bpy=2,2'-bipyridine
cm=centimeter
DBBC=5,15-di(p-benzoato)bacteriochlorin
DBC=5,15-di(p-benzoato)chlorin
DBP=5,15-di(p-benzoato)porphyrin
DLS=dynamic light scattering
DMF=dimethylformamide
DMSO=dimethylsulfoxide
DOPC=1,2-dioleoyl-sn-glycero-3-phosphate sodium salt
DOTAP=1,2-dioleoyl-3-trimethylammonium propane
DSPE-PEG$_{2k}$=1,2-distearoyl-sn-glycero-3-phosphoethanolamine-N-[amino(polyethylene glycol)2000]
g=gram
h=hour
Hf=hafnium
IC$_{50}$=fifty percent inhibitory concentration
ICP-MS=inductively coupled plasma-mass spectrometry
kg=kilogram
kVp=peak kilovoltage
Ln=lanthanide
mg=milligram
min=minute
mL=milliliter
mM=millimolar
mmol=millimole
Mn=manganese
MOF=metal-organic framework
MRI=magnetic resonance imaging
m-THPC=tetra(m-hydroxyphenyl)chlorin
MW=molecular weight
NIR=near infrared
nm=nanometer
NMOF=nanoscale metal-organic frameworks
NMR=nuclear magnetic resonance
PBS=phosphate buffered saline
PDI=polydispersity index
PDT=photodynamic therapy
PEG=polyethylene glycol
PS=photosensitizer
Pt=platinum
PVP=polyvinylpyrrolidone
RES=reticuloendothelial system
rpm=revolutions-per-minute
Ru=ruthenium
SBU=secondary building units
sec=seconds
SOSG=singlet oxygen sensor green
TEM=transmission electron microscopy
TFA=trifluoroacetic acid
TBC=5,10,15,20-tetra(p-benzoato)chlorin
TBP=5,10,15,20-tetra(p-benzoato)-porphyrin
X-PDT=X-ray induced photodynamic therapy
Zn=zinc
Zr=zirconium

BACKGROUND

Photodynamic therapy (PDT) can be an effective anticancer treatment option. PDT involves the administration of a tumor-localizing photosensitizer (PS) followed by light activation to generate highly cytotoxic reactive oxygen species (ROS), particularly singlet oxygen ($^1O_2$), which trigger cell apoptosis and necrosis. By localizing both the PS and the light exposure to tumor regions, PDT can selectively kill tumor cells while preserving local tissues. PDT has been used to treat patients with many different types of cancer, including head and neck tumors, breast cancer, gynecological tumors, brain tumors, colorectal cancer, mesothelioma, and pancreatic cancer. The use of PDT for treating cancers in the head and neck is particularly advantageous over traditional treatment modalities, e.g., surgery and irradiation, as PDT causes less destruction of surrounding tissues and reduces aesthetic and functional impairments. Porphyrin molecules such as PHOTOFRIN®, VERTEPORFIN®, FOSCAN®, PHOTOCHLOR®, and TALAPORFIN® are among the most commonly used PSs for PDT. However, although they have efficient photochemistry for ROS generation, their suboptimal tumor accumulation after systemic administration can limit the efficacy of PDT in the clinic.

Accordingly, there is an ongoing need for additional delivery vehicles for improving the delivery (e.g., the targeted delivery) of PS therapeutics. In particular, there is a need for delivery vehicles that can deliver PSs in combination with other therapeutics (e.g., other chemotherapeutics and immunotherapy agents) in order to increase treatment efficacy.

SUMMARY

In some embodiments, the presently disclosed subject matter provides a composition comprising a metal-organic framework (MOF) comprising: a) a photosensitizer; and b) a plurality of metal-containing secondary building units (SBUs) linked together via one or more bridging ligands, wherein the SBUs comprise hafnium (Hf) oxo clusters. In some embodiments, the Hf oxo clusters are $Hf_6$ oxo clusters, $Hf_{12}$ oxo clusters, or a combination thereof.

In some embodiments, each of the one or more bridging ligands comprises an organic compound capable of binding to two or three SBUs. In some embodiments, each of the one or more bridging ligands comprises at least two groups wherein each of said two groups is individually selected from the group comprising a carboxylate, a nitrogen-containing group, a phenol, an acetylacetonate, a phosphonate, and a phosphate.

In some embodiments, at least one of the one or more bridging ligands comprises the photosensitizer or a derivative of the photosensitizer. In some embodiments, at least one of the one or more bridging ligands comprises a porphyrin, a chlorin, a chlorophyll, a phthalocyanine, a ruthenium-bipyridine complex, or an iridium-bipyridine complex. In some embodiments, at least one of the one or more bridging ligands comprises a diphenyl-di(benzoate)porphyrin, a dibenzoato(bipyridine)ruthenium bis(bipyridine), or a dibenzoato(bipyridine)ruthenium bis(phenylpyridine). In some embodiments, at least one of the one or more bridging ligands comprises 5,15-di(p-benzoato)porphyrin (DBP) or a derivative and/or metal complex thereof; 5,15-di(p-benzoato)chlorin (DBC) or a derivative and/or metal complex thereof; 5,15-di(p-benzoato)bacteriochlorin (DBBC) or a derivative and/or metal complex thereof; 5, 10, 15, 20-tetra (p-pyridyl)porphyrin; phthalocyanine-octacarboxylic acid; a platinum or palladium complex of di(5'-benzoatosaly-cylidene)-1,2-cyclohexylidenediamine; a phthalocyanine; or motexafin lutetium.

In some embodiments, the MOF further comprises a non-covalently bound chemotherapeutic agent and/or immunotherapeutic agent. In some embodiments, the MOF further comprises a non-covalently bound immunotherapeutic agent, wherein said immunotherapeutic agent is an IDO inhibitor (IDOi). In some embodiments, the IDOi is selected from the group comprising ICBN24360, 1-methyl-D-tryptophan, and 1-methyl-L-tryptophan.

In some embodiments, the MOF further comprises a polyethylene glycol (PEG) moiety and/or one or more lipid moiety bound covalently or electrostatically.

In some embodiments, the presently disclosed subject matter provides a pharmaceutical formulation comprising a composition comprising a metal-organic framework (MOF) comprising: a) a photosensitizer, and b) a plurality of metal-containing secondary building units (SBUs) linked together via one or more bridging ligands, wherein the SBUs comprise hafnium (Hf) oxo clusters; and a pharmaceutically acceptable carrier.

In some embodiments, the presently disclosed subject matter provides a method for treating a disease in a patient, the method comprising: administering to a patient a composition comprising a metal-organic framework (MOF) comprising: a) a photosensitizer, and b) a plurality of metal-containing secondary building units (SBUs) linked together via one or more bridging ligands, wherein the SBUs comprise hafnium (Hf) oxo clusters; and exposing at least a portion of the patient to ionizing irradiation energy.

In some embodiments, the disease is selected from a head and neck cancer, breast cancer, prostate cancer, a glioblastoma, a gynecological tumor, a brain tumor, colorectal cancer, and pancreatic cancer. In some embodiments, the disease is a metastatic cancer.

In some embodiments, the method further comprises administering to the patient an immunotherapy agent. In some embodiments, the immunotherapy agent is selected from the group comprising a PD-1/PD-L1 antibody, an IDO inhibitor, CTLA-4 antibody, a OX40 antibody, a TIM3 antibody, a LAG3 antibody, an siRNA targeting PD-1/PD-L1, an siRNA targeting IDO and an siRNA targeting CCR7.

In some embodiments, the presently disclosed subject matter provides a composition comprising a metal-organic framework (MOF) comprising a plurality of metal-containing secondary building units (SBUs) linked together via one or more organic bridging ligands, wherein the SBUs comprise hafnium (Hf) oxo clusters, further wherein said Hf oxo clusters comprise $Hf_{12}$ oxo clusters. In some embodiments, at least one of the one or more bridging ligands comprises a diphenyl-di(benzoate)porphyrin, a dibenzoato(bipyridine)ruthenium bis(bipyridine), a dibenzoatoaniline, a dibenzoatoanthracene, or a dibenzoato(bipyridine)-ruthenium bis (phenylpyridine). In some embodiments, at least one of the one or more bridging ligands is 5, 15-di(p-benzoato)porphyrin (DBP) or a derivative and/or metal complex thereof. In some embodiments, the MOF has a structure of the formula $Hf_{12}(\mu_3\text{-O})_8(\mu_3\text{-OH})_8(\mu_2\text{-OH})_6(DBP)_9$.

Accordingly, it is an object of the presently disclosed subject matter to provide MOFs comprising photosensitizers and/or scintillators and/or X-ray absorbing moieties, nanoparticles thereof, and pharmaceutical formulations thereof, as well as methods of using and use of such compositions in treating disease.

An object of the presently disclosed subject matter having been stated hereinabove, and which is achieved in whole or in part by the presently disclosed subject matter, other objects will become evident as the description proceeds when taken in connection with the accompanying drawings and examples as best described hereinbelow.

BRIEF DESCRIPTION OF THE DRAWINGS

(FIG. 6A) a structure viewed from the [100] direction; (FIG. 6B) a structure viewed from the [110] direction; (FIG. 6C) a ball-stick model of $M_6(\mu_3\text{-}O)_4(\mu_3\text{-}OH)_4(\text{carboxylate})_{12}$ (M=Hf or Zr) secondary building unit (SBU); (FIG. 6D) a tetrahedral cavity, and (FIG. 6E) an octahedral cavity. Polyhedra: $Hf^{4+}$ or $Zr^{4+}$ with eight coordinating oxygen atoms.

FIGS. 7A and 7B show graphs of: (FIG. 7A) radioluminescence signals of a hafnium metal-organic framework (Hf-MOF), a zirconium metal-organic framework (Zr-MOF) and control samples (from left to right): hafnium oxide (HfO₂) and zirconium oxide (ZrO₂) colloidal nanoparticles, bridging ligand (H₂L) alone, H₂L+HfO₂ colloid, H₂L+ZrO₂ colloid, Hf-MOF, and Zr-MOF; and (FIG. 7B) radioluminescence signals of Hf-MOF and Zr-MOF with different concentrations and different radiation tube voltages. For FIG. 7A, the concentrations of H₂L or Hf or Zr in the samples are 1.2 millimolar (mM). The X-ray dosages are 1 Gray (Gy) per 10 seconds (sec) with effective x-ray energy 18.9 kiloelectronvolts (keV) (40 kilovolts (kV) tube voltage, 0.08 milliampere (mA) tube current) and detection gain of 200. For FIG. 7B, data is provided by the following: Hf-MOF at 30 kV (squares); Hf-MOF at 50 kV (circles); Hf-MOF at 80 kV (triangles); Zr-MOF at 30 kV (squares); Zr-MOF at 50 kV (circles); and Zr-MOF at 80 kV (triangles).

(FIG. 12B) the linear fit of change in optical density (Δ(OD)) against irradiation dose at 439 nanometers (nm); and (FIG. 12C) Δ(OD) against irradiation dose at 439 nm.

(FIG. 13B) the cytotoxicity of human laryngeal cancer (SQ20B) cells treated with NMOF (P-MOF or a ruthenium-bipyridine-based metal-organic framework (Ru-MOF) and X-ray irradiation or P-MOF and light emitting diode (LED) light irradiation with or without beef as block.

(FIG. 18A) the tumor growth curves of SQ20B tumor bearing mice treated with phosphate buffered saline (PBS; filled squares), a di(p-benzoato)porphyrin metal-organic framework (P-MOF; open circles for a 2.0 gray (Gy) per fraction irradiation dose or filled triangles for a 0.5 Gy per fraction irradiation dose), or a ruthenium-bipyridine metal-organic framework (Ru-MOF; open triangles) at a ligand dose of 10 micromole per kilogram (μmol/kg); (FIG. 18B) the tumor growth curves of SQ20B tumor bearing mice treated with PBS (filled squares) or P-MOF (open circles) at a ligand dose of 10 μmol/kg and X-ray irradiation; (FIG. 18C) the tumor growth curves of U87 tumor bearing mice treated with PBS (filled squares) or P-MOF (open circles) at a ligand dose of 10 μmol/kg and X-ray irradiation; (FIG. 18D) the tumor growth curves of PC-3 tumor bearing mice treated with PBS (filled squares) or P-MOF (open circles), at a ligand dose of 10 μmol/kg and X-ray irradiation; and (FIG. 18E) the tumor growth curves of CT26 tumor bearing mice treated with PBS (filled squares) or P-MOF, at a ligand dose of 10 μmol/kg (open circles) or 1 μmol/kg (filled triangles) and X-ray irradiation. For FIG. 18A, the treatments started when the tumors reached 100 cubic millimeters ($mm^3$). For FIG. 18B, the treatments started when the tumors reached 250 $mm^3$. For FIG. 18C, the treatments started when the tumors reached ~100 $mm^3$. For FIG. 18D, the treatments started when the tumors reached 100 $mm^3$. For FIG. 18E, the treatments started when the tumors reached 150 $mm^3$. For FIGS. 18A-18E, the X-ray irradiation was carried out on mice 12 hours post the intratumoral injection of PBS or NMOFs on three consecutive days.

(FIG. 25A) calculated fractions of X-ray photons with different energy after penetrating selected attenuators; (FIG. 25B) calculated X-ray spectra from tungsten (W)-target sources at 120 peak kilovoltage (kVp) after being filtered by copper attenuators; (FIG. 25C) calculated X-ray spectra from W-target sources at 120 kVp after filtered by copper attenuators, normalized by total photon counts; (FIG. 25D) calculated X-ray mass energy absorption coefficients of hafnium (Hf) and water; (FIG. 25E) calculated ratios of X-ray mass energy absorption coefficients of Hf and water; and (FIG. 25F) calculated penetration depths of X-ray photons at different energies.

(FIG. 26B) the in vivo anticancer efficacy of tetrabenzoatoporphyrin-hafnium metal-organic frameworks (TBP-Hf) using different X-ray delivery parameters on CT26 subcutaneous tumor bearing mouse models. Phosphate buffered saline (PBS) was used as a control treatment (filled squares). For FIG. 26A P-MOF was intratumorally injected to the mice at a ligand dose of 10 micromoles per kilogram (μmol/kg). For FIG. 26B, TBP-Hf was intratumorally injected to the mice at a ligand dose of 10 μmol/kg or 20 μmol/kg. After 12 hours, the tumors were irradiated using two different X-ray delivery parameters: (1) 225 peak kilovoltage (kVp), 13 milliampere (mA), 0.3 millimeter (mm) Cu filter, and 0.5 Gy/fraction (open circles) and (2) 120 kVp, 20 mA, 2-mm Cu filter, and 1 Gy/fraction (filled triangles). For FIG. 26A, P-MOF was injected once followed by three daily X-ray irradiations. For FIG. 26B, TBO-Hf was injected once followed by five daily X-ray irradiations.

FIG. 31 is a schematic diagram showing the chemical structures of exemplary boron-dipyridine (BODIPY) derivative and disalicylidene-1,2-cyclohexylidenediamine complex photosensitizers and/or bridging ligands according to the presently disclosed subject matter.

FIG. 34A is a schematic drawing of a structural model of a hafnium oxo cluster having a formula $Hf_{12}(\mu_3\text{-O})_8(\mu_3\text{-OH})_8(\mu_2\text{-OH})_6(RCO_2)_{18}$.

FIG. 34B is a schematic drawing of the side view of a nanosheet comprising the oxo clusters shown in FIG. 34A. The hafnium twelve ($Hf_{12}$) oxo clusters align with c axis of the crystal structure, forming double-stack layers of $Hf_{12}(\mu_3\text{-O})_8(\mu_3\text{-OH})_8(\mu_2\text{-OH})_6(DBA)_6$, and are further cross-linked by 2,5-di(p-benzoato)aniline (DBA) ligands to make $Hf_{12}(\mu_3\text{-O})_8(\mu_3\text{-OH})_8(\mu_2\text{-OH})_6(DBA)_9$. Black or gray are arbitrarily assigned to illustrate the packing of the layers in an ABAB pattern. Rods represent ligands.

FIG. 35A a schematic diagram showing the dosing schedule of an in vivo anti-tumor efficacy study of nano metal-organic frameworks (nMOFs), X-ray irradiation, and anti-PD-L1 antibodies (α-PD-L1) in CT26 tumor bearing mice.

FIG. 35B shows the tumor growth curves of the right tumors of CT26 tumor-bearing mice treated with metal-organic framework (MOF) nanoparticles comprising hafnium six oxo clusters and 2,5-di(p-benzoato)aniline (DBA) ligands ($Hf_6$-DBA) with (left pointing triangles) or without (upward pointing triangles) anti-PD-L1 antibody, MOF nanoparticles comprising hafnium 12 oxo clusters and DBA ($Hf_{12}$-DBA) with (stars) or without (squares) anti-PD-L1 antibody, anti-PD-L1 antibody (right pointing triangles), or phosphate buffered saline (PBS, open circles) with (+) or without (−) X-ray irradiation. Treatment began at day 7 after tumor inoculation when the tumor reached a volume of 100-150 cubic millimeters ($mm^3$). X-ray irradiation was carried out on mice 12 hours after the intratumoral (i.t.) injection of PBS or nanoparticles on ten consecutive days at a dose of 1 gray (Gy)/fraction (120 peak kilovoltage (kVp), 20 milliampere (mA), 2-millimeter (mm) copper (Cu) filter). Antibody was given every three days at a dose of 75 micrograms (μg)/mouse. N=5.

FIG. 35C shows the tumor growth curves of the left tumors of CT26 tumor-bearing mice treated with metal-organic framework (MOF) nanoparticles comprising hafnium six oxo clusters and 2,5-di(p-benzoato)aniline (DBA) ligands ($Hf_6$-DBA) with (left pointing triangles) or without (upward pointing triangles) anti-PD-L1 antibody, MOF nanoparticles comprising hafnium 12 oxo clusters and DBA (Hf$_{12}$-DBA) with (stars) or without (squares) anti-PD-L1 antibody, anti-PD-L1 antibody (right pointing triangles), or phosphate buffered saline (PBS, open circles) with (+) or without (−) X-ray irradiation. Treatment began at day 7 after tumor inoculation when the tumor reached a volume of 100-150 cubic millimeters (mm$^3$). X-ray irradiation was carried out on mice 12 hours after the intratumoral (i.t.) injection of PBS or nanoparticles on ten consecutive days at a dose of 1 gray (Gy)/fraction (120 peak kilovoltage (kVp), 20 milliampere (mA), 2-millimeter (mm) copper (Cu) filter). Antibody was given every three days at a dose of 75 micrograms (μg)/mouse. N=5.

FIG. 41A is a schematic drawing showing the dosing schedule of an in vivo study of the efficacy of nano metal-organic frameworks (nMOFs) anti-PD-L1 antibody (α-DP-L1), and X-ray irradiation on a bilateral 4T1 tumor model.

FIG. 41B is a graph showing the tumor growth curves of the right tumors in 4T1 bilateral tumor-bearing mice treated with nano metal-organic frameworks (nMOFs) comprising hafnium twelve di(p-benzoato)porphyrin (Hf$_{12}$-DBP) with anti-PD-L1 antibodies and X-ray irradiation (circles); Hf$_{12}$-DBP and anti-PD-L1 antibodies without X-ray irradiation (downward pointing triangles); Hf$_{12}$-DBP and X-ray irradiation (upward pointing triangles); anti-PD-L1 antibodies and X-ray irradiation (diamonds), or phosphate buffered saline (PBS) and X-ray irradiation (squares). Treatment began at day 10 after tumor inoculation when the tumor reached a volume of 100-150 cubic millimeters (mm$^3$). X-ray irradiation was carried out on mice 12 hours after the intratumoral (i.t.) injection of PBS or nanoparticles on ten consecutive days at a dose of 1 gray (Gy)/fraction (225 peak kilovoltage (kVp), 13 milliampere (mA), 0.2-millimeter (mm) copper (Cu) filter). Antibody was given every three days at a dose of 75 micrograms (μg)/mouse. N=5.

FIG. 41C is a graph showing the tumor growth curves of the left tumors in 4T1 bilateral tumor-bearing mice treated with nano metal-organic frameworks (nMOFs) comprising hafnium twelve di(p-benzoato)porphyrin (Hf$_{12}$-DBP) with anti-PD-L1 antibodies and X-ray irradiation (circles); Hf$_{12}$-DBP and anti-PD-L1 antibodies without X-ray irradiation (downward pointing triangles); Hf$_{12}$-DBP and X-ray irradiation (upward pointing triangles); anti-PD-L1 antibodies and X-ray irradiation (diamonds), or phosphate buffered saline (PBS) and X-ray irradiation (squares). Treatment began at day 10 after tumor inoculation when the tumor reached a volume of 100-150 cubic millimeters (mm$^3$). X-ray irradiation was carried out on mice 12 hours after the intratumoral (i.t.) injection of PBS or nanoparticles on ten consecutive days at a dose of 1 gray (Gy)/fraction (225 peak kilovoltage (kVp), 13 milliampere (mA), 0.2-millimeter (mm) copper (Cu) filter). Antibody was given every three days at a dose of 75 micrograms (μg)/mouse. N=5.

FIG. 43A is a schematic drawing showing the dosing schedule of an in vivo study of the efficacy of nano metal-organic frameworks (nMOFs); antibody and X-ray irradiation on a bilateral SCCVII tumor model.

FIG. 43B is a graph showing the tumor growth curves of right tumors in SCCVII tumor-bearing mice treated with nano metal-organic frameworks (nMOFs) comprising hafnium twelve/di(p-benzoato)porphyrin (Hf$_{12}$-DBP) with (circles, rightward pointing triangles, diamonds) or without (upward pointing triangles) antibody, anti-PD-L1 antibody (leftward pointing triangles), or phosphate buffered saline (PBS) with (+) (downward pointing triangles) or without (−) (squares) X-rays irradiation. Treatment began at day 8 after tumor inoculation when the tumor reached a volume of 100-150 cubic millimeters (mm$^3$). X-ray irradiation was carried out on mice 12 hours after the intratumoral (i.t.) injection of PBS or nanoparticles on ten consecutive days at a dose of 1 gray (Gy)/fraction (225 peak kilovoltage (kVp), 13 milliampere (mA), 0.2-millimeter (mm) copper (Cu) filter). Antibody was given every three days at a dose of 75 micrograms (μg)/mouse. N=5.

FIG. 43C is a graph showing the tumor growth curves of left tumors in SCCVII tumor-bearing mice treated with nano metal-organic frameworks (nMOFs) comprising hafnium twelve/di(p-benzoato)porphyrin (Hf$_{12}$-DBP) with (circles, rightward pointing triangles, diamonds) or without (upward pointing triangles) antibody, anti-PD-L1 antibody (leftward pointing triangles), or phosphate buffered saline (PBS) with (+) (downward pointing triangles) or without (−) (squares) X-rays irradiation. Treatment began at day 8 after tumor inoculation when the tumor reached a volume of 100-150 cubic millimeters (mm$^3$). X-ray irradiation was carried out on mice 12 hours after the intratumoral (i.t.) injection of PBS or nanoparticles on ten consecutive days at a dose of 1 gray (Gy)/fraction (225 peak kilovoltage (kVp), 13 milliampere (mA), 0.2-millimeter (mm) copper (Cu) filter). Antibody was given every three days at a dose of 75 micrograms (μg)/mouse. N=5.

FIG. 44A is a schematic drawing showing the dosing schedule of an in vivo study of the efficacy of nano metal-organic frameworks (nMOFs) antibody, and X-ray irradiation on a bilateral CT26 tumor model.

FIG. 44B is a graph showing the tumor growth curves of right tumors in CT26 tumor-bearing mice treated with nano metal-organic frameworks (nMOFs) comprising hafnium twelve/di(p-benzoato)porphyrin (Hf$_{12}$-DBP) with anti-PD-1 antibody and irradiation (upward pointing triangles); HF$_{12}$-DBP with anti-CTLA-4 antibody and irradiation (circles); Hf12-DBP with anti-PD-L1 antibody and irradiation (downward pointing triangles); or anti-PD-L1 antibody (squares) with X-ray irradiation. Treatment began at day 8 after tumor inoculation when the tumor reached a volume of 100-150 cubic millimeters (mm$^3$). X-ray irradiation was carried out on mice 12 hours after the intratumoral (i.t.) injection of nanoparticles on ten consecutive days at a dose of 1 gray (Gy)/fraction (225 peak kilovoltage (kVp), 13 milliampere (mA), 0.2-millimeter (mm) copper (Cu) filter). Antibody was given every three days at a dose of 75 micrograms (μg)/mouse. N=5.

FIG. 44C is a graph showing the tumor growth curves of left tumors in CT26 tumor-bearing mice treated with nano metal-organic frameworks (nMOFs) comprising hafnium twelve/di(p-benzoato)porphyrin (Hf$_{12}$-DBP) with anti-PD-1 antibody and irradiation (upward pointing triangles); HF$_{12}$-DBP with anti-CTLA-4 antibody and irradiation (circles); Hf12-DBP with anti-PD-L1 antibody and irradiation (downward pointing triangles); or anti-PD-L1 antibody (squares) with X-ray irradiation. Treatment began at day 8 after tumor inoculation when the tumor reached a volume of 100-150 cubic millimeters (mm$^3$). X-ray irradiation was carried out on mice 12 hours after the intratumoral (i.t.) injection of nanoparticles on ten consecutive days at a dose of 1 gray (Gy)/fraction (225 peak kilovoltage (kVp), 13 milliampere (mA), 0.2-millimeter (mm) copper (Cu) filter). Antibody was given every three days at a dose of 75 micrograms (μg)/mouse. N=5.

DETAILED DESCRIPTION

Figure 1:
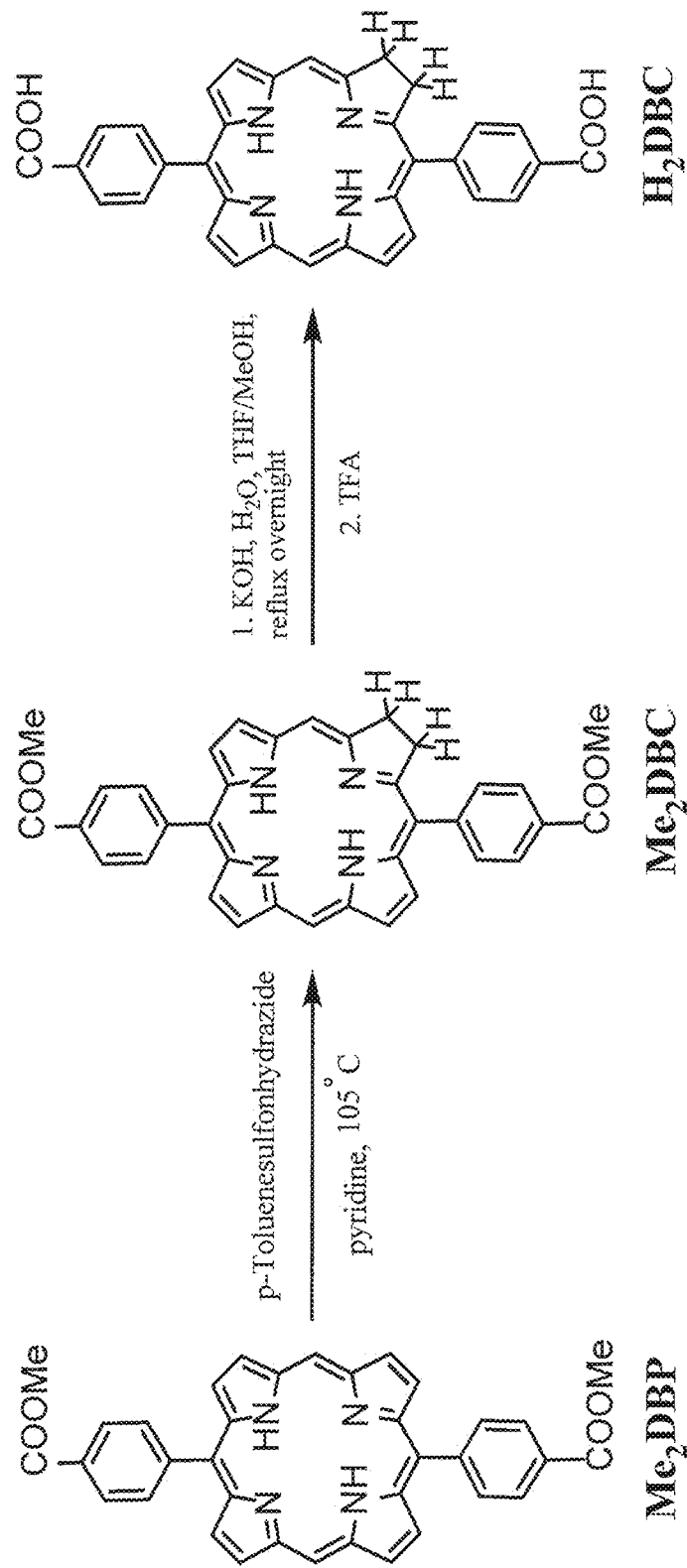
FIG. 1 is a schematic diagram showing the synthesis of the 5,15-di(p-benzoato)chlorin bridging ligand ($H_2DBC$).
Figure 2A:
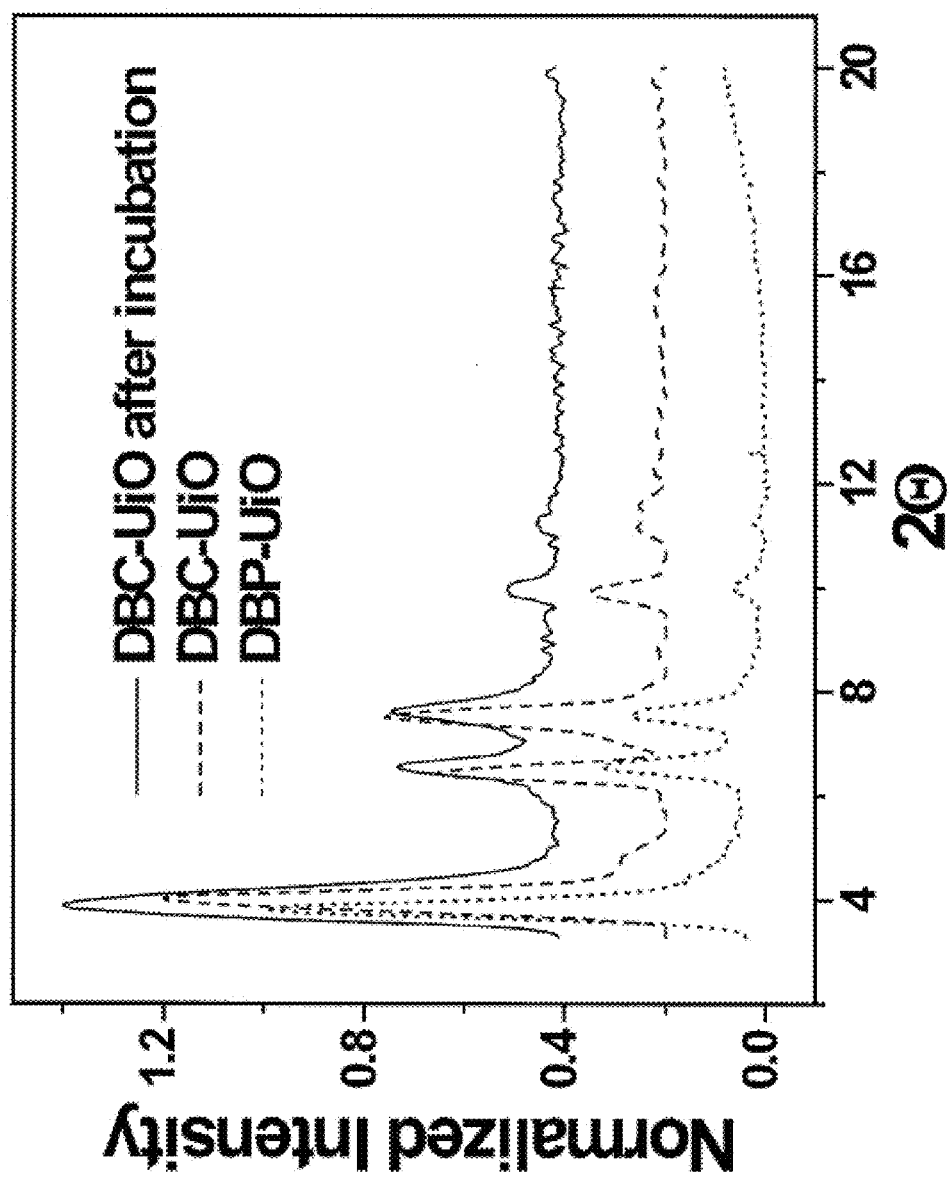
FIG. 2A shows a powder X-ray diffraction (PXRD) pattern of a di(p-benzoato)porphyrin metal-organic framework (DBP-UiO; dotted line) and a di(p-benzoato)chlorin metal-organic framework (DBC-UiO) before (dashed line) and after (solid line) incubation in cell culture medium.
Figure 2B:
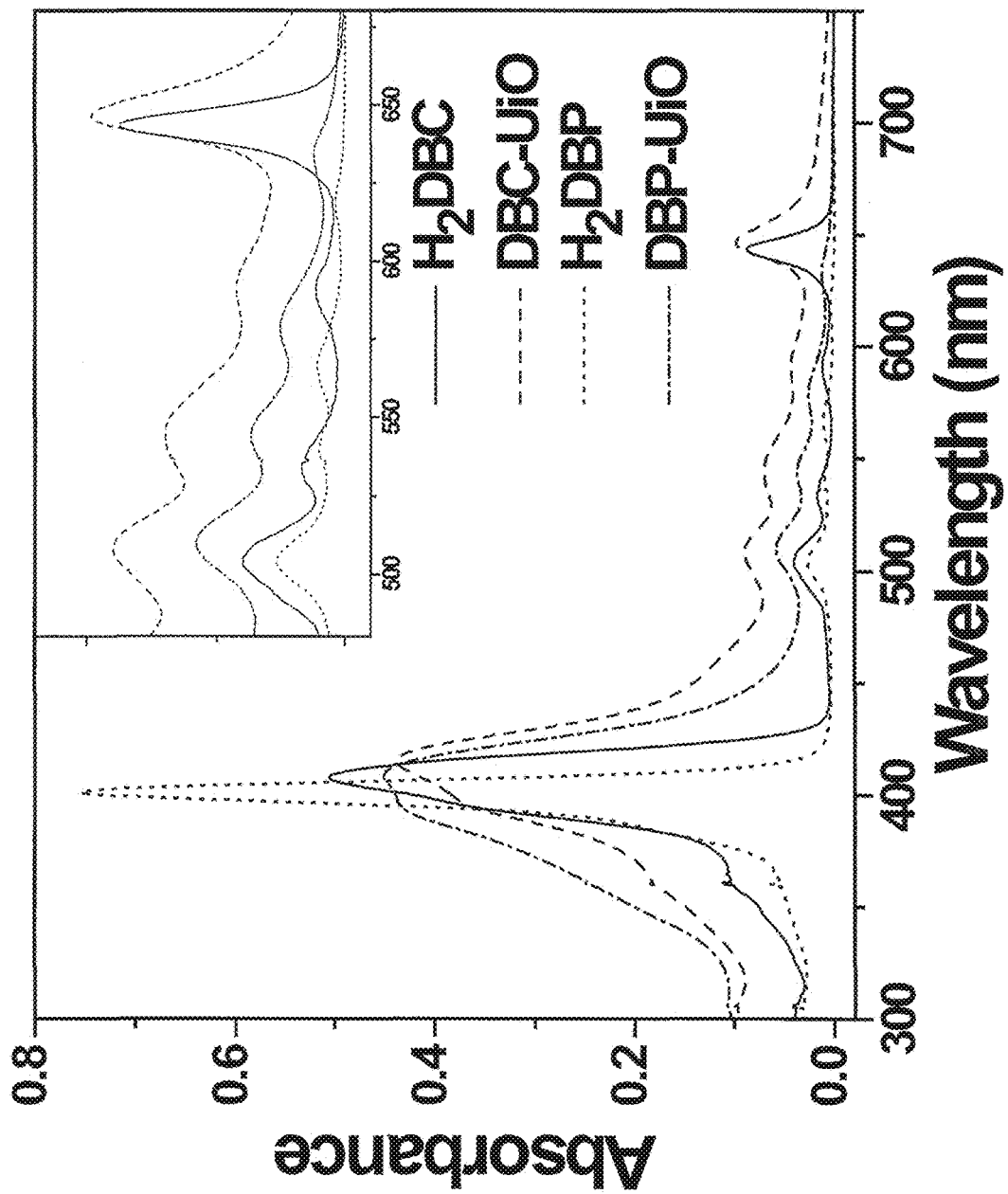
FIG. 2B shows an ultraviolet-visible (UV-vis) absorption spectra of di(p-benzoato)chlorin ($H_2DBC$; solid line), DBC-UiO (dashed line), di(p-benzoato)porphyrin ($H_2DBP$; dotted line) and DBP-UiO (dotted and dashed line) in dimethylformamide (DMF) or 0.67 millimolar (mM) phosphate buffered saline (PBS).
Figure 2C:
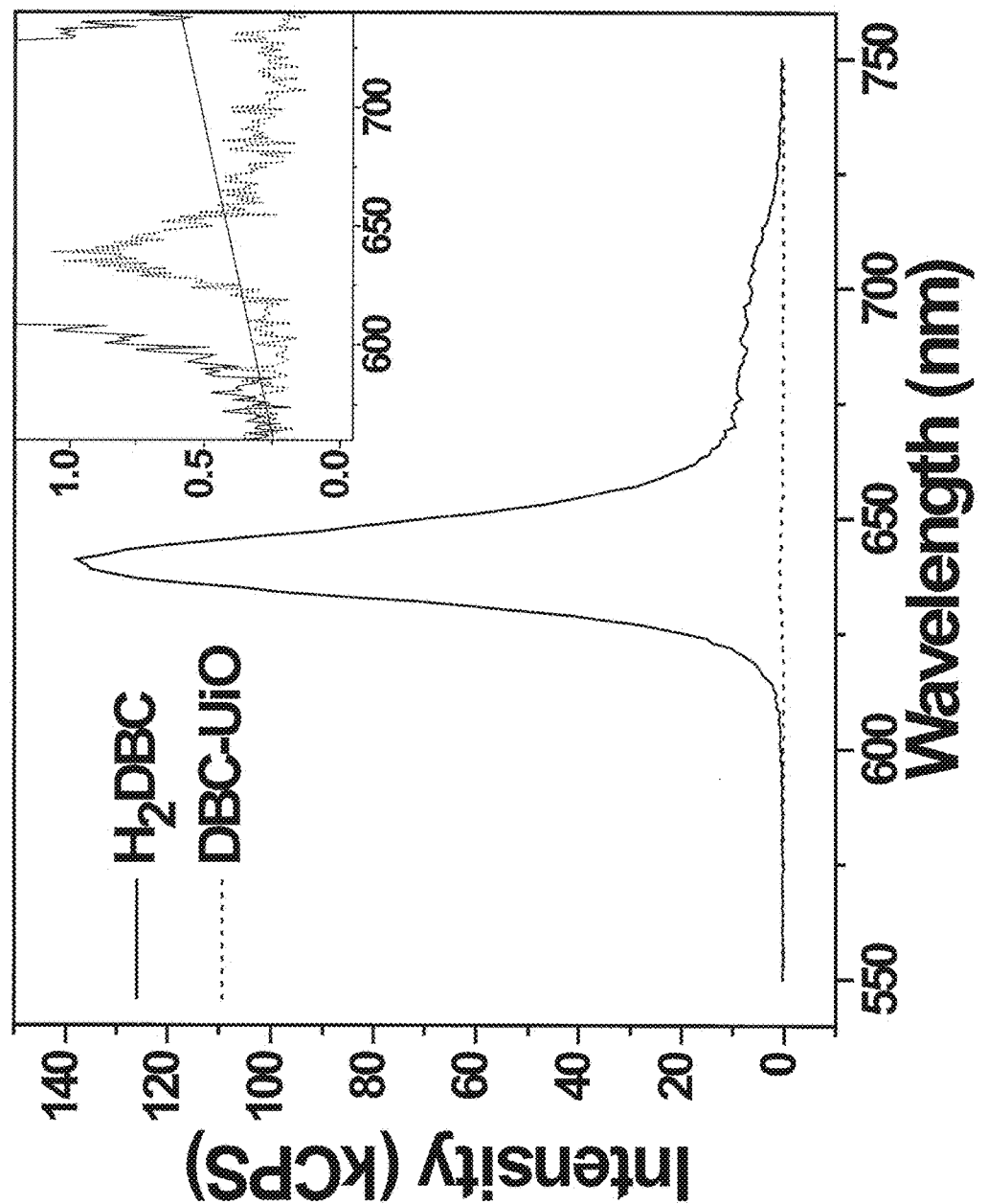
FIG. 2C is a graph showing the steady-state fluorescence of 1 micromolar (μM) H₂DBC (solid line) and DBC-UiO (dotted line) in aqueous solutions.
Figure 2D:
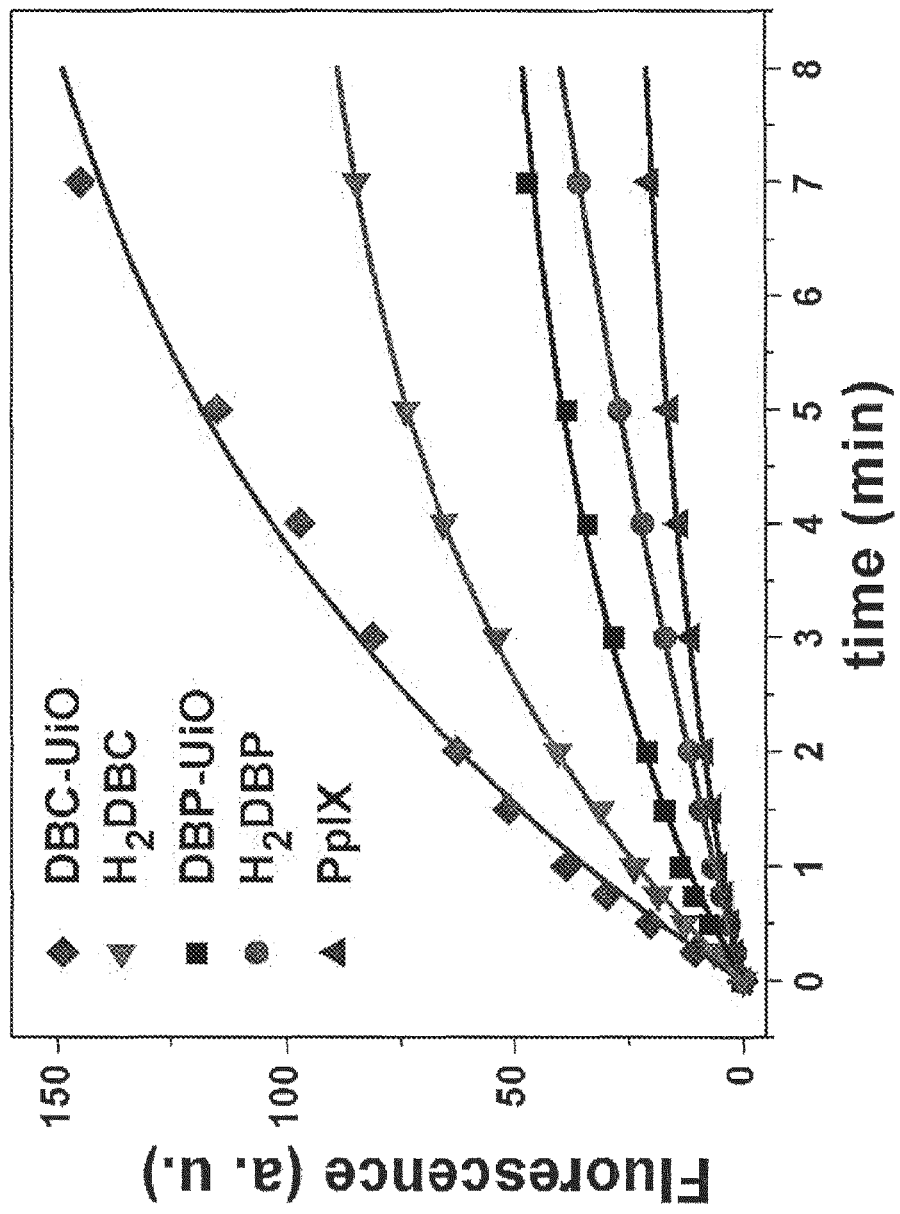
FIG. 2D is a graph showing singlet oxygen ($^1O_2$) generation of DBC-UiO (diamonds), H₂DBC (left pointing triangles), DBP-UiO (squares), H₂DBP (circles) and protoporphyrin IX (PpIX; upward pointing triangles) at an irradiance of 0.1 watts per square centimeter (W/cm²). DBC-UiO and H₂DBC are irradiated with a 650 nanometer (nm) light emitting diode (LED), while the others are irradiated with a 640 nm LED. The symbols (e.g., the squares, triangles, etc.) are experimental data and the solid lines are fitted curves.

In some embodiments, the presently disclosed subject matter provides metal-organic frameworks (MOFs) comprising photosensitizers. The MOFs can also include moieties capable of absorbing X-rays and/or scintillation. Optionally, the photosensitizer or a derivative thereof can form a bridging ligand of the MOF. Further optionally, the MOF can comprise inorganic nanoparticles in the cavities or channels of the MOF or can be used in combination with an inorganic nanoparticle. In some embodiments, the presently disclosed subject matter provides methods of using MOFs and/or inorganic nanoparticles in photodynamic therapy, X-ray induced photodynamic therapy, radiotherapy (RT), radiodynamic therapy (RDT), or radiotherapy-radiodynamic therapy (RT-RDT), either with or without the co-administration of one or more immunotherapeutic agent and/or one or more chemotherapeutic agent.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a metal ion" includes a plurality of such metal ions, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc) in the backbone of a ring structure. Nitrogen-containing heteroaryl moieties include, but are not limited to, pyridine, imidazole, benzimidazole, pyrazole, pyrazine, triazine, pyrimidine, and the like.

"Aralkyl" refers to an -alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH=CH—CH=CH—; —CH=CH—$CH_2$—; —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The term "amino" refers to the group —$N(R)_2$ wherein each R is independently H, alkyl, substituted alkyl, aryl, substituted aryl, aralkyl, or substituted aralkyl. The terms "aminoalkyl" and "alkylamino" can refer to the group —$N(R)_2$ wherein each R is H, alkyl or substituted alkyl, and wherein at least one R is alkyl or substituted alkyl. "Arylamine" and "aminoaryl" refer to the group —$N(R)_2$ wherein each R is H, aryl, or substituted aryl, and wherein at least one R is aryl or substituted aryl, e.g., aniline (i.e., —$NHC_6H_5$).

The term "thioalkyl" can refer to the group —SR, wherein R is selected from H, alkyl, substituted alkyl, aralkyl, substituted aralkyl, aryl, and substituted aryl. Similarly, the terms "thioaralkyl" and "thioaryl" refer to —SR groups wherein R is aralkyl and aryl, respectively.

The terms "halo", "halide", or "halogen" as used herein refer to fluoro, chloro, bromo, and iodo groups.

The terms "hydroxyl" and "hydroxy" refer to the —OH group.

The terms "mercapto" or "thiol" refer to the —SH group.

The terms "carboxylate" and "carboxylic acid" can refer to the groups —C(=O)O⁻ and —C(=O)OH, respectively. The term "carboxyl" can also refer to the —C(=O)OH group. In some embodiments, "carboxylate" or "carboxyl" can refer to either the —C(=O)O⁻ or —C(=O)OH group.

The term "acetylacetonate" refers to the anion formed by deprotonating the group —C(=O)$CH_2$C(=O)$CH_3$.

The term "phosphonate" refers to the —P(=O)$(OR)_2$ group, wherein each R can be independently H, alkyl, aralkyl, aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "phosphate" refers to the —OP(=O)$(OR')_2$ group, where R' is H or a negative charge.

The terms "bonding" or "bonded" and variations thereof can refer to either covalent or non-covalent bonding. In some cases, the term "bonding" refers to bonding via a coordinate bond. The term "conjugation" can refer to a bonding process, as well, such as the formation of a covalent linkage or a coordinate bond.

As used herein, the term "metal-organic framework" refers to a solid two- or three-dimensional network comprising both metal and organic components, wherein the organic components include at least one, and typically more than one carbon atom. In some embodiments, the material is crystalline. In some embodiments, the material is amorphous. In some embodiments, the material is porous. In some embodiments, the metal-organic matrix material is a coordination polymer, which comprises repeating units of coordination complexes comprising a metal-based secondary building unit (SBU), such as a metal ion or metal complex, and a bridging polydentate (e.g., bidentate or tridentate) organic ligand. In some embodiments, the material contains more than one type of SBU or metal ion. In some embodiments, the material can contain more than one type of organic bridging ligand.

The term "nanoscale metal-organic framework" can refer to a nanoscale particle comprising an MOF.

A "coordination complex" is a compound in which there is a coordinate bond between a metal ion and an electron pair donor, ligand or chelating group. Thus, ligands or chelating groups are generally electron pair donors, molecules or molecular ions having unshared electron pairs available for donation to a metal ion.

The term "coordinate bond" refers to an interaction between an electron pair donor and a coordination site on a metal ion resulting in an attractive force between the electron pair donor and the metal ion. The use of this term is not intended to be limiting, in so much as certain coordinate bonds also can be classified as having more or less covalent character (if not entirely covalent character) depending on the characteristics of the metal ion and the electron pair donor.

As used herein, the term "ligand" refers generally to a species, such as a molecule or ion, which interacts, e.g., binds, in some way with another species. More particularly, as used herein, a "ligand" can refer to a molecule or ion that binds a metal ion in solution to form a "coordination complex." See Martell, A. E., and Hancock, R. D., *Metal Complexes in Aqueous Solutions*, Plenum: New York (1996), which is incorporated herein by reference in its entirety. The terms "ligand" and "chelating group" can be used interchangeably. The term "bridging ligand" can refer to a group that bonds to more than one metal ion or complex, thus providing a "bridge" between the metal ions or complexes. Organic bridging ligands can have two or more groups with unshared electron pairs separated by, for example, an alkylene or arylene group. Groups with unshared electron pairs, include, but are not limited to, —$CO_2H$, —$NO_2$, amino, hydroxyl, thio, thioalkyl, —$B(OH)_2$, —$SO_3H$, $PO_3H$, phosphonate, and heteroatoms (e.g., nitrogen, oxygen, or sulfur) in heterocycles.

The term "coordination site" when used herein with regard to a ligand, e.g., a bridging ligand, refers to a unshared electron pair, a negative charge, or atoms or functional groups cable of forming an unshared electron pair or negative charge (e.g., via deprotonation under at a particular pH).

The terms "nanoscale particle," nanomaterial," and "nanoparticle" refer to a structure having at least one region with a dimension (e.g., length, width, diameter, etc.) of less than about 1,000 nm. In some embodiments, the dimension is smaller (e.g., less than about 500 nm, less than about 250 nm, less than about 200 nm, less than about 150 nm, less than about 125 nm, less than about 100 nm, less than about 80 nm, less than about 70 nm, less than about 60 nm, less than about 50 nm, less than about 40 nm, less than about 30 nm or even less than about 20 nm). In some embodiments, the dimension is between about 20 nm and about 250 nm (e.g., about 20, 30, 40, 50, 60, 70, 80, 90, 100, 110, 120, 130, 140, 150, 160, 170, 180, 190, 200, 210, 220, 230, 240, or 250 nm).

In some embodiments, the nanoparticle is approximately spherical. When the nanoparticle is approximately spherical, the characteristic dimension can correspond to the diameter of the sphere. In addition to spherical shapes, the nanomaterial can be disc-shaped, plate-shaped (e.g., hexagonally plate-like), oblong, polyhedral, rod-shaped, cubic, or irregularly-shaped.

The nanoparticle can comprise a core region (i.e., the space between the outer dimensions of the particle) and an outer surface (i.e., the surface that defines the outer dimensions of the particle). In some embodiments, the nanoparticle can have one or more coating layers surrounding or partially surrounding the nanoparticle core. Thus, for example, a spherical nanoparticle can have one or more concentric coating layers, each successive layer being dispersed over the outer surface of a smaller layer closer to the center of the particle.

In some embodiments, the presently disclosed nanoparticles can comprise a solid metal-organic framework (MOF) matrix, which are two- or three-dimensional networks of SBUs linked together by bridging ligands. The MOF can comprise one or more pores or hollow interior regions. The MOF matrix can be amorphous or crystalline. In some embodiments, the nanoparticle core further comprises one or more PSs, X-ray absorbing agents, scintillation agents and/or other therapeutic agents (e.g., anticancer or immunotherapy agents), which can be physically trapped within the matrix, coordinated to a metal ion of the matrix, or chemically bonded (e.g., to a organic bridging ligand in the matrix or a compound in a layer dispersed over the nanoparticle core) via a covalent or ionic bond. In some embodiments, a photosensitizer or a derivative thereof can be an organic bridging ligand or attached to an organic bridging ligand within a metal-organic matrix material that forms the core of the nanoparticle, while the metal of the SBU acts as a scintillator. Alternatively the scintillator, X-ray absorbing agent and/or PS can be entrapped within the MOF or covalently attached to the MOF.

"Embedded" can refer to a agent that is bound, for example covalently bound or bound via a coordinative bond, inside the core of the particle (e.g., to a coordination site of a bridging ligand or to a metal ion of an SBU). Alternatively, agents can be "sequestered", "entrapped", or "trapped" (i.e., non-covalently encapsulated) inside pores, cavities or channels in the core of an MOF particle or interact with a MOF material via hydrogen bonding, London dispersion forces, or any other non-covalent interaction.

The terms "polymer" and "polymeric" refer to chemical structures that have repeating units (i.e., multiple copies of a given chemical substructure). Polymers can be formed from polymerizable monomers. A polymerizable monomer is a molecule that comprises one or more moieties that can react to form bonds (e.g., covalent or coordination bonds) with moieties on other molecules of polymerizable monomer. In some embodiments, each polymerizable monomer molecule can bond to two or more other molecules/moieties. In some cases, a polymerizable monomer will bond to only one other molecule, forming a terminus of the polymeric material.

Polymers can be organic, or inorganic, or a combination thereof. As used herein, the term "inorganic" refers to a compound or composition that contains at least some atoms other than carbon, hydrogen, nitrogen, oxygen, sulfur, phosphorous, or one of the halides. Thus, for example, an inorganic compound or composition can contain one or more silicon atoms and/or one or more metal atoms.

As used herein "organic polymers" are those that do not include silica or metal atoms in their repeating units. Exemplary organic polymers include polyvinylpyrrolidone (PVO), polyesters, polyamides, polyethers, polydienes, and the like. Some organic polymers contain biodegradable linkages, such as esters or amides, such that they can degrade overtime under biological conditions.

The term "hydrophilic polymer" as used herein generally refers to hydrophilic organic polymers, such as but not limited to, polyvinylpyrrolidone (PVP), polyvinylmethylether, polymethyloxazoline, polyethyloxazoline, polyhydroxy-propyloxazoline, polyhydroxypropylmethacrylamide, polymethyacrylamide, polydimethylacrylamide, polyhydroxylpropylmethacrylate, polyhydroxy-ethylacrylate, hydroxymethylcellulose, hydroxyethylcellulose, polyethylene-imine (PEI), polyethyleneglycol (i.e., PEG) or another hydrophilic poly(alkyleneoxide), polyglycerine, and polyaspartamide. The term "hydrophilic" refers to the ability of a molecule or chemical species to interact with water. Thus, hydrophilic polymers are typically polar or have groups that can hydrogen bond to water.

The term "photosensitizer" (PS) refers to a chemical compound or moiety that can be excited by light of a particular wavelength, typically visible or near-infrared (NIR) light, and produce a reactive oxygen species (ROS). For example, in its excited state, the photosensitizer can undergo intersystem crossing and transfer energy to oxygen ($O_2$) (e.g., in tissues being treated by PDT) to produce ROSs, such as singlet oxygen ($^1O_2$). Any known type of a photosensitizer can be used in accordance with the presently disclosed subject matter. In some embodiments, the photosensitizer is a porphyrin, a chlorophyll, a dye, or a derivative or analog thereof. In some embodiments, porphyrins, chlorins, bacteriochlorins, or porphycenes can be used. In some embodiments, the photosensitizer can have one or more functional groups, such as carboxylic acid, amine, or isothiocyanate, e.g., for using in attaching the photosensitizer to another molecule or moiety, such as an organic bridging ligand or a SBU, and/or for providing an additional site or sites to enhance coordination or to coordinate an additional metal or metals. In some embodiments, the photosensitizer is a porphyrin or a derivative or analog thereof. Exemplary porphyrins include, but are not limited to, hematoporphyrin, protoporphyrin and tetraphenylporphyrin (TPP). Exemplary porphyrin derivatives include, but are not limited to, pyropheophorbides, bacteriochlorophylls, chlorophyll a, benzoporphyrin derivatives, tetrahydroxyphenyl chlorins, purpurins, benzochlorins, naphthochlorins, verdins, rhodins, oxochlorins, azachlorins, bacteriochlorins, tolyporphyrins and benzobacteriochlorins. Porphyrin analogs include, but are not limited to, expanded porphyrin family members (such as texaphyrins, sapphyrins and hexaphyrins), porphyrin isomers (such as porphycenes, inverted porphyrins, phthalocyanines, and naphthalocyanines), and TPP substituted with one or more functional groups.

The term "cancer" as used herein refers to diseases caused by uncontrolled cell division and/or the ability of cells to metastasize, or to establish new growth in additional sites. The terms "malignant", "malignancy", "neoplasm", "tumor," "cancer" and variations thereof refer to cancerous cells or groups of cancerous cells.

Particular types of cancer include, but are not limited to, skin cancers (e.g., melanoma), connective tissue cancers (e.g., sarcomas), adipose cancers, breast cancers, head and neck cancers, lung cancers (e.g., mesothelioma), stomach cancers, pancreatic cancers, ovarian cancers, cervical cancers, uterine cancers, anogenital cancers (e.g., testicular cancer), kidney cancers, bladder cancers, colon cancers, prostate cancers, central nervous system (CNS) cancers, retinal cancer, blood, neuroblastomas, multiple myeloma, and lymphoid cancers (e.g., Hodgkin's and non-Hodgkin's lymphomas).

The term "metastatic cancer" refers to cancer that has spread from its initial site (i.e., the primary site) in a patient's body.

The terms "anticancer drug", "chemotherapeutic," and "anticancer prodrug" refer to drugs (i.e., chemical compounds) or prodrugs known to, or suspected of being able to treat a cancer (i.e., to kill cancer cells, prohibit proliferation of cancer cells, or treat a symptom related to cancer). In some embodiments, the term "chemotherapeutic" as used herein refers to a non-PS molecule that is used to treat cancer and/or that has cytotoxic ability. Such more traditional or conventional chemotherapeutic agents can be described by mechanism of action or by chemical compound class, and can include, but are not limited to, alkylating agents (e.g., melphalan), anthracyclines (e.g., doxorubicin), cytoskeletal disruptors (e.g., paclitaxel), epothilones, histone deacetylase inhibitors (e.g., vorinostat), inhibitors of topoisomerase I or II (e.g., irinotecan or etoposide), kinase inhibitors (e.g., bortezomib), nucleotide analogs or precursors thereof (e.g., methotrexate), peptide antibiotics (e.g., bleomycin), platinum based agents (e.g., cisplatin or oxaliplatin), retinoids (e.g., tretinoin), and vinka alkaloids (e.g., vinblastine).

The term "scintillator" refers to a moiety or compound that exhibits luminescence (emits light, e.g., light in the visible or NIR range) when excited by ionizing irradiation energy, such as x-rays, gamma (γ) rays, beta (β) irradiation, neutron beam irradiation, electron beam irradiation, or proton irradiation II. General Considerations Photodynamic therapy (PDT) is a phototherapy that combines three non-toxic components—a photosensitizer (PS), a light source, and tissue oxygen—to cause toxicity to malignant and other diseased cells. The most widely accepted mechanism of PDT involves energy transfer from the light-excited PS to oxygen molecules in the tissue to generate reactive oxygen species (ROS), particularly singlet oxygen ($^1O_2$), which induces cellular toxicity. PDT can lead to localized destruction of diseased tissues via selective uptake of the PS and/or local exposure to light, providing a minimally invasive cancer therapy.

Selective delivery of chemotherapeutics to tumors is preferred for successful chemotherapy. Similarly, localization of PSs in tumors is preferred for effective PDT. However, many PSs are hydrophobic in nature, which not only leads to insufficient tumor localization, but also causes PS aggregation to diminish the PDT efficacy. Significant synthetic modifications are thus preferred for rendering these PSs more effective PDT agents in vivo.

An alternative approach is to use nanocarriers to selectively deliver therapeutic or PDT agents to tumors via the enhanced permeation and retention effect (EPR) and sometimes, via active tumor targeting with small molecule or biologic ligands that bind to overexpressed receptors in cancers.

Nanoscale metal-organic frameworks (NMOFs), constructed from metal ion/ion clusters and organic bridging ligands can be used as a nanocarrier platform for therapeutic and imaging agents. Compared to other nanocarriers, NMOFs combine many beneficial features into a single delivery platform, including tunable chemical compositions and crystalline structures; high porosity; and bio-degradability.

II.A. Porphyrin-Based NMOFs for Photodynamic Therapy

According to one exemplary embodiment of the presently disclosed subject matter, described further hereinbelow in the Examples, a Hf-porphyrin NMOF was prepared and used as a PS for PDT of resistant head and neck cancer. Without wishing to be bound to any one theory, it is believed that incorporation of a porphyrin-derived bridging ligand into a robust and porous UiO (named for Universitetet I Oslo (Norwegian for University of Oslo)) NMOF structure with suitable morphologies and dimensions can give several advantages over other nanoparticle PDT agents. First, the PS molecules or moieties can be well-isolated in the NMOF framework to avoid aggregation and self-quenching of the excited states. Second, coordination of porphyrin ligands to heavy metal (e.g., Hf) centers can promote intersystem crossing to enhance ROS generation efficiency. Third, the porous NMOF structure can provide a pathway for facile diffusion of ROS (such as singlet oxygen ($^1O_2$)) out of the NMOF interior to exert cytotoxic effects on cancer cells. Further, an unprecedentedly high PS loading can be achieved to provide effective PDT of difficult-to-treat cancers.

Accordingly, in some embodiments, the presently disclosed subject matter provides a MOF comprising SBUs linked together via porphyrin-based bridging ligands, e.g., porphyrins, derivatives of porphyrins, and/or metal complexes thereof.

II.B. Chlorin-Based NMOFs for Photodynamic Therapy of Colon Cancers

In another exemplary embodiment, the presently disclosed subject matter provides a chlorin-based NMOF, such as DBC-UiO, with photophysical properties suitable for use in treating tumors. For example, as described hereinbelow in the Examples, DBC-UiO can be used to treat colon cancer in two colorectal adenocarcinoma mouse models.

Hematoporphyrin derivatives were developed as the first generation PSs, leading to the clinical application of the first PDT agent PHOTOFRIN®. However, the photophysical properties of porphyrins are not preferred for certain applications, with the absorption peaks typically near the high energy edge of the tissue-penetrating window (600-900 nm) and small extinction coefficient (ε) values. Reduction of porphyrins to chlorins has been shown to shift the absorption to a longer wavelength with a concomitant increase in ε. For instance, reduction of 5,10,15,20-m-tetra(hydroxyphenyl) porphyrin to its chlorin derivative red-shifts the last Q-band from 644 to 650 nm along with a dramatic enhancement in ε from 3400 $M^{-1} \cdot cm^{-1}$ to 29600 $M^{-1} \cdot cm^{-1}$.

Accordingly, in some embodiments, the presently disclosed subject matter provides a MOF comprising SBUs linked together via chlorin-based bridging ligands or ligands based on other reduced forms of porphyrins, such as bacteriochlorin.

II.C. Synergistic Assembly of Heavy Metal Clusters and Luminescent Organic Bridging Ligands in Metal-organic Frameworks for X-Ray Scintillation X-ray scintillators are widely used in X-ray dosimetry and imaging. Sensitive detection of X-rays reduces the patient exposure while maintaining or improving the image quality. A number of solid-state inorganic materials with lanthanides as light emitters, such as LaOBr:Tm, $Gd_2O_2S$:Tb, and M'-$YTaO_4$, have been developed as efficient X-ray-to-light converters. Nanophosphors have also been employed as molecular probes for a dual modality X-ray and optical imaging, referred to as X-ray luminescence computed tomography (XLCT). By taking advantage of the long penetration depth of X-ray and low optical auto-fluorescence background, XLCT can provide a highly sensitive molecular imaging technique. Additionally, nanoparticles based on solid state scintillators have been attached with singlet oxygen sensitizers for X-ray induced PDT (X-PDT).

Organic crystals such as anthracene can also serve as radiation scintillators, particularly for detecting low-energy β-rays and neutrons due to their high scattering cross sections for electrons and neutrons and low rates of backscattering. However, organic scintillators can be ineffective for X-ray detection (<100 keV) due to their low X-ray scattering cross sections. Metal-organic frameworks (MOFs) can provide a class of crystalline materials that are built from well-defined molecular bridging ligands and metal/metal cluster connecting nodes. MOFs thus can be a tunable platform for the co-assembly of organic scintillator molecules and metal cluster nodes of high atomic numbers (Z) within a highly ordered structure. For instance, Zn MOFs for radioluminescence induced by fast proton, neutron, electron and γ-rays have been reported in U.S. Pat. No. 7,985,868, which is incorporated by reference herein in its entirety.

According to some exemplary embodiments of the presently disclosed subject matter, MOFs with high Z metal clusters, for example, $M_6(\mu_3\text{-O})_4(\mu_3\text{-OH})_4(\text{carboxylate})_{12}$ (M=Hf or Zr) or an $M_{12}$ oxo cluster as connecting nodes and an anthracene-based emitter as the bridging ligand are described herein. With Z=72 for Hf and Z=40 for Zr, Hf and Zr clusters serve as efficient absorbers of X-rays (or other ionizing irradiation energy). Upon photoelectric absorption of X-rays in the 20-200 keV range, outer-shell electrons of $Hf^{4+}$ and $Zr^{4+}$ ions are ejected as fast electrons which interact with the anthracene based linkers to generate luminescence signals from their electronic excited states. The high Z metal clusters and emissive bridging ligands thus work synergistically to lead to highly efficient X-ray (or other ionizing irradiation energy) induced luminescence in the easily detectable visible spectrum.

II.D. NMOFs for Highly Efficient X-ray Induced Photodynamic Therapy

Radiotherapy is one of the most common and efficient cancer treatment modalities. In cancer radiotherapy, tumors are irradiated with high-energy radiation (for example, X-rays) to destroy malignant cells in a treated volume. NMOFs enable the treatment of deep cancer by the combination of radiotherapy and PDT. According to some embodiments of the presently disclosed subject matter, NMOFs having SBUs with high Z metal ions (e.g., Zr or Hf) can serve as effective X-ray antenna by absorbing X-ray photons and converting them to fast electrons through the photoelectric effect. The generated electrons then excite multiple PSs in the MOF through inelastic scattering, leading to efficient generation of hydroxy radicals and $^1O_2$. Additional embodiments can comprise NMOFs with SBUs comprising lanthanide metals (such as La, Ce, Pr, Nd, Pm, Sm, Eu, Gd, Tb, Dy, Ho, Er, Tm, Yb, and Lu), Ba, Ta, W, Re, Os, Ir, Pt, Au, Pb, and Bi, or any metal ion that strongly absorbs x-ray radiation.

In some embodiments, NMOFs constructed from heavy metals such as Hf and Bi as metal connecting points and porphyrin-derivatives, chlorin-derivatives, or metal-containing dyes, including $Ru(bpy)_3^{2+}$ and $Ir(pph)_2(bpy)^+$ (bpy is 2,2'-bipyridine and pph is 2-phenylpyridine), as bridging ligands are provided according to the presently disclosed subject matter. The application of such NMOFs in X-ray induced PDT/RT is demonstrated further hereinbelow in the Examples. These NMOFs are able to excite the photosensitizers with X-ray energy for subsequent singlet oxygen generation, thus serving as efficient therapeutic agents for X-ray induced PDT. The advantages of this class of NMOFs can include: 1) the combination of two effective treatments (radiation therapy and PDT); 2) a modality capable and efficient for deep cancer treatment; 3) a lowered risk of radiation damage to healthy tissue; and 4) a simple, relatively inexpensive and efficient treatment.

In certain embodiments, the presently disclosed nanoscale metal-organic frameworks can comprise or further comprise a polyoxometalate (POM), such as a tungsten, molybdenum, or niobate polyoxometalate, a metallic nanoparticle, such as a gold, palladium, or platinum nanoparticle, or a metal oxide nanoparticle, such as a hafnium oxide or niobium oxide nanoparticle, located in the MOF cavities or channels.

II.E. NMOFs for Radiotherapy and Radiotherapy-Radiodynamic Therapy

As also described further hereinbelow, Hf NMOFs, including UiO-66, UiO-67, and amino UiO-68 were synthesized. These NMOFs were constructed from Hf metal clusters and ligands with negligible photosensitization properties. The ability of Hf metal clusters to absorb ionizing irradiation energy, such as X-rays, γ-rays, β-irradiation, neutron beam irradiation, electron beam irradiation, or proton irradiation, coupled with rapid diffusion of ROS (particularly hydroxyl radical (.OH)) out of the MOF channels enabled highly effective radiotherapy. $HfO_2$ nanoparticles with amorphous structures were also used as comparisons. In some embodiments, the Hf metal cluster absorbed ionizing irradiation energy (e.g., X-ray photons) leading to RT via the production of ROS (e.g.,.OH radicals) and RDT by exciting the photosensitizers within the NMOFs to generate ROS (e.g., singlet oxygen ($^1O_2$)).

II.F. Combined PDT and Immunotherapy

PDT can selectively kill tumor cells while preserving adjacent normal tissue. PDT does not incur cross-resistance with radiotherapy or chemotherapy, and therefore, is useful in the treatment of cancer patients who have not responded significantly to traditional radiotherapy and/or chemotherapy. PDT can provoke a strong acute inflammatory reaction observed as localized edema at the targeted site. The inflammation elicited by PDT is a tumor antigen nonspecific process orchestrated by the innate immune system. PDT is particularly effective in rapidly generating an abundance of alarm/danger signals, such as damage-associated molecular patterns (DAMPs), at the treated site that can be detected by the innate immunity alert elements. PDT-mediated enhancement of antitumor immunity is believed due to the stimulation of dendritic cells by dead and dying tumor cells and can be accompanied by the recruitment and activation of CD8+ cytotoxic T cells (CTLs) followed by the formation of immune memory cells and resistance to subsequent tumor growth.

According to some embodiments of the presently disclosed subject matter, DBP-MOF and other NMOFs of the presently disclosed subject matter can be used to effect combined PDT and immunotherapy. A number of inorganic, organic, and hybrid materials are known to strongly absorb near-infrared light to generate single oxygen. The therapeutic use of such PDT materials can be combined with immune checkpoint inhibitor therapy. Exemplary photosensitizers for such combination therapy include, but are not limited to: upconversion nanoparticles, such as $NaYF_4$ (for example, doped at a ratio of Y:Yb:Er=78%:20%:2%), combined with chlorin e6 or MC540; photosensitizers-embedded in silica-based nanoparticles, such as 2-devinyl-2-(1-hexyloxyethyl) pyropheophorbide (HPPH) loaded silica nanoparticles; polymer micelle loaded photosensitizers, such as Zn(II) phthalocyanine loaded in $DSPE-PEG_{5k}$ polymer micelles; liposome based photosensitizer delivery systems, such as 5,10,15,20-tetrakis(m-hydroxyphenyl)chlorin encapsulated in a liposome and 5-aminolevulinic acid (ALA) encapsulated liposome; human serum albumin based photosensitizer delivery systems, such as HSA-pheophorbide a conjugate particles; dendrimer based photosensitizer delivery systems, such as PEG-attached poly(propyleneimine) or poly(amido amine) loaded with rose bengal and PpIX; porphyrin-, chlorin- or bacteriochlorin-conjugated phospholipid based bilayer delivery systems, such as porphyrin-lipid conjugates (pyrolipid) self-assembly nanovesicles (Porphysome) and NCP@Pyrolipid.

II.G. Combined X-PDT or RT-RDT and Immunotherapy

According to some embodiments of the presently disclosed subject matter, X-ray-induced (or other ionizing irradiation energy-induced) PDT or RT-RDT can be combined with inhibitor-based immunotherapy to cause systemic rejection of established tumors using adaptive immune response, e.g., cytotoxic T cells. When combined with immunotherapeutic agents, not only the effective eradication of primary tumor, but also suppression/eradication of distant metastatic tumor can be accomplished using NMOF-based X-PDT or RT-RDT effects. In some embodiments, the antitumor efficacy can be enhanced by adding chemotherapeutics that are known to cause immunogenic cell death.

A number of inorganic materials are known to strongly absorb X-rays (or other ionizing irradiation energy) and convert the absorbed energy to visible and near-infrared light. The emitted near-infrared light from these scintillating nanomaterials can then be absorbed by the nearby photosensitizers to enable X-ray (or other ionizing irradiation energy) induced PDT effects. In some embodiments, the absorbed energy can lead to the production of ROS and/or the excitation of nearby photosensitizers, leading to the production of ROS. Other types of materials can also achieve X-ray induced PDT or RT-RDT. When this X-ray induced PDT or RT-RDT is combined with immune checkpoint inhibitors, excellent radioimmunotherapy can be obtained. Examples of X-ray scintillating nanomaterials include, but are not limited to: $LnO_3$:Ln' nanoparticles, $LnO_2S$ Ln' nanoparticles or $LnX_3$:Ln' nanoparticles, where Ln=Y, La, Ce, Pr, Nd, Sm, Eu, Gd, Tb, Dy, Ho, Er, Tm, Yb, Lu, Ln'=Ce, Pr, Eu, Tb, etc. and X=F, Cl, Br, and I; X-ray scintillator MOFs, such as $M_6(\mu_3-O)_4(\mu_3-OH)_4L_6$, where M=Hf, Zr, or Ce; and L=9,10-anthracenylbisbenzoic acid and other formulations of MOFs containing heavy metal secondary building units; Lanthanide based MOFs, the SBU include but not limited to: $Ln_4(\mu_4-OH_2)(CO_2)_8(SO_4)_4$, [Ln(OH$_2$)(CO$_2$)$_3$]$_n$ (infinite 1-D chain), [Ln(OH$_2$)(CO$_2$)$_4$]$_n$(infinite 1-D chain), [Ln(CO2)$_3$-Ln(OH$_2$)$_2$(CO$_2$)$_3$]$_n$ (infinite 1-D chain), where Ln=La, Ce, Pr, Nd, Sm, Eu, Gd, Tb, Dy, Ho, Er, Tm, Yb, Lu and/or their mixture combination; the bridging ligands include but not limited to [1,4-benzoic dicarboxylate], [2,5-dimethoxy-1,4-benzenedicarboxylate], [1,3,5-benzoic tricarboxylate], [1,3,5-benzenetrisbenzoate], [5-(pyridin-4-yl)isophthalic acid], [4,4',4"-S-triazine-2,4,6-triyl tribenzoate], [biphenyl-3,4',5-tricarboxylate], [4,4'-[(2,5-Dimethoxy-1,4-phenylene)di-2,1-ethenediyl]bis-benzoic acid], etc.; quantum dots, such as ZnS:M quantum dots (M=Cu, Co, Mn, Eu, etc.) or carbon dots; gold nanoparticles, or platinum or other third-row metal particles; and other X-ray scintillators, such as $SrAl_2O_4$:$Eu^{2+}$; $NaYF_4$:$Tb^{3+}$, $Er^{3+}$.

Figure 27:
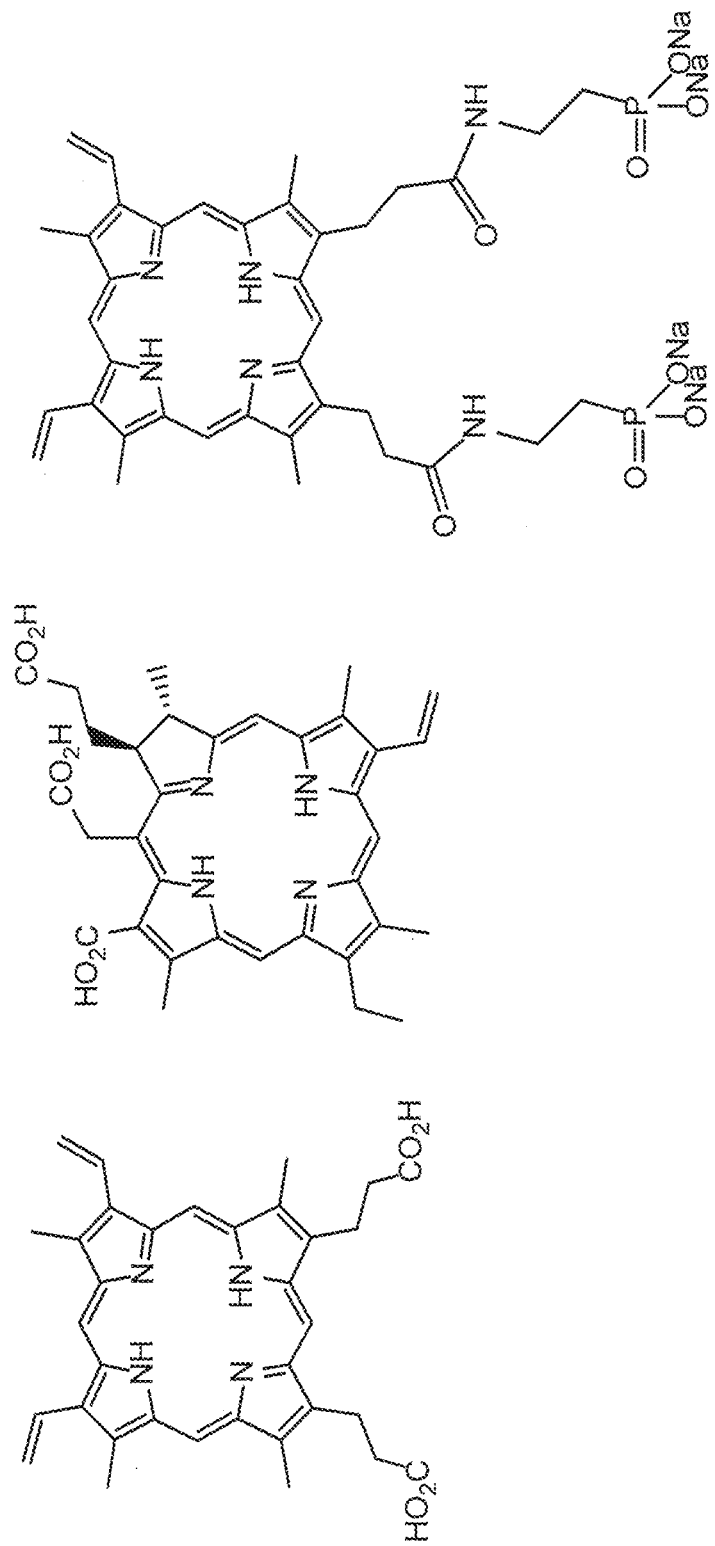
FIG. 27 is a schematic diagram showing the chemical structures of exemplary photosensitizers according to embodiments of the presently disclosed subject matter.
Figure 28:
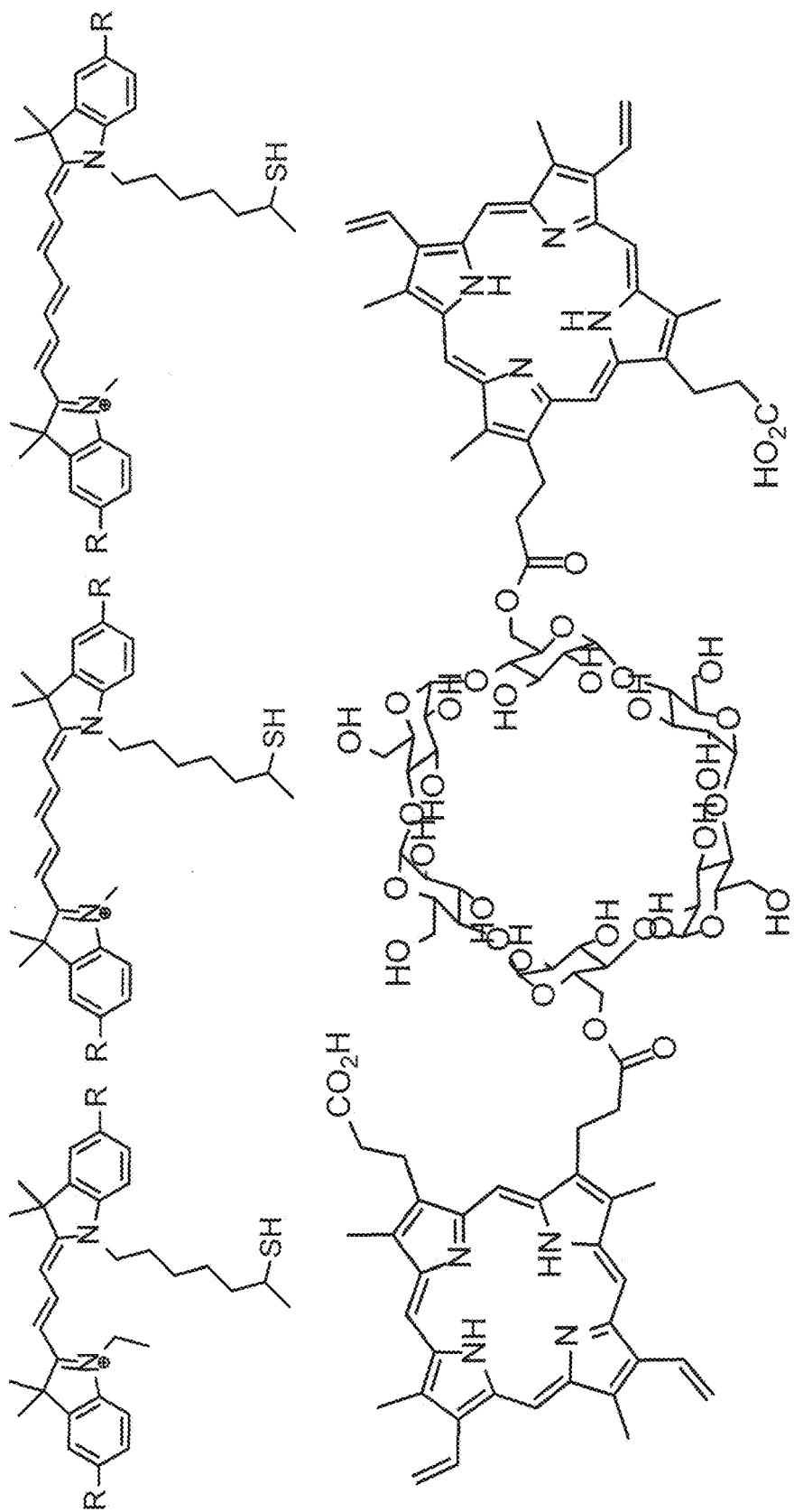
FIG. 28 is a schematic diagram showing the chemical structures of further exemplary photosensitizers according to embodiments of the presently disclosed subject matter.

Examples of photosensitizers conjugated to X-ray scintillating nanoparticles for use in X-ray induced PDT or RT-RDT include, but are not limited to: photosensitizers coordinatively bonded to a particle surface, where the coordination methods include but are not limited to carboxylate or phosphate coordination (such as via the coordination of a carboxylate or phosphate group on the PS to open metal sites (e.g., $Ln^{3+}$, $Zn^{2+}$, $Al^{3+}$, etc.) on nanoparticles); thiol coordination to nanoparticles, (via PSs containing thiols conjugating to nanoparticles through the coordination of thiol groups to Au (in gold nanoparticles) or, for example, Zn, Cd, in quantum dots); polymer conjugation and surface coating, for example, via covalently conjugating PSs to oligomers or polymers with functional groups (e.g., cyclodextrin, polyethylene glycol (PEG), poly (maleic acid) derivatives, etc.) and conjugating the scintillator particles through coordination of additional functional groups (e.g., carboxylates, thiols, hydroxyls, amines, etc.) to the metals on a particle surface, for example using photosensitizers such, but not limited to, any of those shown in FIGS. 27 and 28, covalently bonding to a MOF ligand, for example via amide conjugation, ester conjugation, thiourea conjugation, "click chemistry", disulfide bond conjugation, etc.; surface modification of porous materials and entrapment, mesoporous silica coating and entrapment, and MOF coating and entrapment, for example with photosensitizers entrapped in the pores of the silica layer.

II.H. Refinement of X-ray Set-ups for X-ray Induced Photodynamic Therapy.

In some embodiments of the presently disclosed subject matter, the X-ray (or other ionzing irradiation energy) source can be refined to enhance the X-PDT or RT-RDT effects to enable more efficient cancer cell killing. In some embodiments, the X-ray irradiator can include a panoramic irradiator comprising at least one X-ray source inside a shielded enclosure, the one or more sources each operable to emit X-ray flux across an area equal to the proximate facing surface area of the tumor. See U.S. Patent Application Publication No. 2010/0189222 and WO 2011/049743, each of which is incorporated by reference herein in its entirety.

An X-ray generator based on a tungsten target emission is suited for this application. The output energy typically ranges from 100 to 500 kV. In certain embodiments, at least one removable attenuator or filter of selected materials, which contains at least one metal with atomic number >20, is involved in this application. Each attenuator could be a flat board or a board with gradient thickness. See U.S. Pat. No. 7,430,282 incorporated by reference herein in its entirety. The attenuator could be also modulated with periodically spaced grids/holes. The output X-ray energy can be adjusted after filtration by the attenuator to maximize the energy absorption of radiosensitizers/radioscintillators in this application. An X-ray bandpass filter with an x-ray refractive lens for refracting x-rays can also be used. See WO2008/102632, incorporated by reference herein in its entirety.

III. Metal-Organic Frameworks (MOFs)

In accordance with some embodiments of the presently disclosed subject matter, a photosensitizer and/or an X-ray absorbing moiety/scintillator can be combined in a MOF or NMOF carrier platform, e.g., for use in PDT, RT, RDT, X-ray induced PDT, combined RT and X-PDT, or RT-RDT. Accordingly, in some embodiments, the presently disclosed subject matter provides a MOF comprising: a photosensitizer (PS); and a plurality of metal-containing secondary building units (SBUs) linked together via bridging ligands. In some embodiments, the PS is incorporated in the MOF, i.e., via covalent attachment to a bridging ligand of the MOF, by coordinative bonding with a metal in a SBU of the MOF (including embodiments wherein the PS or a derivative thereof is a bridging ligand), or wherein the PS is non-covalently sequestered within pores or cavities in the MOF. Thus, in some embodiments, the presently disclosed subject matter can provide a MOF nanoparticle (i.e., a NMOF), comprising a PS incorporated within the core of the MOF nanoparticle (e.g., as opposed to being bound or otherwise associated with a non-MOF coating layer of a MOF nanoparticle).

The SBUs of the MOF can contain any suitable SBU. For example, suitable SBUs can include, but are not limited to, Zr-oxo clusters, Hf-oxo clusters, Zn-oxo clusters, Ti-oxo clusters, Cu-carboxylate paddlewheels, and others. However, the SBUs are not limited to these species. In some embodiments, the SBU includes a metal cation capable of absorbing x-rays. In some embodiments, the SBUs can contain a metal ion of a metal from the group comprising Hf, a lanthanide metal (i.e., La, Ce, Pr, Nd, Pm, Sm, Eu, Gd, Tb, Dy, Ho, Er, Tm, Yb, and Lu), Ba, Ta, W, Re, Os, Ir, Pt, Au, Pb, and Bi. In some embodiments, the SBUs can comprise anions selected from oxide and OH$^-$. In some embodiments, the MOF comprises Hf oxo cluster SBUs. In some embodiments, the Hf oxo clusters are $Hf_6$ oxo clusters, $Hf_{12}$ oxo clusters, or a combination thereof.

Any suitable bridging ligand or ligands can be used. In some embodiments, each bridging ligand is an organic compound comprising multiple coordination sites. The coordination sites can each comprise a group capable of forming a coordinate bond with a metal cation or a group capable of forming such a group. Thus, each coordination site can comprise an unshared electron pair, a negative charge, or an atom or functional group capable of forming an unshared electron pair or negative charge. Typical coordination sites include, but are not limited to functional groups such as carboxylate and derivatives there (e.g., esters, amides, anhydrides), nitrogen-containing groups (e.g., amines, nitrogen-containing aromatic and non-aromatic heterocycles), alcohols, phenols and other hydroxyl-substituted aromatic groups; ethers, phosphonates, phosphates, thiols, and the like.

In some embodiments, each bridging ligand comprises between 2 and 10 coordination sites (i.e., 2, 3, 4, 5, 6, 7, 8, 9, or 10 coordination sites). In some embodiments, each bridging ligand is capable of binding to two or three SBUs. For example, the bridging ligand can be a di-carboxylate porphyrin derivative, wherein each of the two carboxylate groups can form a coordinate bond to the metal ion of two separate SBUs, while the porphyrin nitrogen atoms can form coordinate bonds to another cation or cations (e.g., another metal cation).

In some embodiments, each bridging ligand comprises at least two groups wherein each of said two groups is individually selected from the group comprising a carboxylate, an aromatic or non-aromatic nitrogen-containing group (e.g., pyridine, piperidine, indole, acridine, quinolone, pyrrole, pyrrolidine, imidazole, pyrimidine, pyridazine, pyrazine, a triazole, and oxazole), a phenol, an acetylacetonate (acac), a phosphonate, and a phosphate. In some embodiments, at least one bridging ligand is a carboxylate-containing ligand, a pyridine-containing bridging ligand, a phenol-containing ligand, an acetylacetonate-containing bridging ligand, a phosphonate-containing bridging ligand, or a phosphate-containing bridging ligand. In some embodiments, at least one bridging ligand comprises at least two carboxylate groups.

In some embodiments, at least one of the bridging ligands comprises the PS or a derivative of the PS. For example, the bridging ligand can include a PS that is derivatized to include one or more covalently attached groups (e.g., carboxylate-containing groups, aromatic or non-aromatic nitrogen-containing groups, phenol-containing groups, acetylacetonate-containing groups, phosphonate-containing groups or phosphate-containing groups) for forming coordinative bonds to metal ions in SBUs. In some embodiments, such groups are directly substituted on the PS. In some embodiments, the PS is derivatized by being covalently attached to another compound containing such groups, e.g., via an amide, ester, thiourea or another suitable bond, with or without an intermediate linker group containing an alkylene or arylene moiety. In some embodiments, the PS is derivatized by being complexed to an organic compound containing groups for forming coordinative bonds with metal ions in SBUs. In some embodiments, the PS already contains groups for forming coordinative bonds to the metal ions in the SBUs.

Any suitable PS can be used for or as part of the bridging ligand. In some embodiments, at least one bridging ligand comprises a porphyrin, a chlorin, a chlorophyll, a phthalocyanine, a ruthenium-bipyridine complex, or an iridium-bipyridine complex. In some embodiments, at least one bridging ligand comprises a diphenyl-di(benzoate)porphyrin, a dibenzoato(bipyridine)ruthenium bis(bipyridine), tetra(benzoate)porphyrin, a dibenzoatoaniline, or a dibenzoato(bipyridine)ruthenium bis(phenylpyridine). In some embodiments, at least one bridging ligand is the complex formed from ruthenium (II) bis(2,2'-dipyridine) and a dicarboxylate of 5,5'-bisphenyl-2,2'-pyridine. Thus, in some embodiments, at least one bridging ligand is:

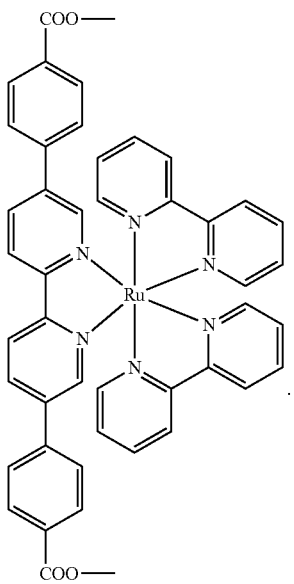

Scheme 1. Exemplary DBP, DBC, and DBCC ligands.

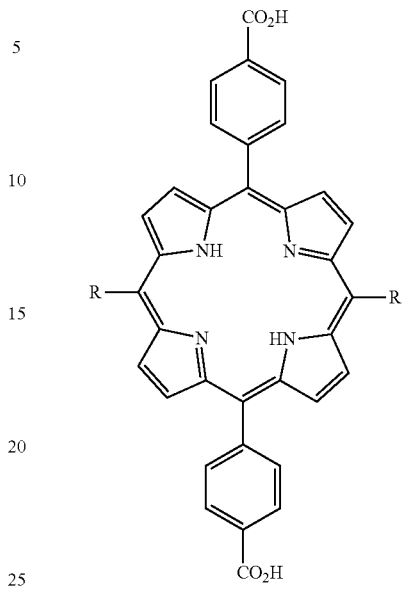

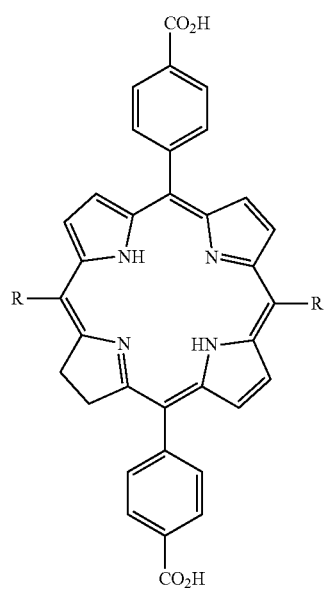

In some embodiments, at least one bridging ligand is a porphyrin-based ligand, a chlorin-based ligand, a bacteriochlorin-based ligand, a large-ring π-conjugation system, a boron-dipyrromethene (BODIPY) derivative or a disalycilidene-1,2-cyclohexylidenediamine derivative. In some embodiments, at least one bridging ligand is selected from the group comprising, but not limited to, 5, 15-di(p-benzoato)porphyrin (DBP) or a derivative and/or a metal complex thereof; 5,15-di(p-benzoato)chlorin (DBC) or a derivative and/or metal complex thereof; 5, 15-di(p-benzoato) bacteriochlorin (DBBC) or a derivative and/or a metal complex thereof; 5, 10, 15, 20-tetra(p-benzoato)porphyrin or a derivative and/or a metal complex thereof; 5, 10, 15, 20-tetra(p-pyridyl)porphyrin, phthalocyanine-octacarboxylic acid, optionally complexed with a metal; a platinum or palladium complex of di(5'-benzoatosalycylidene)-1,2-cyclohexylidenediamine; and a phthalocyanine, optionally substituted with a metal; and motexafin lutetium. Structures of exemplary DBP, DBC, and DBBC ligands are shown in Schemes 1 and 2, below. Scheme 1 shows the structures of, from left to right, DBP, DBC, and DBBC ligands, wherein the core DBP, DBC, and DBBC structure can be optionally substituted at the 10 and 20 positions with aryl or substituted aryl R groups. Suitable R aryl groups include, but are not limited to phenyl, hydroxylphenyl, and pentafluorophenyl. However, the R groups can include other aromatic groups (e.g., naphthyl, etc.) and/or other aryl-group substituents, e.g., other halogens, alkyl groups, etc. Further, the core DBP, DBC, and DBBC ligand can include additional aryl group substituents on the benzoate groups at the 5 and 15 positions and/or on the nitrogen-atom containing rings. As indicated in Scheme 2, the DBP, DBC, and DBBC ligands can also include a metal ion complexed by the nitrogen atoms of the porphyrin, chlorin or bacteriochlorin ring. Suitable metals M, include, but are not limited to, Pt, Pd, Zn, Mn, Fe, Sn, and Cu.

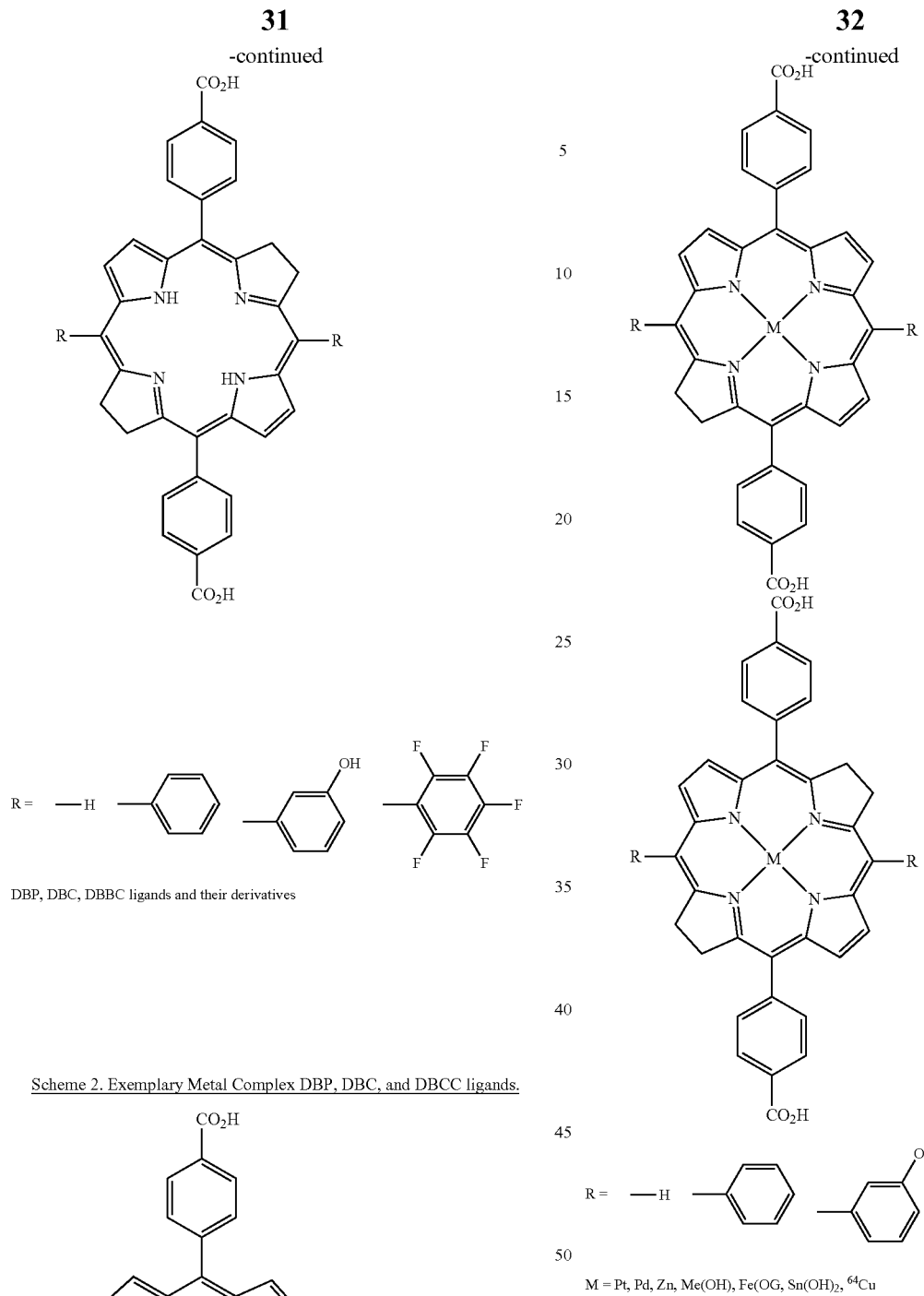

Scheme 2. Exemplary Metal Complex DBP, DBC, and DBCC ligands.

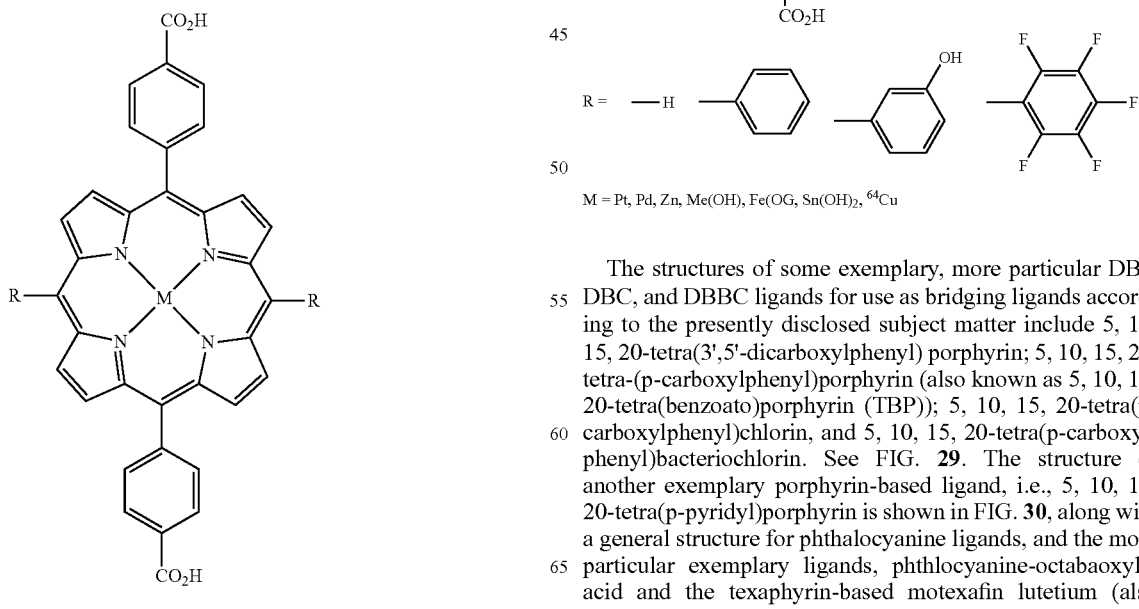

M = Pt, Pd, Zn, Me(OH), Fe(OG), Sn(OH)$_2$, $^{64}$Cu

Figure 29:
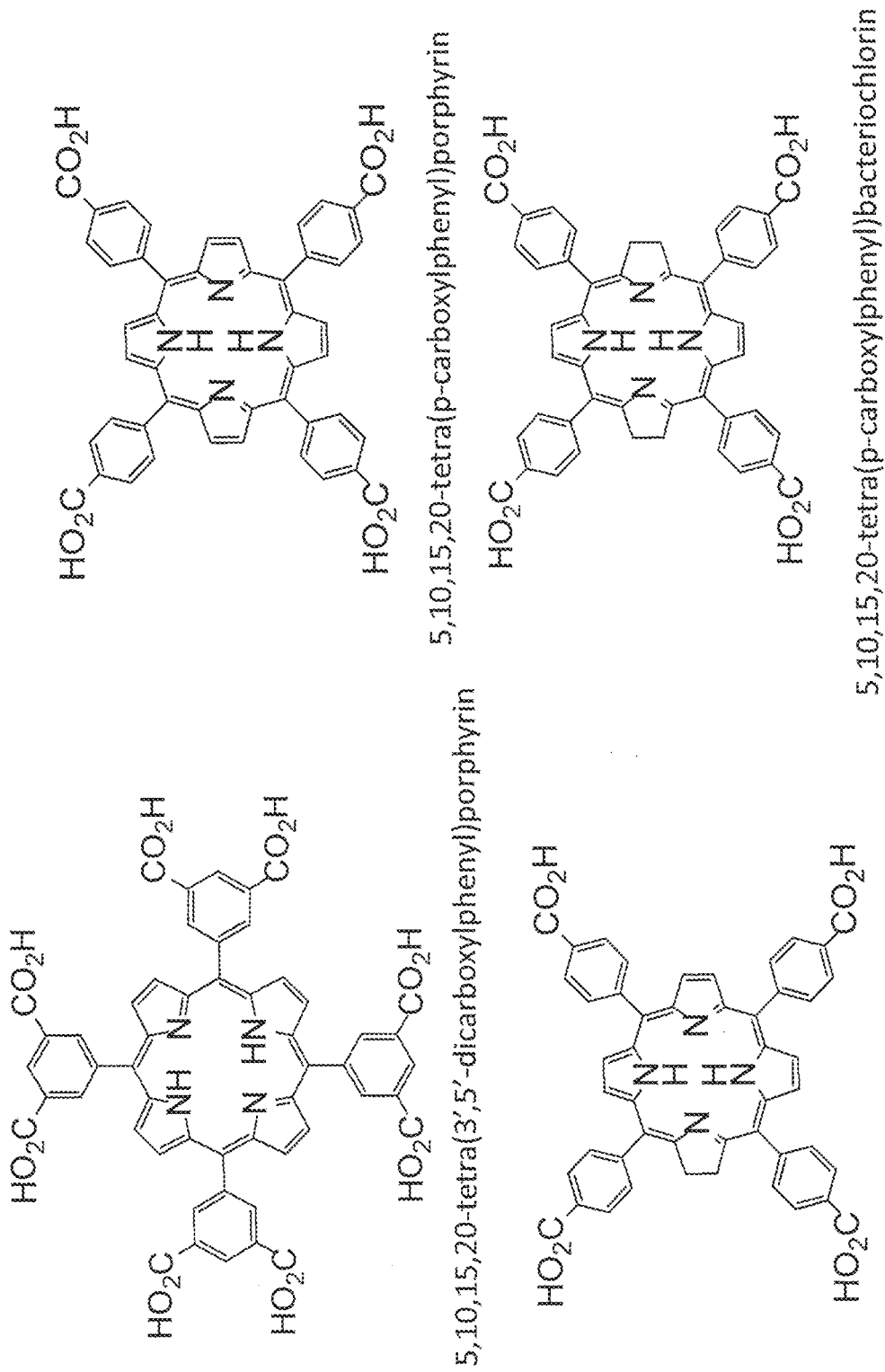
FIG. 29 is a schematic diagram showing the chemical structures of exemplary porphyrin, chlorin, and bacteriochlorin-based photosensitizers and/or bridging ligands according to embodiments of the presently disclosed subject matter.
Figure 30:
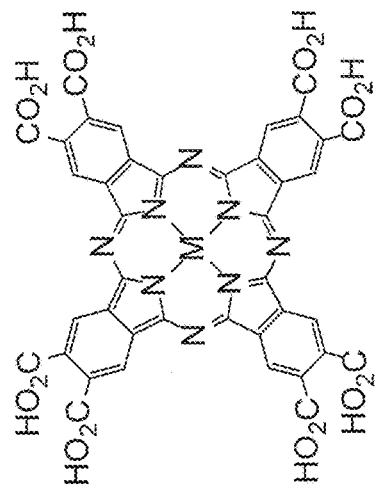
FIG. 30 is a schematic diagram showing the chemical structures of some additional exemplary photosensitizers and/or bridging ligands according to embodiments of the presently disclosed subject matter.
Figure 30:
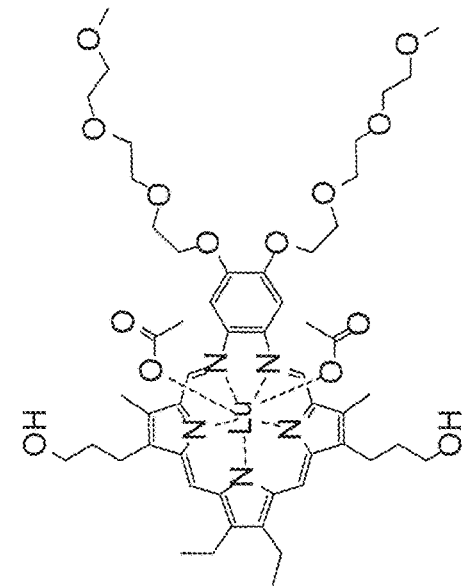
Figure 30:
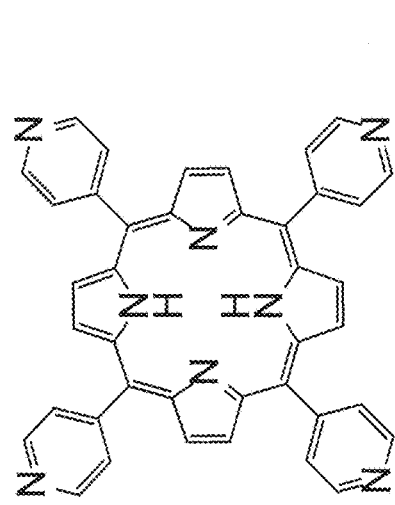
Figure 30:
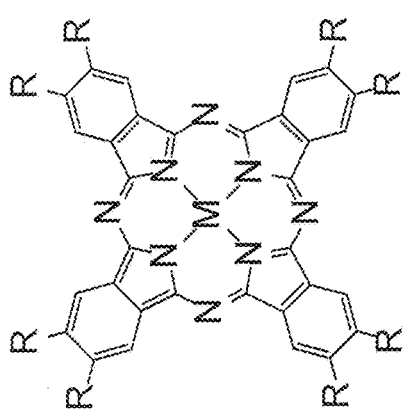

The structures of some exemplary, more particular DBP, DBC, and DBBC ligands for use as bridging ligands according to the presently disclosed subject matter include 5, 10, 15, 20-tetra(3',5'-dicarboxylphenyl) porphyrin; 5, 10, 15, 20, tetra-(p-carboxylphenyl)porphyrin (also known as 5, 10, 15, 20-tetra(benzoato)porphyrin (TBP)); 5, 10, 15, 20-tetra(p-carboxylphenyl)chlorin, and 5, 10, 15, 20-tetra(p-carboxylphenyl)bacteriochlorin. See FIG. 29. The structure of another exemplary porphyrin-based ligand, i.e., 5, 10, 15, 20-tetra(p-pyridyl)porphyrin is shown in FIG. 30, along with a general structure for phthalocyanine ligands, and the more particular exemplary ligands, phthlocyanine-octabaoxylic acid and the texaphyrin-based motexafin lutetium (also known as Lutrin). As indicated in FIG. 30, phthalocyanine ligands can optionally be complexed structure to a metal ion M, e.g., Pt, Pd, Zn. The R groups of the general phthalocyanine ligand can be any suitable aryl group substituent, e.g., carboxyl, hydroxyl, halo, alkyl, phosphate, etc. In some embodiments, at least two R groups of the phthalocyanine are carboxyl.

The structure of the exemplary disalicylidene-1,2-cyclohexylidenediamine bridging ligand di-(5'benzoatosalicylidene)-1,2-cyclohexylidenediamine is shown on the right-hand side of FIG. 31. As indicated in FIG. 31, the ligand can optionally be complexed to a metal M, such as, Pt or Pd. Additionally, although not shown in FIG. 31, the carbon atoms of the cyclohexyl group and/or the phenyl rings can optionally be substituted with one or more alkyl or aryl group substituents.

FIG. 31 also shows, on the left-hand side, the structure for BODIPY derivative-based bridging ligands. The aromatic substituents $R_1$, $R_2$, and $R_3$ of the BODIPY structure can include any suitable aryl group substituent. As indicated in FIG. 31, in some embodiments, the $R_1$ groups are carboxyl-substituted aryl or alkaryl groups, e.g., —$C_6H_4(CO_2H)$, or CH=CH—$C_6H_4(CO_2H)$.

Figure 32:
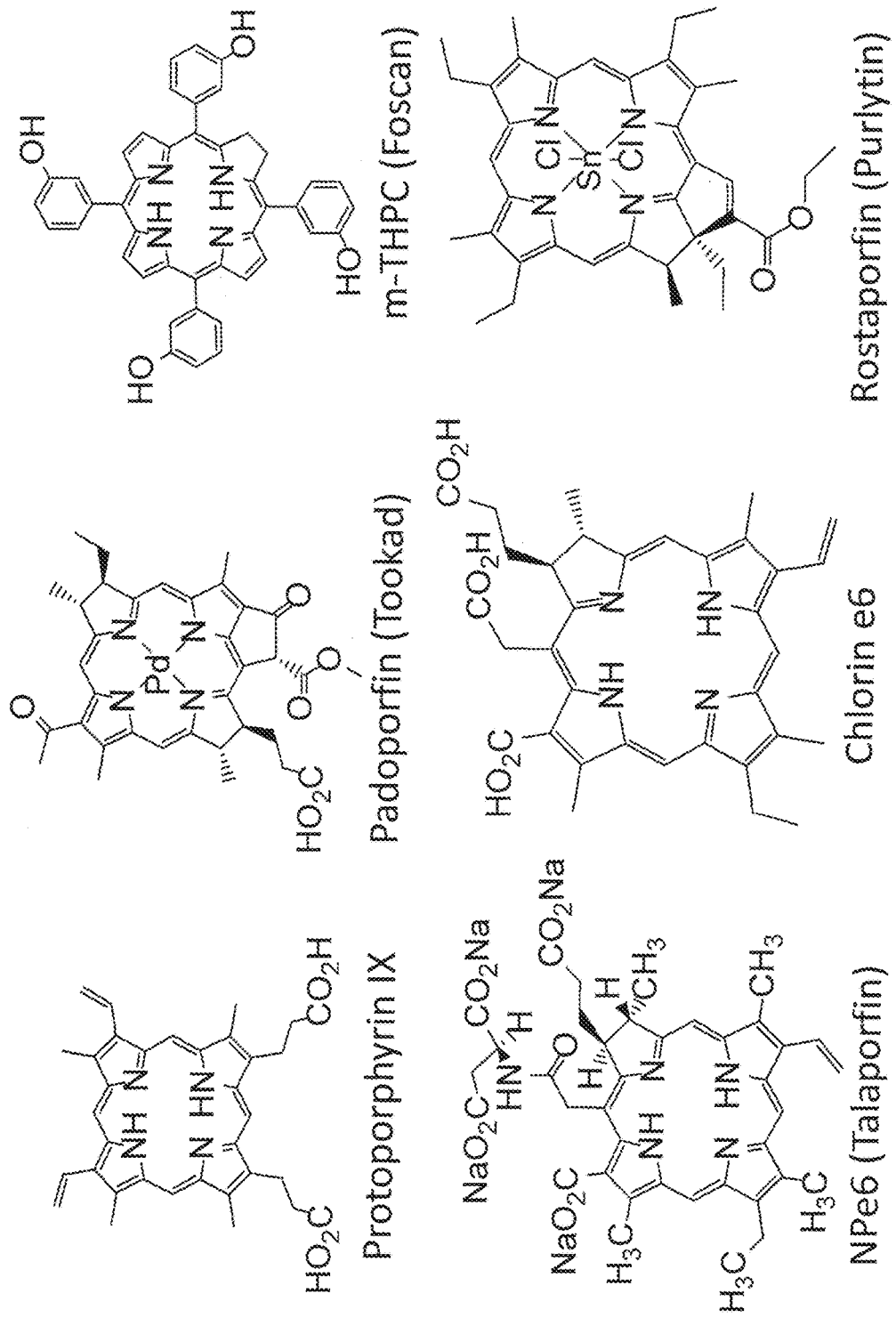
FIG. 32 is a schematic diagram showing the chemical structures of exemplary dye-based photosensitizers for use according to the presently disclosed subject matter.

In some embodiments, the PS and/or at least one of the bridging ligands is selected from the group comprising, but not limited Protoporphyrin IX, Padoporfin; tetra(m-hydroxyphenyl)chlorin (m-THPC); NPe6, Chlorin e6, Rostaporfin and derivatives thereof. The structures of these exemplary ligands/PSs are shown in FIG. 32.

In some embodiments, the PS is a covalently attached dye, e.g. a dye covalently attached to a di-carboxylate-di-phosphonate-, di-phosphate- or dipyridine-containing organic bridging ligand. The type of covalent attachment can be determined based on the available functional groups (e.g., carboxylate, thiol, hydroxyl, amino) on the dye, using conventional conjugation strategies known in the art. For example, if the dye contains an amino group, it can be covalently attached to a bridging ligand via a thiourea or amide. If the dye contains a carboxyl group, it can be covalently attached to the bridging ligand via an amide linkage formed by condensation of the carboxyl group and an amino group present on the bridging ligand, optionally by first transforming the carboxyl group into an activated ester, such as a succinimidyl ester. In some embodiments, the dye is covalently attached to the MOF (e.g., to the bridging ligand of the MOF) via an amide or a thiourea bond.

In some embodiments, MOF contains at least one bridging ligand that comprises a para-terphenyldicarboxylic acid or para-quaterphenyldicarboxylic acid (i.e., ($HO_2C)C_6H_4$—$C_6H_4$—$C_6H_4$—$C_6H_4CO_2H$) derivative. In some embodiments, the derivative is a para-terphenyldicarboxylic acid or para-quaterphenyldicarboxylic acid covalently attached to a PS at a site on one of the phenyl rings (e.g., at a carbon atom of an interior phenyl ring of the para-terphenyldicarboxylic acid or para-quaterphenyldicarboxylic acid). In some embodiments, the MOF comprises:

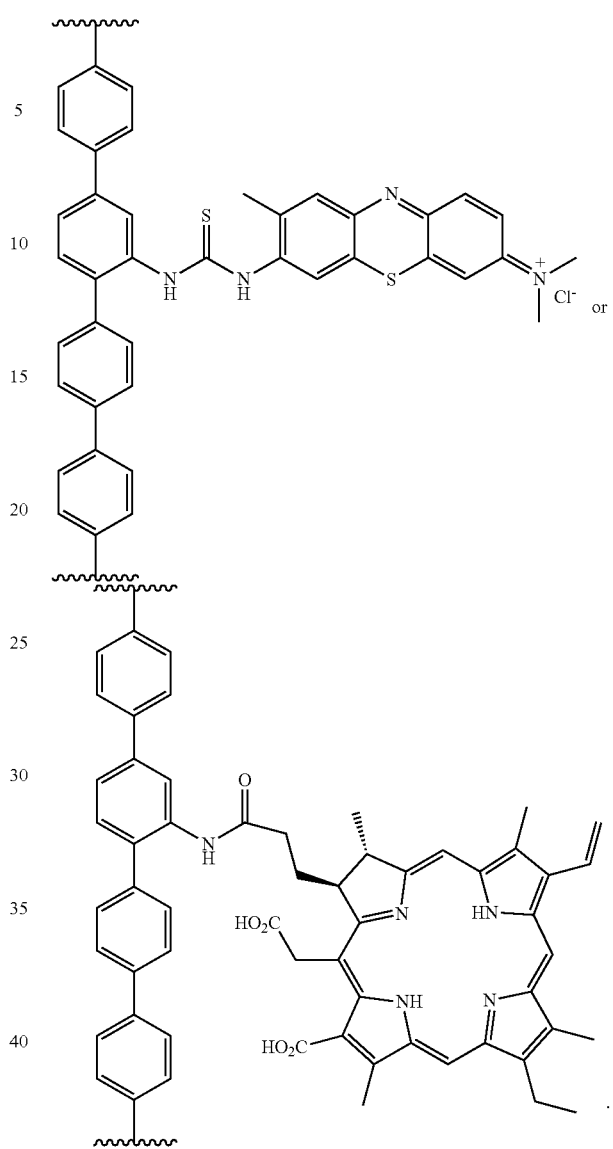

In some embodiments, the PS is a dye that is non-covalently trapped within the MOF, e.g., sequestered within cavities or pores in the MOF. Any suitable dye can be used. Dyes for use in the presently disclosed MOFs, either for covalent attachment to a bridging ligand or for use as non-covalently trapped PSs include, but are not limited to, toluidine blue, methylene blue, Nile blue, hypericin, Cy3, Cy3.5, Cy5, Cy5.5, Cy7, and a chalcogenapyrylium. The structures of exemplary dyes for use as PSs according to the presently disclosed subject matter are shown in FIG. 32.

In some embodiments, the MOF can further comprise another therapeutic agent, e.g., non-covalently entrapped in the MOF. In some embodiments, the other therapeutic agent is a chemotherapeutic agent or an immunotherapeutic agent, such as one of those listed elsewhere herein. In some embodiments, the MOF can comprise another non-covalently bound agent selected from the group comprising, but not limited to, a platinum-based drug (e.g., cisplatin or oxaliplatin), temozolomide, doxorubicin, camptothecin, paclitaxel, pemetrexed, methotrexate, or an IDO inhibitor, optionally wherein the IDO inhibitor is selected from the group comprising ICBN24360, NLG-919, 1-methyl-D-tryptophan and 1-methyl-L-tryptophan.

In some embodiments, the MOF comprises a non-covalently bound immunotherapeutic agent. In some embodiments, the immunotherapeutic agent is an IDO inhibitor (IDOi). In some embodiments, the IDOi is selected from the group including, but not limited to ICBN24360, 1-methyl-D-tryptophan, and 1-methyl-L-tryptophan.

In some embodiments, the MOF can further comprise a moiety comprising a hydrophilic polymer, such as, but not limited to, a polyethylene glycol (PEG) moiety or polyvinylpyrolidine (PVP), bound covalently or electrostatically. In some embodiments, the MOF can be further coated with a lipid or lipids, such as, but not limited to, DOTAP, DOPC, and DSPE-PEG.

In some embodiments, the MOF is in the form of a nanoparticle. In some embodiments, the nanoscale particle can have an average diameter of less than about 250 nm. In some embodiments, the average diameter is between about 20 and about 200 nm. In some embodiments, the nanoscale particle has an average diameter of between about 20 nm and about 180 nm (e.g., about 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, or about 180 nm). In some embodiments, the nanoscale particle has an average diameter of between about 20 nm and about 140 nm. In some embodiments, the particle can have a plate-like morphology.

In some embodiments, the presently disclosed subject matter provides a composition comprising a MOF comprising a plurality of metal-containing SBUs linked together via one or more organic bridging ligands, wherein the SBUs comprise hafnium (Hf) oxo clusters, and further wherein said Hf oxo clusters comprise $Hf_{12}$ oxo clusters. Any suitable bridging ligand can be used. In some embodiments, at least one of the one or more bridging ligands comprises a diphenyl-di(benzoate)porphyrin, a dibenzoato(bipyridine) ruthenium bis(bipyridine), or a dibenzoato(bipyridine)-ruthenium bis(phenylpyridine). In some embodiments, at least one of the one or more bridging ligands is 5, 15-di(p-benzoato)porphyrin (DBP) or a derivative and/or metal complex thereof. In some embodiments, the MOF has a structure of the formula $Hf_{12}(\mu_3-O)_8(\mu_3-OH)_8(\mu_2-OH)_6$ $(DBP)_9$. In some embodiments, the MOF further comprises a non-covalently bound immunotherapeutic agent (e.g., an IDOi).

In some embodiments, the presently disclosed subject matter comprises a pharmaceutical formulation comprising one of the nanoscale particles described herein and a pharmaceutically acceptable carrier. In some embodiments, the pharmaceutically acceptable carrier is pharmaceutically acceptable in humans.

IV. Methods of Using MOFs for Photodynamic Therapy and X-Ray Induced Photodynamic Therapy, Radiotherapy, Radiodynamic Therapy, and/or Radiotherapy-Radiodynamic Therapy In some embodiments, the presently disclosed subject matter provides methods of using MOFs and/or inorganic nanoparticles in photodynamic therapy, X-ray induced photodynamic therapy, radiotherapy, radiodynamic therapy, or radiotherapy-radiodynamic therapy (RT-RDT), either with or without the co-administration of one or more immunotherapeutic agent and/or one or more chemotherapeutic agent. For instance, in some embodiments, the presently disclosed subject matter provides MOFs comprising PSs for use in treating a disease, e.g., cancer or a pathogenic infection, via photodynamic therapy. Thus, in some embodiments, the presently disclosed subject matter provides a method for treating a disease in a patient in need of treatment of the disease, wherein the method comprises: administering to the patient an MOF comprising a photosensitizer and a plurality of SBUs linked together via bridging ligands; and illuminating the patient with visible or near infrared (NIR) light. In some embodiments, at least one or more bridging ligand is or comprises the PS or a derivative thereof. In some embodiments, the PS is embedded or non-covalently trapped within the MOF (e.g., in pores or cavities in the MOF matrix).

The patient can be illuminated, for example, on a portion of the anatomy affected the disease or near a site affected by the disease. In some embodiments, the patient is illuminated on a portion of the anatomy selected from, but not limited to, the skin or the gastrointestinal tract. In some embodiments, the patient's blood is illuminated.

In some embodiments, the disease is cancer. For example, the disease can be selected from the group comprising a head tumor, a neck tumor, breast cancer, a gynecological tumor, a brain tumor, colorectal cancer, lung cancer, mesothelioma, a soft tissue sarcoma, and pancreatic cancer. In some embodiments, the method can further comprise administering to the patient an additional cancer treatment (e.g., surgery, a conventional chemotherapeutic agent, etc.).

In some embodiments, the presently disclosed subject matter provides a method for treating a disease (e.g., cancer) using X-ray induced (or other ionizing irradiation energy induced) PDT and/or RT-RDT, wherein the absorption of X-rays (or other ionizing irradiation energy) by a moiety present on an MOF can provide the light or energy required for PDT or RT-RDT. Such methods can be suitable, for example, when the site of disease is not near the surface of the patient's anatomy or is otherwise not able to be illuminated sufficiently by visible or NIR light. The method can involve administering to a patient in need of treatment a MOF comprising a photosensitizer, a plurality of SBUs linked by organic bridging ligands, and a moiety capable of absorbing x-rays or other ionizing irradiation energy; and exposing at least a portion of the patient to ionizing irradiation energy (e.g., irradiating at least a portion of the patient with x-rays (e.g., in one to fifty fractions)). In some embodiments, the SBUs of the MOF contain metal cations capable of absorbing x-rays or other ionizing irradiation energy, such as gamma rays, beta irradiation, neutron beam irradiation, electron beam irradiation, or proton irradiation. In some embodiments, the SBUs comprise Hf oxo clusters (e.g., $Hf_{12}$ oxo clusters, $Hf_6$ oxo clusters or a combination thereof). In some embodiments, one or more of the bridging ligands comprises an anthracene-based linker, such as 9,10-anthracenyl bis(benzoic acid). In some embodiments, the disease is selected from a head tumor, a neck tumor, breast cancer, a gynecological tumor, a brain tumor, colorectal cancer, lung cancer, mesothelioma, a soft tissue sarcoma, and pancreatic cancer. In some embodiments, the disease is selected from a head and neck cancer, a breast cancer, a prostate cancer, a glioblastoma, a gynecological tumor, a brain tumor, colorectal cancer, and pancreatic cancer. In some embodiments, the disease is a metastatic cancer. In some embodiments, the method can further comprise administering to the patient an additional cancer treatment.

According to some embodiments of the presently disclosed subject matter, the use of an immunotherapy agent can enhance the PDT, RT, RDT, X-ray induced PDT, or RT-RDT treatment. Thus, in some embodiments, the methods described above can further comprise administering to the patient an immunotherapy agent, such as, but not limited to a PD-1/PD-L1 antibody, an IDO inhibitor, CTLA-4 antibody, an OX40 antibody, a TIM3 antibody, a LAG3 antibody, an siRNA targeting PD-1/PD-L1, an siRNA targeting IDO and an siRNA targeting CCR7, as well as any other immunotherapy agent as recited elsewhere herein or that is known in the art.

In some embodiments, the presently disclosed subject matter provides a method of treating a disease (e.g., cancer) that combines X-ray induced PDT or RT-RDT and immunotherapy. Accordingly, in some embodiments, the presently disclosed subject matter provides a method comprising: administering to a patient a scintillator and a nanoparticle comprising a photosensitizer; irradiating at least a portion of the patient with X-rays or other ionizing irradiation energy (e.g., in one to fifty fractions); and administering to the patient an immunotherapy agent.

In some embodiments, the disease is cancer, for example, selected from a head tumor, a neck tumor, breast cancer, a gynecological tumor, a brain tumor, colorectal cancer, lung cancer, mesothelioma, a soft tissue sarcoma, skin cancer, connective tissue cancer, adipose cancer, lung cancer, stomach cancer, anogenital cancer, kidney cancer, bladder cancer, colon cancer, prostate cancer, central nervous system cancer, retinal cancer, blood cancer, neuroblastoma, multiple myeloma, lymphoid cancer and pancreatic cancer. In some embodiments, the disease is metastatic cancer.

In some embodiments, the method can further comprise administering to the patient an additional cancer treatment. The additional cancer treatment can be selected on the basis of the cancer being treated and/or on other factors, such as the patient's treatment history, overall health, etc., in accordance with the best judgement of the treating physician. The additional cancer treatment can be selected from the group including, but not limited to, surgery, radiotherapy, chemotherapy, toxin therapy, immunotherapy, cryotherapy and gene therapy. In some embodiments, the additional cancer treatment can comprise administering to the patient a conventional chemotherapeutic, such as, but not limited to, oxaliplatin, doxorubicin, daunorubicin, docetaxel, mitoxanthrone, paclitaxel, digitoxin, digoxin, and septacidin or another conventional chemotherapeutic known in the art. In some embodiments, the additional cancer treatment can involve administering to the patient a drug formulation selected from the group comprising a polymeric micelle formulation, a liposomal formulation, a dendrimer formulation, a polymer-based nanoparticle formulation, a silica-based nanoparticle formulation, a nanoscale coordination polymer formulation, a nanoscale metal-organic framework formulation, and an inorganic nanoparticle (gold, iron oxide nanoparticles, etc.) formulation. In some embodiments, the drug formulation can be a formulation including a conventional chemotherapeutic.

The immunotherapy agent for use according to the presently disclosed subject matter can be any suitable immunotherapy agent known in the art. Immunotherapeutic agents suitable for use in the presently disclosed subject matter include, but are not limited to: PD-1, PD-L1, CTLA-4, IDO and CCR7 inhibitors, that is, a composition that inhibits or modifies the function, transcription, transcription stability, translation, modification, localization, or secretion of a polynucleotide or polypeptide encoding the target or a target associated ligand, such as anti-target antibody, a small molecule antagonist of the target, a peptide that blocks the target, a blocking fusion protein of the target, or siRNA/shRNA/microRNA/pDNA suppressing the target. Antibodies that can be used according to the presently disclosed subject matter include, but are not limited to: anti-CD52 (Alemtuzumab), anti-CD20 (Ofatumumab), anti-CD20 (Rituximab), anti-CD47 antibodies, anti-GD2 antibodies, etc. Conjugated monoclonal antibodies for use according to the presently disclosed subject matter include, but are not limited to: radiolabeled antibodies (e.g., Ibritumomab tiuxetan (Zevalin), etc.), chemolabeled antibodies (antibody-drug conjugates (ADCs)), (e.g., Brentuximab vedotin (Adcetris), Ado-trastuzumab emtansine (Kadcyla), denileukin diftitox (Ontak) etc.). Cytokines for use according to the presently disclosed subject matter include, but are not limited to: interferons (i.e., IFN-α, INF-γ), interleukins (i.e. IL-2, IL-12), TNF-α, etc. Other immunotherapeutic agents for use according to the presently disclosed subject matter include, but are not limited to, polysaccharide-K, neoantigens, etc.

In some embodiments, the immunotherapy agent can be selected from the group comprising an anti-CD52 antibody, an anti-CD20 antibody, an anti-CD20 antibody, anti-CD47 antibody an anti-GD2 antibody, a radiolabeled antibody, an antibody-drug conjugate, a cytokine, polysaccharide K and a neoantigen. Suitable cytokine immunotherapy agents can be, for example, an interferon (IFN), an interleukin (IL), or tumor necrosis factor alpha (TNF-α). In some embodiments, the cytokine immunotherapy agent is selected from IFN-α, INF-γ, IL-2, IL-12 and TNF-α. In some embodiments, the immunotherapy agent is selected from the group comprising a PD-1 inhibitor, a PD-L1 inhibitor, a CTLA-4 inhibitor, an IDO inhibitor, and a CCR7 inhibitor.

The patient can be exposed to the ionizing irradiation energy in any suitable manner and/or using any suitable equipment. In some embodiments, the patient can be irradiated with X-rays in any suitable manner and/or using any suitable equipment, such as that currently being used for delivering X-rays in a medical or veterinary setting. In some embodiments, the X-ray source and/or output can be refined to enhance disease treatment. For instance, the X-rays can be generated using a peak voltage, current and/or, optionally, a filter chosen to minimize DNA damage in the patient due to X-ray irradiation and maximize X-ray absorption by the scintillator.

In some embodiments, the patients are irradiated with a linear accelerator (LINAC), using conventional techniques, Intensity-Modulated Radiation Therapy (IMRT), Image Guided Radiation Therapy (IGRT), or Stereotactic Body Radio Therapy (SBRT), a $^{60}$Co radiation source, an implanted radioactive seed such as the ones used in brachytherapy, an orthovoltage or supervoltage X-ray irradiator, a high energy electron beam generated from LINAC, or a proton source. In some embodiments, the irradiating can comprise generating X-rays using a tungsten or another metal target, Cobalt-60 sources (cobalt unit), linear accelerators (linacs), Ir-192 sources, and Cesium-137 sources. In some embodiments, the irradiating comprises passing the X-rays (e.g., the X-rays generated using a tungsten target) through a filter prior to irradiation the patient. In some embodiments, the filter can comprise an element with an atomic number of at least 20. In some embodiments, the filter comprises copper (Cu). In some embodiments, the filter can have a thickness that is less than about 5 millimeters (mm). In some embodiments, the filter can have a thickness of less than about 4 mm (e.g., less than about 3 mm, less than out 1 mm, less than about 0.5 mm, less than about 0.4 mm, less than about 0.3 mm, less than about 0.2 mm, or less than about 0.1 mm).

The X-rays can be generated using a peak voltage, current and/or, optionally, a filter chosen to minimize DNA damage in the patient due to X-ray irradiation and maximize X-ray absorption by the scintillator. In some embodiments, the X-rays are generated using a peak voltage that is less than about 230 kVp. In some embodiments, the peak voltage is less than about 225 kVp, less than about 200 kVp, less than about 180 kVp, less than about 160 kVp, less than about 140 kVp, less than about 120 kVp, less than about 100 kVp, or less than about 80 kVp. In some embodiments, the X-rays are generated using a peak voltage that is about 120 kVp.

In some embodiments, X-rays are generated by placing radioactive sources inside the patient on a temporary or permanent basis. In some embodiments, the NMOF is injected along with the implantation of a radioactive source.

In some embodiments, the γ-rays generated by a LINAC pass through an energy modulator (filter) before irradiating the patient, optionally wherein the filter comprises one or more element(s) with atomic number(s) of at least 20, further optionally wherein the filter comprises copper. In some embodiments, the filter has a thickness that is less than 5 mm, less than 4 mm, less than 3 mm, less than 2 mm, less than 1 mm, less than 0.5 mm, less than 0.4 mm, less than 0.3 mm, less than 0.2 mm, less than 0.1 mm.

Any suitable scintillator can be used. In some embodiments, the scintillator comprises a lanthanide (i.e., La, Ce, Pr, Nd, Pm, Sm, Eu, Gd, Tb, Dy, Ho, Er, Tm, Yb, or Lu). The scintillator can be, for example, a lanthanide nanoparticle (e.g., co-administered with the MOF comprising the photosensitizer and/or attached to the MOF comprising the photosensitizer). For example, the lanthanide nanoparticles can be trapped in cavities or pores within the MOF comprising the photosensitizer. In some embodiments, the lanthanide is the metal of the SBUs of the MOF comprising the photosensitizer. In some embodiments, the lanthanide nanoparticle can be a lanthanide core-shell nanoparticle, further optionally wherein the shell of the lanthanide core-shell nanoparticle comprises a lanthanide chalcogenide. In some embodiments, the scintillator comprises a lanthanide aluminum garnet or a lanthanide fluoride.

Other suitable scintillators include, but are not limited to, carbon dots; core-shell nanoparticles wherein the shell comprises zinc sulfide and the core comprises a transition metal or lanthanide metal; and/or nanoparticles comprising gold, platinum, or iridium.

In some embodiments, the scintillator can comprise a MOF comprising hafnium (Hf), zirconium (Zr), or cerium (Ce). In some embodiments, the scintillator comprises $M_6(\mu_3-O)_4(\mu_3-OH)_4L_6$, wherein M is hafnium, zirconium, or cerium, and L is 9,10-anthracenylbisbenzoic acid. In some embodiments, the scintillator comprises a $Hf_{12}$ oxo cluster. In some embodiments, the scintillator can comprise a MOF comprising Hf, Zr, or Ce, and the photosensitizer is covalently bound to the MOF. The photosensitizer can be bound to the organic bridging ligands of the MOF e.g., through amide conjugation, ester conjugation, thiourea conjugation, click chemistry, or disulfide bond conjugation.

In some embodiments, the photosensitizer is bound to the scintillator through a coordinate bond. For example, in some embodiments, the photosensitizer comprises a carboxylate, thiol, hydroxy, amino or phosphate group; the scintillator comprises a metal (e.g., the metal of a MOF SBU); and the carboxylate, thiol, hydroxyl, amino or phosphate group is bound to the metal via a coordinative bond. Thus in some embodiments the photosensitizer can be the binding ligand of a scintillator MOF.

In some embodiments, the photosensitizer and the scintillator are linked and the linkage can comprise a moiety such as a cyclodextrin, polyethylene glycol, poly(maleic acid), or a $C_2$-$C_{15}$ linear or branched alkyl chain. In some embodiments, the photosensitizer comprises one of the structures shown in FIG. 27 or 28 or a deprotonated form of such a structure.

In some embodiments, the scintillator can be encapsulated in a MOF or in mesoporous silica. In some embodiments, the photosensitizer is also trapped in the pores of the mesoporous silica or covalently attached to the MOF.

In some embodiments, the presently disclosed subject matter provides for additional methods of treating disease (e.g., cancer) via the combination of nanoparticle chemotherapeutic agents and immunotherapy agents. Thus, in some embodiments, the presently disclosed subject matter provides methods of treating a disease (e.g., cancer) in a patient, the method comprising: administering to a patient a nanoparticle chemotherapy agent; and administering to a patient an immunotherapy agent. In some embodiments, the nanoparticle chemotherapy agent comprises an MOF of the presently disclosed subject matter (e.g., an MOF comprising a photosensitizer). In some embodiments, the method further comprises illuminating the patient with visible or NIR light or irradiating at least a portion of the patient with X-rays. In some embodiments, the MOF further comprises a scintillator. In some embodiments, a chemotherapeutic agent, such as, but not limited to, oxaliplatin, doxorubicin, daunorubicin, docetaxel, mitoxanthrone, paclitaxel, digitoxin, digoxin, and septacidin or another conventional chemotherapeutic known in the art is entrapped in the MOF.

V. Formulations

The compositions of the presently disclosed subject matter comprise in some embodiments a composition that includes a pharmaceutically acceptable carrier. Any suitable pharmaceutical formulation can be used to prepare the compositions for administration to a subject. In some embodiments, the composition and/or carriers can be pharmaceutically acceptable in humans.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the subject; and aqueous and non-aqueous sterile suspensions that can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are sodium dodecyl sulfate (SDS), in one example in the range of 0.1 to 10 mg/ml, in another example about 2.0 mg/ml; and/or mannitol or another sugar, for example in the range of 10 to 100 mg/ml, in another example about 30 mg/ml; and/or phosphate-buffered saline (PBS).

It should be understood that in addition to the ingredients particularly mentioned above, the formulations of this presently disclosed subject matter can include other agents conventional in the art having regard to the type of formulation in question. For example, sterile pyrogen-free aqueous and non-aqueous solutions can be used.

VI. Subjects

The methods and compositions disclosed herein can be used on a sample either in vitro (for example, on isolated cells or tissues) or in vivo in a subject (i.e. living organism, such as a patient). In some embodiments, the subject or patient is a human subject, although it is to be understood that the principles of the presently disclosed subject matter indicate that the presently disclosed subject matter is effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species.

As such, the methods of the presently disclosed subject matter are particularly useful in warm-blooded vertebrates. Thus, the presently disclosed subject matter concerns mammals and birds. More particularly provided are methods and compositions for mammals such as humans, as well as those mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos or as pets (e.g., parrots), as well as fowl, and more particularly domesticated fowl, for example, poultry, such as turkeys, chickens, ducks, geese, guinea fowl, and the like, as they are also of economic importance to humans. Thus, also provided is the treatment of livestock including, but not limited to domesticated swine (pigs and hogs), ruminants, horses, poultry, and the like.

VII. Administration

Suitable methods for administration of a composition of the presently disclosed subject matter include, but are not limited to intravenous and intratumoral injection, oral administration, subcutaneous administration, intraperitoneal injection, intracranial injection, and rectal administration. Alternatively, a composition can be deposited at a site in need of treatment in any other manner, for example by spraying a composition within the pulmonary pathways. The particular mode of administering a composition of the presently disclosed subject matter depends on various factors, including the distribution and abundance of cells to be treated and mechanisms for metabolism or removal of the composition from its site of administration. For example, relatively superficial tumors can be injected intratumorally. By contrast, internal tumors can be treated following intravenous injection.

In one embodiment, the method of administration encompasses features for regionalized delivery or accumulation at the site to be treated. In some embodiments, a composition is delivered intratumorally. In some embodiments, selective delivery of a composition to a target is accomplished by intravenous injection of the composition followed by photodynamic treatment (light irradiation) of the target.

For delivery of compositions to pulmonary pathways, compositions of the presently disclosed subject matter can be formulated as an aerosol or coarse spray. Methods for preparation and administration of aerosol or spray formulations can be found, for example, in U.S. Pat. Nos. 5,858,784; 6,013,638; 6,022,737; and 6,136,295.

VIII. Doses

An effective dose of a composition of the presently disclosed subject matter is administered to a subject. An "effective amount" is an amount of the composition sufficient to produce detectable treatment. Actual dosage levels of constituents of the compositions of the presently disclosed subject matter can be varied so as to administer an amount of the composition that is effective to achieve the desired effect for a particular subject and/or target. The selected dosage level can depend upon the activity (e.g., RT, RDT, PDT, RT-RDT, or X-PDT activity or NMOF loading) of the composition and the route of administration.

After review of the disclosure herein of the presently disclosed subject matter, one of ordinary skill in the art can tailor the dosages to an individual subject, taking into account the particular formulation, method of administration to be used with the composition, and nature of the target to be treated. Such adjustments or variations, as well as evaluation of when and how to make such adjustments or variations, are well known to those of ordinary skill in the art.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

DBP-Hf Based NMOFs for PDT 1.1. Materials and Cell Lines

All of the starting materials were purchased from Sigma-Aldrich (St. Louis, Mo., United States of America) and Thermo Fisher Scientific (Waltham, Mass., United States of America), unless otherwise noted, and used without further purification.

The human head and neck cancer cell line SQ20B (cisplatin-resistant) was kindly provided by Dr. Stephen J. Kron (Department of Molecular Genetics and Cell Biology, The University of Chicago, Chicago, USA). The cells were cultured in DMEM/F12 (1:1) medium (Gibco, Grand Island, N.Y., United States of America) containing 20% fetal bovine serum (FBS, Hyclone, Logan, Utah, United States of America).

Athymic female nude mice (6 weeks, 20-22 g) were provided by Harlan Laboratories, Inc (Dublin, Va., United States of America). The study protocol was reviewed and approved by the Institutional Animal Care and Use Committee (IACUC) at the University of Chicago.

1.2. Synthesis of 5, 15-di(p-benzoato)porphyrin ($H_2DBP$)

Figure 8:
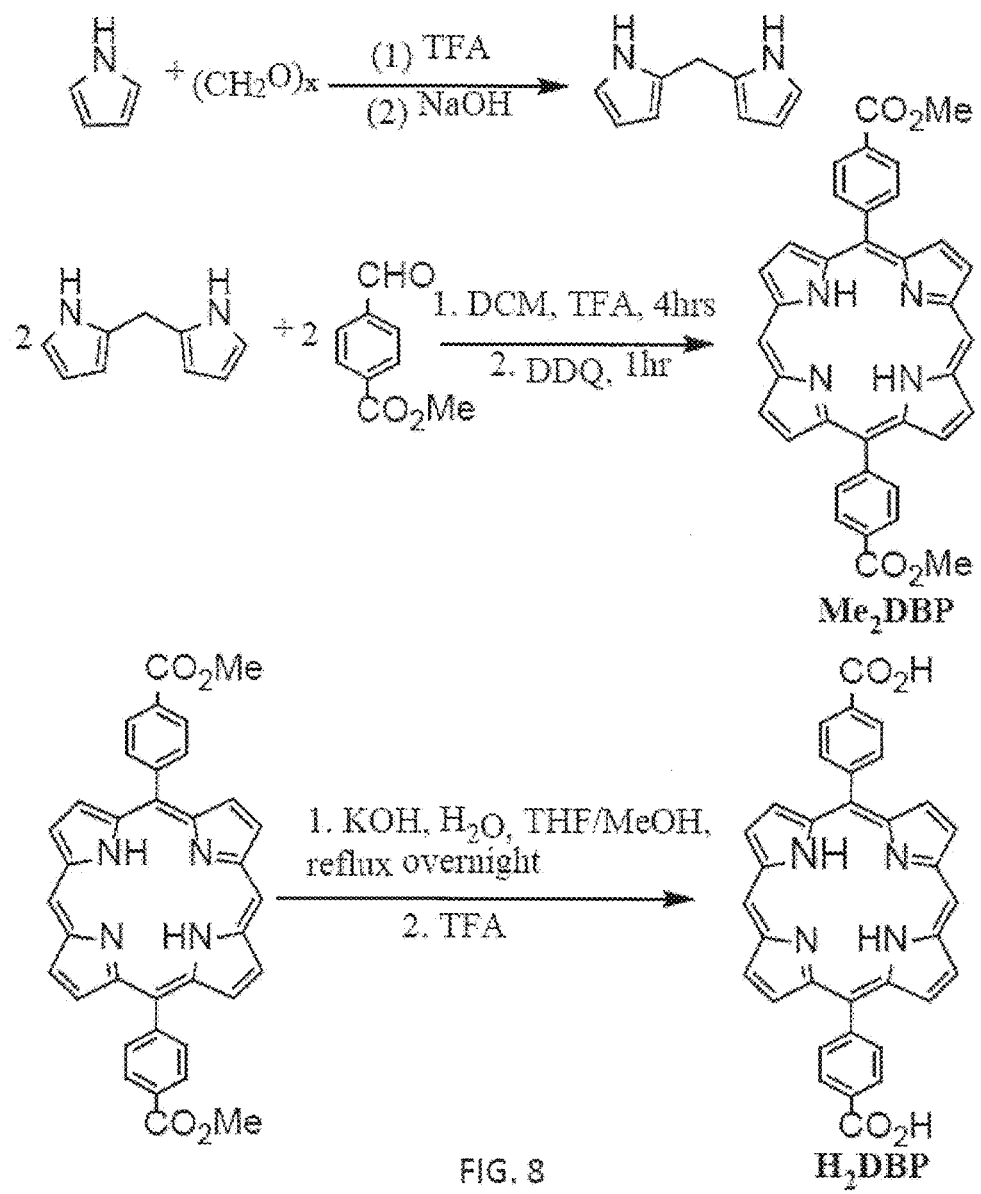
FIG. 8 is a schematic drawing of the synthesis of the 5, 15-di(p-benzoato)porphyrin ligand (H₂DBP).

Dipyrrylmethane was synthesized based on a modified literature procedure as previously reported by Wang et al. (*Synlett* 1995, 1995, 1267). The general synthetic route is shown in FIG. 8. To a 1-liter flask 500 mL of distilled pyrrole (7.2 mol) was added. To the flask paraformaldehyde (1.74 g, 58 mmol by formaldehyde) was added and the mixture was degassed for 15 minutes. The mixture was then heated at 60° C. to dissolve most of the solid. After cooling to room temperature, 0.53 mL of trifluoroacetic acid (TFA) was added slowly to the solution. The reaction mixture was stirred for an hour before the addition of 812 mg of sodium hydroxide, then the mixture was stirred for another 45 minutes. Pyrrole was distilled off under vacuum and the remaining solid was extracted with dichloromethane from water and washed with water twice. The crude product was purified by silica gel column chromatography with chloroform as eluent to afford the off-white product. Yield: 4.94 g, 33.8 mmol (58%). $^1$H-NMR (500 MHz, chloroform-D, ppm): δ =7.72 (s, 2H), 6.61 (d, 2H), 6.15 (d, 2H), 6.03 (s, 2H), 3.94 (s, 2H).

4-(Methoxycarbonyl)benzaldehyde (1.20 g, 7.3 mmol) and dipyrrylmethane (1.07 g, 7.3 mmol) were added to a round bottom flask. To the flask 1 L of anhydrous dichloromethane (DCM) was added. Trifluoroacetic acid (0.34 mL, 4.4 mmol) was added dropwise via a syringe. The mixture was stirred at room temperature for 4 hours. To the reaction mixture, 2.49 g 2,3-dichloro-5,6-dicyano-1,4-benzoquinone (DDQ, 11.0 mmol) was then added and the mixture was stirred for another hour. Triethylamine was added to neutralize the reaction mixture. The solvent was removed with a rotary evaporator, and the 5, 15-di(p-methylbenzoato)porphyrin ($Me_2DBP$) product was purified by column chromatography with chloroform as the eluent. Yield: 810 mg, 1.40 mmol (38%). $^1$H-NMR (500 MHz, chloroform-D, ppm): δ =10.38 (s, 2H), 9.45 (d, 4H), 9.06 (d, 4H), 8.52 (d, 4H), 8.39 (d, 4H), 4.16 (s, 6H), −3.12 (s, 2H).

The aforementioned $Me_2DBP$ (399 mg, 0.69 mmol) was dissolved in a mixture of tetrahydrofuran (THF) and methanol (90 mL, 1:1 vol/vol). A potassium hydroxide aqueous solution (14 mL, 2 M) was then added. The solution was heated to reflux under nitrogen protection overnight. Half of the solvent was removed with a rotary evaporator before the solution was neutralized to pH=3 with trifluoroacetic acid. The dark purple product was collected by centrifugation and washed with water and ether. The solid residue was dried under vacuum to give the pure $H_2DBP$ product in 95% yield (362 mg, 0.66 mmol). $^1$H-NMR (500 MHz, DMSO-$D_6$, ppm): δ =13.35 (s, 2H), 10.71 (s, 2H), 9.71 (d, 4H), 9.08 (d, 4H), 8.45 (m, 8H), −3.26 (s, 2H). $^{13}$C-NMR (125 MHz, DMSO-$D_6$, ppm): δ =168.05 (a), 145.36 (f), 135.35, 133.46, 131.22, 130.78 (b-e), 128.67 (g, j), 118.19 (k), 106.62 (h, i). ESI-MS for $[H_2DBP+H]^+$: 551.1 calc; 551.2 found.

1.3. Synthesis and Characterization of the DBP-UiO NMOF

To a 20-mL glass vial was added 3 mL of $HfCl_4$ solution [2 mg/mL in N,N-dimethylformamide (DMF), 0.018 mmol], 3 mL of the $H_2DBP$ solution (3.5 mg/mL in DMF, 0.018 mmol), and 0.45 mL of acetic acid (7.9 mmol). The reaction mixture was kept in a 90° C. oven for 3 days. The dark red powder was collected by centrifugation and washed with DMF, triethylamine/ethanol (1:20 vol/vol) and ethanol.

The powder X-ray diffraction pattern of DBP-UiO matches that of the Zn-DPDBP-UiO MOF [DPDBP refers to 10, 20-diphenyl-5, 15-di(p-benzoato)porphyrin]. The Zn-DPDBP-UiO MOF adopts a UiO structure with a framework formula of $Zr_6O_4(OH)_4(Zn\text{-}DPDBP)_6$.

Nitrogen adsorption of the NMOF was tested on Autosorb-1 surface area and pore size analyzer (Quantachrome Instruments, Boynton Beach, Fla., United States of America) at 77K. The BET surface area was calculated to be 558 m$^2$/g.

Thermogravimetric analysis on DBP-UiO NMOF was carried out on Shimadzu TGA-50 thermogravimetric analyzer (Shimadzu Corporation, Kyoto, Japan). Heating speed was set to 3° C./min and the sample was heated to 600° C. in air. The weight percentage was plotted against temperature. The normalized percent weight loss from 200° C. to 600° C. was 77%, which corresponded well to the calculated DBP ligand weight loss based on the MOF formula (74%).

A plate-like morphology of DBP-UiO NMOF was confirmed by transmission electron microscopy (TEM, Tecnai F30 and Tecnai Spirit, FEI, Hillsboro, Oreg., United States of America). The distances between SBUs are measured. The particles display a plate-like morphology with thickness of about 10 nm and plate diameter of less than 100 nm. Particle sizes of DBP-UiO NMOFs were determined to be 76.3 nm (PDI=0.103) by dynamic light scattering (DLS, Nano-ZS, Malvern, United Kingdom).

1.4. DBP-UiO Stability

To test the stability of DBP-UiO in physiological environments, the DBP-UiO particles were incubated in RPMI 1640 cell culture medium for 12 h. TEM images displayed an unchanged morphology of NMOFs after incubation.

1.5. Photochemical Properties of $H_2DBP$ and DBP-UiO

The UV-visible absorption spectra of $H_2DBP$ and DBP-UiO were acquired with a UV-vis spectrophotometer (UV-2401 PC, Shimadzu Corporation, Kyoto, Japan). The $H_2DBP$ solution and DBP-UiO NMOF suspension were prepared in 0.67 mM phosphate buffer saline (PBS). The absorption of standard solutions of $H_2DBP$ at concentrations of 0.2, 0.4, 0.6, 0.8, 1, 1.5, 4 and 8 mg/L were acquired and the standard curve was plotted by linear fitting of the absorbance at 402 nm. The extinction coefficients of $H_2DBP$ at 402 nm and 619 nm are $2.2 \times 10^5$ and $1.7 \times 10^3$ $M^{-1}cm^{-1}$, respectively.

The fluorescence spectra of $H_2DBP$ ligand and DBP-UiO NMOF were taken on a spectrofluorophotometer (RF-5301PC, Shimadzu Corporation, Kyoto, Japan). The ligand fluorescence appears at 630 nm (strong) and 690 nm (weak), while DBP-UiO NMOF shows negligible fluorescence.

Time-domain lifetimes were measured on a ChronosBH lifetime fluorimeter (ISS, Inc., Champaign, Ill., United States of America) using Time-Correlated Single Photon Counting (TCSPC) methods. The fluorimeter contained Becker-Hickl SPC-130 detection electronics and an HPM-100-40 Hybrid PMT detector. Tunable picosecond pulsed excitation was provided by a Fianium SC400-2 supercontiuum laser source with integrated pulse picker and AOTF. Emission wavelengths were selected with bandpass filters (Semrock and Chroma). The Instrument Response Function (IRF) was measured to be approximately 120 ps FWHM in a 1% scattering solution of Ludox LS colloidal silica. Lifetimes were fit via a forward convolution method in the Vinci control and analysis software. The fitted lifetimes are listed in Table 1.

TABLE 1

Lifetimes of $H_2DBP$ and DBP-UiO fluorescence in different medium, fitted by software.

| sample | $μ_1$ (ns) | $μ_2$ (ns) | $\bar{τ}$ (ns) |
|---|---|---|---|
| IRF | 0.0074 | N/A | N/A |
| $H_2DBP$_DMF | 11.3 | N/A | N/A |
| $H_2DBP$_aq | 12.4 | 7.86 | 10.9 |
| DBP-UiO_DMF | 0.44 | 1.31 | 0.54 |
| DBP-UiO_aq | 0.21 | 0.70 | 0.26 |

1.6. Singlet Oxygen Generation of $H_2DBP$ and DBP-UiO

A light-emitting diode (LED) array with peak emission at 640 nm was used as the light source of singlet oxygen generation. The irradiance of LED is 100 mW/cm$^2$. Singlet oxygen sensor green (SOSG) reagent (Life Technologies, Carlsbad, Calif., United States of America) was employed for the detection of singlet oxygen. $H_2DBP$ and DBP-UiO samples were prepared in 5 μM solutions/suspensions in HBSS buffer (for DBP-UiO samples, the concentration was calculated as ligand equivalents). To 2 mL each of these solutions/suspensions, SOSG stock solution (5 μL at 5 mM) was added (final concentration=12.5 μM) before fluorescence measurement.

For a typical measurement, fluorescence intensity was acquired on a spectrofluorophotometer (RF-5301PC, Shimadzu Corporation, Kyoto, Japan) with excitation at 504 nm and emission at 525 nm (slit width 3 nm/5 nm for ex/em).

Fluorescence was measured after irradiation by LED for 0 (as background), 10 s, 20 s, 30 s, 1 min, 1.5 min, 2 min, 2.5 min, 3 min, 3.5 min, 4 min, 4.5 min, 5 min, 6 min and 7 min.

As the light intensity and photosensitizer concentration are fixed, for the photoreaction, it is assumed that [PS*] (the concentration of the excited state of the photosensitizer) is a constant. Therefore, the reaction rate equation is:

$$\frac{d[^1O_2]}{dt} = -\frac{d[O_2]}{dt} = k[PS^*][O_2] = k^*[O_2]$$

Where $k^* = k[PS^*]$. Here is a coupled reaction of SOSG to consume singlet oxygen:

$$\frac{d[SOSG^*]}{dt} = k^*[O_2]$$

Where [SOSG*] is the concentration of reacted form of SOSG. Note that $[SOSG^*]=[^1O_2]=c_0(O_2)-[O_2]$, and the fluorescence intensity is proportional to [SOSG*]:

$$I_F = I_0 \varphi_f \varepsilon b [SOSG^*]$$

Where $I_0$ is the incident light intensity, $\varphi_f$ is the fluorescence quantum yield of SOSG*, $\varepsilon$ is the extinction coefficient of SOSG*, and b is the light path length. We can integrate the equation to obtain the correlation of fluorescence intensity $I_F$ and irradiation time t:
In $$\ln\frac{[O_2]}{c_0(O_2)} = -kt$$

$$I_F = A[1 - e^{-kt}]$$

Where A and k are fitting parameters,
$A = \varphi_f I_0 \varepsilon_S b c_0(O_2)$
$k = \varphi_A N_{ir} \varepsilon_{PS} b c(PS)$
Were $I_0$ refers to the incident light intensity in fluorimeter, $\varphi_f$ is the fluorescence quantum yield of SOSG, $\varepsilon_S$ is the extinction coefficient of SOSG at excitation wavelength, b is the light path length, $c_0(O_2)$ is the initial oxygen concentration; $\varphi_A$ is the quantum yield of singlet oxygen generation, $N_{ir}$ is the irradiation light intensity by photons per second, $\varepsilon_{PS}$ is the extinction coefficient of photosensitizer at LED emission wavelength, c(PS) is the photosensitizer concentration. Linear approximations are applied in above equations.

By non-linear regression, obtained is a series of fit curves in the aforementioned form. The fitting parameters are listed in Table 2.

TABLE 2

Fitting parameters of singlet oxygen generation rate.

|  | A | k (s$^{-1}$) | r$^2$ |
|---|---|---|---|
| DBP | 68.3 | 1.5 × 10$^{-3}$ | 0.998 |
| DBP-UiO | 87.6 | 3.3 × 10$^{-3}$ | 0.999 |

1.7. Cellular Uptake of DBP-UiO

SQ20B cells were seeded on 6-well plates at 5×10$^5$ cells/well and further incubated for 24 h. The DBP-UiO samples were added to the cells at a concentration of 30 mg/L. After incubating for 4 h and 12 h, the cells were collected and the cell numbers were counted by hemocytometer. The cells were digested with concentrated nitric acid and subjected to ICP-MS for the determination of the Hf concentration. The cellular uptake amounts were determined to be 433.3±23.8 and 451.4±26.1 ng Hf/10$^5$ cells after 4 h and 12 h incubation, respectively.

1.8. Cytotoxicity

The cytotoxicity of DBP-UiO and H$_2$DBP was evaluated in human head and neck cancer cells SQ20B which are resistant to cisplatin and conventional radiotherapy. SQ20B cells were seeded on 96-well plates at 2000 cells/well. The cells were treated with DBP-UiO and H$_2$DBP at various ligand concentrations (5, 10, 20, 50 and 100 μM base on ligand concentrations) after a 24-h incubation. A further incubation of 4 h was allowed, followed by replacing the culture medium with 100 μL of fresh DMEM/F12 medium. The cells were irradiated with LED light (640 nm) at 100 mW/cm$^2$ for 15 min (total light dose 90 J/cm$^2$) or 30 min (total light dose 180 J/cm$^2$), respectively. The cells without irradiation treatment served as controls. The cells were further incubated to achieve a total incubation time of 72 h with DBP-UiO or H$_2$DBP. The cell viability was detected by (3-(4,5-dimethylthiazol-2-yl)-5-(3-carboxymethoxyphenyl)-2-(4-sulfophenyl)-2H-tetra-zolium) (MTS) assay (Promega, Madison, Wis., United States of America).

1.9. In Vivo Efficacy

The PDT efficacy of DBP-UiO was investigated using SQ20B subcutaneous xenograft murine models. Tumor bearing mice were established by subcutaneous inoculation of SQ20B cell suspension (5×10$^6$ cells per mouse) into the right flank region of 6-week athymic female nude mice. Three groups were included for comparison: PBS as control, H$_2$DBP, and DBP-UiO. When tumors reached 100 mm$^3$, PBS, H$_2$DBP, and DBP-UiO were intratumorally injected to animals at a DBP dose of 3.5 mg/kg. At 12 h post-injection, mice were anesthetized with 2% (v/v) isoflurane and tumors were irradiated with a 640 nm LED for 30 min. The light intensity was measured as 100 mW/cm$^2$, and the total light dose was 180 J/cm$^2$. Both injection and PDT were performed once.

To evaluate the therapeutic efficacy, tumor growth and body weight evolution were monitored. The tumor size was measured with a digital caliper every day. Tumor volumes were calculated as follows: (width$^2$×length)/2. Finally, all mice were sacrificed on Day 8, and the excised tumors were photographed and weighed. Tumors were fixed with formalin. Paraffin-embedded 5 μm tumor sections were stained with hematoxylin and erosin (H&E) and observed with light microscopy (Pannoramic Scan Whole Slide Scanner, Perkin Elmer, Waltham, Mass., United States of America).

The histologies of tumor slices of all three groups were observed after PDT treatment. The dominant normal tumor cells are observed in control and ligand treated groups. Prevailing apoptosis/necrosis of tumor cells were observed in tumor slices from NMOF group and massive inflammatory cells indicated the immunoresponse after PDT. The blood vessels in tumor tissue in NMOF treated group are destroyed after PDT while not disturbed in control and ligand treated groups.

1.10. Synthesis of Bi-DBP NMOF

To a 4-mL glass vial 0.5 mL of Bi(NO$_3$)$_3$.5H$_2$O solution (2.4 mg/mL in DMF, 2.5 μmol), 0.5 mL of H$_2$DBP solution (2.8 mg/mL in DMF, 2.5 μmol) and 4 μL of trifluoroacetic acid (0.05 mmol) was added. The reaction mixture was kept in an 80° C. oven for 3 days. The purple powder was collected by centrifugation and washed with DMF, triethylamine/ethanol (1:100 vol/vol) and ethanol. Bi-DBP NMOF display a nanorod morphology as revealed by TEM.

Example 2

Summary of Characterization of DBP MOF

As described in Example 1 a porphyrin derivative, 5,15-di(p-benzoato)porphyrin ($H_2DBP$), was synthesized by a condensation reaction between 4-(methoxycarbonyl)-benzaldehyde and dipyrrylmethane, and characterized by $^1H$ and $^{13}C$ NMR spectroscopy and mass spectrometry. The linearly aligned dicarboxylate groups of the DBP ligand can allow the construction of a DBP-UiO NMOF with the framework formula of $Hf_6(\mu_3-O)_4(\mu_3-OH)_4(DBP)_6$. DBP-UiO was synthesized by a solvothermal reaction between $HfCl_4$ and $H_2DBP$ in N, N-dimethylformamide (DMF) at 80° C. The resulting dark purple powder was washed with copious amounts of DMF, 1% triethylamine in ethanol (v/v), and ethanol successively before being dispersed in ethanol as a stock suspension.

Initially, based the single crystal structure of an analog of DBP-UiO, $Zr_6(\mu_3-O)_4(\mu_3-OH)_4(Zn-DPDBP)_6$ (i.e., Zn-DP-DBP-UiO, wherein DPDBP is 5,15-di(p-benzoato)-10,20-diphenyl-porphyrin) and similarities in the lengths of DPDBP and DBP and powder X-ray diffraction (PXRD) patterns of Zn-DPDBP-UiO and DBP-UiO, it was believed that DBP-UiO adopts a UiO-type MOF structure that is built from 12-connected $Hf_6(\mu_3-O)_4(\mu_3-OH)_4(carboxylate)_{12}$ secondary building units (SBUs) and DBP bridging ligands. Without wishing to be bound by theory, it is thought that the high SBU connectivity and strong Zr/Hf-carboxylate bond are responsible for the stability of UiO MOFs under a variety of conditions. DBP-UiO has a very open framework structure with triangular channels of 1.6 nm in dimensions as well as octahedral and tetrahedral cavities of 2.8 nm and 2.0 nm in dimensions, respectively. Later studies indicated that this DBP-UiO has a $Hf_{12}$ oxo cluster SBU. The synthesis of a Hf-DBP MOF with a $Hf_6$ oxo cluster SBU is described below in Example 19.

DBP-UiO particles display a plate morphology by transmission electron microscopy (TEM). Nitrogen adsorption measurements gave a BET surface area of 558 $m^2/g$ for DBP-UiO. The composition of DBP-UiO was confirmed by thermal gravimetric analysis and inductively coupled plasma-mass spectrometry (ICP-MS), giving DBP loading of 77 wt % (calcd 73%) and Hf content of 24.3% (calcd 23.7%), respectively.

Individual SBUs are clearly visible in high-resolution TEM images of DBP-UiO. The distances between SBUs are measured to be approximately 2.7 nm, which are consistent with the calculated distance of 2.77 nm based on the X-ray structure model. Fast Fourier transform (FFT) of the high-resolution TEM image displays a 3-fold symmetry for the nanoplates, consistent with the cubic crystal system of the DBP-UiO. The dimensions of the nanoplates are measured to be ~100 nm in diameter and ~10 nm in thickness. Such thin plates consist of only 4-5 sets of (111) packing layer (d111=2.2 nm). Dynamic light scattering (DLS) measurements gave an average diameter of 76.3 nm for the particles. Notably, the nanoplate morphology is particularly advantageous for generating ROS for PDT. It has been established that the diffusion length of $^1O_2$ is no more than 90-120 nm in aqueous environment and can be as short as ~20 nm inside cells. Therefore, nanoplates as thin as 10-nm in thickness are preferable for transporting $^1O_2$ from the NMOF interior to the cell cytoplasm to exert cytotoxic effects.

The UiO framework is typically stable in aqueous solution. DBP-UiO was incubated in RPMI 1640 cell culture medium for 12 h to determine its stability in physiologically relevant media. TEM images showed an unaltered morphology of the nanoplates and FFT proved that the crystalline structure of DBP-UiO remained intact. The PXRD patterns of the NMOF samples before and after incubation in RPMI 1640 medium are identical, further confirming structural stability of DBP-UiO in physiological environments.

The UV-visible absorption spectra of $H_2DBP$ and DBP-UiO in phosphate buffer saline (PBS) buffers (pH=7.4) are compared. $H_2DBP$ shows a Soret band at 402 nm and four Q-bands at 505, 540, 566, and 619 nm. The extinction coefficients of $H_2DBP$ at 402 nm and 619 nm are $2.2\times10^5$ and $1.7\times10^3$ $M^{-1}cm^{-1}$, respectively. DBP-UiO shows slight red shifts for all Q-bands, with the peaks appearing at 510, 544, 579, and 634 nm. Without wishing to be bound by any one theory, it is thought that the red-shifts probably result from the coordination of the carboxylate groups of DBP ligands to $Hf^{4+}$ centers. The Soret band of DBP-UiO is significantly broadened, presumably due to inequivalent ligand environments in thin nanoplates as well as potential framework distortion in thin MOF structures.

Singlet oxygen generation efficiencies of $H_2DBP$ and DBP-UiO were determined using Singlet Oxygen Sensor Green (SOSG, Life Technologies). After exposure to a LED light source (peak emission at 640 nm, energy irradiance of 100 $mW/cm^2$), the chemiluminescent reagent SOSG reacted with $^1O_2$ to generate green fluorescence which was quantified with a fluorimeter. The fluorescence intensity was plotted against irradiation time. The $^1O_2$ generation was depicted with an exponential function that corresponded to a pseudo first-order process. The $^1O_2$ generation curve was fitted with the following equation:

$$I_F = A(1-e^{-kt}) \quad (1)$$

Where $I_F$ is fluorescence intensity and t represents irradiation time while A and k are fitting parameters (for detailed derivations, see SI). The fitted equations for $H_2DBP$ and DBP-UiO are:

$$I_{H2DBP} = 68.3 \times (1-e^{-0.0015t}) \quad (2)$$

$$I_{DBP-UiO} = 87.6 \times (1-e^{-0.0031t}) \quad (3)$$

As the irradiance and the photosensitizer concentrations are constants in our experiments, k is an indicator of the efficiency of singlet oxygen generation. DBP-UiO is thus at least twice as efficient as H2DBP in generating $^1O_2$, presumably owing to heavy $Hf^{4+}$ centers facilitating the intersystem crossing from the $^1DBP$ to $^3DBP$ excite state. Consistent with this, the $^1DBP$ emission intensity at 640 nm greatly diminished for DBP-UiO (by a factor of ~250) with a lifetime reduction from 10.9 ns for H2DBP to 0.26 ns for DBP-UiO.

The PDT efficacy of DBP-UiO was tested on resistant head and neck cancer. Head and neck cancer refers to a group of biologically similar cancers that arise in the head or neck region (including, but not limited to, nasal cavity sinuses, lips, mouth, salivary glands, throat, and larynx). Since head and neck cancers occur superficially, PDT represents a viable treatment modality.

In vitro PDT was performed on human head and neck cancer cells SQ20B which are resistant to cisplatin and traditional radiation therapy. The tumor cell uptake of DBP-UiO was first evaluated by incubating the SQ20B cancer cells with DBP-UiO (30 μg/mL) for 4 h or 12 h. The Hf concentrations in the cells were determined by ICP-MS. No significant difference was observed between the cells after 4 h and 12 h incubation, showing rapid internalization of DBP-UiO by cancer cells.

To further confirm the PDT efficacy of DBP-UiO, SQ20B cancer cells were treated with $H_2DBP$ or DBP-UiO at various concentrations (5, 10, 20, 50 and 100 µM based on ligand concentrations), the cells were irradiated with LED light (640 nm, 100 mW/cm$^2$) for 15 min (total light dose 90 J/cm$^2$) or 30 min (total light dose 180 J/cm$^2$), respectively. Significant PDT efficacy was observed in DBP-UiO treated groups, even for the group receiving 5 µM photosensitizer dose and 15 minute irradiation. $H_2DBP$-treated groups show moderate PDT efficacy only at 20 µM dose with 30 min light irradiation while no cytotoxicity was observed in dark control or blank control groups. The in vitro PDT efficacy of BCP-UiO is superior to that of other small molecule PDT agents; for example, PHOTOFRIN® shows modest PDT efficacy at 8.5 µM dose with 100 J/cm$^2$ light dose on HT29 colon cancer cells.

In vivo experiments on SQ20B subcutaneous xenograft murine models were carried out. The mice were treated with PBS control, DBP-UiO (3.5 mg DBP/kg) or $H_2DBP$ (3.5 mg/kg) by intratumoral injection. Twelve hours post injection, each mouse was irradiated at the tumor site with light (180 J/cm$^2$) for 30 min. For comparison, PHOTOFRIN® is typically administered by intraperitoneal injection at 10 mg/kg in tumor bearing mice and with light irradiation of 135 J/cm$^2$. The tumors of mice treated with DBP-UiO started shrinking 1 day post DBP-UiO administration and PDT. Among the four tumors in the DBP-UiO group, two tumors were completely eradicated by single DBP-UiO administration and single PDT while the sizes of the other two tumors decreased from ~150 mm$^3$ to ~3 mm$^3$. The tumor growth of mice treated with $H_2DBP$ was slightly suppressed after PDT, however accelerated after 5 days and exhibited no difference to the control group at the endpoint. After local administration, DBP-UiO could be efficiently internalized by the tumor cells and induce cytotoxicity upon irradiation while the free ligand might be cleared away from the tumor sites before irradiation. No skin/tissue damage was observed after PDT treatment on all mice. Histologies of tumor slices showed macrophage infiltration in tumors of the DBP-UiO treated group and indicated that significant fractions of tumor cells were undergoing apoptosis/necrosis Example 3

DPDBP-UiO NMOF 3.1. Synthesis of DPDBP-UiO NMOF

Figure 9:
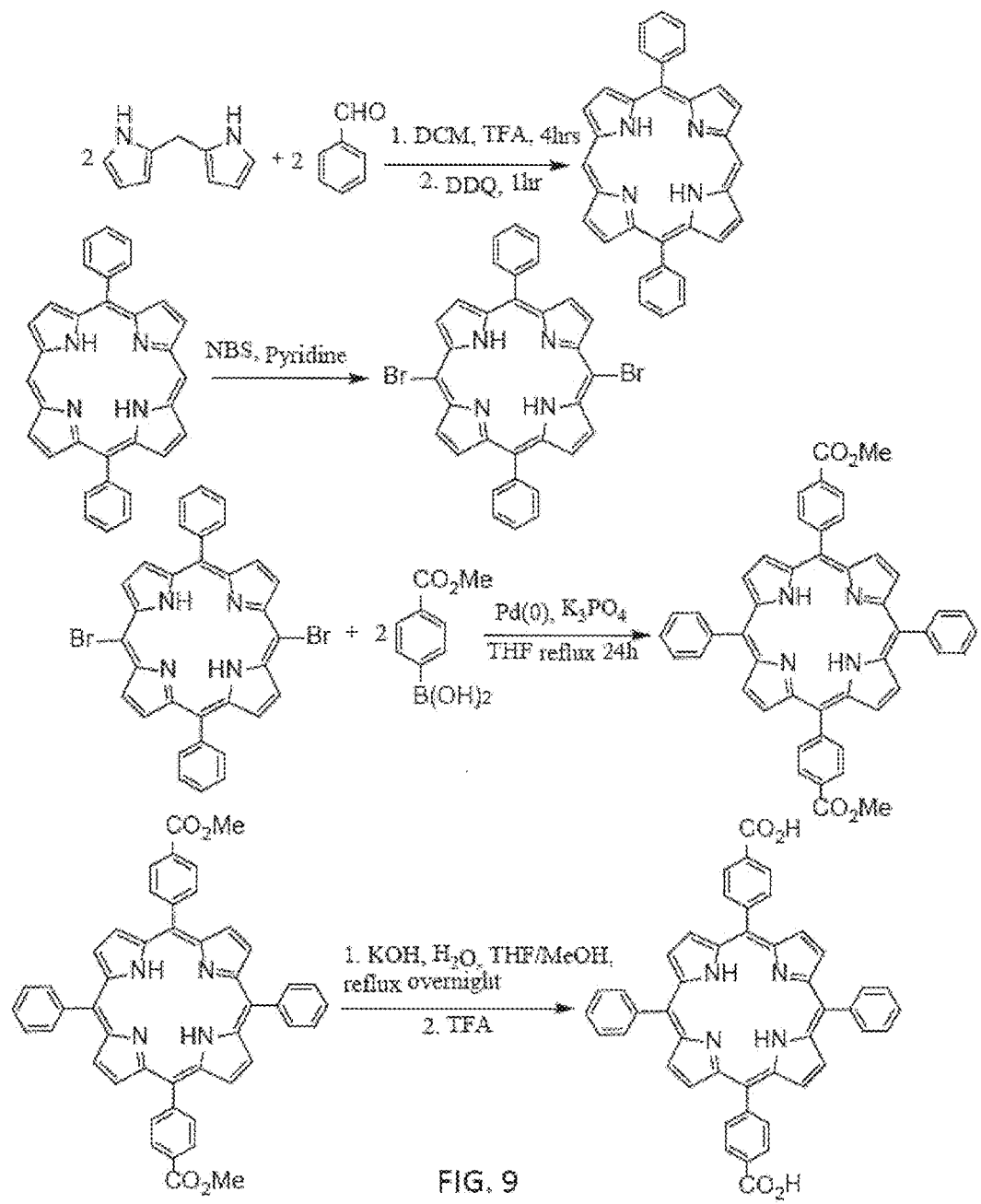
FIG. 9 is a schematic drawing of the synthesis of the 10, 20-diphenyl-5, 15-di(p-benzoato)porphyrin ligand.

A scheme showing the synthesis of 10,20-diphenyl-5,15-di(p-benzoato)porphyrin ($H_2DPDBP$) is shown in FIG. 9. More particularly, benzaldehyde (0.65 mL, 6.4 mmol) and dipyrrylmethane (0.94 g, 6.4 mmol) was dissolved in 600 mL anhydrous DCM in a round bottom flask. After nitrogen degas for 15 min, TFA (0.27 mL, 3.5 mmol) was added dropwise via a syringe. The mixture was stirred at room temperature for 4 hours. To the reaction 2.40 g 2,3-dichloro-5,6-dicyano-1,4-benzoquinone (DDQ, 10.6 mmol) was then added and the mixture was allowed to react for another hour before 1 mL of triethylamine was added to neutralize the reaction mixture. The solvent was removed by a rotary evaporator, and the diphenylporphyrin product was purified by column chromatography (1:1 vol/vol hexanes/DCM as eluent). The yield is 36% (534 mg, 1.15 mmol). $^1$H-NMR (chloroform-D): 10.34 (s, 2H), 9.42 (d, 4H), 9.11 (d, 4H), 8.30 (dd, 4H), 7.83 (m, 6H), −3.09 (s, 2H).

A chloroform solution of diphenylporphyrin (342 mg in 165 mL chloroform, 0.74 mmol) was cooled on ice bath. Pyridine (725 µL, 9 mmol) and N-bromosuccinimide (NBS, 284 mg, 1.61 mmol) were then added in sequence. The reaction was stirred on ice and was monitored by thin layer chromatography (TLC). After stirring for 35 minute, 17 mL acetone was added to quench the reaction. The solvent was evaporated on a rotary evaporator, and then vacuum was applied to remove residual pyridine. The product was purified by column chromatography with hexanes/DCM (1:1 vol/vol) as eluent. The yield is 58% (266 mg, 0.43 mmol). $^1$H-NMR (chloroform-D): 9.63 (d, 4H), 8.86 (d, 4H), 8.18 (dd, 4H), 7.80 (m, 6H), −2.71 (s, 2H).

To a 250-mL round-bottom flask 5,15-dibromo-10,20-diphenylporphyrin (265 mg, 0.43 mmol), 4-(methoxycarbonyl)-phenylboronic acid (187 mg, 1.04 mmol) and potassium phosphate (tribasic, 3.65 g, 17.2 mmol) were added. The mixture was dissolved in 50 mL of THF under nitrogen protection. Tetrakis(triphenylphosphine)-palladium(0) (103 mg, 0.09 mmol) was then added and the mixture was heated to reflux for a 24-hour reaction. The 10, 20-diphenyl-5,15-di(p-methyl-benzoato)porphyrin ($Me_2DPDBP$) product was extracted by DCM/water after reducing original solvent amount by rotary evaporation. Column chromatography was employed to purify the product with chloroform as eluent. The yield is 82% (255 mg, 0.35 mmol). $^1$H-NMR (chloroform-D): 8.89 (d, 8H), 8.49 (d, 4H), 8.35 (d, 4H), 8.26 (d, 4H), 7.80 (m, 6H), 4.15 (m, 6H), −2.73 (s, 2H).

In a round-bottom flask $Me_2DPDBP$ (139 mg, 0.19 mmol) was dissolved in mixture solvent of THF/methanol (1:1 vol/vol, 34 mL). To the solution 6 mL of 3M potassium hydroxide aqueous solution was added. The mixture was heated to reflux in nitrogen protection overnight. After evaporating most of the solvent, 10 mL of water was added and the pH was adjusted to acidic (pH=3) with TFA. The $H_2DPDBP$ solid was collected by centrifugation and was washed with water. $^1$H-NMR (DMSO-$D_6$): 13.32 (s, 2H), 8.85 (s, 8H), 8.37 (dd, 8H), 8.23 (d, 4H), 7.85 (d, 6H), −2.94 (s, 2H).

3.2. Synthesis and Characterization of the DPDBP-UiO NMOF

The DPDBP-UiO NMOF was synthesized with similar method to that of DBP-UiO. To a 20-mL glass vial 4 mL of $HfCl_4$ solution (1 mg/mL in DMF, 0.012 mmol), 1 mL of $H_2DBP$ solution (1.72 mg/mL in DMF, 0.003 mmol), 3 mL of $H_2DPDBP$ solution (2.2 mg/mL in DMF, 0.009 mmol) and 0.36 mL of acetic acid (6.3 mmol) was added. The reaction mixture was kept in a 90° C. oven for 3 days. The dark purple powder was collected by centrifugation and washed with DMF, triethylamine/ethanol (1:20 vol/vol) and ethanol.

The DPDBP-UiO NMOF exhibits a slight distorted UiO structure as manifested by PXRD, showing a similar pattern to that of the Zn-DPDBP-UiO MOF but an extra peak (2Θ=3°). TEM shows that the morphology of DPDBP-UiO is similar to that of DBP-UiO. DLS gives an average diameter of DPDBP-UiO to be 81.2 nm.

Example 4

DHDBP-UiO NMOF 4.1. Synthesis of DHDBP-UiO NMOF

Figure 10:
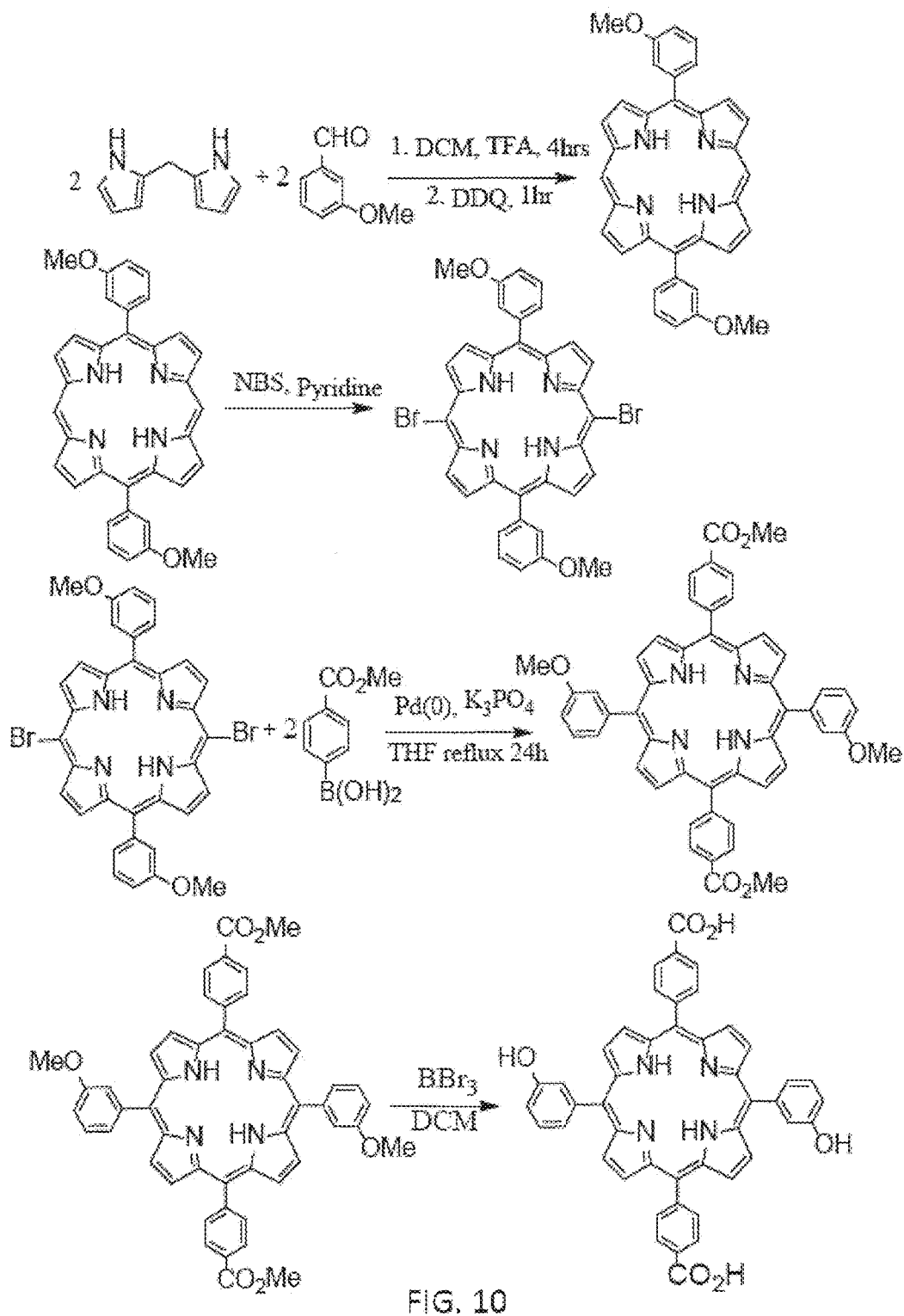
FIG. 10 is a schematic drawing of the synthesis of the 10,20-di(m-hydroxyphenyl)-5, 15-di(p-benzoato)porphyrin ligand.

A scheme showing the synthesis of 10,20-di(m-hydroxyphenyl)-5,15-di(p-benzoato)porphyrin ($H_2DHDBP$) is provided in FIG. 10. More particularly, dipyrrylmethane (635 mg, 4.34 mmol) and m-anisaldehyde (0.53 mL, 4.34 mmol)

was dissolved in 430 mL anhydrous dichloromethane in a round bottom flask. After nitrogen degas for 15 min, TFA (0.20 mL, 2.6 mmol) was added dropwise via a syringe. The mixture was stirred at room temperature for 4 hours. To the reaction 1.47 g 2,3-dichloro-5,6-dicyano-1,4-benzoquinone (DDQ, 6.5 mmol) was then added and the mixture was allowed to react for another hour before 1 mL of triethylamine was added to neutralize the reaction mixture. The solvent was removed by a rotary evaporator, and the 5, 15-di(m-methoxyphenyl)porphyrin product was purified by column chromatography (1:1 vol/vol hexanes/DCM as eluent). The yield is 28% (311 mg, 0.60 mmol). $^1$H-NMR (chloroform-D): 10.34 (s, 2H), 9.41 (d, 4H), 9.15 (d, 4H), 7.88 (m, 4H), 7.72 (t, 2H), 7.38 (dd, 2H), 4.05 (s, 6H), −3.12 (s, 2H).

A chloroform solution of di(m-methoxyphenyl)porphyrin (311 mg in 150 mL chloroform, 0.60 mmol) was cooled on ice bath. Pyridine (690 µL, 8.6 mmol) and NBS (268 mg, 1.52 mmol) were then added in sequence. The reaction was stirred on ice and was monitored by TLC. After stirring for 45 minute, 15 mL acetone was added to quench the reaction. The solvent was evaporated on a rotary evaporator, and then vacuum was applied to remove residual pyridine. The product was purified by column chromatography with hexanes/DCM (1:1 vol/vol) as eluent. The yield is 92% (374 mg, 0.55 mmol). $^1$H-NMR (chloroform-D): 9.59 (d, 4H), 8.87 (d, 4H), 7.74 (d, 2H), 7.70 (s, 2H), 7.65 (t, 2H), 7.34 (dd, 2H), 3.99 (s, 6H).

To a 250-mL round-bottom flask 5,15-dibromo-10,20-di (m-methoxyphenyl)-porphyrin (374 mg, 0.55 mmol), 4-(methoxycarbonyl)-phenylboronic acid (215 mg, 1.19 mmol) and potassium phosphate (tribasic, 4.70 g, 22 mmol) were added. The mixture was dissolved in 50 mL of anhydrous THF under nitrogen protection. Tetrakis(triphenylphosphine)-palladium(0) (133 mg, 0.12 mmol) was then added and the mixture was heated to reflux for a 24-hour reaction. The product was extracted by DCM/water after reducing original solvent amount by rotary evaporation. Column chromatography was employed to purify the product with chloroform as eluent. The yield is 76% (331 mg, 0.42 mmol). $^1$H-NMR (chloroform-D): 8.89 (d, 4H), 8.77 (d, 4H), 8.42 (d, 4H), 8.28 (d, 4H), 7.78 (d, 2H), 7.75 (s, 2H), 7.63 (t, 2H), 7.32 (dd, 2H), 4.09 (s, 6H), 3.97 (s, 6H), −2.83 (s, 2H).

In a round-bottom flask 5, 15-di(methyl-benzoato)-10, 20-di(m-methoxyphenyl)porphyrin (331 mg, 0.42 mmol) was dissolved in 20 mL of anhydrous DCM. The solution was cooled on dry ice/acetone bath before boron bromide (0.45 mL, 4.7 mmol) was added dropwise. The mixture was brought back to room temperature and was stirred overnight. The reaction solution was then poured into 100 mL of ice water and was filtered on vacuum. The H$_2$DHDBP product was washed with sodium bicarbonate solution until the wash color change to slight purple, then followed by water wash. $^1$H-NMR (DMSO-D$_6$): 9.97 (s, 2H), 8.86 (d, 8H), 8.28 (d, 4H), 8.13 (d, 4H), 7.60 (m, 6H), 7.23 (d, 2H), −2.95 (s, 2H).

4.2. Synthesis and Characterization of DHDBP-UiO NMOF

The DPDBP-UiO NMOF was synthesized with similar method to that of DBP-UiO. To a 20-mL glass vial 3 mL of HfCl$_4$ solution (2 mg/mL in DMF, 0.019 mmol), 1 mL of H$_2$DBP solution (1.8 mg/mL in DMF, 0.003 mmol), 2 mL of H$_2$DHDBP solution (2.3 mg/mL in DMF, 0.006 mmol) and 0.27 mL of acetic acid (4.7 mmol) was added. The reaction mixture was kept in a 90° C. oven for 3 days. The dark purple powder was collected by centrifugation and washed with DMF, triethylamine/ethanol (1:20 vol/vol) and ethanol. TEM shows that the morphology of DHDBP-UiO is similar to that of DBP-UiO and DPDBP-UiO. DLS gives an average diameter of DHDBP-UiO to be 66.3 nm.

Example 5

Chlorin-Based NMOFs and Use in Photodynamic Therapy of Colon Cancers

Partial reduction of 5, 15-di(p-methylbenzoato)porphyrin (Me$_2$DBP) with toluenesulfonhydrazide yielded 5, 15-di(p-methylbenzoato)chlorin (Me$_2$DBC) in 26% yield. See FIG. 1. Base-catalyzed hydrolysis of Me$_2$DBC afforded 5, 15-di (p-benzoato)chlorin (H$_2$DBC) in 88% yield. Me$_2$DBC and H$_2$DBC were characterized by NMR and mass spectrometry. A solvothermal reaction between HfCl$_4$ and H$_2$DBC in DMF led to the dark purple powdery product of DBC-UiO which was washed with copious amounts of DMF, 1% triethylamine (NEt$_3$) in ethanol (v/v), and ethanol successively and stored as a stock suspension in ethanol.

As indicated in FIGS. 2A-2D, powder X-ray diffraction (PXRD) indicated that DBC-UiO adopts the same UiO-type structure as DBP-UiO, due to the geometric similarity between the DBC and DBP ligands. Initially, it was believed that the Hf$_6$(µ$_3$-O)$_4$(µ$_3$-OH)$_4$ secondary building units (SBUs) in DBC-UiO are connected by DBC ligands to afford a UiO framework of Hf$_6$(µ$_3$-O)$_4$(µ$_3$-OH)$_4$(DBC)$_6$. The Hf content was determined by inductively coupled plasma-mass spectrometry (ICP-MS) to be 24.0% (23.8% calculated) whereas a DBC weight loss of 64% (72% calculated) was observed in thermogravimetric analysis. Based on later analysis regarding DBP-UiO (see Example 19, below), it is believed that DBC-UiO contain Hf$_{12}$ oxo clusters.

Transmission electron microscopy (TEM) of DBC-UiO reveals a nanoplate morphology similar to that of DBP-UiO. The plate diameters are 100~200 nm, while the thickness varies from 3.3 to 7.5 nm by direct observation of the particles lying perpendicular to the TEM grid. Notably, since the calculated distances between neighboring (111) packing layers (d$_{111}$) of the UiO structure are 2.2 nm, the ultra-thin plates consist of only 2-4 sets of (111) packing layers. Such plates are even thinner than DBP-UiO of ~10 nm in thickness, further facilitating the ROS diffusion during PDT. Dynamic light scattering (DLS) measurements of DBC-UiO gave an average diameter of 128.5 nm with a polydispersity index of 0.17 and a ζ potential of −10.2 mV in phosphate buffer saline (PBS).

UV-visible absorption spectroscopy confirmed the photophysical properties of chlorin-based PSs. See FIGS. 2A-2D. H$_2$DBC has a split Soret band at $\lambda_{max}$=408 nm and four Q-bands at 504, 534, 591, and 643 nm. DBC-UiO shows slight red-shifts for all Q-bands compared to H$_2$DBC, with the peaks at 508, 545, 592, and 646 nm. The lowest energy Q-band of DBC-UiO has thus red-shifted by 13 nm from DBP-UiO, with an ε value of 24600 M$^{-1}$·cm$^{-1}$. H$_2$DBC has an ε value of 21800 M$^{-1}$·cm$^{-1}$ for the lowest energy Q-band.

H$_2$DBC exhibited a fluorescence peak at ~641 nm. See FIGS. 2A-2D. However, DBC-UiO fluorescence was ~200 fold weaker than H$_2$DBC, due to an enhanced intersystem crossing upon coordination of DBC ligands to Hf$^{4+}$ ions via the carboxylate groups. Consistent with this, DBC-UiO has a slightly shorter fluorescence lifetime of 7.88 ns compared to H$_2$DBC (8.15 ns) by Time-Correlated Single Photon Counting measurements. See Table 3.

TABLE 3

Lifetimes of H$_2$DBC, DBC-UiO and HfCl$_4$+ DBC control fluorescence in different medium, fitted by software.

| sample | μ$_1$ (ns) | μ$_2$ (ns) | μ$_3$ (ns) | τ̄ (ns) |
|---|---|---|---|---|
| IRF | 0.0086 | N/A | N/A | N/A |
| H$_2$DBC__HBSS | 5.80 | 8.77 | N/A | 8.15 |
| DBC-UiO__HBSS | 3.27 | 8.26 | 0.14 | 7.88* |
| HfCl$_4$ + DBC__HBSS | 6.12 | 8.78 | N/A | 8.13 |
| H$_2$DBC__DMF | 8.27 | N/A | N/A | N/A |
| DBC-UiO__DMF | 3.24 | 8.54 | 0.19 | 8.16* |
| HfCl$_4$ + DBC__DMF | 2.41 | 7.97 | 0.38 | 7.32 |

*These average lifetimes are fitted with only μ$_1$ and μ$_2$, the μ$_3$ of these sets are known to be from scattering.

Singlet Oxygen Sensor Green (SOSG) was employed to determine $^1$O$_2$ generation efficiencies of H$_2$DBC and DBC-UiO. SOSG reacted with generated $^1$O$_2$ to give green fluorescence ($\lambda_{em}$=525 nm) that was quantified with a fluorometer. For comparison, $^1$O$_2$ generation efficiency of H$_2$DBP, DBP-UiO and protoporphyrin IX (PpIX) were also determined. The fluorescence plotted against irradiation time was fitted with an exponential function (Eq 1):

$$I_F = A(1-e^{-kt}) \tag{Eq 1}$$

indicating a pseudo first-order $^1$O$_2$ generation process. See FIGS. 2A-2D. In Eq 1, $I_F$ is fluorescence intensity and t is irradiation time while A and k are fitting parameters. See Table 4. The total $^1$O$_2$ generation yield was normalized based on that of PpIX to compare the overall photosensitization efficiency. DBC-UiO is ~3 times as efficient as DBP-UiO in generating $^1$O$_2$.

TABLE 4

Fitting parameters for $^1$O$_2$ generation curves.

| | A | k (min$^{-1}$) | Relative yield |
|---|---|---|---|
| H$_2$DBC | 102 | 0.25 | 4.3 |
| DBC-UiO | 195 | 0.18 | 7.3 |
| H$_2$DBP | 101 | 0.06 | 1.8 |
| DBP-UiO | 55.9 | 0.24 | 2.4 |
| PpIX | 26.6 | 0.19 | 1 |

The stability of DBC-UiO in biological media was confirmed by culturing the NMOF in RPMI 1640 cell culture medium for 12 h. The morphology of NMOFs did not change by TEM, while high resolution TEM images along with their fast-Fourier transform patterns indicate the retention of NMOF crystallinity. The PXRD pattern of DBC-UiO did not change after incubation in RPMI 1640 cell medium, further proving the framework stability of DBC-UiO in biological environments.

DBC-UiO has a crystalline and stable structure to avoid self-quenching even at 64% PS loading, enhanced intersystem crossing to increase $^1$O$_2$ generation efficiency, and porous framework and nanoplate morphology to facilitate $^1$O$_2$ diffusion, and preferred photophysical properties. DBC-UiO is effective against murine and human colorectal cancers. PDT is used in the clinic to treat colon cancer by delivering light through an endoscope. It is also known that PDT treatment of primary colon tumors can elicit an immunogenic response against metastatic tumors.

Figure 3:
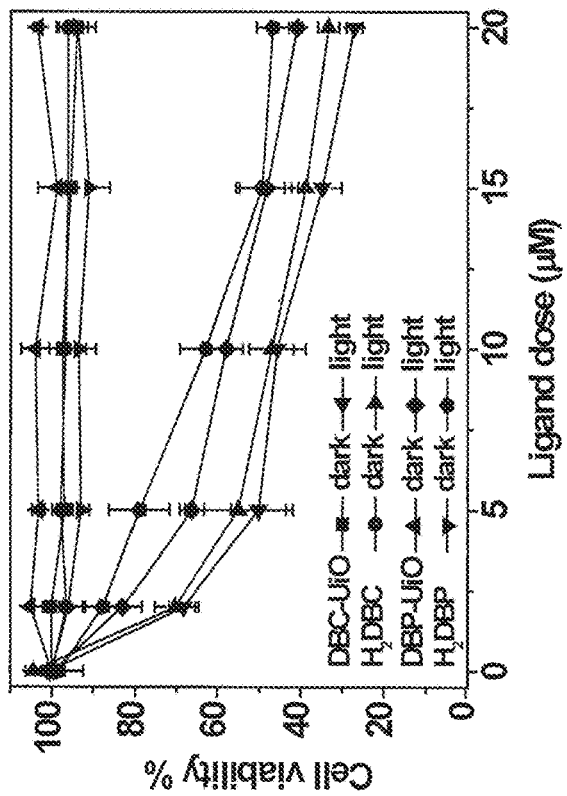
FIG. 3 is a pair of graphs of photodynamic therapy (PDT) cytotoxicity of a di(p-benzoato)chlorin metal-organic framework (DBC-UiO), a di(p-benzoato)porphyrin metal-organic framework (DBP-UiO), a di(-p-benzoato)chlorin (H₂DBC), and di(p-benzoato)porphyrin (H₂DBP) at different photosensitizer (PS) concentrations in CT26 colon carcinoma cells (left) and HT29 colon carcinoma cells (right). For both left graph and right graph, percentage cell viability is shown for DBC-UiO with light illumination (left-pointing triangles) and without light illumination (i.e., dark; squares); for H₂DBC with light illumination (circles) and without (right-pointing triangles); for DBP-UiO with light illumination (upward-pointing triangles) and without (diamonds); and for H₂DBP with light illumination (downward-pointing triangles) and without (pentagons).
Figure 3:
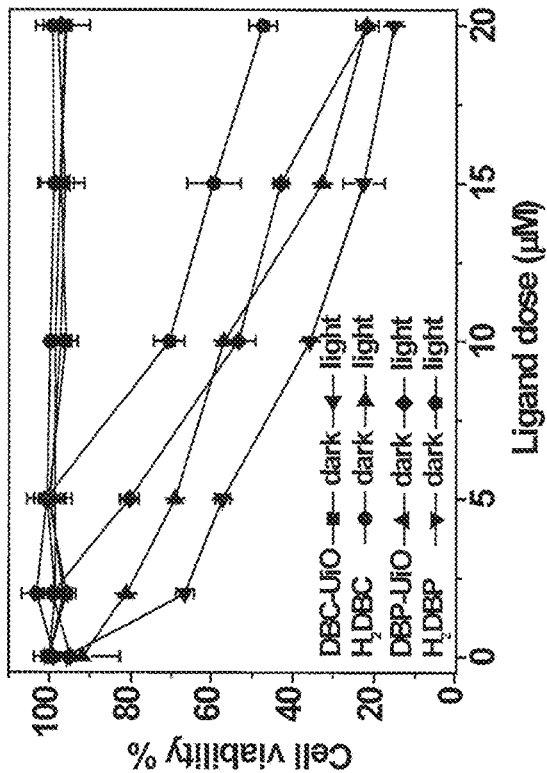

The tumor cell uptake of NMOFs was evaluated by incubating CT26 cells with DBP-UiO or DBC-UiO at a Hf concentration of 50 μM for 4 h. The Hf contents in CT26 cells were determined to be (3.44±0.13) and (2.35±0.08) nmol/10$^5$ cells for DBP-UiO and DBC-UiO, respectively, by ICP-MS. The in vitro PDT efficacy of DBC-UiO against colon cancer cells was investigated and compared with DBP-UiO and their corresponding free ligands. NMOFs or free ligands were incubated with CT26 or HT29 cells at various concentrations, and the cells were irradiated with LED light at a total light dose of 90 J/cm$^2$ (0.1 W/cm$^2$, and 15 min. DBP-UiO and H$_2$DBP: 640 nm; DBC-UiO and H$_2$DBP: 650 nm). DBC-UiO outperformed DBP-UiO by effectively killing both cancer cell lines at low NMOF and light doses. See FIG. 3. Free ligand treated groups also showed moderate PDT efficacy, while no cytotoxicity was observed in dark control or PBS control groups. The IC$_{50}$ values of DBC-UiO, H$_2$DBC, DBP-UiO, and H$_2$DBP in CT26 cells with irradiation were calculated to be 5.1±0.2, 8.5±0.1, 10.4±0.5, and 20.0±3.1 μM, respectively. The IC$_{50}$ values of DBC-UiO, H$_2$DBC, DBP-UiO, and H$_2$DBP in HT29 cells with irradiation were calculated to be 6.0±1.5, 7.5±2.3, 13.1±2.2, and 17.0±4.0 μM, respectively.

Both apoptosis and immunogenic cell death (ICD) contribute to the superior in vitro PDT efficacy. CT26 cells were incubated with 5 μM DBC-UiO or H$_2$DBC followed by light irradiation at 0.1 W/cm$^2$ for 15 min (90 J/cm$^2$). The apoptosis induced by PDT treatment was determined with the Alexa Fluor 488 Annexin V/dead cell apoptosis kit by flow cytometry. No apoptosis or necrosis was observed for cells treated with DBC-UiO or H$_2$DBC in the dark while significant amounts of cells underwent apoptosis when treated with DBC-UiO or H$_2$DBC upon light irradiation. Calreticulin (CRT) is a distinct biomarker exposed on the surface of cells undergoing ICD. The CRT expression was determined by flow cytometry and immunofluorescence to assess the ICD induced by DBC-UiO induced PDT. CT26 cells were treated with 5 μM DBC-UiO or H$_2$DBC followed by light irradiation at 0.1 W/cm$^2$ for 15 min (90 J/cm$^2$). For flow cytometry analysis, cells were collected and stained with Alexa Fluor 488-CRT antibody and propidium iodide (PI). The fluorescence intensity of stained cells was gated on PI-negative cells. For immunostaining analysis, the cells were stained with AlexaFluor 488-CRT conjugated antibody and DAPI nuclei stain, and observed using confocal laser scanning microscopy (CLSM). Cells treated with DBC-UiO or H$_2$DBC without light irradiation or treated with PBS with light irradiation showed no surface CRT expression while significant amounts of CRT were detected on the surface of cells upon irradiation. This result indicates that ICD was involved in the cytotoxicity induced by PDT of DBC-UiO and H$_2$DBC.

Figure 4:
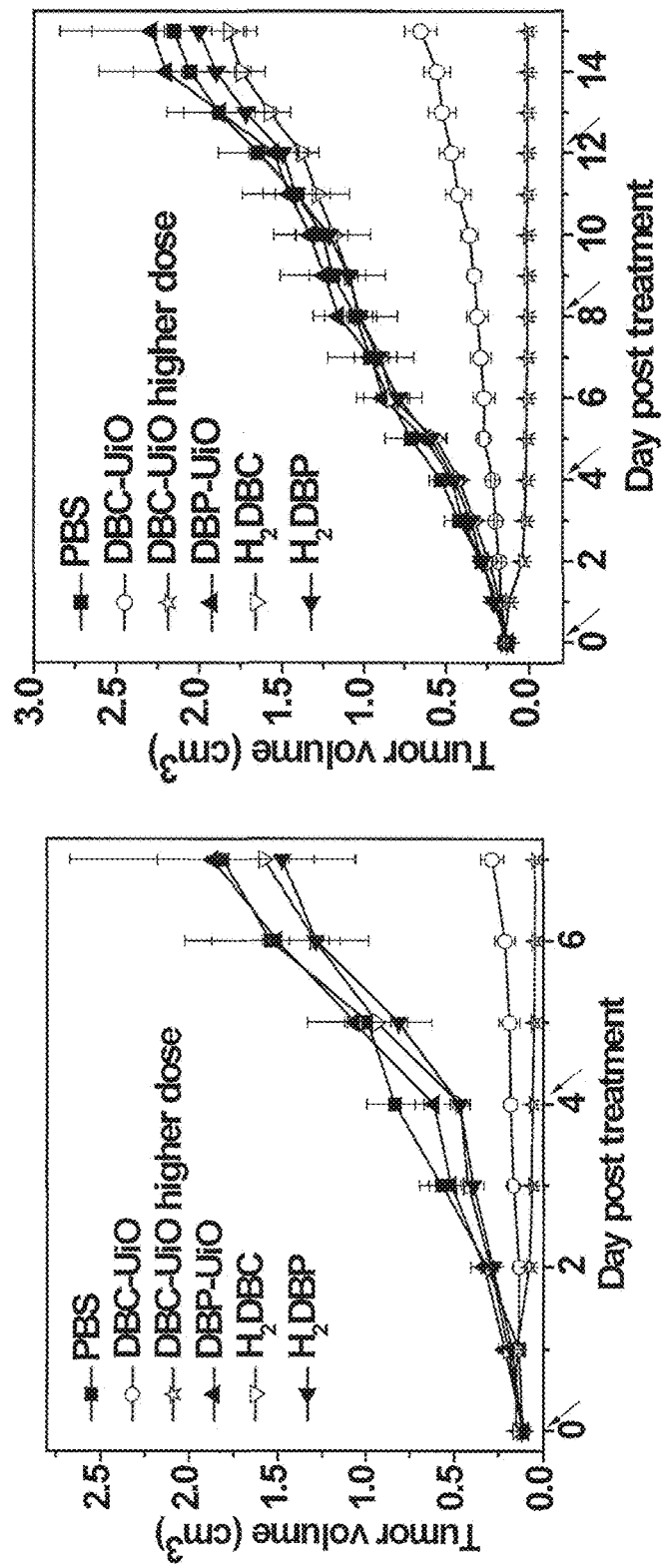
FIG. 4 is a pair of graphs showing the tumor growth inhibition curves after photodynamic therapy (PDT) treatment in a CT26 colon carcinoma model (left graph) and a HT29 colon carcinoma model (right graph). In both graphs; tumor volumes (in cubic centimeters (cm³)) are provided for the following treatments: a control (phosphate buffered saline (PBS); filled squares), a di(p-benzoato)chlorin metal-organic framework (DBC-UiO; open circles); a higher dose of DBC-UiO (open stars); a di(p-benzoato)porphyrin metal-organic framework (DBP-UiO; filled upward-pointing triangles); di(p-benzoato)chlorin (H₂DBC; open downward-pointing triangles) and di(p-benzoato)porphyrin (H₂DBP; filled left-pointing triangles).

In vivo anticancer efficacy experiments on subcutaneous flank tumor mouse models of CT26 and HT29 were performed. The mice were intratumorally injected with (1) PBS control, (2) DBC-UiO, (3) DBP-UiO, (4) H$_2$DBC, or (5) H$_2$DBP at a ligand dose of 1 mg/kg or (6) DBC-UiO at a ligand dose of 3.5 mg/kg. Twelve hours post injection, each mouse in group (1)-(5) was irradiated at the tumor site with light (0.1 W/cm$^2$) for 15 min (90 J/cm$^2$) and the mice in group (6) received light irradiation (0.1 W/cm$^2$) for 30 min (180 J/cm$^2$). For (1) to (5) groups on the CT26 model, mice are treated again 4 days after first treatment, while for (1) to (5) groups on HT29 model, mice are treated every 4 days for total 4 treatments. As depicted in FIG. 4, the tumor growth of mice treated with DBC-UiO (1 mg/kg DBC dose) was effectively inhibited in both models. DBP-UiO and the two PS ligands failed to suppress the tumor growth in either model, due to low PS and light doses. Higher doses of DBC-UiO and light irradiation led to effective tumor regression in HT29 with single treatment and in CT26 with two treatments. The weights and sizes of tumors treated with DBC-UiO at the endpoint were also significantly smaller than the other groups. Histology of frozen tumor slices further confirmed that only DBC-UiO treatment caused apoptosis/necrosis of tumors but not in DBP-UiO or the two PS ligands.

Example 6

MOFs for X-ray Scintillation

Figures 5A, 5B:
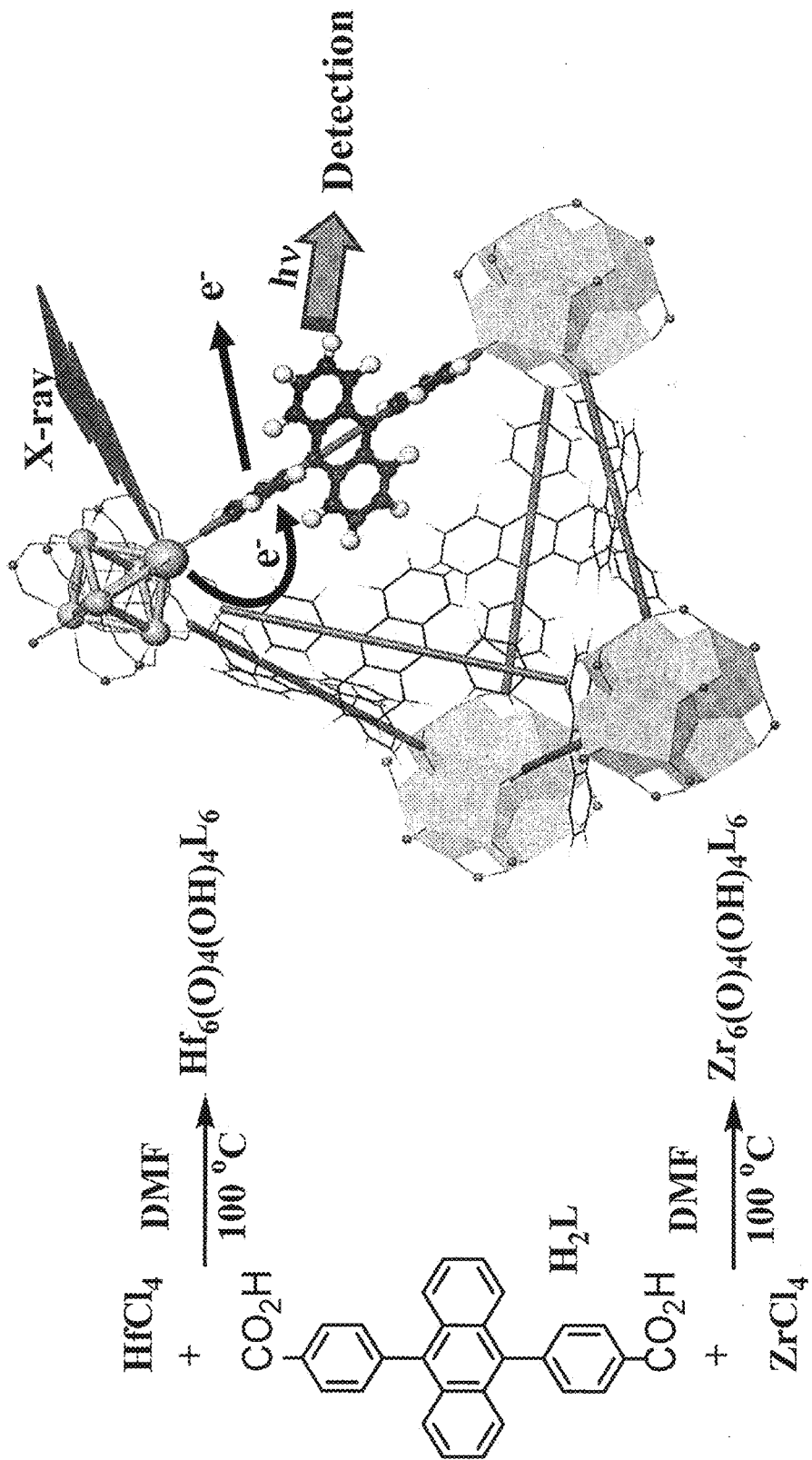
FIG. 5A is a schematic diagram of the synthesis of hafnium metal-organic framework (Hf-MOF) and zirconium metal-organic framework (Zr-MOF).
FIG. 5B is a schematic diagram of the X-ray induced generation of fast photo-electrons from heavy metals followed by scintillation of the anthracene based linkers in the visible spectrum.
Figure 6B:
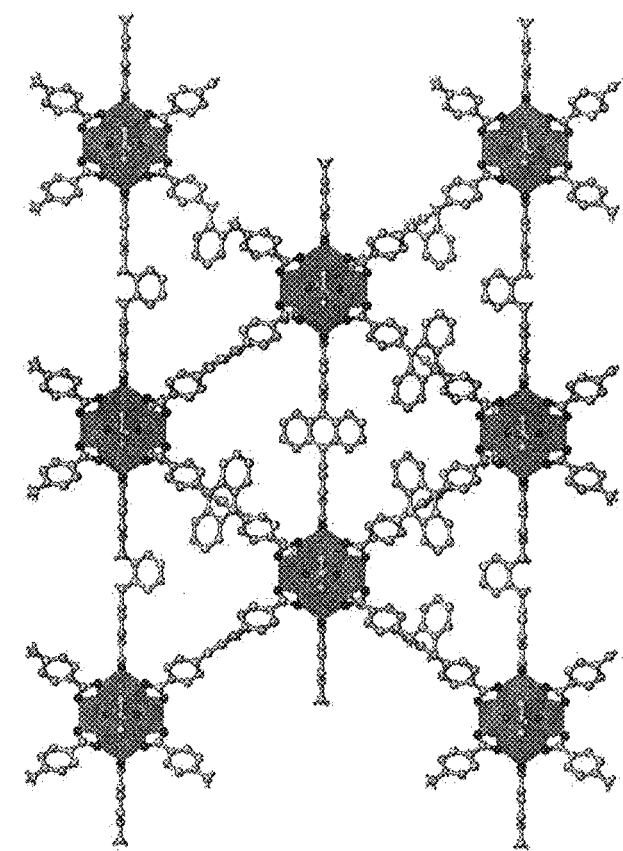
FIGS. 6A-6E show schematic drawings of structural models of a hafnium metal-organic framework (Hf-MOF) and a zirconium metal-organic framework (Zr-MOF), including.
Figure 6A:
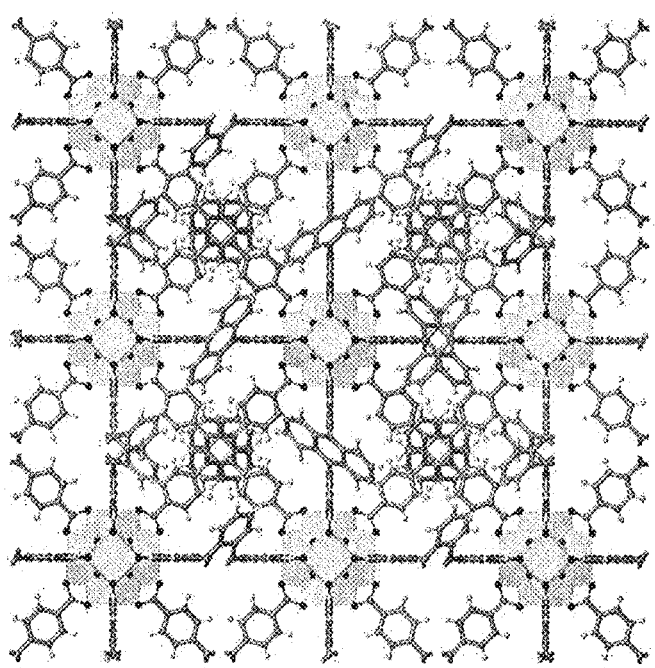
Figure 6C:
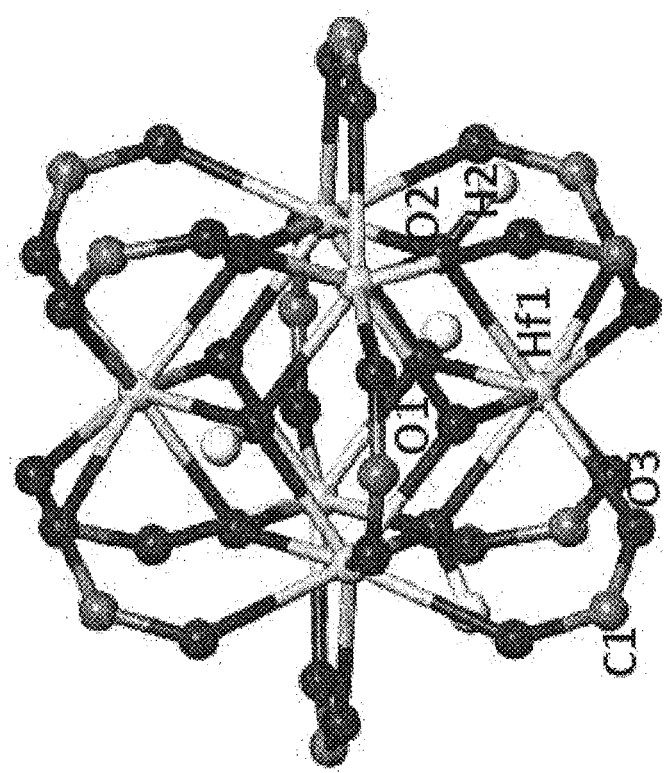
Figures 6D, 6E:
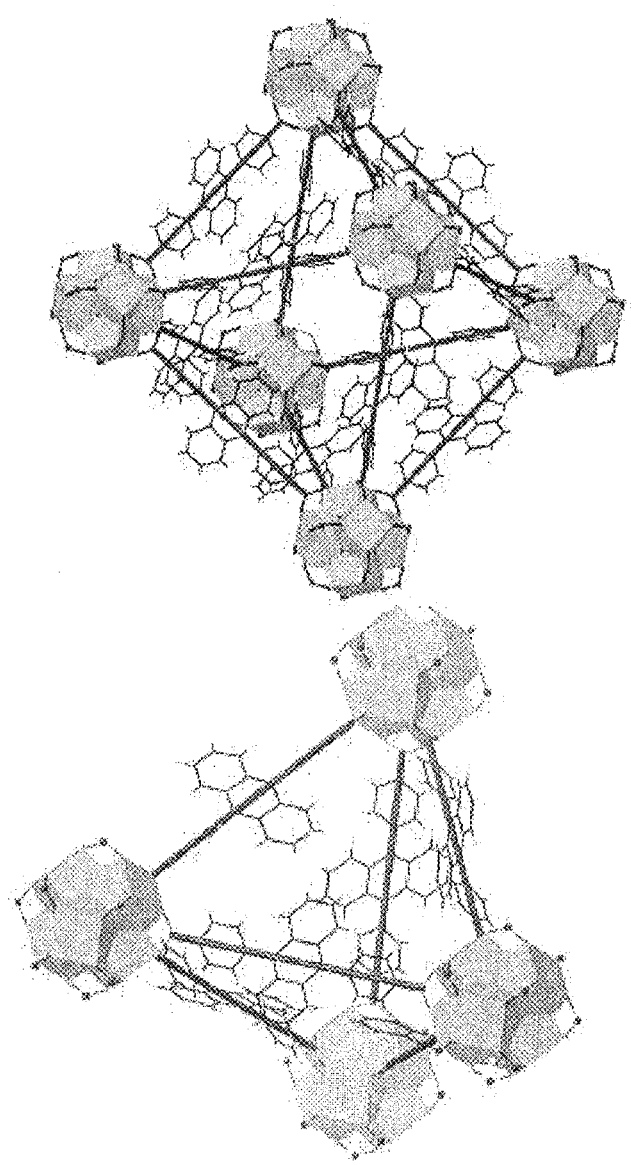

UiO frameworks (Hf-MOF and Zr-MOF) built from a linear dicarboxylate ligand and the $M_6(\mu_3-O)_4(\mu_3-OH)_4$(carboxylate)$_{12}$ SBU (M=Hf or Zr) or an $M_{12}$ oxo cluster can be suitable for use according to the presently disclosed subject matter because of their high chemical stability and structural predictability. The 9,10-anthacenyl bis(benzoic acid) ($H_2L$) was prepared in a high yield following the procedure of Hauptvogel et al. (*Inorg. Chem.* 2011, 50, 8367). Hf-MOF and Zr-MOF were synthesized by treating $H_2L$ with $HfCl_4$ or $ZrCl_4$ in DMF at 100° C. for 2 days. The resulting white crystalline solids were washed with copious amounts of DMF, methanol, and water. The crystal structures of these two MOFs were revealed by the similarities of their PXRD patterns to the simulated pattern from a UiO MOF that is built from the amino-terphenyldicarboxylate ligand of the same length as L. See FIGS. 5A and 5B. Both MOFs adopt the UiO framework structure of the fcu topology by connecting the $M_6(\mu_3-O)_4(\mu_3-OH)_4$(carboxylate)$_{12}$ SBU with the linear L linkers. See FIGS. 5A and 5B. Within every SBU, $M^{4+}$ was placed on the six vertices of an octahedron. The faces of the octahedron were bridged by a $\mu_3-O^{2-}$ or a $\mu_3-OH^-$ alternately. The edges of the octahedron were bridged by a carboxylate group with each oxygen coordinating to one $M^{4+}$, finishing an 8-coordinated environment for each $M^{4+}$ ion. See FIGS. 6A-6E. Because of the steric bulk of the L ligand, non-interpenetrated structures were obtained based on systematic absences of the PXRD patterns. The open-framework possesses a 60.5% void space, as calculated by PLATON, and a triangular open channel with 1.2 nm edge length. For every SBU, there is one octahedral cavity with a diameter of 0.8 nm and two tetrahedral cavities with a diameter of 0.6 nm. See FIGS. 6A-6E. TEM and SEM images of Hf-MOF and Zr-MOF showed octahedral microcrystals of ~1 μm in dimensions. Nitrogen adsorption measurements on the MOFs gave BET surface areas of 2187 $m^2/g$ and 2776 $m^2/g$ for Hf-MOF and Zr-MOF, respectively. The pore-size distribution functions of both MOFs showed maxima at around 0.6 nm, 0.8 nm and 1.2 nm, consistent with the cavity and channel sizes derived from the crystal structural models.

Fluorescence spectra of suspensions of Hf-MOF (0.04 mM of L ligand) in water, DMF, and THF were taken with an excitation wavelength of 368.8 nm. The maxima of the emission spectra shift to longer wavelengths as the polarity of the solvent increases (430 nm in THF, 435 nm in DMF, and 469 nm in water), as predicted by the general solvent effect. Such an observation supports the accessibility of the anthracene sites in the MOFs to solvent molecules. The excitation spectra of the MOFs in more polar solvents also exhibit less defined vibrational fine structure due to stronger coupling of the solvent bath modes to the molecular electronic and vibrational coordinates. Suspensions of Zr-MOF (0.04 mM of L ligand) in water and DMF showed similar emission spectra as Hf-MOF. In contrast, $H_2L$ particles which are insoluble in water showed only moderate dependence of emission on solvent, due to the inability of solvent molecules to access the interiors of the ligand particles.

Fluorescence lifetimes of Hf-MOF, Zr-MOF, and $H_2L$ suspensions in water were also examined. All of the suspended samples showed bi-exponential fluorescence decays and the weighted lifetimes of the samples were calculated based on the fittings. Hf-MOF and Zr-MOF possess significantly longer lifetime (6.19 ns and 5.96 ns, respectively) than $H_2L$ particles (2.0 ns). Without being bound to any one theory, it is believed that this difference results from a combination of a solvent effect on excited state lifetime and the exciton migration in the densely packed $H_2L$ particles. The mobile excited state can move and be trapped and quenched at a defect site in a $H_2L$ particle, while site isolation of anthracene moieties in the MOFs reduces the excited state mobility, leading to an enhanced lifetime of the excited state. Consistent with this, the DMF solution of $H_2L$ exhibits longer excited state lifetimes (5.34 ns) than those of DMF suspensions of Hf-MOF (4.06 ns) and Zr-MOF (3.92 ns). Previous studies indicated that the free rotation of anthracene in the structure can reduce its luminescence signal.

The heavy metal clusters in the MOF structure serve as an effective X-ray antenna due to their high Z numbers. The outer-shell electrons of $Hf^{4+}$ and $Zr^{4+}$ ions are ejected as fast electrons upon the X-ray absorption through the photoelectric effect. The generated photo-electrons then experience inelastic scattering in a framework, and transfer their energy to the L ligands, bringing them to excited states which decay and emit the visible photons for detection. X-ray luminescence of the MOF particles (200 μL suspensions in water) were tested with clinical superficial therapy system. Both Hf-MOF and Zr-MOF exhibit bright radioluminescence in the visible spectrum upon X-ray excitation. See FIGS. 6A-6E.

Hf-MOF exhibited higher radioluminescence signal than Zr-MOF under the same experimental conditions due to higher X-ray scattering cross section of Hf than Zr (for example, the average energy attenuation coefficient ranges for Hf from ~110 to 18 $cm^2/g$ and for Zr~23 to 16 $cm^2/g$ in the 15-30 keV range). As control experiments, neither the anthracenyl ligand $H_2L$ by itself nor metal oxide ($HfO_2$ or $ZrO_2$) nanoparticles produce significant amount of optical signal, indicating the synergistic roles played by both heavy metal antenna and organic emitters in the MOF assemblies. Hf-MOF (1.2 mM L or Hf) produced a signal that is ~24 times of the signal generated by $H_2L$ alone, while the Zr-MOF produced as signal of ~11 times the amount. For comparison, the widely used inorganic scintillator NaI(Tl) has a light output of 2.3 times of that of the anthracene crystal, while practical organic liquid and plastic scintillators all have lower light outputs than the anthracene crystal. In contrast, a physical mixture of colloidal metal oxide ($HfO_2$ or $ZrO_2$) and ligand $H_2L$ only generate luminescence slightly higher than that of $H_2L$ (~1.3 times for $HfO_2+H_2L$ and ~1.2 times for $ZrO_2+H_2L$). Additional control experiments with $HfOCl_2$ and $ZrOCl_2$ solutions and $Me_2L$ (methyl ester of the L ligand) were also performed. Again negligible luminescence was generated by the solution samples as compared to that of the MOF samples.

Radioluminescence of MOF suspensions in ethanol was also measured with slightly lower luminescence as compared to that obtained in aqueous solution under the same experimental condition. Such solvent dependence indicates interactions between solvent molecules and the generated fast electrons which determine the overall X-ray-to-photon conversion efficiency. To eliminate the solvent effect, the radioluminescence of dry MOF samples in the absence of any solvent molecules was measured. ~15 times more MOFs were used than were used in suspension measurements, to get sufficient volumes of the materials for the measurements. The resulting luminescence signals of the MOFs are ~1200 times more intense for the Hf-MOF and ~2400 times more intense for the Zr-MOF than those signals obtained from aqueous suspensions. The integration time (or dosage) of the measurement was decreased from 10 sec to 0.01 sec and the detection gain was reduced from 200 to 50 to avoid saturating the detector. The solid samples can generate much more (80 to 160 times) radioluminescence in the absence of solvent molecules, which, without wishing to be bound by theory, is consistent with a secondary fast electron induced luminescence as the major mechanism of X-ray to visible light conversion.

Different concentrations of Hf-MOF and Zr-MOF samples in aqueous suspensions were exposed to X-rays with effective energies of 14.8, 16.2 and 29.8 keV (with the delivered dose of ~0.025, 0.25 and 0.05 Gy per 10 seconds based on the tube voltage of 30, 50 and 80 kV and the tube current 7.6, 30 and 8 mA) for a further systematic study. As shown in FIGS. 7A and 7B, the observed radioluminescence signals of MOFs vary linearly with the nanoparticle concentrations for all the three X-ray energies. It was also confirmed that increase of dose leads to the increase of signal from MOFs; the more X-ray photons absorbed, the more visible photons generated. The spectrum of X-ray induced luminescence from these MOF samples was measured with a custom-made system. Samples showed radioluminescence peaks ranging between 400-600 nm. Optical stability of the radioluminescence against X-ray damage was also examined. The cumulative dose of up to 300 Gy was delivered to Zr-MOF and Hf-MOF samples, and X-ray luminescence was examined by very low-dose X-ray irradiation (~0.25 μGy) before and after ultra-high-dose delivery. No substantial decrease of the X-ray induced luminescence was observed.

Example 7

RuBipyL-UiO NMOF 7.1. Synthesis of [Ru(bipy)$_2$(bpy-dc)]C$_2$(RuBipyL)

Figure 11:
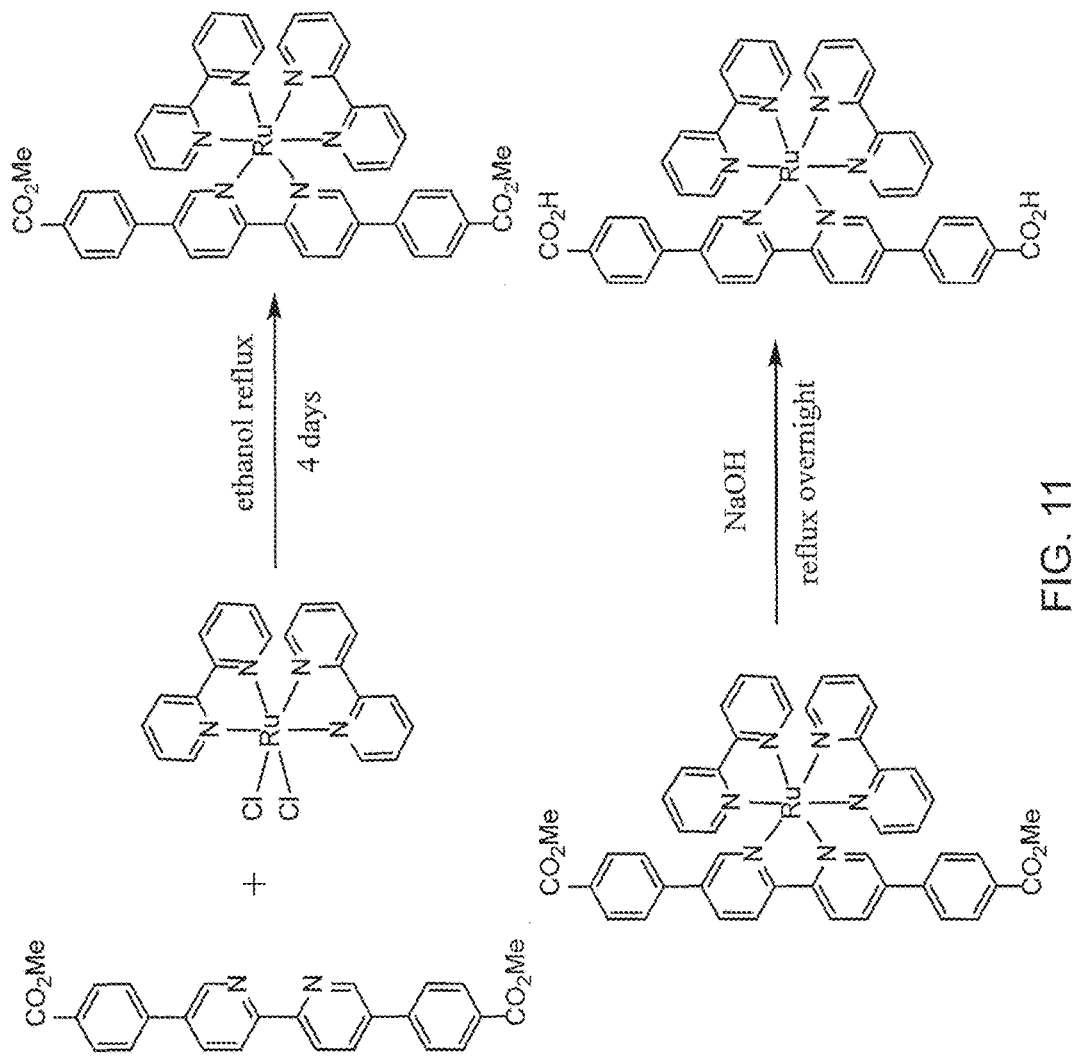
FIG. 11 is a schematic drawing of the synthesis of a ruthenium bipyridine complex-based bridging ligand, [Ru(bipy)₂(bpy-dc)]Cl₂(RuBipyL).

5,5'-bis(4-methoxycarboxylphenyl)-2,2'-bipyridine (bpy-de) was prepared in a reported method. As shown in FIG. 11, in a round-bottom flask bpy-de (195 mg, 0.46 mmol) and ruthenium(II) bis(2,2'-bipyridine) dichloride (206 mg, 0.43 mmol) were dissolved in 30 mL of ethanol and refluxed under nitrogen protection for 4 days. The solution was then cooled down, filtered and concentrated in vacuo. Diethyl ether (30 mL) was added to the concentrated solution to afford the product Me$_2$-RuBipyL as a red precipitate (175 mg, 45%). $^1$H NMR (500 MHz, DMSO-d6): 9.06 (d, 2H, J=8.5 Hz), 8.87 (d, 2H, J=8.0 Hz), 8.84 (d, 2H, J=8.0 Hz), 8.60 (dd, 2H, J=8.5 Hz, 2.0 Hz), 8.22 (td, 2H, J=8.0 Hz, 1.2 Hz), 8.18 (td, 2H, J=8.0 Hz, 1.2 Hz), 8.02 (d, 4H, J=8.5 Hz), 7.95 (d, 2H, J=5.5 Hz), 7.84 (d, 2H, J=5.5 Hz), 7.80 (d, 2H, J=2.0 Hz), 7.66 (d, 4H, J=8.5 Hz), 7.59 (td, 2H, J=6.5 Hz, 1.0 Hz), 7.55 (td, 2H, J=6.5 Hz, 1.0 Hz), 3.89 (s, 6H).

Me$_2$-RuBipyL (175 mg, 0.19 mmol) was dissolved in 20 mL of 3M NaOH solution in ethanol/water (1:1 vol/vol) and refluxed overnight. The solution was then cooled down and neutralized with 2M HCl (aq). The solvent was removed on vacuo. The resulting solid was then dissolved in ethanol and filtered. The filtration was concentrated to afford the product RuBipyL as a red solid (146 mg, 90%). $^1$H NMR (500 MHz, DMSO-d6): 13.24 (br s, 2H), 9.06 (d, 2H, J=8.5 Hz), 8.88 (d, 2H, J=8.0 Hz), 8.85 (d, 2H, J=8.0 Hz), 8.59 (dd, 2H, J=8.0 Hz, 1.5 Hz), 8.22 (t, 2H, J=8.0 Hz), 8.18 (t, 2H, J=8.0 Hz), 8.00 (d, 4H, J=8.0 Hz), 7.95 (d, 2H, J=5.0 Hz), 7.84 (d, 2H, J=5.5 Hz), 7.81 (d, 2H, J=1.5 Hz), 7.63 (d, 4H, J=8.5 Hz), 7.60 (t, 2H, J=6.5 Hz), 7.56 (t, 2H, J=6.5 Hz).

7.2. Synthesis and Characterization of the RuBipyL-UiO NMOF

To a 2-mL glass vial 1.51 mg RuBipyL (1.7 μmol), 0.5 mL of HfCl$_4$ solution (1.4 mg/mL in DMF, 2.2 μmol) and 8 μL of trifluoroacetic acid (0.10 mmol) was added. The reaction mixture was kept in a 100° C. oven for 4 days. The orange powder was collected by centrifugation and washed with DMF, triethylamine/ethanol (1:100 vol/vol) and ethanol.

Methods for x-ray induced photodynamic therapy are described, for example, in US Patent Application Publication Nos.: 2007/0218049, 2002/0127224 and 2011/0238001, each of which is incorporated by reference herein in its entirety.

7.3. X-ray Induced Singlet Oxygen Generation

Conventional PDT:

In a 2-dram vial an aqueous solution of 4-nitroso-N,N-dimethylanaline (RNO, 25 μM), histidine (10 mM) and MOF sample (P-MOF or Ru-MOF, 5 μM) was prepared. The solution absorption at 439 nm was monitored by a UV-vis spectrophotometer. The solution was irradiated by LED light (for P-MOF, 640 nm 100 mW LED; for Ru-MOF, white light LED with a 400 nm long pass filter) for 0, 2, 5, 10, 15, 20, 30 min. The decrease of absorption at 439 nm (ΔOD) was plotted against irradiation time. The relative 1O2 generation rate was evaluated by linear fitting of the data. The fit equations are as below:

$$\text{P-MOF: } y=0.00178t \quad (1)$$

$$\text{Ru-MOF: } y=0.0105t \quad (2)$$

Where y is the decrease of absorption (a.u.) and t is irradiation time (min).

Figure 12A:
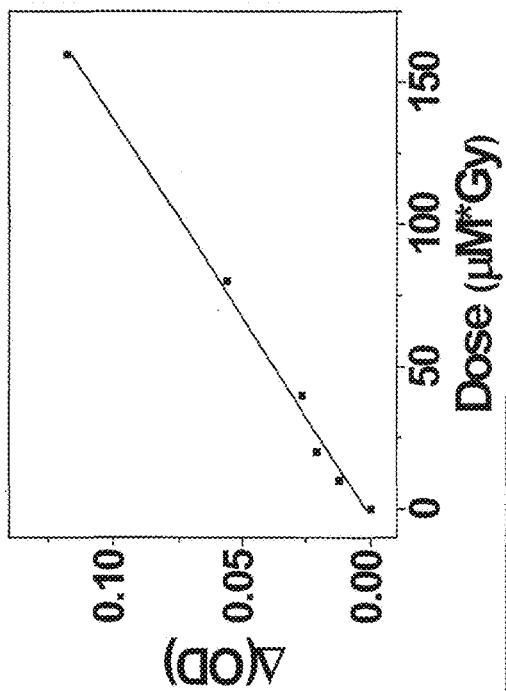
FIGS. 12A-12C are a set of graphs of (FIG. 12A) a di(p-benzoate)porphyrin metal-organic framework (P-MOF) conventional photodynamic therapy (PDT) fit curve.
Figure 12B:
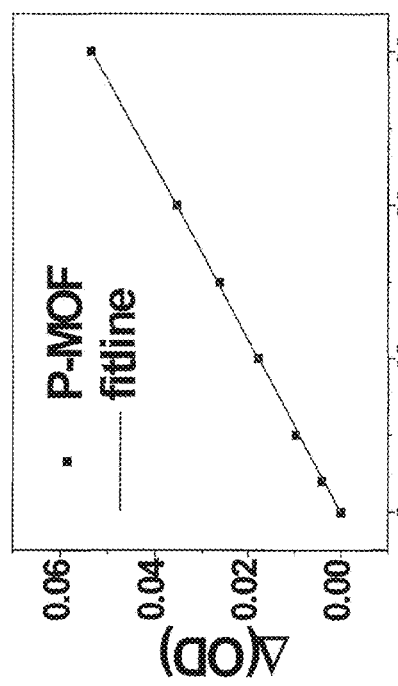
Figure 12C:
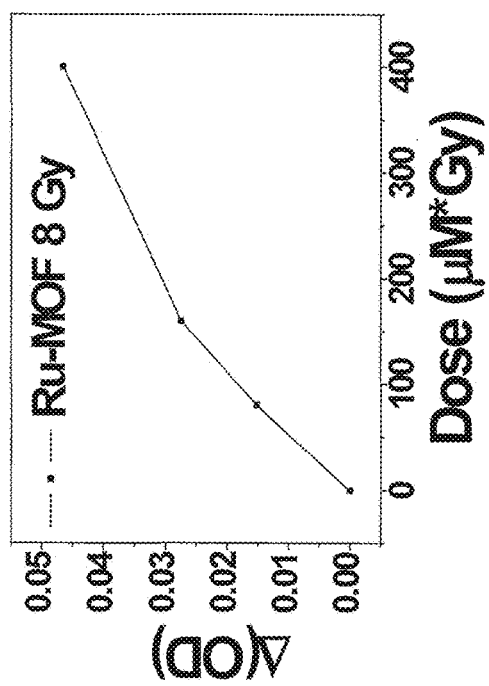

X-PDT:

The MOF samples were prepared in aqueous solutions (10, 20 or 50 μM) in presence of 25 μM of RNO and 10 mM of histidine. For P-MOF, 1, 2, or 4 Gy of X-ray irradiation was applied. For Ru-MOF, all the samples are given 8 Gy of X-ray dose. The UV-vis absorption spectra of the solutions were taken by a spectrophotometer. The results of these studies are shown in FIGS. 12A-12C.

7.4. Cellular Uptake of P-MOF and Ru-MOF

The cellular uptake of DBP-UiO NMOF (P-MOF) and RuBipyL-UiO NMOF (Ru-MOF) was evaluated in three cancer cell lines including murine colorectal adenocarcinoma CT26, human glioblastoma U87, and human head and neck cancer SQ20B. The cells were incubated with P-MOF or Ru-MOF at a Hf concentration of 50 μM for 4 h. The cells were collected and the cell numbers were counted by a hemocytometer. Concentrated nitric acid was used to digest the cells and the metal concentrations were determined by ICP-MS.

Both P-MOF and Ru-MOF were efficiently taken up by the cancer cells with uptake efficiencies ranging from ~5-30%. The Hf concentrations for P-MOF and Ru-MOF in CT26, U87, and SQ20B cells were 3.44±0.13 and 6.08±0.10, 1.27±0.07 and 4.26±0.53, and 1.02±0.32 and 4.64±0.61 nmol/$10^5$ cells, respectively.

In addition, the molar ratios of Hf to Ru for Ru-MOF taken up by CT26, U87, and SQ20B cells were calculated to be 1.05±0.12, 1.01±0.11, and 0.98±0.09, respectively, which were in accordance with those for intact Ru-MOF, suggesting the Ru-MOF was internalized by the cells in its intact forms.

7.5. Cytotoxicity
7.5.1. Cell-line-dependent Cytotoxicity of UiO NMOFs

The cytotoxicity of P-MOF and Ru-MOF upon X-ray irradiation was evaluated against ten different human cancer cell lines, including four HNSCC (SQ20B, JSQ3, SCC61, HNSCC135), two glioblastoma (GBM, U251, U87), one colon cancer cell (HT29), one cisplatin-resistant ovarian cancer cell (OCa, A2780cisR), one breast cancer cell (MCF-7), and one pancreatic cancer cell (PDAC, BxPC-3). Various X-ray irradiation doses ranging from 0-1 Gy were applied to determine the X-ray irradiation dose dependent cytotoxicity. P-MOF or Ru-MOF were incubated with the cells at a ligand concentration of 10 µM for 4 h, and the cell culture medium was replaced with fresh medium followed by X-ray irradiation. An X-ray beam with 250 kVp and 10 mA current were used for the irradiation. After irradiation, the cells were further incubated for 72 h before determining the cell viability by MTS assay. The results are shown in Table 5.

No cytotoxicity was observed for cells treated with PBS and X-ray irradiation up to 1 Gy. Both P-MOF and Ru-MOF exhibited efficient cancer cell killing at extremely low X-ray doses against a panel of different human cancer cell lines.

TABLE 5

Cell viability (%) of different cell lines receiving NMOF and X-ray treatment.

| | Ru-MOF | | P-MOF | | | |
|---|---|---|---|---|---|---|
| | 0.5 Gy | 1 Gy | 0.5 Gy | 1 Gy | 180 J/cm² | X-ray [a] |
| SQ20B | 28.1 ± 0.2 | 17.2 ± 0.5 | 25.9 ± 2.9 | 19.5 ± 2.4 | 44.4 ± 3.2 | 0.30 |
| JSQ3 | 41.3 ± 9.8 | 24.7 ± 2.4 | 42.3 ± 6.4 | 23.8 ± 6.0 | 70.8 ± 9.2 | 0.20 |
| SCC61 | 26.2 ± 0.4 | 18.3 ± 3.7 | 32.1 ± 2.1 | 18.9 ± 2.1 | 67.9 ± 5.8 | 0.13 |
| HNSCC135 | 32.4 ± 3.9 | 23.7 ± 1.8 | 33.2 ± 4.8 | 18.7 ± 2.5 | 62.1 ± 7.6 | 0.18 |
| U251 | 42.5 ± 1.3 | 31.0 ± 2.6 | 43.8 ± 1.8 | 38.0 ± 1.6 | 67.1 ± 0.4 | 0.16 |
| U87 | 16.2 ± 3.5 | 10.7 ± 2.5 | 18.9 ± 2.7 | 11.5 ± 2.9 | 57.0 ± 0.2 | 0.17 |
| HT29 | 18.5 ± 4.8 | 9.3 ± 1.6 | 18.3 ± 0.7 | 10.1 ± 2.4 | 39.4 ± 5.6 | 0.17 |
| A2780cisR | 20.6 ± 1.3 | 14.5 ± 3.2 | 23.9 ± 2.5 | 15.4 ± 2.1 | 42.2 ± 4.7 | 0.16 |
| MCF-7 | 43.4 ± 3.2 | 34.0 ± 1.8 | 42.1 ± 2.0 | 36.2 ± 0.9 | 58.9 ± 2.7 | 0.16 |
| BxPC-3 | 55.0 ± 5.8 | 45.0 ± 0.8 | 67.5 ± 1.2 | 57.5 ± 2.2 | 74.4 ± 4.8 | 0.17 |

[a] X-ray dose (Gy) needed to achieve similar cytotoxicity as 180 J/cm² light irradiation (clinically used irradiation dose for PDT).

7.5.2. NMOF Concentration-dependent Cytotoxicity

The NMOF concentration-dependent cytotoxicity was evaluated on U87 cells. P-MOF was incubated with the cells at various ligand concentrations ranging from 0 to 15 µM for 4 h followed by X-ray irradiation at 0.5 Gy. An X-ray beam with 250 kVp and 10 mA current were used for the irradiation. After irradiation, the cells were further incubated for 72 h before determining the cell viability by MTS assay.

The cytotoxicity of P-MOF was concentration dependent when dosing at lower than 10 µM. No significant difference of cytotoxicity was observed between 10 µM and 15 µM. See FIG. 12A.

7.5.3. Tissue Penetration of X-ray Induced Cytotoxicity

Figures 13A, 13B:
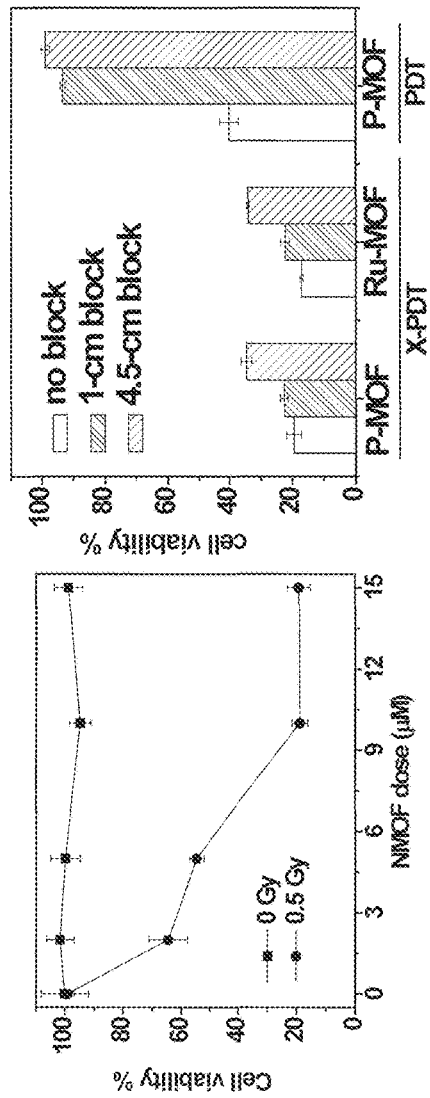
FIGS. 13A-13B are a pair of graphs showing (FIG. 13A) the nanoscale metal-organic framework (NMOF) concentration-dependent cytotoxicity of a di(p-benzoato)porphyrin metal-organic framework (P-MOF) in human glioblastoma (U87) cells with 0.5 gray (Gy) X-ray irradiation (circles) and without X-ray irradiation (squares)
Figure 14A:
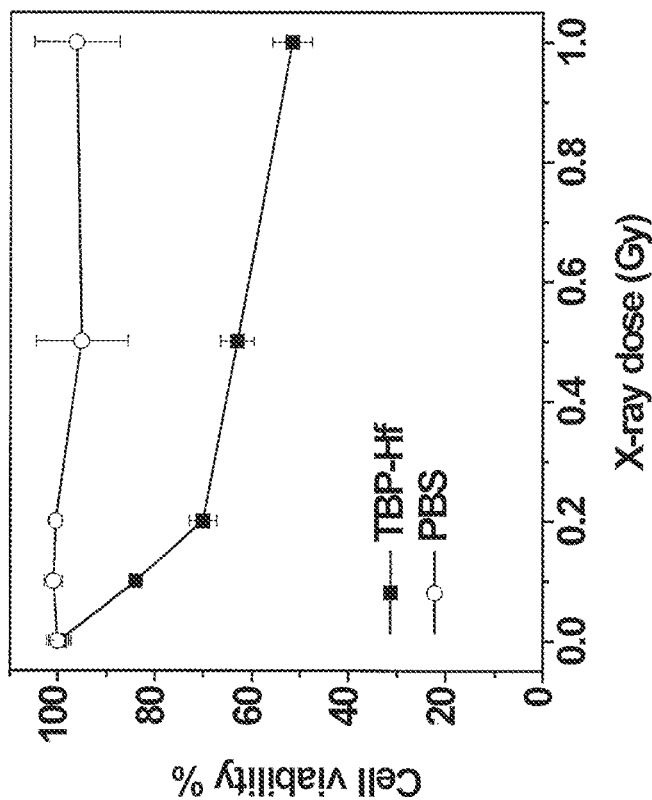
FIGS. 14A-14F are a set of graphs showing the cytotoxicity of a tetra(benzoate)porphyrin-hafnium (TBP-Hf) metal-organic framework (MOF) upon X-ray irradiation against GL261 glioma cells (FIG. 14A), U251 glioblastoma cells (FIG. 14B), U87 primary glioblastoma cells (FIG. 14C), CT26 colon carcinoma cells (FIG. 14D), TUBO breast cancer cells (FIG. 14E), and TRAMP-C2 prostate cancer cells (FIG. 14F). TBP-Hf NMOFs were incubated with the cells at a Hf dose of 10 micromolar (μM) for 4 hours (h) followed by X-ray irradiation at different doses. The cell viability was evaluated by (3-(4,5-dimethylthiazol-2-yl)-5-(3-carboxymethoxyphenyl)-2-(4-sulfophenyl)-2H-tetra-zolium) (MTS) after 72 h.
Figure 14B:
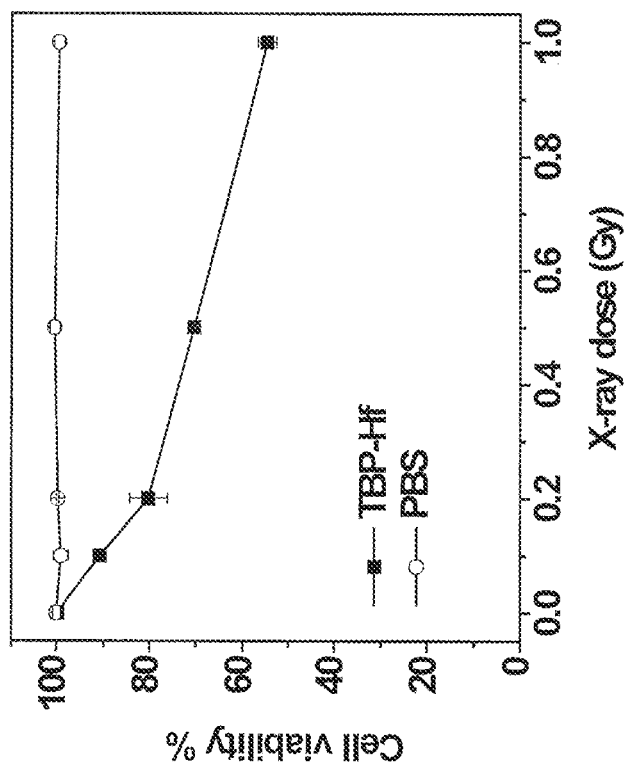
Figures 14C, 14D:
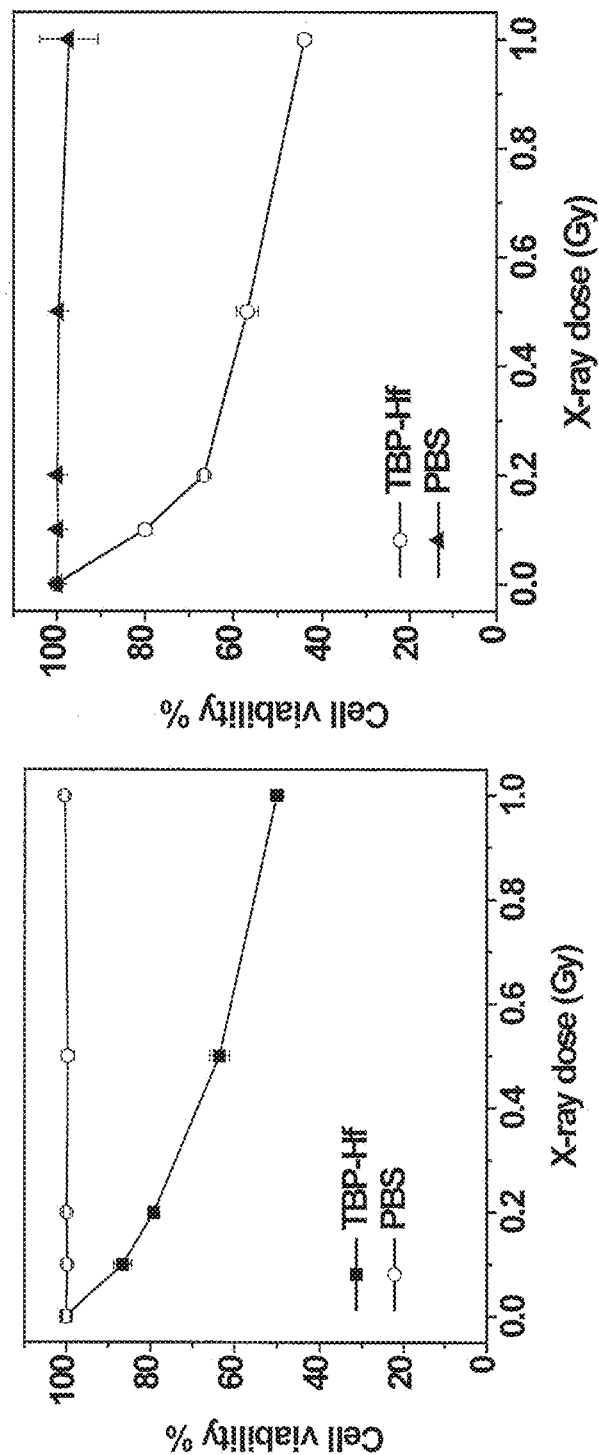
Figures 14E, 14F:
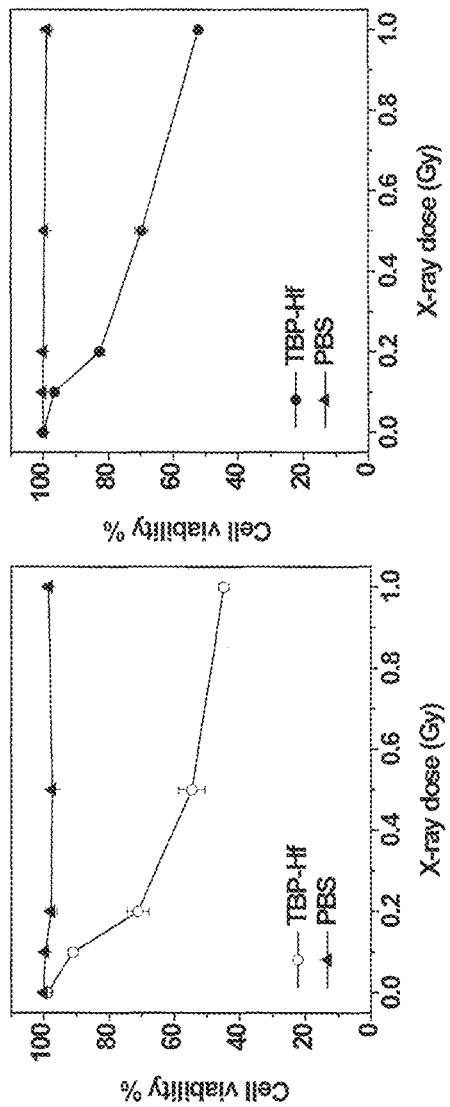

X-ray has large tissue penetration depth while visible light or NIR has tissue penetration depth less than 1 cm. A piece of beef with 1 cm in thickness or a stack of beef of 4.5 cm in thickness was used to cover the cells during in vitro LED light irradiation or X-ray irradiation to mimic deep tumor environments, and to evaluate the cytotoxicity of P-MOF or Ru-MOF at a ligand concentration of 10 µM. After the irradiation (0.5 Gy for X-PDT and 180 J/cm² for PDT), the cells were further incubated for 72 h before determining the cell viability by MTS assay. No cytotoxicity was observed for light activated PDT blocked by 1-cm or 4.5-cm beef because the light cannot penetrate the tissue. The X-ray induced cancer cell killing was only slightly impacted by the beef blocks, effectively killing >65% cells with a 4.5-cm block (compared to ~80-83% cell killing without the beef block). See FIGS. 13A and 13B.

Example 8

TBP-Hf NMOF

8.1. Synthesis and Characterization of TBP-Hf NMOF.

To a 2-dram glass vial was added 1 mL of HfCl$_4$ solution [2 mg/mL in N,N-diethylformamide (DEF), 6.2 µmol], 1 mL of tetra(benzoate)porphyrin (H$_4$TBP) solution (1.9 mg/mL in DEF, 2.4 µmol), and 60 mg of benzoic acid (0.49 mmol). The reaction mixture was kept in a 120° C. oven for 2 days. The violet powder was collected by centrifugation and washed with DMF, triethylamine/ethanol (1:20 vol/vol) and ethanol.

The powder X-ray diffraction pattern of TBP-Hf NMOF matches the pattern simulated from the reported structure for the TBP-Zr MOF.

Nanorod morphology of TBP-Hf NMOF was confirmed by transmission electron microscopy (TEM, Tecnai F30 and Tecnai Spirit, FEI, Hillsboro, Oreg., United States of America). The distances between neighboring lattice fringes are measured to be 1.61 nm, which matches the d$_{001}$=1.66 nm of the reported structure. The particles display a rod-like morphology with width of about 20-30 nm and length of about 50-100 nm.

The cytotoxicity of TBP-Hf NMOF upon X-ray irradiation was evaluated against two human GBM cell lines (U87 and U251), one murine GBM cell line (GL261), one murine colorectal adenocarcinoma cell line (CT26), one murine breast cancer cell line (TUBO), and one murine prostate cancer cell line (TRAMP-C2). Various X-ray irradiation doses ranging from 0-1 Gy were applied to determine the X-ray irradiation dose dependent cytotoxicity. See FIGS. 14A-14F. TBP-Hf NMOFs were incubated with the cells at a Hf concentration of 10 µM for 4 h, and the cell culture medium was replaced with fresh medium followed by X-ray irradiation. An X-ray beam with 225 kVp and 13 mA current were used for the irradiation. After irradiation, the cells were further incubated for 72 h before determining the cell viability by MTS assay.

No cytotoxicity was observed for cells treated with PBS and X-ray irradiation up to 1 Gy. TBP-Hf NMOFs also exhibited efficient cancer cell killing at extremely low X-ray doses against a panel of different cell lines.

The cytotoxicity of TBP-Hf NMOF upon X-ray irradiation was further evaluated against two human GBM cell lines (U87 and U251) and one murine GBM cell line (GL261) and compared with P-MOF. Various X-ray irradiation doses ranging from 0-1 Gy were applied to determine the X-ray irradiation dose dependent cytotoxicity. TBP-Hf NMOFs or P-MOF were incubated with the cells at a PS ligand concentration of 10 μM for 4 h, and the cell culture medium was replaced with fresh medium followed by X-ray irradiation. An X-ray beam with 225 kVp and 13 mA current were used for the irradiation. After irradiation, the cells were further incubated for 72 h before determining the cell viability by MTS assay.

No cytotoxicity was observed for cells treated with PBS and X-ray irradiation up to 1 Gy. TBP-Hf NMOFs exhibited more efficient cancer cell killing than P-MOF at extremely low X-ray doses against a panel of different GBM cell lines.

Example 9

X-ray Sensitization with UiO NMOFs

Three Hf NMOFs including UiO-66, UiO-67, and amino UiO-68 were synthesized, which were constructed from Hf metal clusters and ligands with negligible photosensitization properties. In addition, $HfO_2$ nanoparticles with amorphous structures which are in the clinical trial as radiosensitizers were also used as comparisons.

9.1. Synthesis and Characterization of UiO-66, UiO-67, and Amino UiO-68 Hf NMOFs Hf-UiO-66 (UiO-66)

A solution of $HfCl_4$ (3.52 mg/mL in DMF, 0.6 mL, 6.59 mol) and a solution of terephthalic acid ($H_2DBC$, 20 mg/mL in DMF, 0.2 mL, 24.1 μmol) were mixed in a 1-dram vial. To the solution 25 μL of acetic acid was added. White powdery product was afforded after 18 h reaction in a 90° C. oven and was collected by centrifugation. The mother liquor was kept in at 90° C. for another 6 h to afford additional powdery product. The two portions of the product were combined and washed with DMF and ethanol.

Hf-UiO-67 (UiO-67)

A solution of $HfCl_4$ (4 mg/mL in DMF, 0.5 mL, 6.24 μmol) and a solution of 4,4-biphenyl dicarboxylic acid ($H_2BPDC$, 6 mg/mL in DMF, 0.5 mL, 12.4 μmol) were mixed in a 1-dram vial. To the solution 20 μL of acetic acid was added. The mixture was heated in a 90° C. oven for 18 hours and the white powdery product was collected by centrifugation and was washed with DMF and ethanol.

Amino UiO-68

Figure 15:
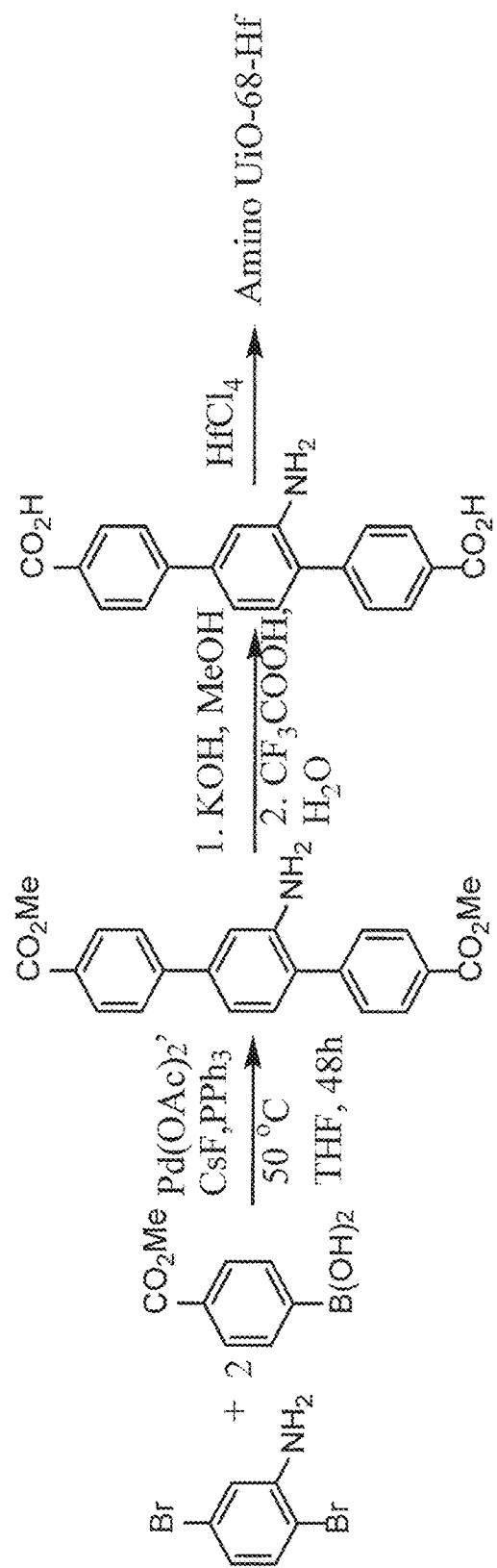
FIG. 15 is a schematic diagram showing the synthesis of the amino-triphenyldicarboxylic acid (amino-TPDC) ligand and UiO nanoscale metal-organic framework (NMOF).

A synthetic scheme for Amino UiO-68 is shown in FIG. 15. Briefly, 2,5-dibromoaniline (2.00 g, 8.0 mmol), 4-(methoxycarbonyl)-phenylboronic acid (4.40 g, 24.5 mmol) and CsF (5.82 g, 38 mmol) were suspended in 50 mL of anhydrous tetrahydrofuran (THF) under nitrogen protection in a 100 mL round-bottom flask. Pd(OAc)$_2$ (0.60 g, 2.7 mmol) and PPh$_3$ (1.61 g, 6.1 mmol) were then added. The mixture was heated at 50° C. for 48 h. The product was purified by water/dichloromethane extraction and silica gel column chromatography (dichloromethane: ethyl ether=50:1 with 0.2%-0.5% triethylamine). Yield: 58%. $^1$H NMR (Chloroform-D): δ =8.10 (m, 4H), 7.65 (d, 2H), 7.57 (d, 2H), 7.22 (d, 1H), 7.09 (d, 1H), 7.01 (s, 1H), 3.93 (two overlapping singlets, 6H), 3.88 (s, 2H).

The amino-triphenyldicarboxyl methyl ester from above (1.68 g, 4.65 mmol) was suspended in 200 mL of THF and heated to 40° C. To the suspension 100 mL of 5.5 M KOH methanol solution was added and the resulting mixture was stirred at 40° C. for 18 hours. A white solid was collected by centrifugation, and then treated with 12 mL of trifluoroacetic acid in 100 mL of THF at room temperature for 2 h. The yellow solid product (amino-TPDC) was isolated by vacuum filtration and washed with THF, methanol and ether. Yield: 80%. $^1$H NMR (DMSO-d6): δ =12.97 (br, 2H), 8.03 (m, 4H), 7.74 (d, 2H), 7.61 (d, 2H), 7.16 (d, 2H), 7.02 (dd, 1H), 5.12 (br, 2H). $^{13}$C NMR (DMSO-d6): δ=167.66, 167.63 (COOH), 146.24 ($C_{1'}$), 145.00 ($C_{1''}$), 144.25 ($C_1$), 139.96 ($C_{4'}$), 131.31 ($C_{6'}$), 130.40, 130.28 ($C_{3''}$, $C_3$), 129.98, 129.54 ($C_{4''}$, $C_4$), 129.19 ($C_{2''}$), 126.97 ($C_2$), 125.04 ($C_{2'}$), 115.96 ($C_{5'}$), 114.26 ($C_{3'}$).

DMF solutions of $HfCl_4$ (3 mL, 1.4 mg/mL, 18 μmol) and amino-TPDC (3 mL, 2 mg/mL, 18 μmol) were added to a 20 mL glass vial and the mixture was diluted to 10 mL, followed by the addition of 750 μL of acetic acid. The mixture was kept in an 80° C. oven for 5 days. The product was collected by centrifugation and washed with DMF, 5% triethylamine ethanolic solution and ethanol, yielding UiO NMOFs with a light yellow color (Yield: ~20%).

9.2. Cellular Uptake

The cellular uptake of three NMOFs and $HfO_2$ nanoparticles was first evaluated on SQ20B cells. NMOFs or $HfO_2$ nanoparticles were incubated with SQ20B cells at a Hf concentration of 50 μM for 4 h. The cells were collected and the cell numbers were counted by a hemocytometer. Concentrated nitric acid was used to digest the cells and the metal concentrations were determined by ICP-MS.

Figure 16:
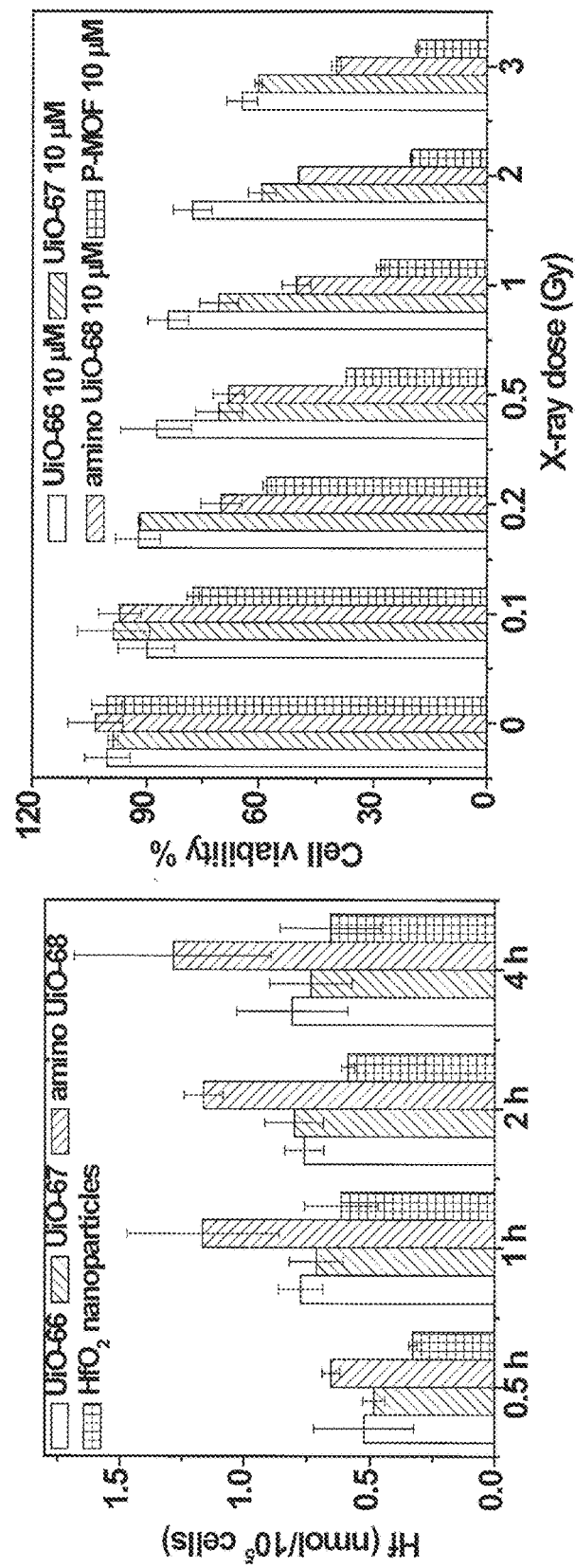
FIG. 16 is a pair of graphs showing (left) cellular uptake amounts of UiO-66 (open bars), UiO-67 (bars with lines going from bottom left to top right), amino UiO-68 (bars with lines going from top left to bottom right), and HfO₂ (bars with squares) nanoparticles in SQ20B head and neck cancer cells after 4 hour incubation, where the hafnium (Hf) concentrations were determined by inductively coupled plasma-mass spectrometry (ICP-MS); and (right) cytotoxicity of UiO-66 (open bars), UiO-67 (bars with lines going from bottom left to top right), amino UiO-68 (bars with lines going from top left to bottom right), and P-MOF (bars with squares) against SQ20B cells. The cells were incubated with NMOFs at a Hf concentration of 10 micromolar (μM) and treated with X-ray irradiation at different doses. The cell viability was determined by (3-(4,5-dimethylthiazol-2-yl)-5-(3-carboxymethoxyphenyl)-2-(4-sulfophenyl)-2H-tetrazolium) (MTS) assay.

Three NMOFs and $HfO_2$ nanoparticles can be efficiently taken up by the cells within the 4-h incubation period. The cellular uptake amounts of NMOFs and $HfO_2$ nanoparticles were in the order of amino UiO-68>UiO-67≈UiO-66≈$HfO_2$ nanoparticles. See FIG. 16, left panel.

9.3. In Vitro Radiosensitization

The cytotoxicity of the three Hf NMOFs and $HfO_2$ nanoparticles induced by X-ray irradiation was evaluated against SQ20B cells. The cells were incubated with UiO-66, UiO-67, amino UiO-68, or $HfO_2$ nanoparticles at different Hf concentrations for 4 h followed by X-ray irradiation at different doses. An X-ray beam with 225 kVp and 13 mA current was used for the irradiation. After irradiation, the cells were further incubated for 72 h before determining the cell viability by MTS assay.

Amino UiO-68 NMOF exhibited radiosensitization capability as evidenced by the efficient cancer cell killing (>50%) at an X-ray irradiation dose higher than 1 Gy. UiO-66, UiO-67, and $HfO_2$ nanoparticles showed modest radiosensitization characteristics. See FIG. 16, right panel. Without being bound to any one theory, it is believed that the higher cellular uptake, distinct thin plate-like morphology, and larger pores/channels of amino UiO-68 contributed to the preferable radiosensitization. However, P-MOF induced significantly higher cell killing than amino UiO-68 NMOF, suggesting other mechanisms besides radiosensitization can be involved in the efficient cancer cell killing process.

X-ray irradiation causes double-strand break (DSB) of DNA in the nucleus. H2AFX is a sensitive target for evaluating DSBs in the cells. The DSB caused by Ru-MOF upon irradiation and P-MOF upon LED light irradiation (630 nm) was investigated by H2AFX assay in SQ20B cells. For X-ray irradiation, SQ20B cells were incubated with Ru-MOF at a Hf concentration of 10 μM for 4 h followed by X-ray irradiation at 0, 0.1, 0.2, 0.5, and 1 Gy. SQ20B cells incubated with PBS with 1 Gy X-ray irradiation served as a control. For LED light irradiation, SQ20B cells were incubated with P-MOF at a Hf concentration of 10 μM for 4 h followed by LED light irradiation at a fluence rate of 100 mW/cm$^2$ for 30 min (180 J/cm$^2$). H2AFX assays were carried out immediately after X-ray or light irradiation. The nuclei were stained with DAPI. The cells were imaged with CLSM. Red fluorescence indicated the DSBs stained with antibody-labeled H2AFX. No DSB was observed for cells treated with Ru-MOF and 0.1 Gy X-ray irradiation. With the increase of X-ray dose, significant DSB in the nucleus was observed as low as 0.2 Gy. No DSB was observed in PBS treated cells with 1 Gy irradiation or P-MOF treated cells with LED light irradiation at 180 J/cm$^2$. Without being bound to any one theory, these results were taken to imply that DSB is involved in the cell killing of Ru-MOF induced by X-ray irradiation while conventional PDT at 180 J/cm$^2$ caused no DSB.

Example 10

X-ray Induced Photodynamic Therapy (X-PDT)

$^1O_2$ generation in live cells was detected by SOSG. Briefly, SQ20B cells were seeded in a petri dish and grown for 24 h. The medium was then replaced with fresh medium containing 1 μM SOSG to preload the cells with SOSG. After incubating for 30 min, the cells were washed by PBS three times to remove excess SOSG. The cells were incubated with PBS, P-MOF, or Ru-MOF at a Hf dose of 10 μM for 4 h followed by washing with PBS three times to remove excess NMOFs. X-ray irradiation was applied to cells at a dose of 1 Gy. CLSM was used to visualize the $^1O_2$ generated in the live cells by detecting the green fluorescence inside the cells (ex/em: 504/525 nm). Green fluorescence was not observed in cells treated with P-MOF or Ru-MOF without X-ray irradiation or treated with PBS and X-ray irradiation.

Green fluorescence was observed in the cells treated with P-MOF and X-ray irradiation or Ru-MOF and X-ray irradiation, suggesting that $^1O_2$ was generated by internalized NMOFs with X-ray irradiation.

Example 11

Biodistribution of NMOFs after Intratumoral Injection

Murine adenocarcinoma cells CT26 were subcutaneously injected to the right flank region of BALB/c mice (1 million cells/mouse). After the tumor size reached 100 mm$^3$, 50 μL of P-suspension was intratumorally injected to the mice at a Hf dose of 10 μmol/kg. Mice were sacrificed right after injection and 12 h post injection. Mice received X-ray irradiation at 2 Gy at the tumor site 12 h post injection and then sacrificed 36 h, 60 h, 84 h, 108 h, and 132 h post injection. For each group and time point, three mice were sacrificed. Blood, heart, liver, spleen, lung, kidney, and bladder were harvested for the determination of Hf concentrations by ICP-MS. The tumors were harvested and homogenized with saturated $K_3PO_4$. The DBP ligand was further extracted by DMSO followed by centrifugation. The supernatant was subjected to UV-Vis to determine the DBP ligand concentration in the tumors. The precipitate was lyophilized, digested by concentrated nitric acid, and subjected to ICP-MS to determine the Hf concentrations in the tumors.

Figure 17:
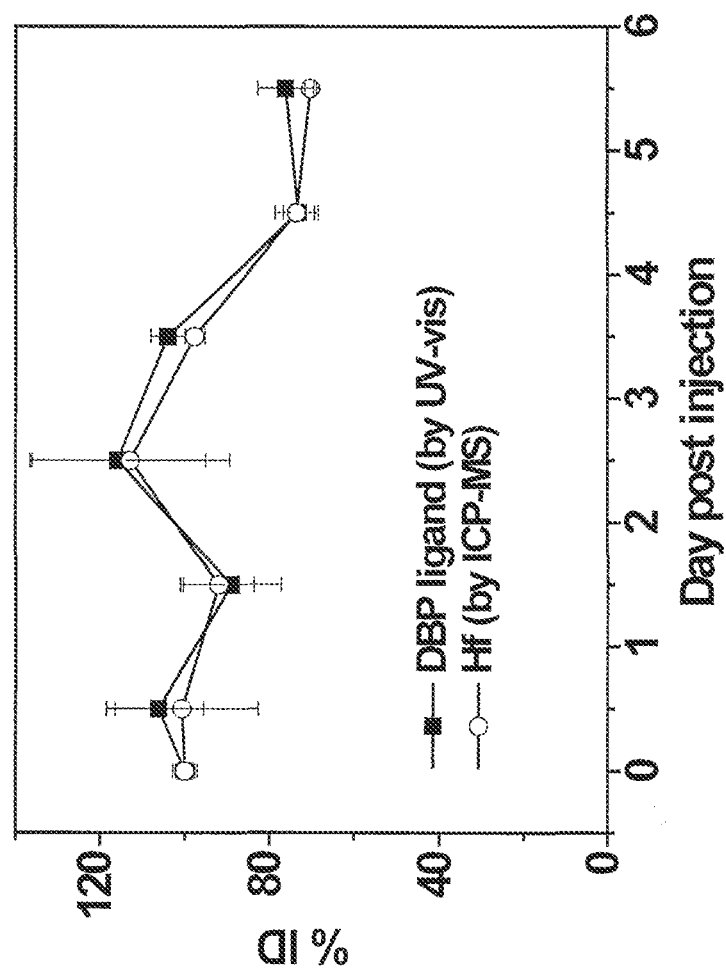
FIG. 17 is a graph showing the tumor retention of a di(p-benzoato)porphyrin metal-organic framework (P-MOF) in terms of hafnium (Hf; open circles) and di(p-benzoato)porphyrin (DBP) ligand (filled squares) after intratumoral injection to CT26 tumor bearing mice.
Figures 18A, 18B:
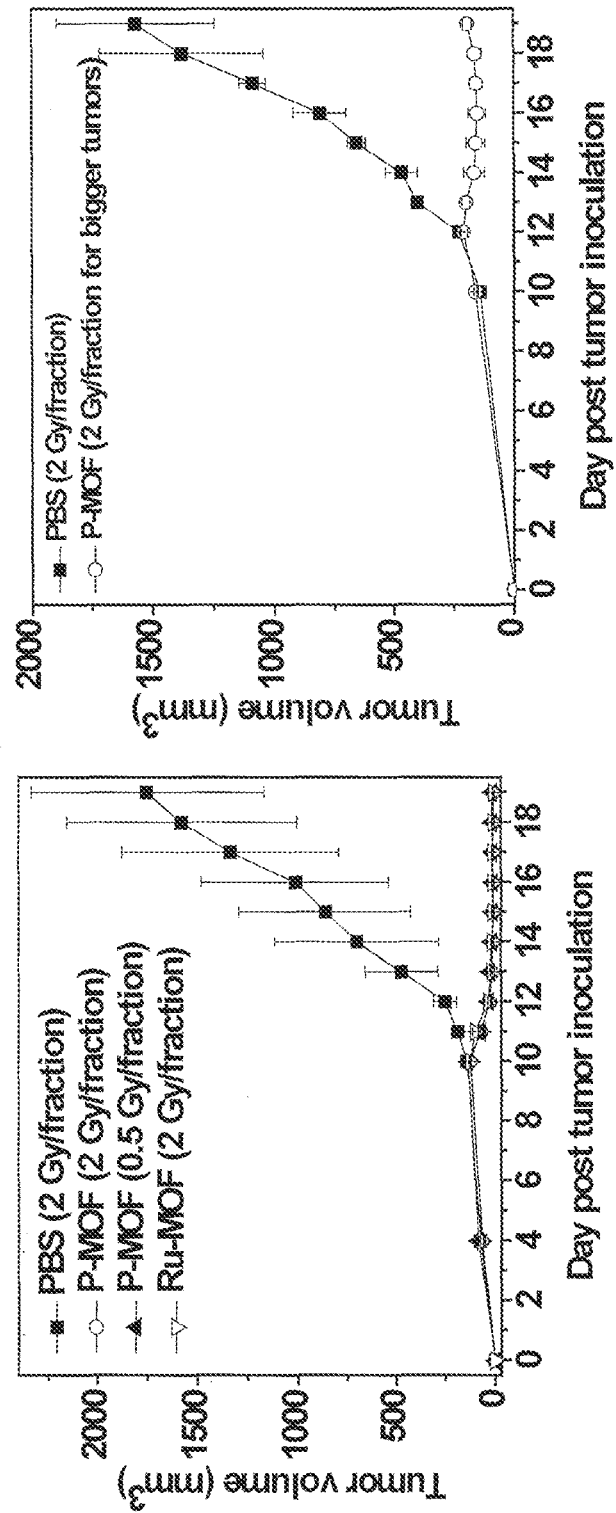
FIGS. 18A-18E are a set of graphs showing.
Figures 18C, 18D:
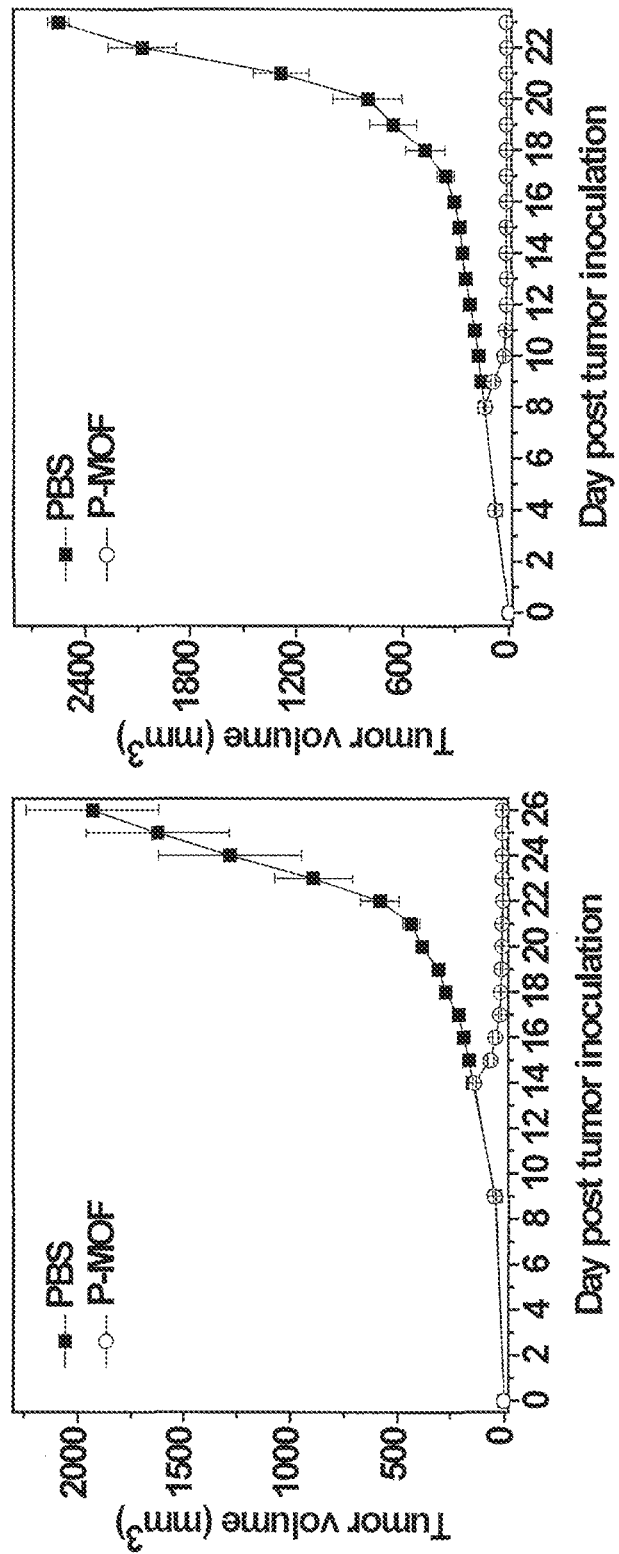
Figure 18E:
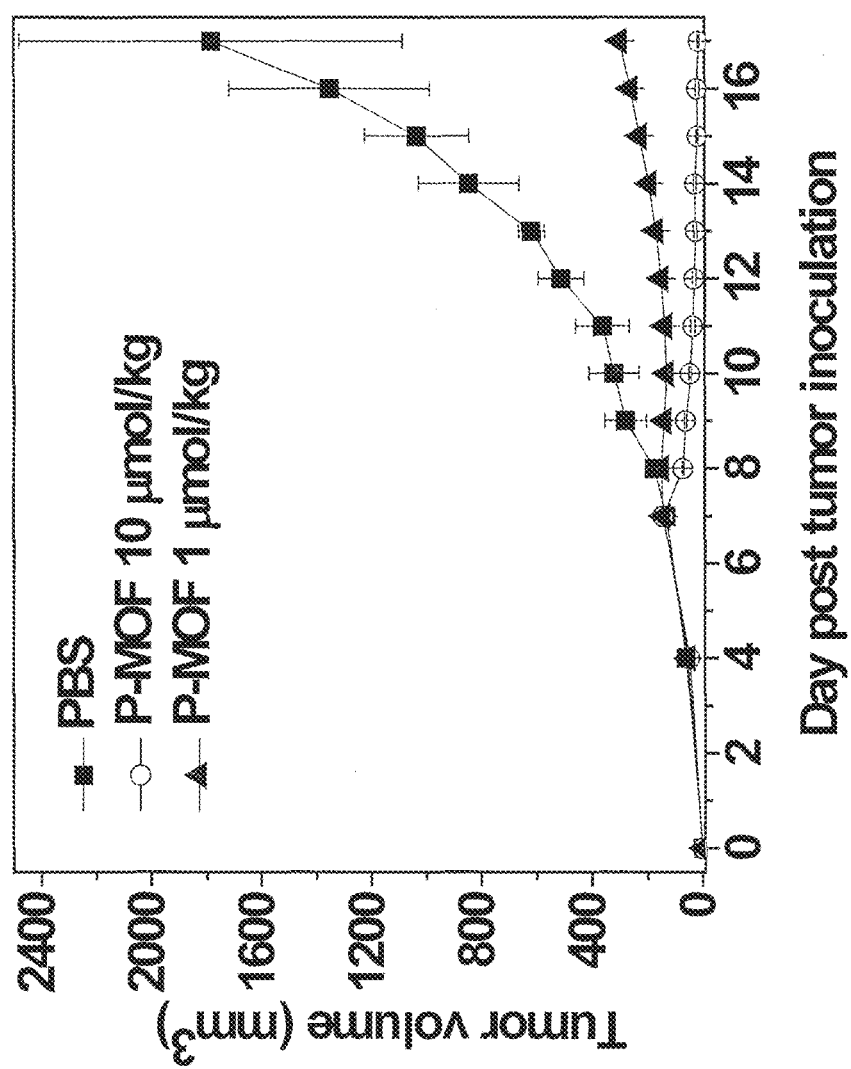

Negligible Hf was observed in blood, heart, liver, spleen, lung, kidney, and bladder over time. As shown in FIG. 17, the molar ratio of DBP ligand to Hf maintained constantly at ~1 over time, suggesting that P-MOF was intact 5.5 days post intratumoral injection. However, NMOF concentrations in the tumors decreased over time and showed a significant drop 4.5 day post injection with less than 75% ID remained in the tumors.

Example 12

In Vivo Anticancer Efficacy of X-ray Induced Therapy 12.1 In Vivo Anticancer Efficacy on Subcutaneous Xenograft of SQ20B Mouse Models Tumor bearing mice were established by subcutaneous inoculation of SQ20B cell suspension (5×10$^6$ cells per mouse) into the right flank region of 6-week athymic male nude mice. Four groups were included for comparison: (1) PBS+2 Gy/fraction for three fractions (2) P-MOF 10 μmol/kg+2 Gy/fraction for three fractions (3) Ru-MOF 10 μmol/kg+2 Gy/fraction for three fractions (4) P-MOF 10 μmol/kg+0.5 Gy/fraction for three fractions. When tumors reached 100 mm$^3$, P-MOF, Ru-MOF, or PBS was intratumorally injected at a Hf dose of 10 μmol/kg. In order to investigate if P-MOF can lead to tumor inhibition in bigger tumors, P-MOF was intratumorally injected at a Hf dose of 10 μmol/kg when tumors reached 250 mm$^3$. Twelve hour post-injection, mice were anesthetized with 2% (v/v) isoflurane and tumors were irradiated with image-guided X-ray at 225 kVp and 13 mA. The NMOFs were injected once followed by three daily X-ray irradiations. To evaluate the therapeutic efficacy, tumor growth and bodyweight evolution were monitored. The tumor size was measured with a digital caliper every day. Tumor volumes were calculated as follows: (width$^2$×length)/2. All mice were sacrificed on Day 19 post tumor inoculation.

NMOFs led to successful tumor regression at extremely low X-ray doses without causing significant toxicity as evidenced by the unappreciable difference in body weight evolution and histology of major organs compared to control group. See FIGS. 18A-18E. For the study that started with 100 mm$^3$ tumors, the tumor weights in NMOF groups were 53~65-fold lower than the control group.

12.2. In Vivo Anticancer Efficacy on Subcutaneous Xenograft of U87 Mouse Models

Tumor bearing mice were established by subcutaneous inoculation of U87 cell suspension (5×10$^6$ cells per mouse) into the right flank region of 6-week athymic male nude mice. Two groups were included for comparison: (1) PBS+ 0.5 Gy (2) P-MOF 10 μmol/kg+0.5 Gy. When tumors reached 100 mm$^3$, P-MOF or PBS was intratumorally injected at a Hf dose of 10 μmol/kg. Twelve hour post-injection, mice were anesthetized with 2% (v/v) isoflurane and tumors were irradiated with image-guided X-ray at 225 kVp and 13 mA. The NMOFs were injected once followed by single X-ray irradiations. To evaluate the therapeutic efficacy, tumor growth and bodyweight evolution were monitored. The tumor size was measured with a digital caliper every day. Tumor volumes were calculated as follows: (width$^2$×length)/2. All mice were sacrificed on Day 26 post tumor inoculation.

Single NMOF injection and single X-ray irradiation at extremely low dose (0.5 Gy) led to successful tumor regression. See FIGS. 18A-18E. The tumor weights in NMOF groups were 51-fold lower than the control group.

12.3. In Vivo Anticancer Efficacy on Subcutaneous Xenograft of PC-3 Mouse Models Tumor bearing mice were established by subcutaneous inoculation of SQ20B cell suspension (5×10$^6$ cells per mouse) into the right flank region of 6-week athymic male nude mice. Four groups were included for comparison: (1) PBS+2 Gy/fraction for three fractions (2) P-MOF 10 μmol/kg+0.5 Gy/fraction for three fractions. When tumors reached 100 mm$^3$, P-MOF, Ru-MOF, or PBS was intratumorally injected at a Hf dose of 10 µmol/kg. Twelve hour post-injection, mice were anesthetized with 2% (v/v) isoflurane and tumors were irradiated with image-guided X-ray at 225 kVp and 13 mA. The NMOFs were injected once followed by three daily X-ray irradiations. To evaluate the therapeutic efficacy, tumor growth and bodyweight evolution were monitored. The tumor size was measured with a digital caliper every day. Tumor volumes were calculated as follows: (width$^2$×length)/2. All mice were sacrificed on Day 19 post tumor inoculation.

NMOFs led to successful tumor regression at extremely low X-ray doses without causing significant toxicity as evidenced by the unappreciable difference in body weight evolution compared to control group. See FIGS. 18A-18E.

12.4. Anticancer Effect on Subcutaneous CT26 Mouse Models

Tumor bearing mice were established by subcutaneous inoculation of CT26 cell suspension (2×10$^6$ cells per mouse) into the right flank region of 6-week male BALB/c mice. Three groups were included for comparison: (1) PBS+0.5 Gy/fraction for three fractions (2) P-MOF 10 µmol/kg+0.5 Gy/fraction for three fractions (3) P-MOF 1 µmol/kg+0.5 Gy/fraction for three fractions. When tumors reached 150 mm$^3$, P-MOF, or PBS was intratumorally injected at a Hf dose of 10 µmol/kg or 1 µmol/kg. Twelve hour post-injection, mice were anesthetized with 2% (v/v) isoflurane and tumors were irradiated with image-guided X-ray at 225 kVp and 13 mA. The NMOFs were injected once followed by three daily X-ray irradiations. To evaluate the therapeutic efficacy, tumor growth and bodyweight evolution were monitored. The tumor size was measured with a digital caliper every day. Tumor volumes were calculated as follows: (width$^2$×length)/2. All mice were sacrificed on Day 19 post tumor inoculation.

NMOFs injected at a dose of 10 µmol/kg led to successful tumor regression at extremely low X-ray doses without causing significant toxicity as evidenced by the unappreciable difference in body weight evolution compared to control group. See FIGS. 18A-18E. NMOFs injected at a dose of 1 µmol/kg also led to successful tumor inhibition at extremely low X-ray doses.

Example 13

In Vivo Anticancer Efficacy and Abscopal Effect of NMOFs in Combination with Immunotherapy 13.1. Synthesis and Characterization of P-MOF/INCB24360

To a 2-dram glass vial was added 2.28 mg of INCB24360 (8.4 µmol) that was obtained from MedKoo Biosciences (Chapel Hill, N.C., United States of America) and 1.0 mL of P-MOF suspension (2.0 mg/mL in ethanol). After dissolution of INCB24360 with help of sonication, 1.0 mL of water was added. The mixture was stirred in dark for 12 hours. The loaded MOF was collected by centrifugation and was washed by 50% ethanol (v/v) and water.

Thermogravimetric analysis (TGA) was carried out on P-MOF samples before and after INCB24360 loading on Shimadzu TGA-50 thermogravimetric analyzer (Shimadzu Corporation, Kyoto, Japan). Heating speed was set to 3° C./min and the sample was heated to 700° C. in air. The weight percentage was plotted against temperature. Pure INCB24360 has a weight loss of ~90% at ~200° C. The drug loading was calculated to be 9.4% by weight following the equation below:

$$\text{loading wt \%} = \left(1 - \frac{\text{remaining wt \% after loading}}{\text{remaining wt \% before loading}}\right) * 100\%$$

13.2. Anticancer and Abscopal Effect on Subcutaneous CT26 and TUBO Mouse Models

The anticancer efficacy and abscopal effect of NMOFs in combination with IDO inhibitor (INCB24360) was evaluated against two immunocompetent mouse models including CT26 and TUBO flank tumor bearing BALB/c mice. Tumor bearing mice were established by subcutaneous inoculation of CT26 or TUBO cell suspension (2×10$^6$ cells per mouse) into the right flank region and CT26 or TUBO cell suspension (4×10$^5$ cells per mouse) into the left flank region of the same mouse. Two or three groups were included for comparison: (1) PBS+0.5 Gy (2) P-MOF 10 µmol/kg+0.5 Gy (3) P-MOF/INCB224360 10 µmol/kg+0.5 Gy. When tumors reached ~100 mm$^3$, P-MOF, P-MOF/INCB24360 or PBS was intratumorally injected at a Hf dose of 7 µmol/kg equivalent to INCB24360 dose of 2 µmol/kg. Twelve hour post-injection, mice were anesthetized with 2% (v/v) isoflurane and tumors were irradiated with image-guided X-ray at 225 kVp and 13 mA. The NMOFs were injected once followed by daily X-ray irradiations on three consecutive days. To evaluate the therapeutic efficacy, tumor growth and bodyweight evolution were monitored. The tumor size was measured with a digital caliper every day. Tumor volumes were calculated as follows: (width$^2$×length)/2.

Figure 19:
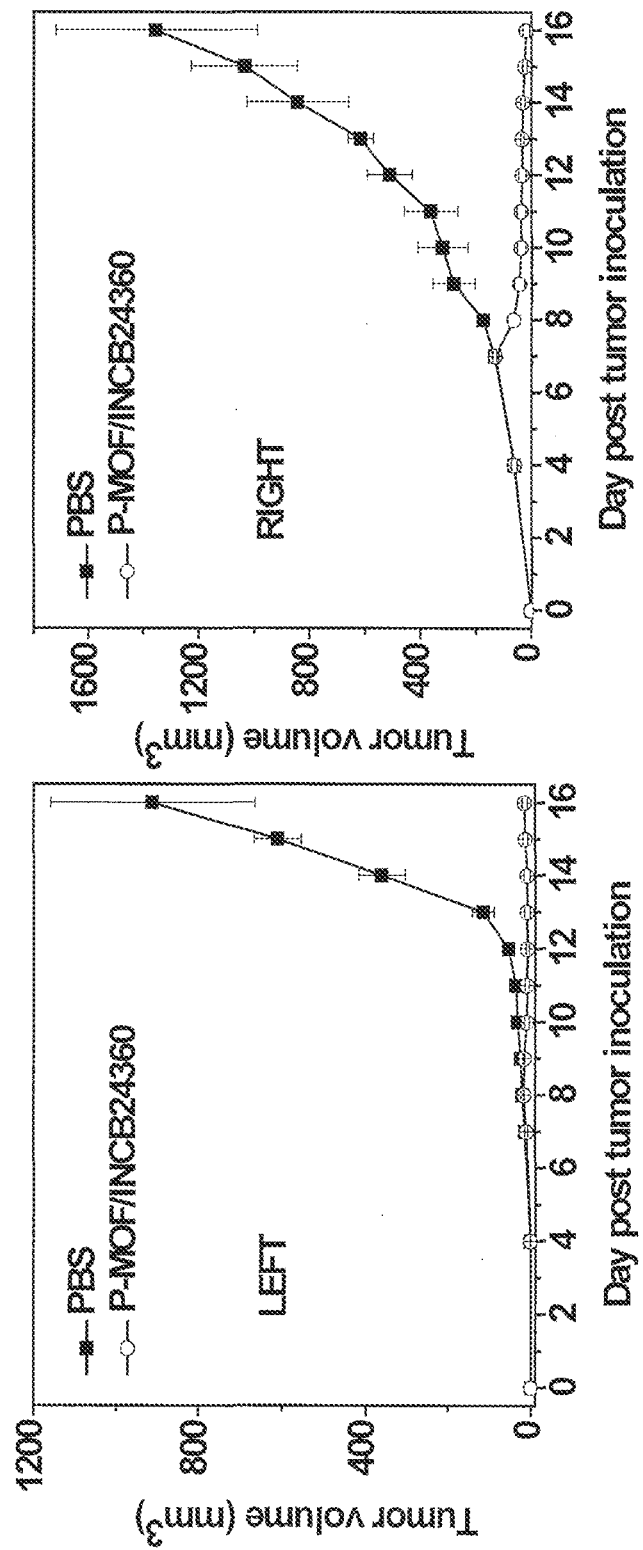
FIG. 19 is a pair of graphs showing the tumor growth curves of CT26 tumor bearing mice treated with phosphate buffered saline (PBS; squares) or a di(p-benzoato)porphyrin metal-organic framework (P-MOF) and an IDO1 inhibitor immunotherapy agent (INCB24360) (P-MOF/INCB24360; open circles) at a ligand dose of 7 micromoles per kilogram (μmol/kg) and X-ray irradiation. The treatments started when the tumors reached ~100 cubic millimeters ($mm^3$). The X-ray irradiation (0.5 Gy/fraction) was carried out on mice 12 hours (h) post the intratumoral injection of PBS or nanoscale metal-organic frameworks (NMOFs) on three consecutive days. The growth curves in the graph on the right side is for the treated tumor (right side of mouse), while the growth curves in the graph on the left side is for the untreated, distant tumor on the left side of the mouse.
Figure 20:
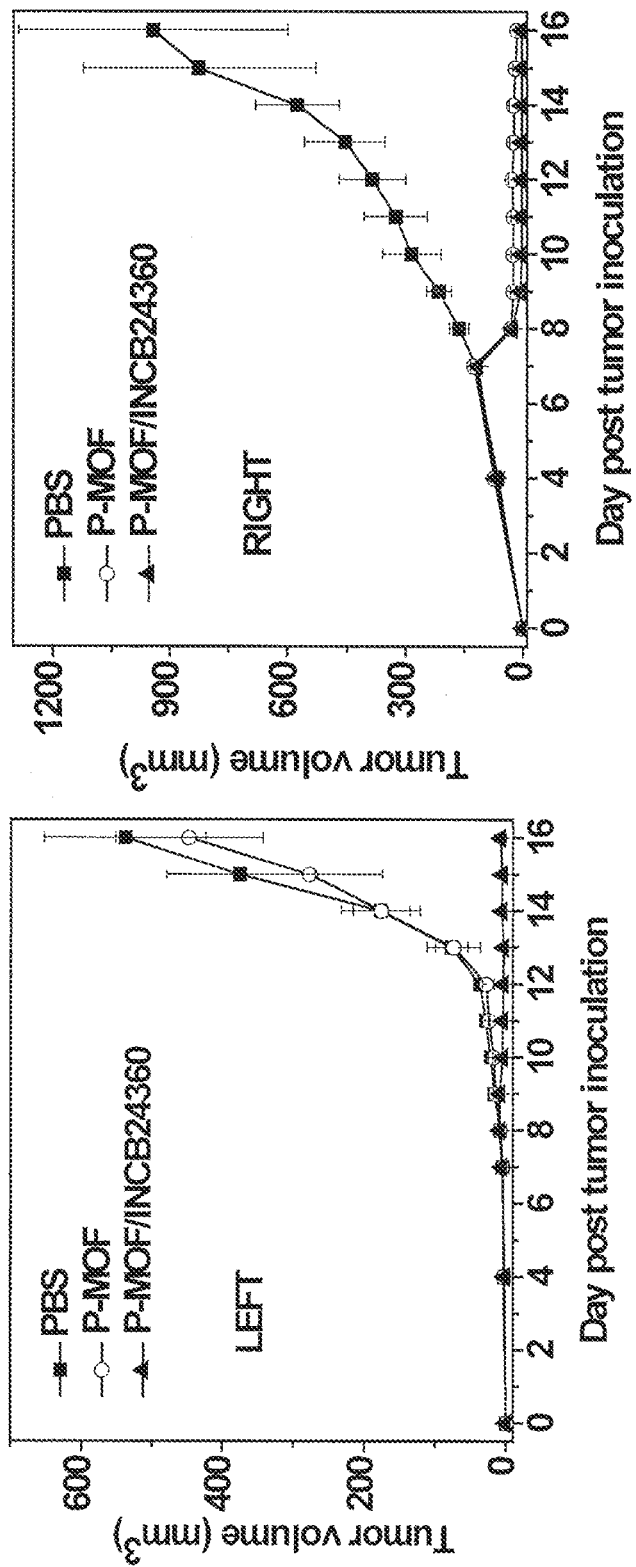
FIG. 20 is a pair of graphs showing the tumor growth curves of TUBO tumor bearing mice treated with phosphate buffered saline (PBS; filled squares), a di(p-benzoato)porphyrin metal-organic framework (P-MOF; open circles), or P-MOF and IDO1 inhibitor immunotherapy agent INCB24360 (P-MOF/INCB24360; filled triangles) at a ligand dose of 7 micromoles per kilogram (μmol/kg) and X-ray irradiation. The treatments started when the tumors reached ~100 cubic millimeters ($mm^3$). The X-ray irradiation (0.5 Gy/fraction) was carried out on mice 12 hours (h) post the intratumoral injection of PBS or nanoscale metal-organic frameworks (NMOFs) on three consecutive days. The growth curves in the graph on the right side is for the treated tumor (right side of mouse), while the growth curves in the graph on the left side is for the untreated, distant tumor on the left side of the mouse.

Local injection of P-MOF/INCB24360 plus X-ray irradiation at low X-ray dose not only led to the tumor regression on the treated right tumors but also shrank the distant left tumors, suggesting the combination therapy successfully evoked immunoresponse in immunocompetent mouse models of both colon and breast cancer. See FIGS. 19 and 20.

13.3. Anticancer and Abscopal Effect on Subcutaneous TRAMP-C2 Mouse Models

The anticancer efficacy and abscopal effect of NMOFs in combination with IDO inhibitor (INCB24360) was evaluated against subcutaneous TRAMP-C2 tumor bearing C57BL/6 mice. Tumor bearing mice were established by subcutaneous inoculation of TRAMP-C2 cell suspension (5×10$^6$ cells per mouse) into the right flank region and TRAMP-C2 cell suspension (1×10$^6$ cells per mouse) into the left flank region of the same mouse. Three groups were included for comparison: (1) PBS+0.5 Gy (2) P-MOF 3.5 µmol/kg+0.5 Gy (3) P-MOF/INCB224360 3.5 µmol/kg+0.5 Gy. When tumors reached ~200 mm$^3$, P-MOF, P-MOF/INCB24360 or PBS was intratumorally injected at a Hf dose of 3.5 µmol/kg equivalent to INCB24360 dose of 1 µmol/kg. Twelve hour post-injection, mice were anesthetized with 2% (v/v) isoflurane and tumors were irradiated with image-guided X-ray at 225 kVp and 13 mA. The NMOFs were injected every other day for a total three injections. X-ray irradiation was performed daily on six consecutive days. To evaluate the therapeutic efficacy, tumor growth and bodyweight evolution were monitored. The tumor size was measured with a digital caliper every day. Tumor volumes were calculated as follows: (width$^2$×length)/2.

Figure 21:
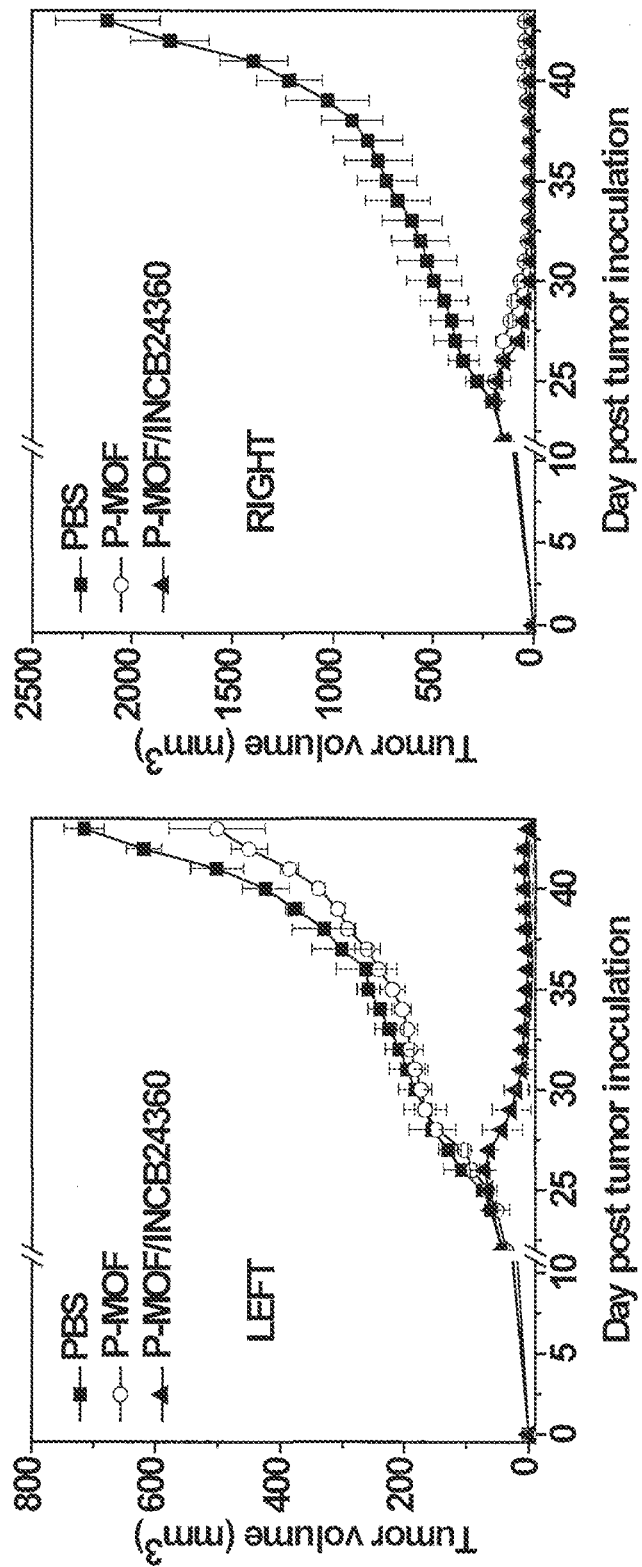
FIG. 21 is a pair of graphs showing the tumor growth curves of TRAMP-C2 tumor bearing mice treated with phosphate buffered saline (PBS), a di(p-benzoato)porphyrin metal-organic framework (P-MOF; open circles), or P-MOF and IDO1 inhibitor immunotherapy agent INCB24360 (P-MOF/INCB24360; filled triangles) at a ligand dose of 3.5 micromoles per kilogram (μmol/kg) and X-ray irradiation. The treatments started when the tumors reached 200 cubic millimeters ($mm^3$). The growth curves in the graph on the right side is for the treated tumor (right side of mouse), while the growth curves in the graph on the left side is for the untreated, distant tumor on the left side of the mouse.

Local injection of P-MOF/INCB24360 plus X-ray irradiation at low X-ray dose not only led to complete tumor eradication of the treated right tumors but also completely eradicated the distant left tumors, suggesting the combination therapy successfully evoked immunoresponse in immunocompetent mouse models of prostate cancer. See FIG. 21.

13.4. Anticancer and Abscopal Effect on Subcutaneous MC38 Mouse Models

The anticancer efficacy and abscopal effect of NMOFs in combination with IDO inhibitor (INCB24360) was evaluated against subcutaneous MC38 tumor bearing C57BL/6 mice. Tumor bearing mice were established by subcutaneous inoculation of MC38 cell suspension ($2\times10^6$ cells per mouse) into the right flank region and MC38 cell suspension ($4\times10^5$ cells per mouse) into the left flank region of the same mouse. Three groups were included for comparison: (1) PBS+0.5 Gy (2) P-MOF 3.5 µmol/kg+0.5 Gy (3) P-MOF/INCB224360 3.5 µmol/kg+0.5 Gy. When tumors reached ~250 mm³, P-MOF, P-MOF/INCB224360 or PBS was intratumorally injected at a Hf dose of 3.5 µmol/kg equivalent to INCB24360 dose of 1 µmol/kg. Twelve hour post-injection, mice were anesthetized with 2% (v/v) isoflurane and tumors were irradiated with image-guided X-ray at 225 kVp and 13 mA. The NMOFs were injected every other day for a total three injections. X-ray irradiation was performed daily on six consecutive days. To evaluate the therapeutic efficacy, tumor growth and bodyweight evolution were monitored. The tumor size was measured with a digital caliper every day. Tumor volumes were calculated as follows: (width²×length)/2.

Figure 22:
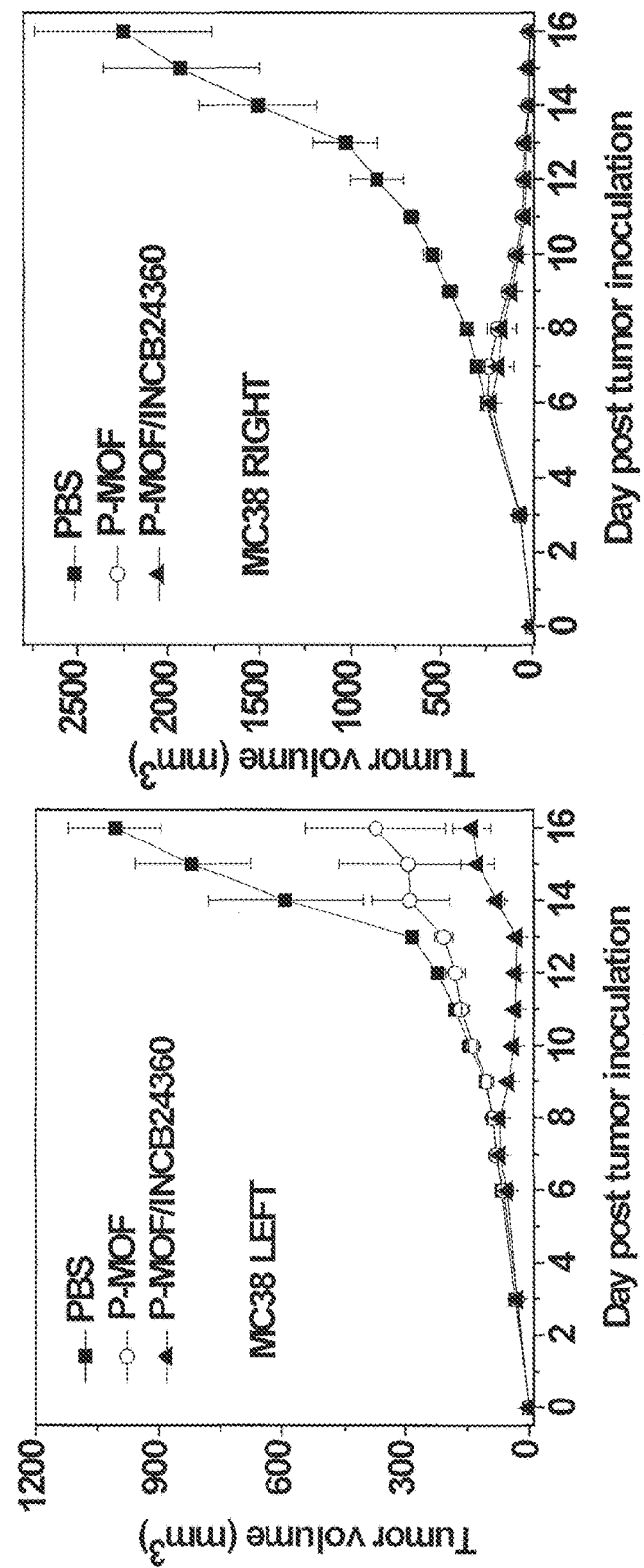
FIG. 22 is a pair of graphs showing the tumor growth curves of MC38 tumor bearing mice treated with phosphate buffered saline (PBS; filled squares), a di(p-benzoato)porphyrin metal-organic framework (P-MOF open circles), or P-MOF and IDO1 inhibitor immunotherapy agent INCB24360 (P-MOF/INCB24360; filled triangles) at a ligand dose of 3.5 micromoles per kilogram (μmol/kg) and X-ray irradiation. The treatments started when the tumors reached 250 cubic millimeters ($mm^3$). The growth curves in the graph on the right side is for the treated tumor (right side of mouse), while the growth curves in the graph on the left side is for the untreated, distant tumor on the left side of the mouse.

Local injection of P-MOF/INCB24360 plus X-ray irradiation at low X-ray dose not only led to tumor regression/eradication of the treated right tumors (two out of three tumors were eradicated), but also shrank the distant left tumors, suggesting the combination therapy successfully evoked immunoresponse in immunocompetent mouse models of colon cancer. See FIG. 22.

13.5. Anticancer and Abscopal Effect on Subcutaneous GL261 Mouse Models

The anticancer efficacy and abscopal effect of NMOFs in combination with IDO inhibitor (INCB24360) was evaluated against subcutaneous GL261 tumor bearing C57BL/6 mice. Tumor bearing mice were established by subcutaneous inoculation of GL261 cell suspension ($2\times10^6$ cells per mouse) into the right flank region and GL261 cell suspension ($4\times10^5$ cells per mouse) into the left flank region of the same mouse. Three groups were included for comparison: (1) PBS+0.5 Gy (2) P-MOF 3.5 µmol/kg+0.5 Gy (3) P-MOF/INCB224360 3.5 µmol/kg+0.5 Gy. When tumors reached ~200 mm³, P-MOF, P-MOF/INCB224360 or PBS was intratumorally injected at a Hf dose of 3.5 µmol/kg equivalent to INCB24360 dose of 1 µmol/kg. Twelve hour post-injection, mice were anesthetized with 2% (v/v) isoflurane and tumors were irradiated with image-guided X-ray at 225 kVp and 13 mA. The NMOFs were injected every other day for a total three injections. X-ray irradiation was performed daily on six consecutive days. To evaluate the therapeutic efficacy, tumor growth and bodyweight evolution were monitored. The tumor size was measured with a digital caliper every day. Tumor volumes were calculated as follows: (width²×length)/2.

Figure 23:
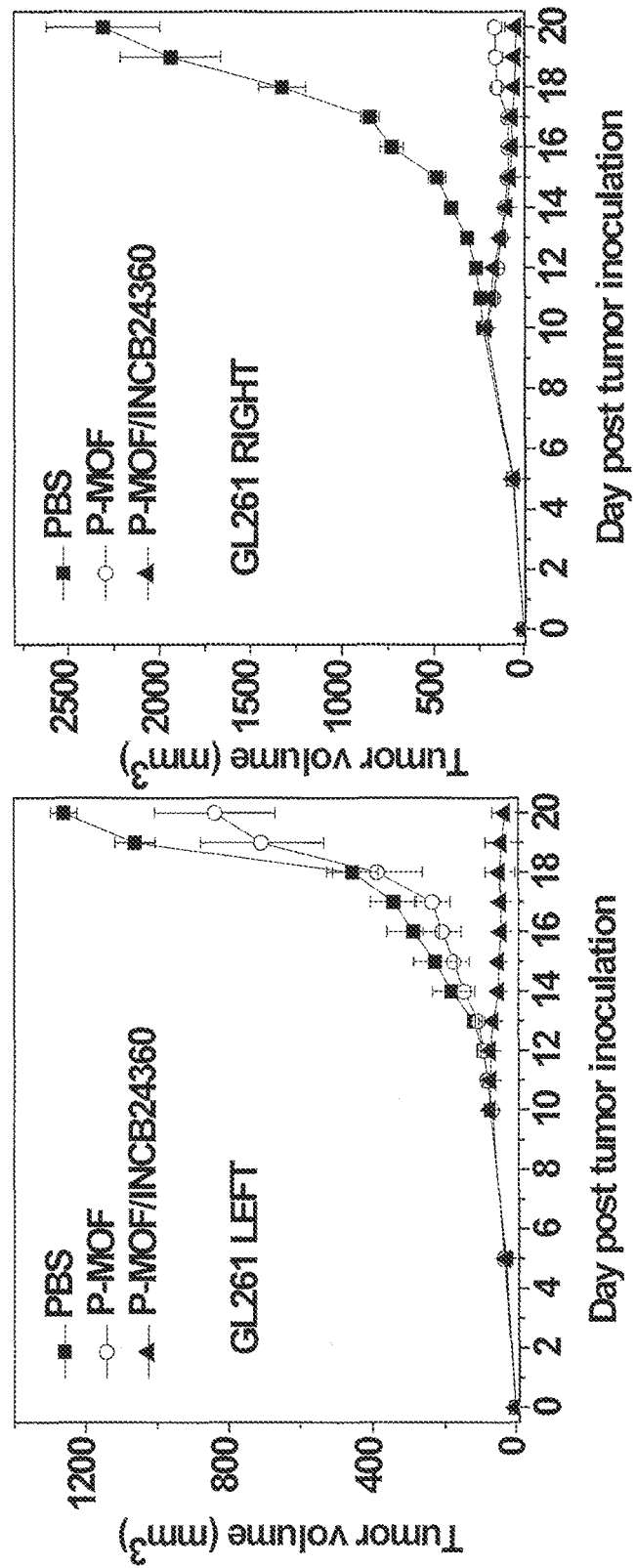
FIG. 23 is a pair of graphs showing the tumor growth curves of MC38 tumor bearing mice treated with phosphate buffered saline (PBS; filled squares), a di(p-benzoato)porphyrin (P-MOF; open circles), or P-MOF and IDO1 inhibitor immunotherapy agent INCB24360 (P-MOF/INCB24360; filled triangles) at a ligand dose of 3.5 micromoles per kilogram (μmol/kg) and X-ray irradiation. The treatments started when the tumors reached 200 cubic millimeters ($mm^3$). The growth curves in the graph on the right side is for the treated tumor (right side of mouse), while the growth curves in the graph on the left side is for the untreated, distant tumor on the left side of the mouse.

Local injection of P-MOF/INCB24360 plus X-ray irradiation at low X-ray dose not only led to tumor regression/eradication of the treated right tumors (two out of three tumors were eradicated), but also shrank/eradicated the distant left tumors (two out of three tumors were eradicated), suggesting the combination therapy successfully evoked immunoresponse in immunocompetent mouse models of glioblastoma cancer. See FIG. 23.

13.6. Anticancer and Abscopal Effect on Subcutaneous TUBO Mouse Models by Combination Therapy of P-MOF/INCB24360 and PD-L1 Antibody The anticancer efficacy and abscopal effect of NMOFs in combination with IDO inhibitor (INCB24360) and PD-L1 antibody was evaluated against subcutaneous TUBO tumor bearing BALB/c mice. Tumor bearing mice were established by subcutaneous inoculation of TUBO cell suspension ($2\times10^6$ cells per mouse) into the right flank region and TUBO cell suspension ($4\times10^5$ cells per mouse) into the left flank region of the same mouse. Three groups were included for comparison: (1) PBS+0.5 Gy (2) P-MOF 3.5 µmol/kg+0.5 Gy+PD-L1 antibody (3) P-MOF/INCB224360 3.5 µmol/kg+0.5 Gy+PD-L1 antibody. When tumors reached ~200 mm³, P-MOF, P-MOF/INCB224360 or PBS was intratumorally injected at a Hf dose of 3.5 µmol/kg equivalent to INCB24360 dose of 1 µmol/kg. Twelve hour post-injection, mice were anesthetized with 2% (v/v) isoflurane and tumors were irradiated with image-guided X-ray at 225 kVp and 13 mA. Twelve hours after X-ray irradiation, 200 µg of PD-L1 antibody was intraperitoneally injected to each mouse in group (2) and (3). The NMOFs and PD-L1 antibody were injected every other day for a total three injections. X-ray irradiation was performed daily on six consecutive days. To evaluate the therapeutic efficacy, tumor growth and bodyweight evolution were monitored. The tumor size was measured with a digital caliper every day. Tumor volumes were calculated as follows: (width²×length)/2.

Figure 24:
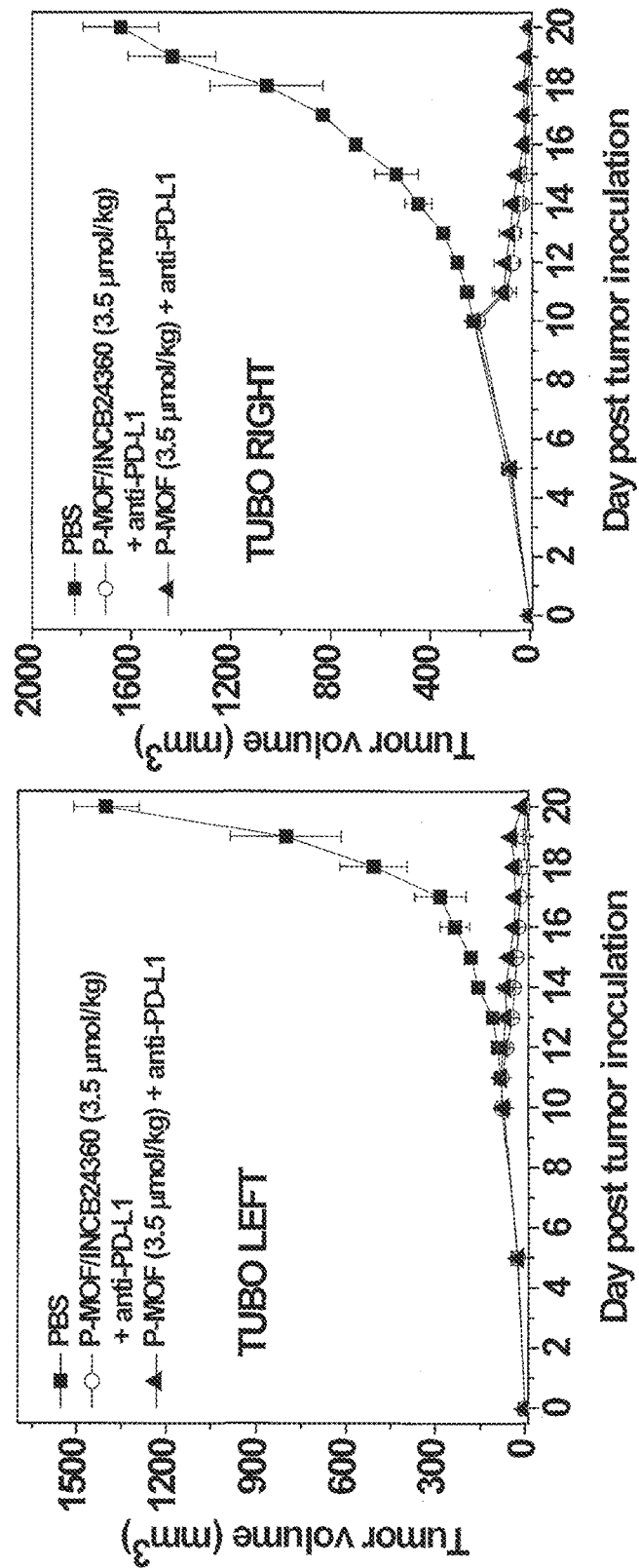
FIG. 24 is a pair of graphs showing the tumor growth curves of TUBO tumor bearing mice treated with phosphate buffered saline (PBS; filled squares), a di(p-benzoato)porphyrin metal-organic framework (P-MOF; open circles), or P-MOF and IDO1 inhibitor immunotherapy agent INCB24360 (P-MOF/INCB24360; filled triangles) at a ligand dose of 3.5 micromoles per kilogram (μmol/kg), X-ray irradiation, and PD-L1 antibody (intraperitoneal (i.p.) injection). The treatments started when the tumors reached 200 cubic millimeters ($mm^3$). The growth curves in the graph on the right side is for the treated tumor (right side of mouse), while the growth curves in the graph on the left side is for the untreated, distant tumor on the left side of the mouse.
Figures 25A, 25B:
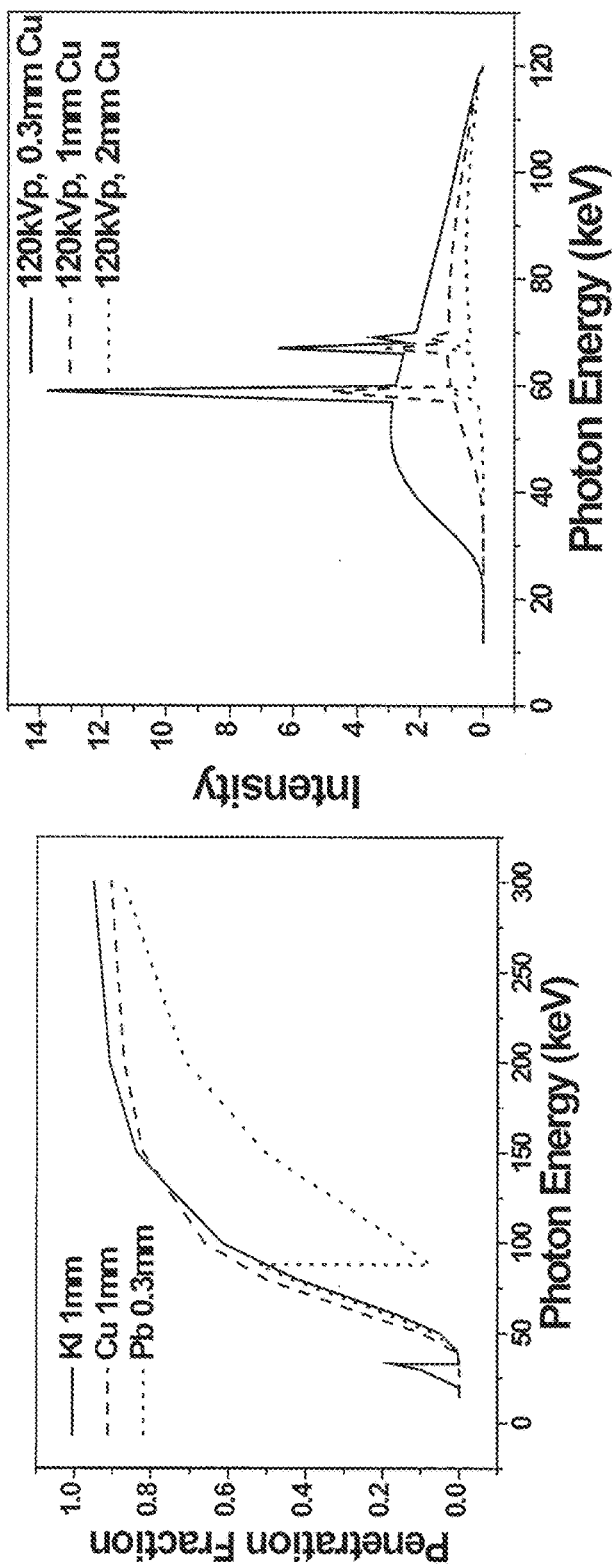
FIGS. 25A-25F are a set of graphs showing.
Figures 25C, 25D:
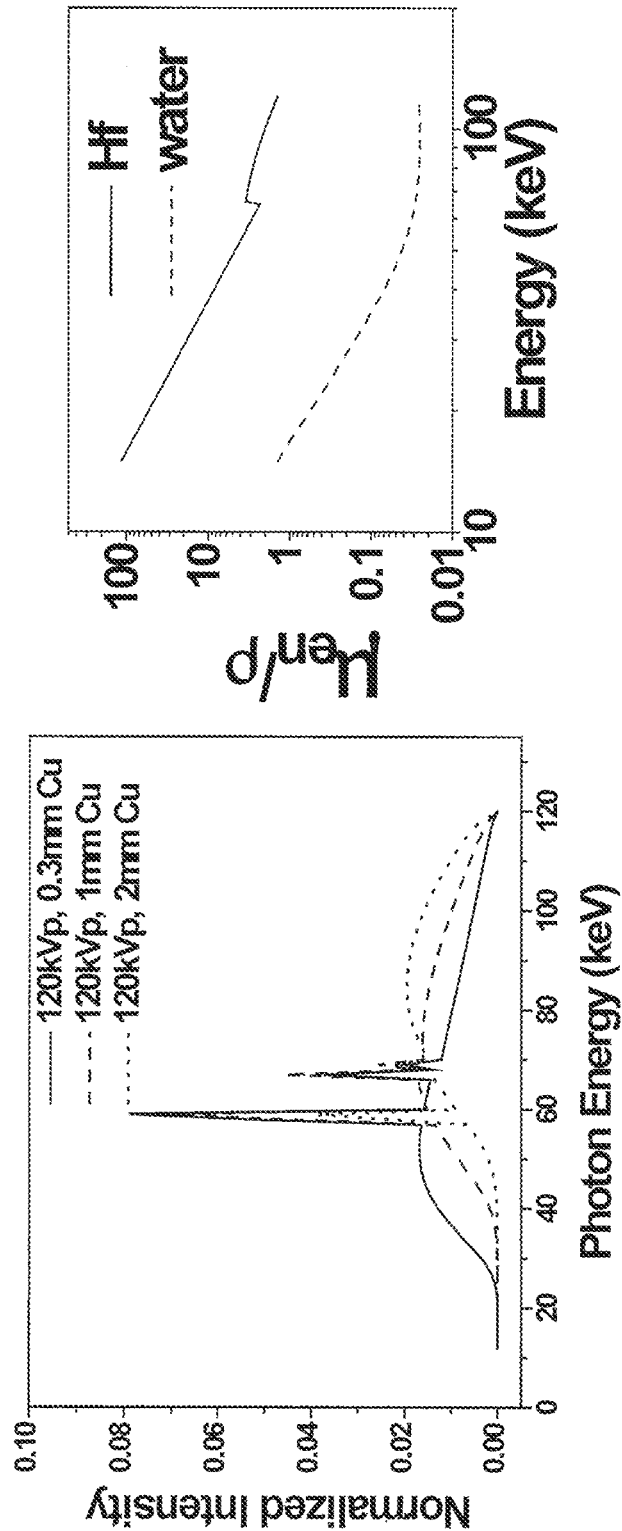
Figure 25F:
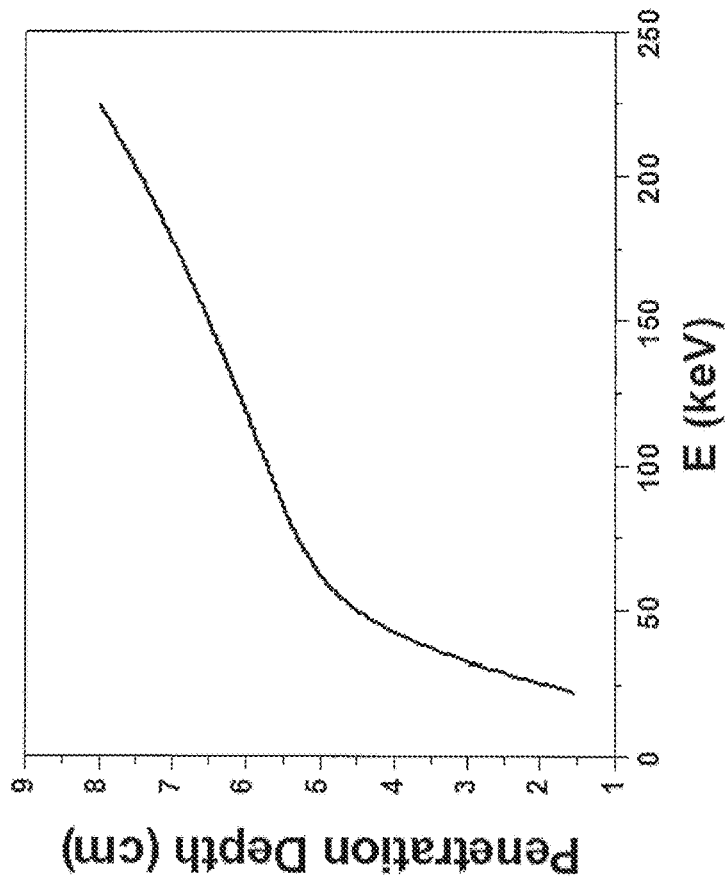
Figure 25E:
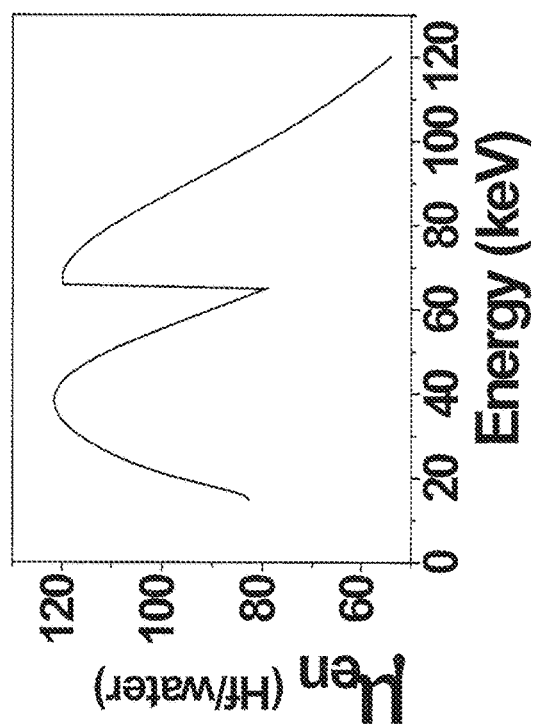

Local injection of P-MOF/INCB24360 plus X-ray irradiation plus PD-L1 antibody dose not only led to complete eradication of the treated right tumors, but also completely eradicated the distant left tumors, suggesting the combination therapy successfully evoked immunoresponse in immunocompetent mouse models of breast cancer. Local injection of P-MOF plus X-ray irradiation plus PD-L1 antibody also led to complete tumor eradication of the treated right tumors and tumor eradication/regression of the distant left tumors (one out of three tumors were eradicated). See FIG. 24.

Example 14

Pegylation of P-MOF

P-MOF (1 mg/mL) in ethanol was mixed with DSPE-PEG2000 (5 mg/mL) in THF at NMOF:DSPE-PEG2000 weight ratio of 1:1, 1:2, 1:5, and 1:10, respectively. The suspension was concentrated by blowing nitrogen to 50 µL and then vortexed for 1 min. One milliliter of water was added to this suspension. The mixture was vortexed for 1 min and sonicated for 5 min to yield PEGylated P-MOF.

The particle sizes and polydispersity index (PDI) of PEGylated P-MOF were determined by dynamic light scattering (DLS) measurements. Table 6 summarizes the Z-average, Number-average, and PDI of PEGylated P-MOF formulated with different weight ratios of NMOF:DSPE-PEG2000. The particle sizes and PDI of P-MOF dispersed in ethanol and water at a concentration of 50 µg/mL were determined as comparisons.

TABLE 6

Z-average, Number-average, and PDI of P-MOF dispersed in ethanol and water and PEGylated P-MOF dispersed in water.

|  | Z-average (nm) | Number-average (nm) | PDI |
|---|---|---|---|
| P-MOF in ethanol | 113.5 | 58.09 | 0.260 |
| P-MOF in water | n.d. | n.d. | 1.000 |
| PEGylated P-MOF (1:1)$^a$ | 148.6 | 112.4 | 0.136 |
| PEGylated P-MOF (1:2)$^a$ | 136.6 | 103.0 | 0.123 |

TABLE 6-continued

Z-average, Number-average, and PDI of P-MOF dispersed in ethanol and water and PEGylated P-MOF dispersed in water.

|  | Z-average (nm) | Number-average (nm) | PDI |
|---|---|---|---|
| PEGylated P-MOF (1:5)[a] | 150.5 | 103.7 | 0.146 |
| PEGylated P-MOF (1:10)[a] | 140.7 | 99.90 | 0.112 |

[a]weight ratio of NMOF to DSPE-PEG2000.

The stability of PEGylation of P-MOF was further evaluated in phosphate buffered solution (PBS). PEGylated P-MOF (50 μg) was centrifuged at 13000 rpm for 15 min. The precipitate was dispersed in 1 mL of PBS followed by sonication for 5 min. The particle sizes and PDI of PEGylated P-MOF in PBS were determined by DLS measurements. As shown in Table 7, the particle sizes of PEGylated P-MOF further decreased after being dispersed in PBS compared to those determined in water, indicating the colloidal stability and the strong interactions between P-MOF and DSPE-PEG. Thus, surface modified NMOFs can have better biocompatibility and blood circulation properties. In some embodiments, they can be administered via systemic injection.

TABLE 7

Z-average, Number-average, and PDI of PEGylated P-MOF dispersed in PBS.

|  | Z-average (nm) | Number-average (nm) | PDI |
|---|---|---|---|
| PEGylated P-MOF (1:1)[a] | 111.0 | 75.19 | 0.148 |
| PEGylated P-MOF (1:2)[a] | 103.8 | 68.47 | 0.109 |
| PEGylated P-MOF (1:5)[a] | 107.1 | 74.65 | 0.094 |
| PEGylated P-MOF (1:10)[a] | 105.9 | 70.47 | 0.105 |

[a]weight ratio of NMOF to DSPE-PEG2000.

Example 15

Refinement of X-ray Set-ups for X-ray Induced Photodynamic Therapy in the Treatment of Superficial Cancers 15.1. In Vivo Anticancer Efficacy of P-MOF on Subcutaneous CT26 Tumor Bearing Mouse Models Using Different X-ray Set-ups.

FIGS. 25A-25F show graphs of: (FIG. 25A) calculated fractions of X-ray photons with different energy after penetrating selected attenuators; (FIG. 25B) calculated X-ray spectra from W-target sources at 120 kVp after being filtered by copper attenuators; (FIG. 25C) calculated X-ray spectra from W-target sources at 120 kVp after filtered by copper attenuators, normalized by total photon counts; (FIG. 25D) calculated X-ray mass energy absorption coefficients of Hf and water; (FIG. 25E) calculated ratios of X-ray mass energy absorption coefficients of Hf and water; and (FIG. 25F) calculated penetration depths of X-ray photons at different energies.

Tumor bearing mice were established by subcutaneous inoculation of CT26 cell suspension ($2 \times 10^6$ cells per mouse) into the right flank region of 6-week male BALB/c mice. Three groups were included for comparison: (1) PBS+0.5 Gy/fraction for three fractions (2) P-MOF 10 μmol/kg+0.5 Gy/fraction for three fractions (3) P-MOF 10 μmol/kg+1 Gy/fraction for three fractions. Group (1) and (2) adopted the following X-ray set-up: 225 kVp, 13 mA, 0.3-mm Cu filter. Group (3) adopted another X-ray set-up: 120 kVp, 20 mA, 2-mm Cu filter. When tumors reached 100 mm, P-MOF or PBS was intratumorally injected at a ligand dose of 10 μmol/kg. Twelve hour post-injection, mice were anesthetized with 2% (v/v) isoflurane and tumors were irradiated with image-guided X-ray. The NMOFs were injected once followed by three daily X-ray irradiations. To evaluate the therapeutic efficacy, tumor growth was monitored. The tumor size was measured with a digital caliper every day. Tumor volumes were calculated as follows: (width$^2$× length)/2.

Figure 26A:
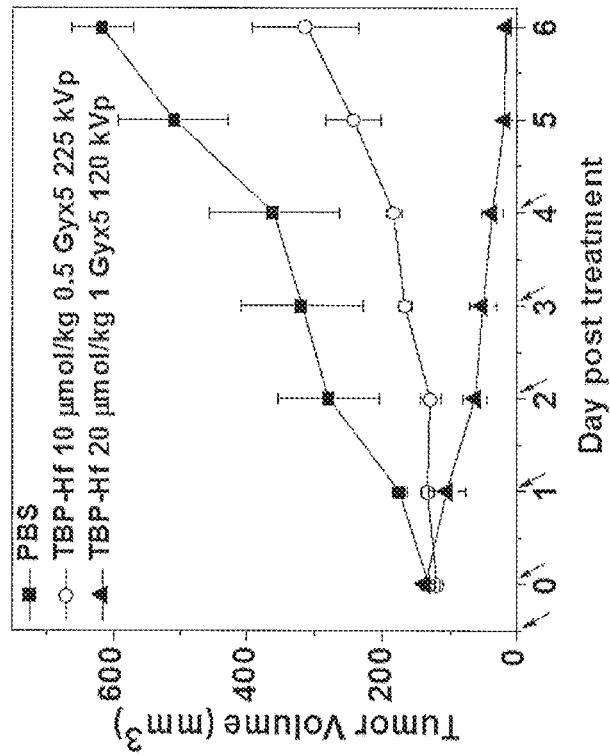
FIGS. 26A-26B are a pair of graphs showing (FIG. 26A) the in vivo anticancer efficacy of a di(p-benzoato)porphyrin metal-organic framework (P-MOF) using different X-ray delivery parameters on CT26 subcutaneous tumor bearing mouse models.
Figure 26B:
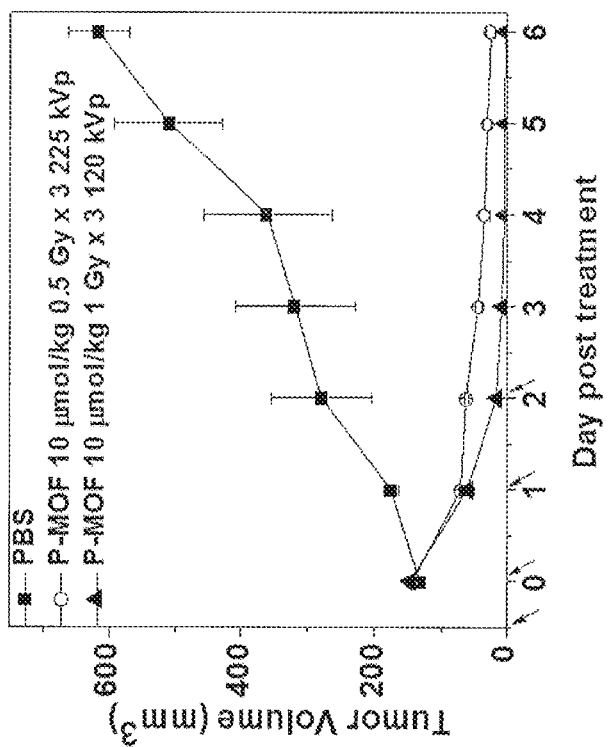

The 225-kVp-X-ray set-up led to significant tumor regression while 120-kVp-X-ray set-up achieved complete tumor eradication on two out of three mice on Day 6 post first treatment. See FIGS. 26A and 26B. Without being bound to any one theory, this result suggested that the therapeutic effect of P-MOF can, in certain embodiments, be further enhanced by the refinement of X-ray delivery parameters.

15.2. In Vivo Anticancer Efficacy of TBP-Hf on Subcutaneous CT26 Tumor Bearing Mouse Models Using Different X-ray Set-ups.

Tumor bearing mice were established by subcutaneous inoculation of CT26 cell suspension ($2 \times 10^6$ cells per mouse) into the right flank region of 6-week male BALB/c mice. Three groups were included for comparison: (1) PBS+0.5 Gy/fraction for three fractions (2) TBP-Hf 10 μmol/kg+0.5 Gy/fraction for five fractions (3) TBP-Hf 20 μmol/kg+1 Gy/fraction for five fractions. Group (1) and (2) adopted the following X-ray set-up: 225 kVp, 13 mA, 0.3-mm Cu filter. Group (3) adopted another X-ray set-up: 120 kVp, 20 mA, 2-mm Cu filter. When tumors reached 100 mm$^3$, TBP-Hf or PBS was intratumorally injected to the mice. Twelve hour post-injection, mice were anesthetized with 2% (v/v) isoflurane and tumors were irradiated with image-guided X-ray. The NMOFs were injected once followed by five daily X-ray irradiations. To evaluate the therapeutic efficacy, tumor growth was monitored. The tumor size was measured with a digital caliper every day. Tumor volumes were calculated as follows: (width$^2$×length)/2.

The 225-kVp-X-ray set-up showed moderate tumor growth inhibition while 120-kVp-X-ray set-up achieved significant tumor regression on CT26 mouse model. See FIGS. 26A and 26B. Again, without being bound by any one theory, this result suggested that, in certain embodiments, the therapeutic effect of TBP-Hf can be enhanced by the refinement of X-ray delivery parameters.

Example 16

In Vivo Anticancer Efficacy of PEG@TBP-Hf on Subcutaneous CT26 Tumor and 4T1 Bearing Mouse Models Tumor bearing mice were established by subcutaneous inoculation of CT26 cell suspension ($2 \times 10^6$ cells per mouse) or 4T1 cell suspension ($5 \times 10^5$ cells per mouse) into the right flank region of 6-week male BALB/c mice. For the CT26 model, three groups were included for comparison: (1) PBS+1 Gy/fraction for five fractions (2) PEGylated TBP-Hf 20 μmol/kg+1 Gy/fraction for five fractions (3) TBP-Hf 20 μmol/kg+1 Gy/fraction for five fractions. The X-ray was delivered at 120 kVp, 20 mA, and with a 2-mm Cu filter. When tumors reached 100 mm$^3$, TBP-Hf, PEGylated TBP-Hf or PBS was intratumorally injected to the mice. Twelve hour post-injection, mice were anesthetized with 2% (v/v)

isoflurane and tumors were irradiated with image-guided X-ray. The NMOFs were injected once followed by five daily X-ray irradiations. To evaluate the therapeutic efficacy, tumor growth was monitored. The tumor size was measured with a digital caliper every day. Tumor volumes were calculated as follows: (width$^2$×length)/2. During the first six days post the first X-ray irradiation, TBP-Hf outperformed PEGylated TBP-Hf in terms of tumor growth regression with a 55% tumor volume reduction on Day 2 post the first irradiation for TBP-Hf and a 44% tumor volume reduction on Day 3 post the first irradiation for PEGylated TBP-Hf. However, after 6 days post the first irradiation when TBP-Hf achieved a 90% tumor volume reduction and PEGylated TBP-Hf achieved an 88% tumor volume reduction, no statistical difference was observed for tumor growth regression between TBP-Hf and PEGylated TBP-Hf up to 9 days post the first irradiation.

For the 4T1 model, three groups were included for comparison: ((1) PBS+1 Gy/fraction for five fractions (2) PEGylated TBP-Hf 20 μmol/kg+1 Gy/fraction for five fractions (3) TBP-Hf 20 μmol/kg+1 Gy/fraction for five fractions. The X-ray was delivered at 120 kVp, 20 mA, and with a 2-mm Cu filter. When tumors reached 100 mm$^3$, TBP-Hf, PEGylated TBP-Hf or PBS was intratumorally injected to the mice. Twelve hour post-injection, mice were anesthetized with 2% (v/v) isoflurane and tumors were irradiated with image-guided X-ray. The NMOFs were injected once followed by five daily X-ray irradiations. To evaluate the therapeutic efficacy, tumor growth was monitored. The tumor size was measured with a digital caliper every day. Tumor volumes were calculated as follows: (width$^2$× length)/2. No difference was observed for tumor growth regression between PEGylated TBP-Hf and TBP-Hf. Both formulations achieved >50% and >80% tumor volume reduction on Day 3 and Day 6 post the first irradiation, respectively.

Example 17

Lipid Coating of MOFs

DOTAP Coating (TBP-Hf@DOTAP)

To a 15 mL centrifuge tube TBP-Hf (0.20 mL, 3 mg/mL in ethanol) and 1,2-di-(9Z-octadecenoyl)-3-trimethylammonium-propane (chloride salt, DOTAP) (3 mL, 5 mg/mL in ethanol) are mixed. The mixture was vortexed and sonicated briefly before 2.0 mL of water was added. The mixture was then vortexed for 1 min and sonicated for 5 min. The coated MOF was isolated by centrifugation and was re-dispersed in 50 mL of 5% glucose aqueous solution.

DOTAP+DOPC Coating (TBP-Hf@DOTAP/DOPC)

To a 15 mL centrifuge tube TBP-Hf (0.20 mL, 3 mg/mL in ethanol), 1,2-di-(9Z-octadecenoyl)-sn-glycero-3-phosphocholine (DOPC, 60 mL, 5 mg/mL in ethanol) and DOTAP (3 mL, 5 mg/mL in ethanol) are mixed. The mixture was vortexed and sonicated briefly before 2.0 mL of water was added. The mixture was then vortexed for 1 min and sonicated for 5 min. The coated MOF was isolated by centrifugation and was re-dispersed in 50 mL of 5% glucose aqueous solution.

DOTAP+DSPE-PEG Coating (TBP-Hf@DOTAP/DSPE-PEG)

To a 15 mL centrifuge tube TBP-Hf (0.20 mL, 3 mg/mL in ethanol), DSPE-PEG$_{2k}$ (0.12 mL, 5 mg/mL in ethanol) and DOTAP (3 mL, 6 mL, 12 mL or 30 mL for different formulations, 5 mg/mL in ethanol) are mixed. The mixture was vortexed and sonicated briefly before 2.0 mL of water was added. The mixture was then vortexed for 1 min and sonicated for 5 min. The coated MOF was isolated by centrifugation, re-dispersed in small amount of water by sonication and frozen in a −20° C. freezer. The purple powder product was finally afforded after lyophilization.

DLS measurement data and zeta (ζ) potential for the lipid coated MOFs are shown below in Table 8.

TABLE 8

Z-average, Number average, PDI, and Zeta Potential of TBP-Hf with Various coatings.

| Sample | Z-average (nm) | PDI | N-average (nm) | ζ-potential (mV) |
|---|---|---|---|---|
| Bare TBP-Hf in ethanol | 103.8 | 0.085 | 72.72 | N/A |
| TBP-Hf@DOTAP | 156.0 | 0.173 | 94.99 | 20.2 |
| TBP-Hf@DOTAP/DOPC | 145.1 | 0.087 | 106.5 | 6.32 |
| TBP-Hf@DOTAP/DSPE-PEG (20:1:10 by mol) | 109.8 | 0.041 | 82.43 | −4.61* |
| TBP-Hf@DOTAP/DSPE-PEG (20:2:10 by mol) | 110.4 | 0.084 | 75.64 | −6.38* |
| TBP-Hf@DOTAP/DSPE-PEG (20:4:10 by mol) | 102.3 | 0.058 | 78.69 | −5.27* |
| TBP-Hf@DOTAP/DSPE-PEG (20:10:10 by mol) | 106.2 | 0.058 | 85.64 | −3.94* |

*for these samples, ζ-potentials are tested in phosphate buffer saline (6.7 mM total phosphate).

Example 18

Radioenhancement by Hf-L MOFs and their Combination with Checkpoint Blockade Immunotherapy Hf$_6$- and Hf$_{12}$-L MOFs were prepared where L is a linear dicarboxylate ligand such as 2,5-di(p-benzoato)aniline (DBA), 4,4'-biphenyldicarboxylate (BPDC), 2, 2'-bipyridine-5, 5'-dicarboxylate (BPyDC), 2,5-di(p-benzoato)anthracene (DBAn), [1,1':4',1"-terphenyl]-4,4"-dicarboxylate, or 4,4'-bis(carboxyphenyl)-2-nitro-1,1'-biphenyl (NO$_2$-QPDC), and their combination with checkpoint blockade immunotherapy.

18.1 Material Synthesis and Characterization

Synthesis of 2,5-di(p-benzoato)aniline (H$_2$DBA) and 2,5-di(p-benzoato) anthracene (H$_2$DBAn)

Synthesis of 2,5-di(p-benzoato)aniline (H$_2$DBA). 2,5-di(p-benzoato)aniline (H$_2$DBA) was synthesized as described previously (He et al., *J. Am. Chem. Soc.* 2014, 136, 5181-5184). $^1$H-NMR (DMSO-d6): δ =12.97 (br, 2H), 8.03 (m, 4H), 7.74 (d, 2H), 7.61 (d, 2H), 7.16 (d, 2H), 7.02 (dd, 1H), 5.12 (br, 2H).

Synthesis of 2,5-di(p-benzoato)anthracene (H$_2$DBAn). 2,5-di(p-benzoato)anthracene (H$_2$DBAn) was synthesized as described previously (Wang et al. *J. Am. Chem. Soc.* 2014, 136, 6171-6174). $^1$H-NMR (DMSO-d6): δ =8.25 (m, 4H), 7.65 (m, 4H), 7.56 (m, 4H), 7.47 (m, 2H).

18.2 Synthesis of Hf-based nMOFs

Synthesis of $Hf_6$-DBA and $Hf_6$-DBAn nMOFs. To a 1 dram glass vial was added 0.5 mL of $HfCl_4$ solution (2.0 mg/mL in DMF), 0.5 mL of the 2,5-di(p-benzoato)aniline ($H_2$DBA) solution (2.0 mg/mL in DMF) or 2,5-di(p-benzoato)anthracene ($H_2$DBAn) solution (2.5 mg/mL in DMF) and 0.5 µL of trifluoroacetic acid. The reaction mixture was kept in a 60° C. oven for 72 h. The white precipitate was collected by centrifugation and washed with DMF, 1% trimethylamine/ethanol solution and ethanol. PXRD patterns indicate that $Hf_6$-DBA and $Hf_6$-DBAn nMOFs adopt UiO MOF structures with the $Hf_6$ SBUs.

Preparation of $Hf_{12}$-DBA nMOF. To a 4 mL glass vial was added 0.5 mL of $HfCl_4$ solution (1.6 mg/mL in DMF), 0.5 mL of the $H_2$DBA solution (1.6 mg/mL in DMF), 75 µL of acetic acid and 5 µL of water. The reaction mixture was kept in an 80° C. oven for 72 hours. The white precipitate was collected by centrifugation and washed with DMF, 1% trimethylamine/ethanol solution and ethanol.

Preparation of $Hf_{12}$-DBAn nMOF. To a 4 mL glass vial was added 0.5 mL of $HfCl_4$ solution (1.6 mg/mL in DMF), 0.5 mL of the $H_2$DBA solution (1.6 mg/mL in DMF), 75 µL of acetic acid and 5 µL of water. The reaction mixture was kept in an 80° C. oven for 72 hours. The white precipitate was collected by centrifugation and washed with DMF, 1% trimethylamine/ethanol solution Preparation of other control particles. Preparation of $Hf_6$-DBA or $Hf_6$-DBAn nMOFs: To a 4 mL glass vial was added 0.5 mL of $HfCl_4$ solution (2.0 mg/mL in DMF), 0.5 mL of the $H_2$DBA solution (2.0 mg/mL in DMF) or $H_2$DBAn solution (2.5 mg/mL in DMF) and 0.5 µL of trifluoroacetic acid. The reaction mixture was kept in a 60° C. oven for 72 hours. The white precipitate was collected by centrifugation and washed with DMF, 1% trimethylamine/ethanol solution and ethanol.

$HfO_2$ nanoparticles were synthesized as described previously (see Pinna et al., Advanced Materials 2004, 16 (23-24), 2196-2200), and used as a control. The crystalline $HfO_2$ nanoparticles have a diameter of 5.2±0.6 nm based on TEM images. Gold nanoparticles (AuNP) were synthesized as described previously (see Ji et al., J. Am. Chem. Soc. 2007, 129, 13939), and used as a control. The crystalline $HfO_2$ nanoparticles have a diameter of 46.5±1.9 nm based on TEM images.

18.3 Structure and Composition Characterization

Figure 33A:
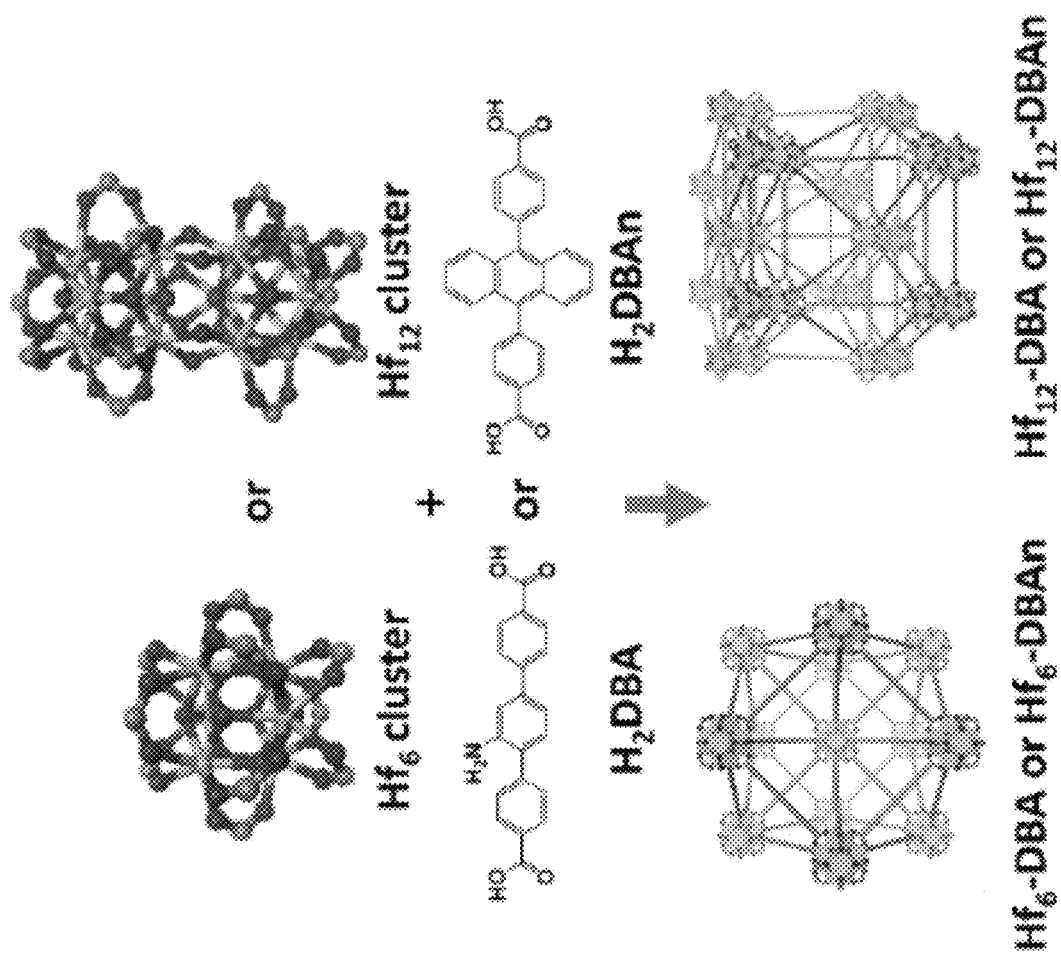
FIG. 33A is a schematic drawing of the synthesis of metal-organic frameworks (MOFs) comprising the following combinations of secondary building units (SBUs) and bridging ligands: hafnium six oxo cluster SBUs and 2,5-di(p-benzoato)aniline (DBA) bridging ligands ($Hf_6$-DBA); hafnium six oxo cluster SBUs and 2,5-di(p-benzoato)anthracene (DBAn) bridging ligands ($Hf_6$-DBAn); hafnium twelve oxo cluster SBUs and DBA bridging ligands ($Hf_{12}$-DBA); and hafnium twelve oxo cluster SBUs and DBAn bridging ligands ($Hf_{12}$-DBAn).
Figure 33C:
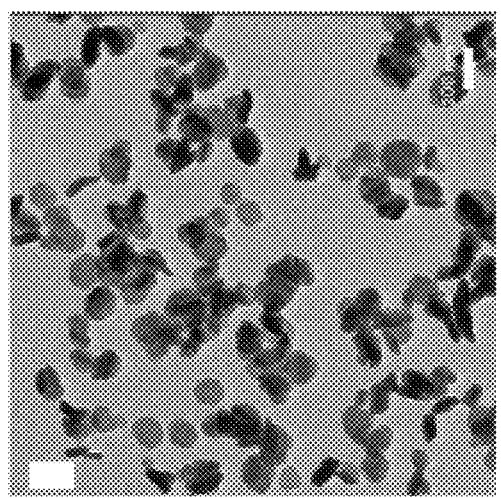
FIG. 33C is a transmission electron microscopy (TEM) image of the metal-organic frameworks (MOFs) described in FIG. 33A that comprise hafnium twelve oxo cluster secondary building units and 2,5-di(p-benzoato)aniline (DBA) bridging ligands ($Hf_{12}$-DBA). The white scale bar in the lower right hand corner of the image represents 100 nanometers (nm).
Figure 33D:
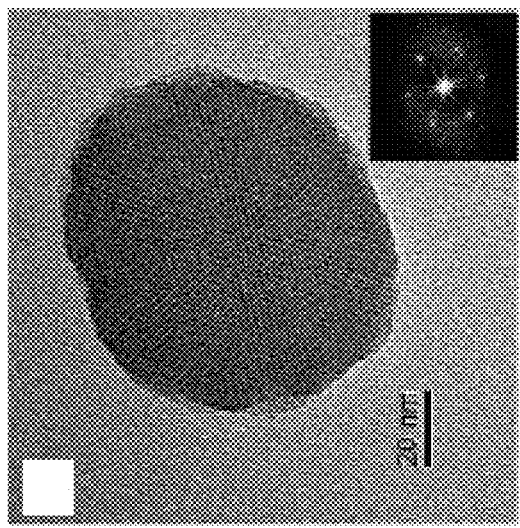
FIG. 33D is a transmission electron microscopy (TEM) image of the metal-organic frameworks (MOFs) described in FIG. 33A that comprise hafnium twelve oxo cluster secondary building units and 2,5-di(p-benzoato)aniline (DBA) bridging ligands ($Hf_{12}$-DBA). The fast Fourier transform (FFT) pattern of the MOF is shown in the inset. The scale bar in the lower left side of the TEM image represents 20 nanometers (nm).
Figure 33B:
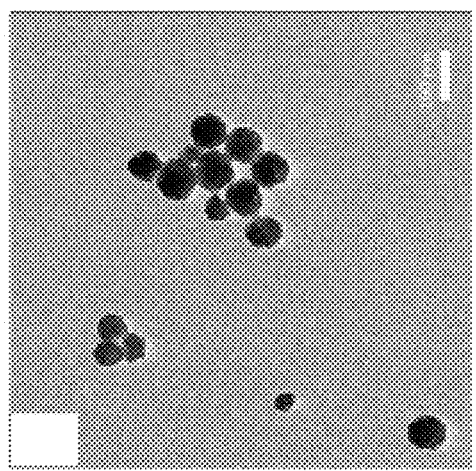
FIG. 33B is a transmission electron microscopy (TEM) image of the metal-organic frameworks (MOFs) described in FIG. 33A that comprise hafnium six oxo cluster secondary building units and 2,5-di(p-benzoato)aniline (DBA) bridging ligands ($Hf_6$-DBA). The white scale bar in the lower right hand corner of the image represents 100 nanometers (nm).
Figure 33E:
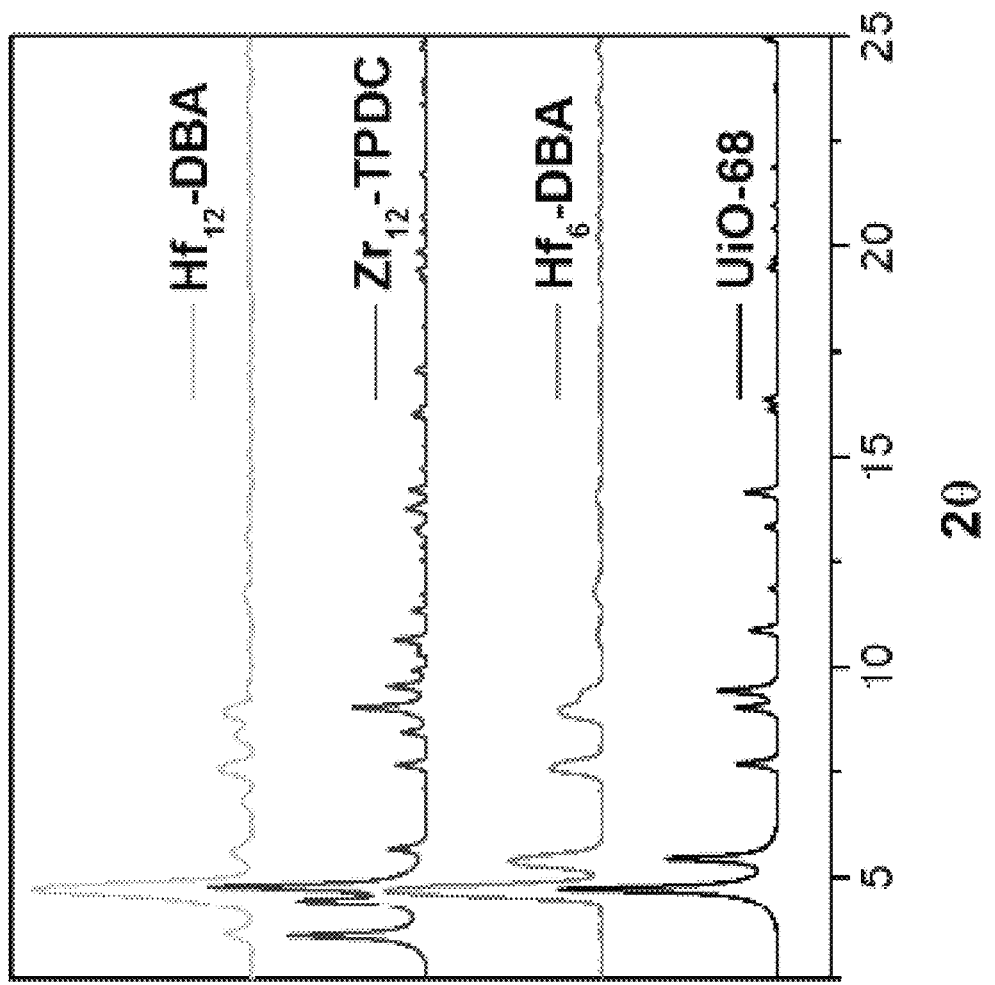
FIG. 33E is a graph showing the powder x-ray diffraction (PXRD) patterns of nano metal-organic frameworks (nMOFs) comprising (1) hafnium six oxo cluster secondary building units (SBUs) and 2,5-di(p-benzoato)aniline (DBA) bridging ligands ($Hf_6$-DBA) and (2) hafnium twelve oxo cluster SBUs and DBA bridging ligands ($Hf_{12}$-DBA). For comparison, the patterns of UiO-68 and a nMOF comprising zinc twelve oxo cluster SBUs and amino-triphenyldicarboxylic acid bridging ligands ($Zr_{12}$-TPDC) are shown.

By tuning the temperature and modulators, two Hf-based nMOFs with different SBUs, $Hf_6$-DBA with a formula of $Hf_6(\mu_3\text{-}O)_4(\mu_3\text{-}OH)_4(DBA)_6$ and $Hf_{12}$-DBA with a formula of $Hf_{12}(\mu_3\text{-}O)_8(\mu_3\text{-}OH)_8(\mu_2\text{-}OH)_6(DBA)_9$, were synthesized via solvothermal reactions. See FIG. 33A. TEM images of $Hf_6$-DBA showed the formation of uniformly spherical NPs with a diameter of approximately 90 nm, while $Hf_{12}$-DBA possessed a plate-like morphology of ~80 nm in diameter and ~30 nm in thickness. Both nMOFs showed good dispersity in ethanol and monodispersity. See FIGS. 33B-33D. DLS measurements gave a Z-average diameter, number-average diameter, and polydispersity index of 139.7±1.1 nm, 116.0±0.9 nm, and 0.07±0.01, respectively, for $Hf_6$-DBA and 132.2±0.3 nm, 102.1±4.1 nm, and 0.08±0.02, respectively, for $Hf_{12}$-DBA. The power X-ray diffraction (PXRD) pattern of $Hf_6$-DBA was identical to that of UiO-68 while the PXRD pattern of $Hf_{12}$-DBA was identical to that of $Zr_{12}$-TPDC (see Inorg. Chem. 2017, 56, 8128-8134), indicative of their crystalline nature and different topological structures. See FIG. 33E. Thermogravimetric analysis results of $Hf_6$-DBA or $Hf_{12}$-DBA matched the weight losses expected for their decomposition to $HfO_2$. Nitrogen sorption measurements showed that $Hf_6$-DBA possessed a BET surface area of 804.4 $m^2$/g whereas $Hf_{12}$-DBA exhibited a BET surface area of 463.9 $m^2$/g.

Figure 34D:
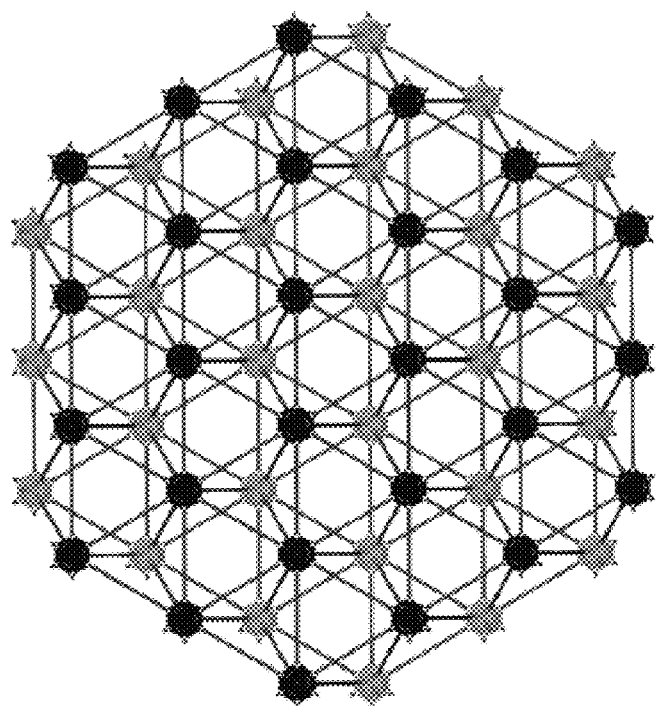
FIG. 34D is a schematic drawing showing the view along c axis of a stack of multiple layers of the nanosheets described in FIG. 34B. Rods in represent the ligands.
Figure 34C:
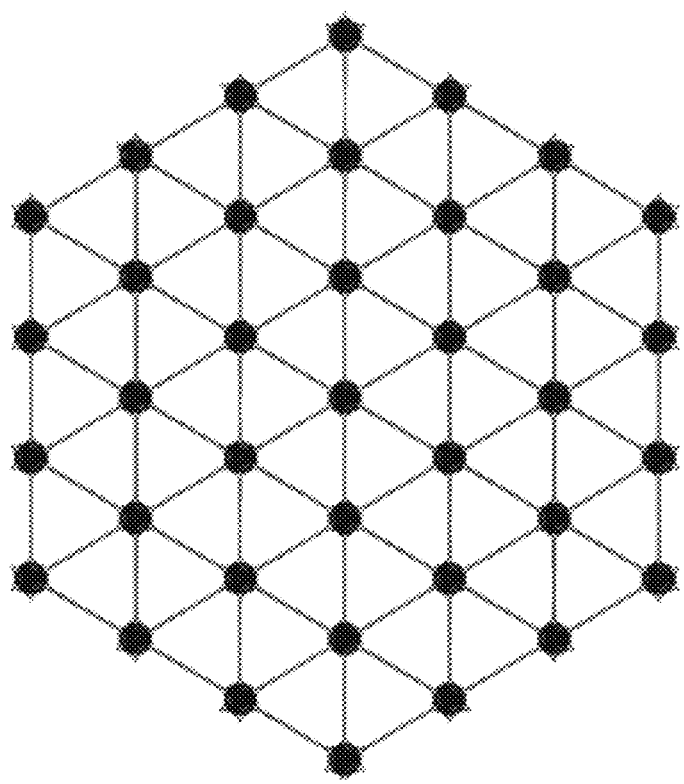
FIG. 34C is a schematic drawing showing the view along c axis of a single layer of the nanosheets described in FIG. 34B. Rods represent ligands.

Both $Hf_{12}$-DBA and $Hf_{12}$-DBAn adopt a layered structure with formula of $Hf_{12}(\mu_3\text{-}O)_8(\mu_3\text{-}OH)_8(\mu_2\text{-}OH)_6(L)_9$ (L=DBA or DBAn). The $Hf_{12}$ SBU is fused from two $Hf_6(\mu_3\text{-}O)_4(\mu_3\text{-}OH)_4(RCO_2)_{12}$ clusters that three carboxylates from each part are substituted by six $\mu_2$-OH bridges (see FIG. 34A), affording an SBU formula of $Hf_{12}(\mu_3\text{-}O)_8(\mu_3\text{-}OH)_8(\mu_2\text{-}OH)_6(RCO_2)_{18}$. Different from $Hf_6$ SBU based cubic (UiO) MOFs, $Hf_{12}$ SBU causes preferential growth perpendicular to the long axis of the SBU, resulting in a hexagonal layered structure. See FIGS. 34B-34D. The characteristic peak at 2Θ=3.50° in PXRD patterns matches the 002 diffraction of the structure ($d_{002}$=2.52 nm). Both $Hf_{12}$-DBA and $Hf_{12}$-DBAn are nanoplates with plate diameters of 75.4±4.0 and 83.5±6.2 nm and thicknesses of 27.6±2.3 and 24.9±1.7 nm, respectively, according to the TEM images.

18.4 Clonegenic Assay

The Clonegenic assay was used to evaluate radioenhancing effects of $HfO_2$, $Hf_6$-DBA, $Hf_{12}$-DBA and AuNP with modified protocol. Generally, cells were seeded in 6-well plates and cultured for 12 h. After incubated with particles at a Hf concentration of 20 µM for 4 h, cells were irradiated upon X-ray (X-RAD 225Cx, GE, Germany), Co-60 isotope gamma ray source or linear accelerator (LINAC) gamma ray at 0, 1, 2, 4, 8 and 16 Gy dose. Cells were trypsinized and counted immediately. 100-200 cells were seeded on 6-well plates and cultured with 2 mL medium for 10-20 days. Once observing cell clone formation, the culture medium was discarded and the plate was rinsed with PBS twice. 500 µL 0.5% crystal violet (50% methanol) were added per well for staining. Then all the wells were rinsed with water and the clones were counted. $Hf_{12}$-DBA displays efficient radiosensitization with radiation enhancement factors (REFs) at 10% survival dose ($D_{10}$) range from 1.47 to 1.66 for different cells, significantly outperforming $HfO_2$, $Hf_6$-DBA and gold nanoparticles at the same Hf/Au doses (see Table 9, below), likely due to the enhanced radical generation by $Hf_{12}$ SBUs and facile ROS diffusion through the porous structure of nMOF nanoplates. The dose-response curves were fitted with the function $F(D)=\exp(-\alpha D-\beta D^2)$, where D is the radiation dose and F(D) is the survival fraction. A greater $\alpha/\beta$ value indicates strong early radiation response. $Hf_{12}$-DBA radiosensitization for $^{60}$Co source γ-ray irradiation (REF=1.10-1.77) is also significantly greater than $HfO_2$, $Hf_6$-DBA and gold nanoparticles. See Table 10, below. As shown in Table 10, 20 µM $HfO_2$ showed only moderate radioenhancing effect compared to water and exhibited much smaller REF10 values than $Hf_6$-DBA and $Hf_{12}$-DBA in all cell lines examined, which is consistent with the APF assay results. Interestingly, at the same Hf concentration, $Hf_{12}$-DBA outperformed $Hf_6$-DBA, with REF10 values from 1.45 to 1.73 compared to those from 1.10 to 1.31 for $Hf_6$-DBA. This was consistent with the APF fluorescence and radioluminescence assay results that showed the $Hf_{12}$ cluster exhibited superior radioenhancement over $Hf_6$, likely due to enhanced X-ray absorption by the electron-dense $Hf_{12}$ clusters and hydroxyl radical diffusion through the pores. Upon irradiation with γ-rays from a $^{60}$Co source, $Hf_{12}$-DBA also exhibited higher radiosensitization (REF10=1.10-1.47) than $HfO_2$ and $Hf_6$-DBA, suggesting that $Hf_{12}$-DBA is compatible with linear accelerators commonly used in the clinic.

TABLE 9

Fitting result of the dose-response curves by clonogenic assay upon X-ray irradiation.

| | α | β | Adj. $r^2$ | α/β | $D_{10}$ | $D_{20}$ | $D_{50}$ | REF |
|---|---|---|---|---|---|---|---|---|
| CT26 | | | | | | | | |
| PBS | 0.02512 | 0.01585 | 0.993 | 1.58 | 11.29 | 9.32 | 5.87 | |
| $Hf_6$-DBA | 0.09444 | 0.01582 | 0.994 | 5.97 | 9.44 | 7.53 | 4.28 | 1.2 |
| $Hf_{12}$-DBA | 0.3055 | 0.0033 | 0.995 | 92.6 | 7.01 | 5 | 2.22 | 1.61 |
| $HfO_2$ | 0.02416 | 0.01696 | 0.991 | 1.42 | 10.96 | 9.06 | 5.72 | 1.03 |
| AuNP | 0.17898 | 0.01009 | 0.997 | 17.7 | 8.65 | 6.56 | 3.27 | 1.31 |
| SQ20B | | | | | | | | |
| PBS | 0.1546 | 0.0058 | 0.98 | 26.6 | 10.64 | 8.01 | 3.91 | |
| $Hf_6$-DBA | 0.2716 | 0.00216 | 0.97 | 125.7 | 7.97 | 5.67 | 2.5 | 1.34 |
| $Hf_{12}$-DBA | 0.3598 | / | 0.99 | / | 6.4 | 4.47 | 1.93 | 1.66 |
| $HfO_2$ | 0.2369 | 0.00306 | 0.98 | 77.4 | 8.73 | 6.28 | 2.82 | 1.22 |
| AuNP | 0.2571 | 0.0028 | 0.991 | 91.8 | 8.22 | 5.88 | 2.62 | 1.29 |
| TUBO | | | | | | | | |
| PBS | 0.05004 | 0.007714 | 0.98 | 6.49 | 14.34 | 11.56 | 6.78 | |
| $Hf_6$-DBA | 0.2229 | 9.45E−04 | 0.99 | 236 | 9.92 | 7.01 | 3.07 | 1.45 |
| $Hf_{12}$-DBA | 0.2624 | / | 0.99 | / | 8.78 | 6.13 | 2.64 | 1.63 |
| $HfO_2$ | 0.129 | 0.00338 | 0.99 | 38.2 | 13.25 | 9.91 | 4.78 | 1.08 |
| AuNP | 0.1646 | 0.00255 | 0.993 | 64.5 | 11.82 | 8.63 | 3.97 | 1.21 |
| Hela | | | | | | | | |
| PBS | 0.07104 | 0.00528 | 0.997 | 13.5 | 15.21 | 11.98 | 6.56 | |
| $Hf_6$-DBA | 0.1475 | 0.00437 | 0.98 | 33.7 | 11.62 | 8.68 | 4.18 | 1.31 |
| $Hf_{12}$-DBA | 0.1719 | 0.00495 | 0.99 | 34.7 | 10.32 | 7.66 | 3.64 | 1.47 |
| $HfO_2$ | 0.0951 | 0.00534 | 0.97 | 17.8 | 13.68 | 10.6 | 5.56 | 1.11 |
| AuNP | 0.18006 | 0.00293 | 0.995 | 61.5 | 10.87 | 7.92 | 3.63 | 1.4 |
| JSQ3 | | | | | | | | |
| PBS | 0.03676 | 0.00699 | 0.993 | 5.26 | 15.71 | 12.77 | 7.67 | |
| $Hf_6$-DBA | 0.13588 | 0.00247 | 0.99 | 55 | 13.59 | 10.02 | 4.7 | 1.16 |
| $Hf_{12}$-DBA | 0.17188 | 0.00725 | 0.98 | 23.7 | 9.55 | 7.19 | 3.51 | 1.65 |
| $HfO_2$ | 0.08438 | 0.00372 | 0.98 | 22.7 | 16 | 12.35 | 6.41 | 1 |
| AuNP | 0.05066 | 0.01099 | 0.995 | 4.61 | 12.35 | 10.01 | 5.96 | 1.27 |
| 4T1 | | | | | | | | |
| PBS | 0.05079 | 0.00613 | 0.996 | 8.29 | 15.68 | 12.58 | 7.27 | |
| $Hf_6$-DBA | 0.15003 | 0.00147 | 0.991 | 102.1 | 13.55 | 9.79 | 4.43 | 1.16 |
| $Hf_{12}$-DBA | 0.20059 | 7.52E−04 | 0.99 | 266.8 | 11.02 | 7.8 | 3.41 | 1.42 |
| $HfO_2$ | 0.1026 | 0.00575 | 0.993 | 17.8 | 12.99 | 10.04 | 5.23 | 1.21 |
| AuNP | 0.1469 | 0.00192 | 0.994 | 76.5 | 13.35 | 9.72 | 4.46 | 1.17 |

TABLE 10

REF at $D_{10}$ by clonogenic assay in a panel of cell lines upon γ-ray irradiation from $^{60}$Co source.

| | 4T1 | TUBO | Hela | CT26 | JSQ3 | SQ20B |
|---|---|---|---|---|---|---|
| $HfO_2$ | 1.06 | 1.03 | 1 | 1.01 | 1 | 1 |
| $Hf_6$-DBA | 1.15 | 1.27 | 1.29 | 1.06 | 1.06 | 1.08 |
| $Hf_{12}$-DBA | 1.26 | 1.44 | 1.77 | 1.14 | 1.1 | 1.23 |

18.5 In Vitro Assays to Assess Radioenhancing Properties

DNA Double-strand Break Detection

The DNA double-strand break (DSB) caused by Hf-based particles upon X-ray was investigated by γ-$H_2AX$ assay (Life Technologies, Carlsbad, Calif., United States of America) in CT26 cells. Cells were cultured in 6 well plates overnight and incubated with particles at a Hf concentration of 20 μM for 4 h followed by X-ray irradiation at 0 and 4 Gy dose (250 kVp, 15 mA, 1 mm Cu filter).

$H_2AX$ assays were carried out immediately after X-ray by both immunostaining analysis and flow cytometry analysis. For immunostaining analysis, the cells were seeded on cover slides and observed under confocal laser scanning microscopy (CLSM). Red fluorescence indicating the DSBs was observed. A highly enhanced DSB level was observed when the cells were treated with induced Hf-based nanoparticles and X-rays, while no red fluorescence was detected in groups either without X-ray irradiation or without Hf-nanoparticle.

For flow cytometry analysis, cells were cultured in 6 well plates overnight and incubated with particles at a Hf concentration of 20 μM for 4 h followed by X-ray irradiation at 0 and 4 Gy dose. Normal CT26 cells served as control. Texas-red fluorescence channel was utilized to gate the DSBs stained with antibody-labeled $H_2AX$. Significant increase of Texas-red fluorescence intensity was observed in both $Hf_{12}$-DBA and $Hf_6$-DBA treated groups compared to groups treated with PBS or $HfO_2$. Hf-based nMOFs show better DNA double strand break effect than control nanoparticles.

CRT Assay

The immunogenic cell death (ICD) induced by Hf-mediated radiation treatment was investigated by detecting cell-surface expression of calreticulin (CRT). CT26 cells were seeded in 6-well plates overnight and incubated with $HfO_2$, $Hf_6$-DBA or $Hf_{12}$-DBA at 20 μM based on Hf concentration for 4 hours followed by treatment of X-ray irradiation at 0 and 4 Gy dose (250 kVp, 15 mA, 1 mm Cu filter). Then cells were cultured in the incubator for another 4 hours before microscope observation. Green fluorescence indicating CRT expression was observed in $Hf_6$-DBA or $Hf_{12}$-DBA samples irradiated by X-ray. Stronger green fluorescence was observed in groups treated with $Hf_{12}$-DBA compared to either $Hf_6$-DBA or $HfO_2$ treated groups under CLSM.

18.6 In Vivo Anti-tumor Cancer Efficacy

The in vivo anticancer efficacy of $Hf_6$-DBA and $Hf_{12}$-DBA on CT26 tumor bearing mice in combination with immune checkpoint blockade was evaluated. A bilateral model was established to assess both the local radiotherapy and the systemic immunotherapy. 5 million cells and 2 million cells were respectively inoculated into right and left side subcutaneous tissue on day 0. When the right tumors reached 100-150 mm³ in volume, particles with Hf amount of 1 μmol was intratumorally injected followed by daily X-ray irradiation at a dose of 1 Gy/fraction (120 kVp, 20 mA, 2 mm-Cu filter) for a total of 10 fractions on CT26 model on consecutive days. See FIG. 35A. Anti-PD-L1, an antibody that can bind the PD-L1 receptor highly expressed on the surface of tumor cell, was given every three days by intraperitoneal injection at a dose of 75 μg/mouse. The tumor sizes were measured with a caliper every day and the tumor volume equals (width²×length)/2. Mice treated with $Hf_6$-DBA (with or without antibody) and $Hf_{12}$-DBA (with or without antibody) were sacrificed on Day 30 while Mice treated with PBS (without irradiation) or antibody (with irradiation) were sacrificed on Day 21. Body weight of each group was monitored and no systemic toxicity was observed in any of the groups as indicated by the steady weight increases for the treated mice.

As shown in FIG. 35B, $Hf_{12}$-DBA has high radioenhancing effect, regressing the local irradiated tumors at 10 Gy of total X-ray doses. In comparison, $Hf_6$-DBA is less effective. More significantly, in combination with an anti-PD-L1 antibody, $Hf_{12}$-DBA not only regressed local, irradiated tumors but also regressed distant, non-irradiated tumors (see FIG. 35C, likely via synergistic actions of $Hf_{12}$-DBA mediated radiotherapy and anti-PD-L1 antibody mediated immunotherapy. The inhibition of distant tumors in $Hf_{12}$-DBA mediated-RT plus checkpoint blockade group indicated effective induction of systemic antitumor immune response.

18.7 Anti-tumor Immunity Analysis

Figure 36A:
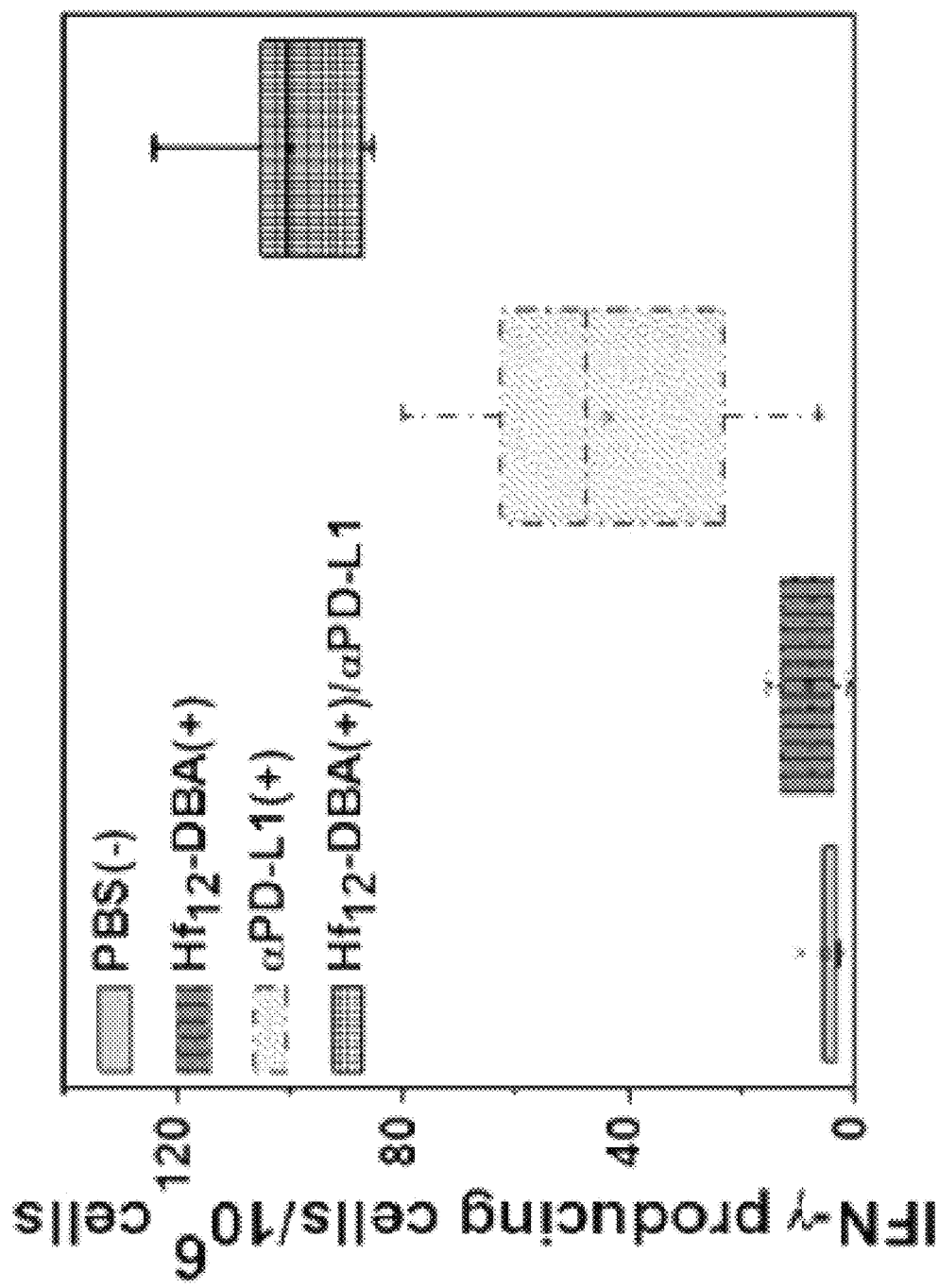
FIG. 36A is a graph showing the percentage of interferon (IFN)-producing cells determined by Enzyme-Linked ImmunoSpot (ELISPOT) with respect to the total number of splenocytes of mice from groups treated with, from left to right, phosphate buffered saline (PBS); metal-organic frameworks (MOFs) comprising hafnium twelve oxo clusters and 2,5-di(p-benzoato)aniline (DBA) ligands (Hf$_{12}$-DBA) and X-rays; anti-PD-L1 antibodies and X-rays; and Hf$_{12}$-DBA combined with anti-PD-L1 antibody and X-ray irradiation. The samples were collected after 5 days post 5 days treatment. N=5.

The anti-tumor immunity of CT26-bearing mice treated with $Hf_{12}$-DBA plus anti-PD-L1 antibody was tested by Enzyme-Linked ImmunoSpot (ELISPOT) and flow cytometry. The presence of tumor-antigen specific cytotoxic T cells was first determined with an IFN-γ ELISPOT assay. At day 10 after the first 5-days consecutive treatment, splenocytes were harvested from CT26-bearing mice and stimulated with antigen-presenting 3T3/NKB cells, which express CT26-derived antigen neu, and the IFN-γ spot forming cells were counted by Immunospot Reader. The number of antigen-specific IFN-γ producing T cells significantly increased in tumor-bearing mice treated with $Hf_{12}$-DBA plus anti-PD-L1 antibody (IFN-γ producing cells/$10^6$ cells=100.2±15.7 compared to the PBS control group (IFN-γ SFC/$10^6$ cells=5.3±2.7) and $Hf_{12}$-DBA (IFN-γ producing cells/$10^6$ cells=8.2±6.1) (see FIG. 36A), suggesting that $Hf_{12}$-DBA with X-ray irradiation plus anti-PD-L1 antibody induce in situ tumor vaccination to effectively generate tumor-specific T cell response.

Figure 36C:
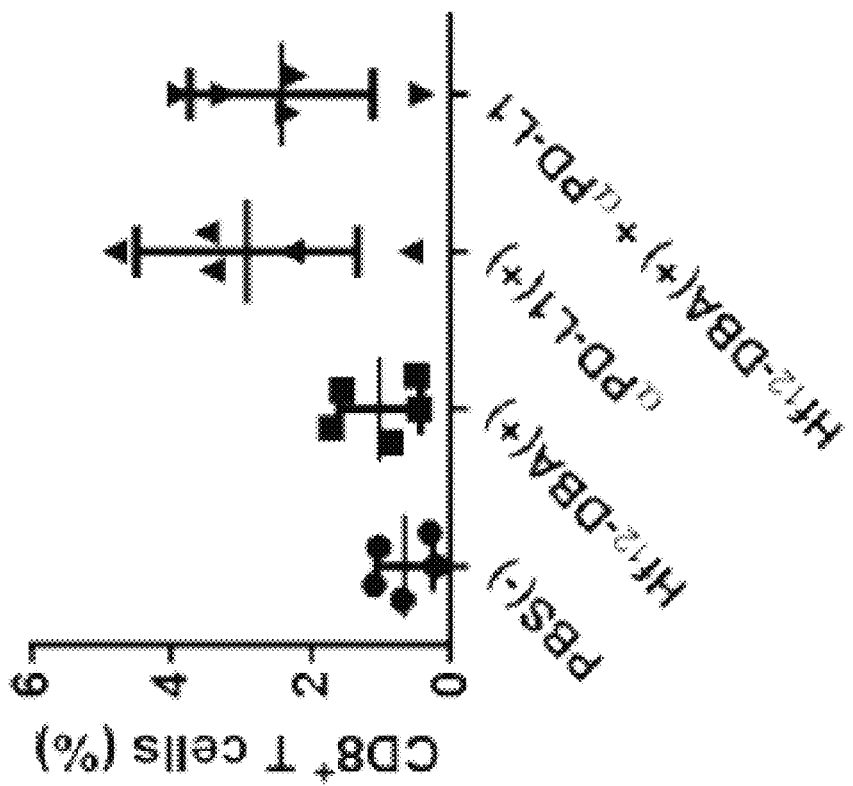
FIG. 36C is a graph showing the percentage of tumor-infiltrating CD8$^+$ T cells with respect to the total number of cells in the right tumor of mice from groups treated with, from left to right, phosphate buffered saline (PBS); metal-organic frameworks (MOFs) comprising hafnium twelve oxo clusters and 2,5-di(p-benzoato)aniline (DBA) ligands (Hf$_{12}$-DBA) and X-rays; anti-PD-L1 antibodies and X-rays; and Hf$_{12}$-DBA combined with anti-PD-L1 antibody and X-ray irradiation. The samples were collected after 5 days post 5 days treatment. N=5.
Figure 36B:
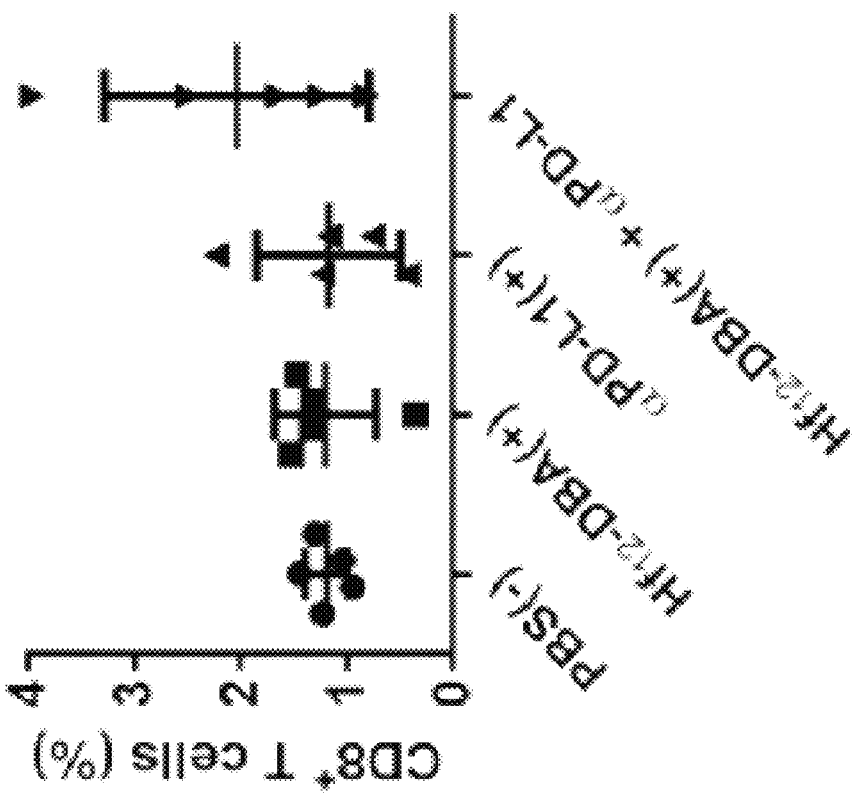
FIG. 36B is a graph showing the percentage of tumor-infiltrating CD8$^+$ T cells with respect to the total number of cells in the left tumor of mice from groups treated with, from left to right, phosphate buffered saline (PBS); metal-organic frameworks (MOFs) comprising hafnium twelve oxo clusters and 2,5-di(p-benzoato)aniline (DBA) ligands (Hf$_{12}$-DBA) and X-rays; anti-PD-L1 antibodies and X-rays; and Hf$_{12}$-DBA combined with anti-PD-L1 antibody and X-ray irradiation. The samples were collected after 5 days post 5 days treatment. N=5.

Infiltrating leukocytes in both the primary and distant tumors were profiled. Specifically, for the primary tumor, the percentage of $CD8^+$ T cells in the total tumor cells significantly increased in both $Hf_{12}$-DBA mediated-RT (2.92±1.58%) and $Hf_{12}$-DBA mediated-RT plus anti-PD-L1 treatment groups (2.42±1.31%) compared to the PBS control group (0.67±0.40%). See FIG. 36C. For the distant tumor, the percentage of $CD8^+$ T cells in the total tumor cells increased in $Hf_{12}$-DBA mediated-RT plus anti-PD-L1 treatment group (2.04±1.24%) compared to $Hf_{12}$-DBA mediated-RT group (1.21±0.48%) and PBS group (1.20±0.20%). See FIG. 36B. These results indicated that a combination of PD-L1 checkpoint blockade and enhanced RT was likely responsible for the suppression of the primary tumor and inhibition of distant tumor. The increased efficacy of $Hf_{12}$-DBA mediated-RT synergized with anti-PD-L1 immune checkpoint blockade to afford systemic antitumor immunity.

Example 19

Figure 38:
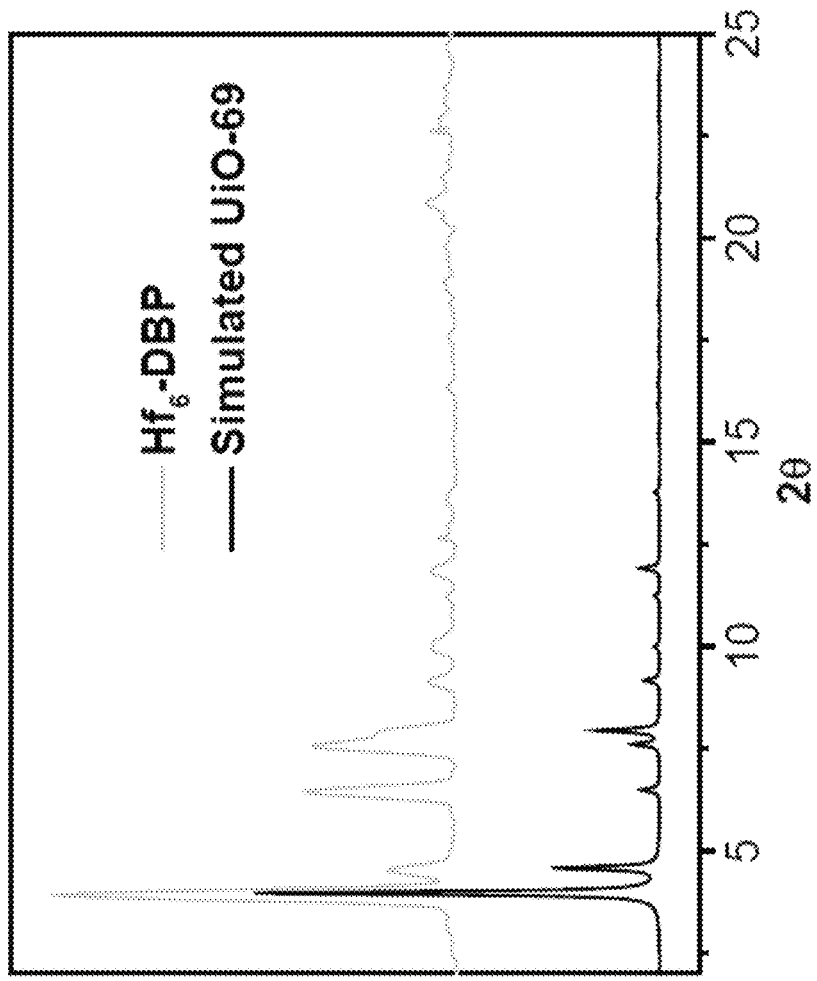
FIG. 38 is a graph showing the powder x-ray diffraction (PXRD) patterns of (top) nano metal-organic frameworks (nMOFs) comprising hafnium six oxo clusters and di(p-benzoato)porphyrin (DBP) ligands (Hf$_6$-DBP) and (bottom) simulated UiO-69.
Figure 37:
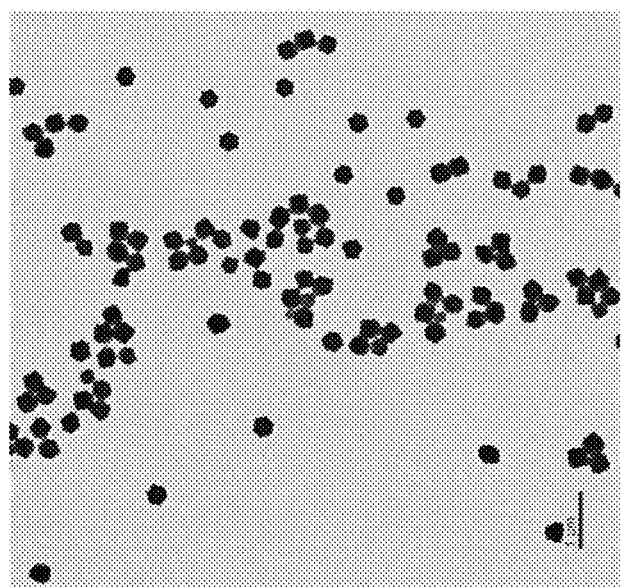
FIG. 37 is a transmission electron microscopy (TEM) image of metal-organic frameworks (nMOFs) comprising hafnium six oxo clusters and di(p-benzoato)porphyrin (DBP) ligands (Hf$_6$-DBP). The scale bar in the lower left of the image represents one micrometer (μm).

Radiotherapy and Radiodynamic Therapy by $Hf_{12}$-DBP nMOF and the Combination with Immune Checkpoint Blockade 19.1 Synthesis and Characterization of $Hf_6$-DBP nMOF To a 4 mL glass vial was added 0.5 mL of $HfCl_4$ solution (3.2 mg/mL in DMF), 0.5 mL of $H_2$DBP-Pt solution (6.0 mg/mL in DMF), 5 μL of trifluoroacetic acid. The reaction mixture was kept in an 120° C. oven for 2 days. The purple precipitate was collected by centrifugation and washed with DMF, 1% trimethylamine/ethanol solution and ethanol. TEM imaging showed that $Hf_6$-DBP nMOF adopted octahedral morphology with a diameter of ~500 nm. See FIG. 37. PXRD studies (see FIG. 38) indicated that $Hf_6$-DBP adopted the same crystal structure as UiO-69. See Manna et al., *Journal of the American Chemical Society* 2016, 138, 7488-7491.

19.2 Preparation of $Hf_{12}$-DBP nMOF $Hf_{12}$-DBP with the framework formula of $Hf_{12}(\mu_3\text{-O})_8(\mu_3\text{-OH})_8(\mu_2\text{-OH})_6(DBP)_{6.8}(AcO)_{3.5}(OH)_{0.9}(OH_2)_{0.9}$ was synthesized through a solvothermal reaction between $HfCl_4$ and 5,15-di(p-benzoato)-porphyrin ($H_2$DBP) in N,N-dimethylformamide (DMF) at 80° C. in 40% yield, with the presence of acetic acid and water. The resulting dark purple powder was washed with copious amounts of DMF, 1% triethylamine in ethanol (v/v), and ethanol in succession before being dispersed in ethanol as a stock suspension. $Zr_{12}$-DBP was synthesized as control particles with similar method to $Hf_{12}$-DBP.

19.3 Composition and Structure Characterization of $Hf_{12}$-DBP

Figure 39A:
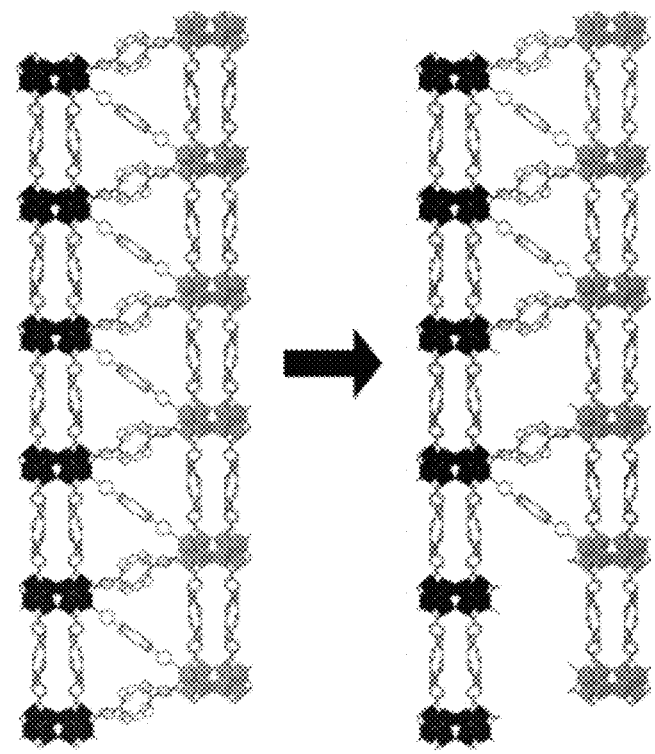
FIG. 39A is schematic drawing showing defects between layers in a metal-organic framework comprising hafnium twelve oxo clusters and di(p-benzoato)porphyrin (DBP) ligands (Hf$_6$-DBP).
Figure 39B:
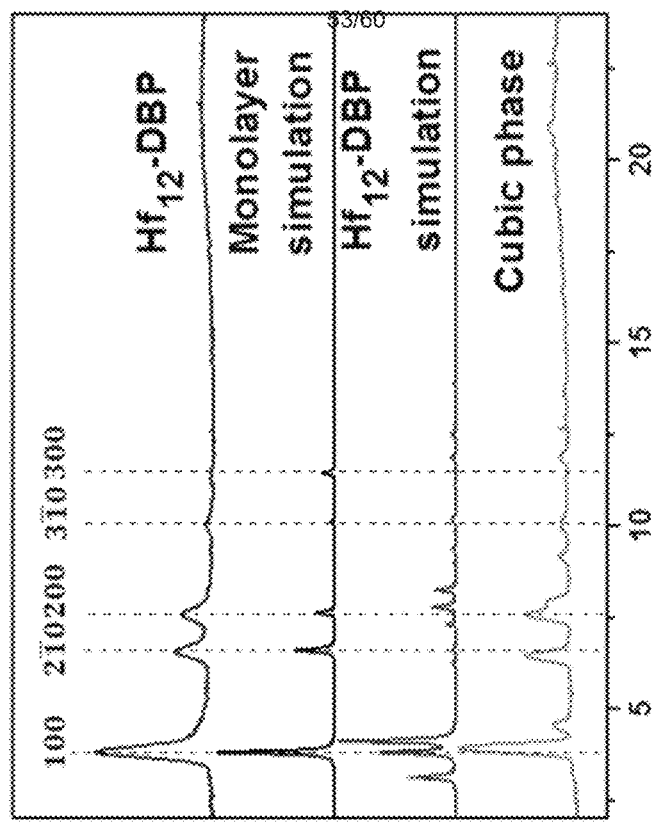
FIG. 39B is a graph showing the powder X-ray diffraction (PXRD) patterns of (top) a metal-organic framework comprising hafnium twelve oxo clusters and di(p-benzoato) porphyrin (DBP) ligands (Hf$_{12}$-DBP); (second to top) a simulated single layer Hf$_{12}$-DBP, (second to bottom) an idealized H$_{12}$-DBP sample, and (bottom) a cubic UiO phase. The diffraction indices along with the dotted droplines are for the peaks in the Hf$_{12}$-DBP structure.
Figure 39D:
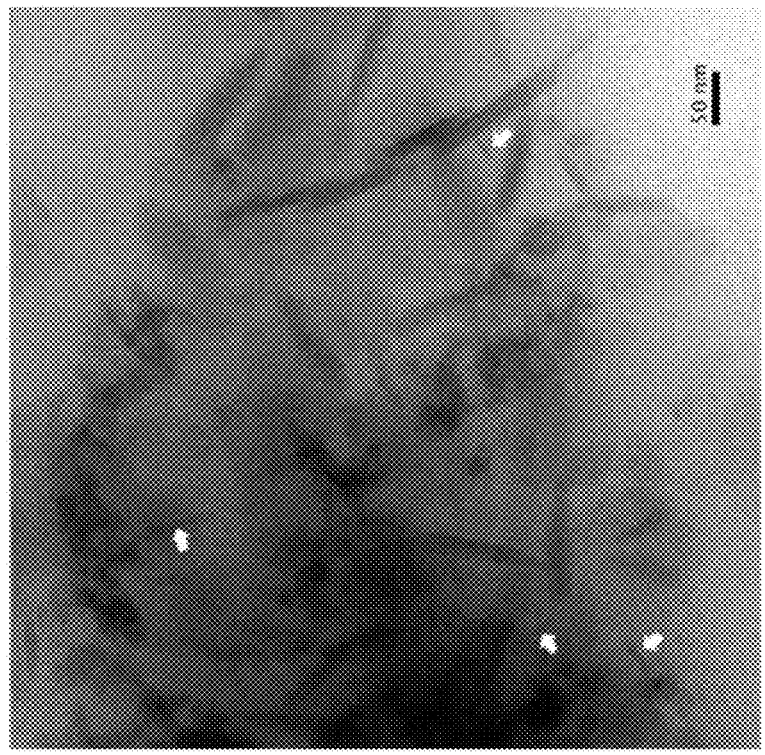
FIG. 39D is a transmission electron microscopy (TEM) image showing the double layer pieces (white arrows) of hafnium twelve oxo clusters and di(p-benzoato)porphyrin (DBP) ligands (Hf$_{12}$-DBP). Three-, four- or multiple layer pieces are also observed in the same sight of view. The scale bar in the lower left represents 50 nanometers (nm).
Figure 39C:
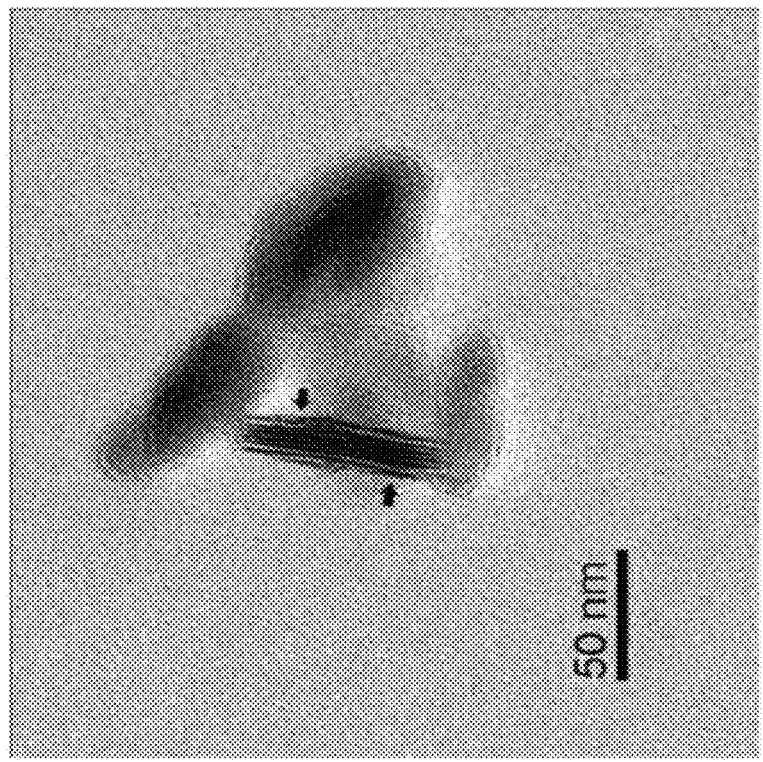
FIG. 39C is a transmission electron microscopy (TEM) image of a "standing" particle of hafnium twelve oxo clusters and di(p-benzoato)porphyrin (DBP) ligands (Hf$_{12}$-DBP) showing the fusing of layers in the particle. Black arrows label the defects of fusing layers. The scale bar in the lower left represents 50 nanometers (nm).

The structure of $Hf_{12}$-DBP was carefully examined and assigned as $Hf_{12}$ SBU-based nanoplates with an idealized formula of $Hf_{12}(\mu_3\text{-O})_8(\mu_3\text{-OH})_8(\mu_2\text{-OH})_6(DBP)_9$ based on powder X-ray diffraction and rotation electron diffraction data of analogous $Hf_{12}$-based nMOFs. See FIGS. 39A-39D. The nMOF structure is highly defected perpendicular to directions of the nanoplates due to missing DBP ligands (see FIG. 39A), affording an empirical formula of $Hf_{12}(\mu_3\text{-O})_8(\mu_3\text{-OH})_8(\mu_2\text{-OH})_6(DBP)_{6.8}(AcO)_{3.5}(OH)_{0.9}(OH_2)_{0.9}$, from a combination of inductively coupled plasma-mass spectrometry (ICP-MS), UV-visible spectroscopy, $^1$H NMR, and thermogravimetric analysis (TGA) measurements. See Table 11, below. The defects disrupt the periodicity along c direction, causing the absence of most of the peaks except those with hk0 indices in the powder X-ray diffraction pattern. See FIG. 39B. The defect behavior was directly visualized by TEM, and occasionally pieces of $Hf_{12}$-DBP nMOFs with as few as two layers were observed. See FIG. 39C.

ICP-MS (Agilent 7700x, Agilent Technologies, Santa Clara, Calif., United States of America) was used to quantify the Hf content in $Hf_{12}$-DBP. The dry MOF sample was digested with a mixture of concentrate nitric acid and hydrofluoric acid ($HNO_3$:HF=99:1 v/v). The digestion is further diluted to appropriate concentration for Hf detection and the concentration was converted to Hf weight percentage in the MOF. The results are listed in Table 11, below.

The dry $Hf_{12}$-DBP sample was digested with $H_3PO_4$/DMSO (85% $H_3PO_4$:DMSO=5:95 v/v) for UV-vis detection of $H_2$DBP. The DBP concentration was calculated based on the standard curve of pure ligand at the same condition, and converted to DBP weight percentage in the MOF. See Table 11.

For NMR analysis, the dry $Hf_{12}$-DBP sample was digested with 85% $D_3PO_4$ in DMSO-$d_6$ (50 mL of $D_3PO_4$, diluted to 1 mL with DMSO-$d_6$). The ratio of acetic acid (AcOH) to DBP was determined by the integral of the AcOH peak at d=1.89 vs. that of the $H_2$DBP peak at d=10.69, and the results are listed in Table 11.

Thermogravimetric analysis was carried out on Shimadzu TGA-50 thermogravimetric analyzer. The sample was heated at 3° C./min to 800° C. in air. The weight loss before 800° C. was 60.5% (calculated 61.0%).

TABLE 11

Compositional analysis of $Hf_{12}$-DBP samples from three different batches.

| | Hf wt % | $H_2$DBPwt % | AcOH:DBP by NMR | Formula |
|---|---|---|---|---|
| 1 | 33.2 | 56.6 | 0.56 | $Hf_{12}(\mu_3\text{-}O)_8(\mu_3\text{-}OH)_8(\mu_2\text{-}OH)_6(DBP)_{6.6}(AcO)_{3.7}(OH)_{1.1}(OH_2)_{1.1}$ |
| 2 | 32.1 | 57.5 | 0.40 | $Hf_{12}(\mu_3\text{-}O)_8(\mu_3\text{-}OH)_8(\mu_2\text{-}OH)_6(DBP)_{7.0}(AcO)_{2.8}(OH)_{1.2}(OH_2)_{1.2}$ |
| 3 | 32.9 | 57.6 | 0.52 | $Hf_{12}(\mu_3\text{-}O)_8(\mu_3\text{-}OH)_8(\mu_2\text{-}OH)_6(DBP)_{6.8}(AcO)_{3.5}(OH)_{0.9}(OH_2)_{0.90}$ |

Figure 40:
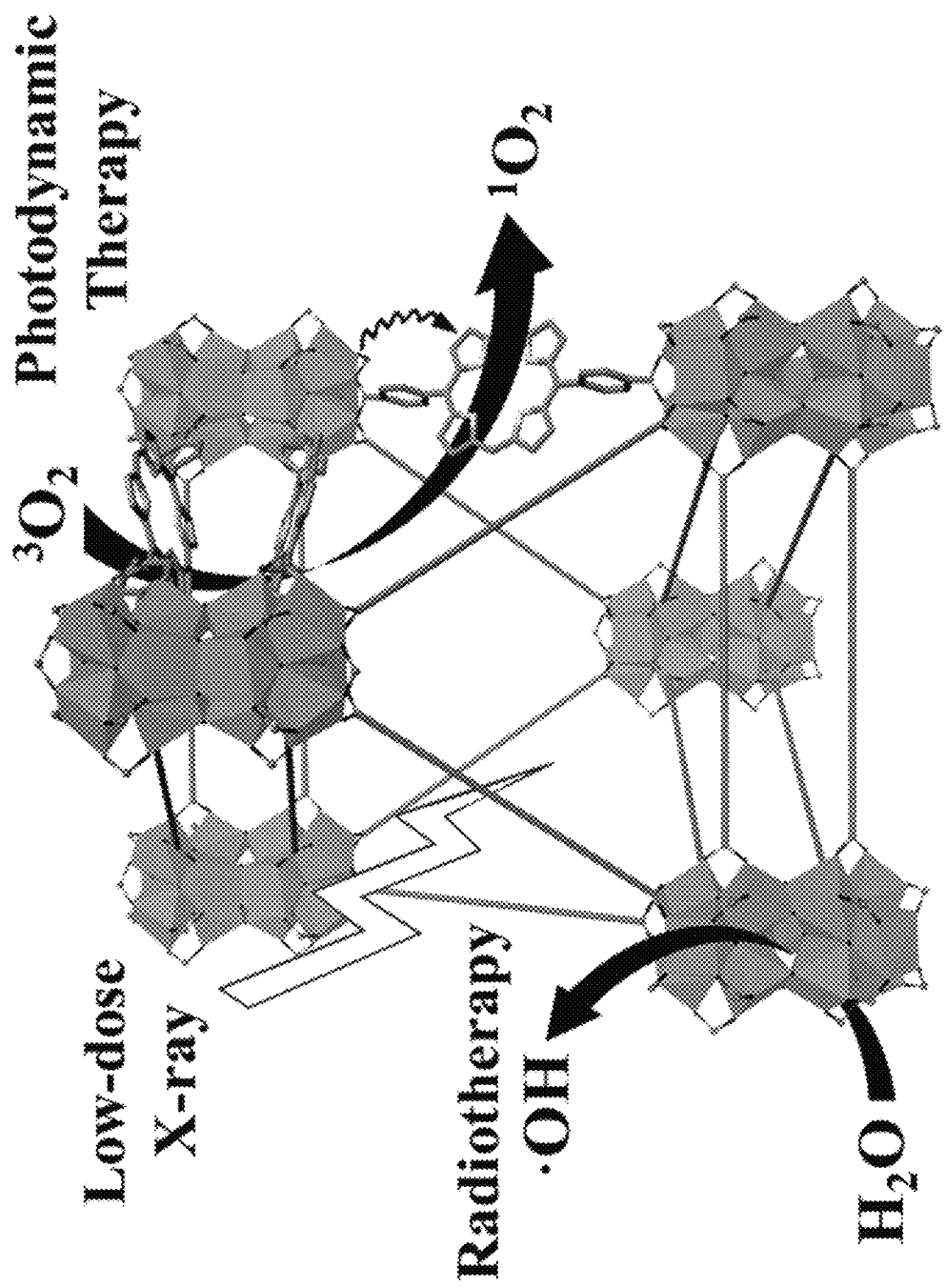
FIG. 40 is a schematic drawing showing a proposed mechanism for X-ray induced radiotherapy-radiodynamic therapy (RT-RDT) by hafnium twelve oxo cluster/di(p-benzoato)porphyrin (Hf$_{12}$-DBP) nano metal-organic frameworks (nMOFs).

19.4 Radiotherapy and Radiodynamic Therapy by $Hf_{12}$-DBP $Hf_{12}$-DBP is constructed from Hf clusters and porphyrin-based photosensitizing ligands. Without being bound by any one theory, it is believed that the Hf clusters efficiently absorb X-ray photons leading to RT (via the production of .OH radicals) and RDT (by exciting the PSs to generate $^1O_2$). See FIG. 40. The RT effect of $Hf_{12}$-DBP was assessed by probing double-strand breaks (DSBs) in DNA, typically caused by OH radicals, and by clonogenic assays. The RDT effect of $Hf_{12}$-DBP was proved by 4-nitroso-N,N-dimethylanaline (RNO) assay, singlet oxygen sensor green (SOSG) detection in live cells, and COX-2 assay to assess $^1O_2$-induced cell membrane damage. When incubated with $Hf_{12}$-DBP and irradiated with X-rays, significant g-H2AX fluorescence indicating DSBs was observed in the nuclei of SQ20B cells. No DSB was observed in PBS treated cells with 1 Gy irradiation.

19.5 Clonegenic Assay

Clonogenic assay was used to determine cell survival after irradiating cells with ionizing radiation. $Hf_{12}$-DBP shows excellent radiosensitization with a radiation enhancement factor (REF) at 10% survival fraction dose ($D_{10}$) ranging from 2.13 to 3.36, much better than $HfO_2$, $Hf_6$-DBA, $Hf_{12}$-DBA, and gold nanoparticles at the same Hf/Au doses. See Table 12, below. RT-RDT contribution is confirmed by fitting the dose-response curves with the function $F(D)=\exp(-\alpha D - \beta D^2)$, where D is the radiation dose and F(D) is the survival fraction. Strikingly, the fitting of concave-shaped dose-response curves of $Hf_{12}$-DBP groups afforded negative β values, indicating RDT damage on cancer cells. Upon γ-ray irradiation $Hf_{12}$-DBP also displays excellent radiosensitization. The REF of $Hf_{12}$-DBP by $^{60}$Co source γ-ray irradiation range from 1.33 to 1.77 (see Table 13, below), and that by LINAC γ-ray irradiation (6 MV) range from 1.88 to 3.29. See Table 14, below.

TABLE 12

Fitting results of the dose-response curves of $Hf_{12}$-DBP by clonogenic assay upon X-ray irradiation.

| | α | β | Adj. $r^2$ | α/β | $D_{10}$ | $D_{20}$ | $D_{50}$ | REF |
|---|---|---|---|---|---|---|---|---|
| CT26 | 0.512 | −0.00715 | 0.993 | −71.6 | 4.82 | 3.3 | 1.38 | 2.34 |
| SQ20B | 0.5061 | −0.00901 | 0.99 | −56.2 | 4.99 | 3.38 | 1.4 | 2.13 |
| TUBO | 0.5677 | −0.00676 | 0.993 | −84 | 4.27 | 2.94 | 1.24 | 3.36 |
| Hela | 0.4137 | −0.00759 | 0.98 | −54.5 | 6.29 | 4.22 | 1.73 | 2.42 |
| JSQ3 | 0.41777 | / | 0.99 | / | 5.51 | 3.85 | 1.66 | 2.85 |
| 4T1 | 0.37389 | −0.00171 | 0.99 | −218.6 | 6.34 | 4.39 | 1.87 | 2.47 |

TABLE 13

REF values of $Hf_{12}$-DBP at $D_{10}$ by clonogenic assay in a panel of cell lines upon γ-ray irradiation from $^{60}$Co source.

| | 4T1 | TUBO | Hela | CT26 | JSQ3 | SQ20B |
|---|---|---|---|---|---|---|
| $HfO_2$ | 1.06 | 1.03 | 1 | 1.01 | 1 | 1 |
| $Hf_{12}$-DBP | 1.43 | 1.72 | 1.77 | 1.56 | 1.33 | 1.46 |

TABLE 14

Fitting results of the dose-response curves of $Hf_{12}$-DBP by clonogenic assay upon γ-ray irradiation from LINAC.

| | α | β | Adj. $r^2$ | α/β | $D_{10}$ | $D_{20}$ | $D_{50}$ | REF |
|---|---|---|---|---|---|---|---|---|
| CT26 | | | | | | | | |
| PBS | 0 | 0.01621 | 0.991 | 0 | 11.92 | 9.96 | 6.54 | |
| $Hf_{12}$-DBP | 0.4249 | −0.00172 | 0.995 | −247 | 5.54 | 3.85 | 1.64 | 2.15 |
| $HfO_2$ | 5.42E−04 | 0.01664 | 0.994 | 0.033 | 11.75 | 9.82 | 6.44 | 1.01 |
| AuNP | 0.06412 | 0.01394 | 0.997 | 4.6 | 10.76 | 8.69 | 5.12 | 1.11 |

TABLE 14-continued

Fitting results of the dose-response curves of $Hf_{12}$-DBP
by clonogenic assay upon γ-ray irradiation from LINAC.

| | α | β | Adj. $r^2$ | α/β | $D_{10}$ | $D_{20}$ | $D_{50}$ | REF |
|---|---|---|---|---|---|---|---|---|
| SQ20B | | | | | | | | |
| PBS | 0.04748 | 0.01316 | 0.998 | 3.61 | 11.55 | 9.4 | 5.67 | |
| $Hf_{12}$-DBP | 0.41298 | −0.0049 | 0.995 | −84.3 | 6 | 4.1 | 1.71 | 1.925 |
| $HfO_2$ | 0.0605 | 0.01321 | 0.997 | 4.58 | 11.11 | 8.98 | 5.31 | 1.04 |
| AuNP | 0.12618 | 0.01141 | 0.998 | 11.1 | 9.71 | 7.57 | 4.03 | 1.19 |
| TUBO | | | | | | | | |
| PBS | 0.09348 | 0.00695 | 0.995 | 13.5 | 12.68 | 9.91 | 5.31 | |
| $Hf_{12}$-DBP | 0.56774 | −0.00676 | 0.993 | −84 | 4.27 | 2.94 | 1.24 | 2.97 |
| $HfO_2$ | 0.13314 | 0.00556 | 0.993 | 23.9 | 11.64 | 8.83 | 4.4 | 1.09 |
| AuNP | 0.13382 | 0.00699 | 0.996 | 19.1 | 10.95 | 8.37 | 4.24 | 1.16 |
| Hela | | | | | | | | |
| PBS | 0.11287 | 0.00554 | 0.993 | 20.4 | 12.6 | 9.67 | 4.94 | |
| $Hf_{12}$-DBP | 0.44131 | −0.00806 | 0.99 | −54.8 | 5.84 | 3.93 | 1.62 | 2.16 |
| $HfO_2$ | 0.08995 | 0.00706 | 0.995 | 12.7 | 12.78 | 10.02 | 5.41 | 1 |
| AuNP | 0.14667 | 0.00451 | 0.995 | 32.5 | 11.58 | 8.66 | 4.19 | 1.09 |
| JSQ3 | | | | | | | | |
| PBS | 0.08061 | 0.01145 | 0.996 | 7.04 | 11.09 | 8.85 | 5.02 | |
| $Hf_{12}$-DBP | 0.40257 | −0.00196 | 0.995 | −205.4 | 5.89 | 4.08 | 1.74 | 1.88 |
| $HfO_2$ | 0.18651 | 0.00484 | 0.997 | 38.5 | 9.84 | 7.26 | 3.41 | 1.13 |
| AuNP | 0.12848 | 0.01413 | 0.996 | 9.09 | 9 | 7.05 | 3.8 | 1.23 |
| 4T1 | | | | | | | | |
| PBS | 0.10083 | 0.00199 | 0.97 | 50.7 | 17.08 | 12.75 | 6.13 | |
| $Hf_{12}$-DBP | 0.52387 | −0.01551 | 0.992 | −33.8 | 5.19 | 3.42 | 1.38 | 3.29 |
| $HfO_2$ | 0.06111 | 0.00545 | 0.997 | 11.2 | 15.7 | 12.47 | 6.99 | 1.09 |
| AuNP | 0.1027 | 4.89E−04 | 0.99 | 210.1 | 20.44 | 14.65 | 6.55 | 1 |

19.6 Radiodynamic Effects

The singlet oxygen ($^1O_2$) generation efficiency of $Hf_{12}$-DBP-Hf upon X-ray irradiation by RDT was determined by 4-nitroso-N,N-dimethylanaline (RNO) assay. The RDT effect was further detected by COX-2 assay which assesses $^1O_2$-induced cell membrane damage causes upregulation of COX-2, a cyclooxygenase responsible for membrane damage repair. The upregulation of COX-2 was directly observed by CLSM after $Hf_{12}$-DBP incubation and X-ray irradiation. No fluorescence signal was observed in cells treated with $Hf_{12}$-DBP without X-ray irradiation group and PBS with or without X-ray irradiation groups. $^1O_2$ generation was also confirmed by singlet oxygen sensor green (SOSG) detection in live cells using CLSM. Green fluorescence was observed only in SQ20B cells treated with $Hf_{12}$-DBP and X-ray irradiation and not PBS or control groups without X-ray irradiation, due to the generation of $^1O_2$ intracellularly by the interaction of $Hf_{12}$-DBP with irradiation.

19.7 In Vivo Anticancer Efficacy-4T1 Bilateral Model

The in vivo anticancer efficacy of $Hf_{12}$-DBP on 4T1 tumor bearing mice was evaluated with the combination of immune checkpoint blockade. A bilateral model was established to assess both the local radiodynamic therapy and the systemic immunotherapy. 2 million cells and 1 million cells were respectively inoculated into right and left side subcutaneous tissue on day 0. When the right tumors reached 100-150 mm³ in volume, $Hf_{12}$-DBP particles with Hf amount of 0.2 μmol was intratumorally injected followed by daily X-ray irradiation at a dose of 1 Gy/fraction (225 kVp, 13 mA, 0.2 mm-Cu filter) for a total of 8 fractions on 4T1 bilateral model on consecutive days. See FIG. 41A. Anti-PD-L1 antibody was given every three days by intraperitoneal injection at a dose of 75 μg/mouse. The tumor sizes were measured with a caliper every day and the tumor volume equals (width²×length)/2. All the mice were sacrificed on Day 28 and tumors were excised from mice immediately following sacrifice and were embedded in optimal cutting temperature compound (OCT) and stored at −80° C. Organs and tumors were then sectioned and stained with hematoxylin and erosin (H&E) and observed with light microscopy (Pannoramic Scan Whole Slide Scanner, Perkin Elmer, Waltham, Mass., United States of America). Body weight of each group was monitored and no systemic toxicity was observed in any of the groups.

As shown in FIGS. 41B and 41C, $Hf_{12}$-DBP effectively regressed right (treated) 4T1 tumors upon X-ray irradiation but did not have significant effects on left (untreated) tumors. Anti-PD-L1 treatment either with or without X-ray irradiation showed moderate anti-tumor efficacy both on primary and distant tumors. When combined with PD-L1 antibody, $Hf_{12}$-DBP effectively regressed treated right primary tumors (99% reduction in tumor size compared to PBS control group) and almost completely eradicated nonirradiated distant left tumors, likely via systemic antitumor immunity from synergistic $Hf_{12}$-DBP-mediated RT-RDT and immune checkpoint blockade.

19.8 In Vivo Anti-metastatic Efficacy-4T1 Orthotopic Model

Figure 42A:
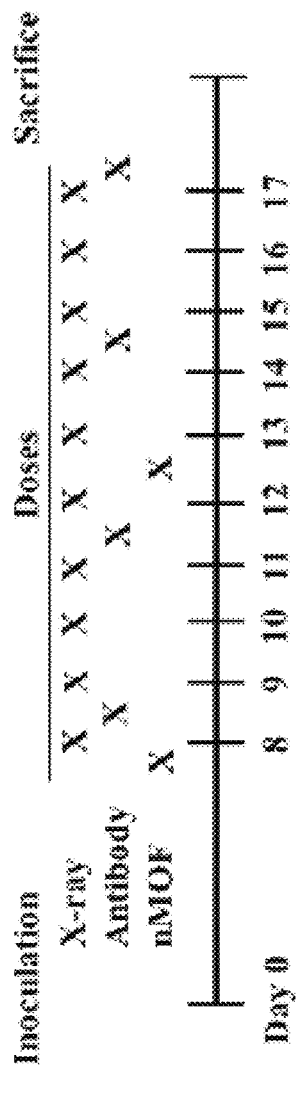
FIG. 42A a schematic drawing showing the dosing schedule of an in vivo study of the efficacy of nano metal-organic frameworks (nMOFs), anti-PD-L1 antibody (Antibody), and X-ray irradiation on a 4T1 orthotopic tumor model.

The antitumor activity and antimetastatic effect of $Hf_{12}$-DBP combined with anti-PD-L1 was investigated on a 4T1 orthotopic model. Two million 4T1 cells were inoculated into the mammary fat pads of female, which can produce spontaneous metastases to the lung. When the orthotopic tumors reached 100-150 mm³ in volume, $Hf_{12}$-DBP particles with Hf amount of 0.2 μmol was intratumorally injected followed by daily X-ray irradiation at a dose of 1 Gy/fraction (225 kVp, 13 mA, 0.2 mm-Cu filter) for a total of 8 fractions on 4T1 bilateral model on consecutive days. See FIG. 42A. Anti-PD-L1 antibody was given every three days by intraperitoneal injection at a dose of 75 μg/mouse. All the mice were sacrificed on Day 24 and tumors were excised from mice immediately following sacrifice and were embedded in optimal cutting temperature compound (OCT) and stored at −80° C. Body weight of each group was monitored and no systemic toxicity was observed in any of the groups. Organs and tumors were then sectioned and stained with hematoxylin and erosin (H&E) and observed with light microscopy (Pannoramic Scan Whole Slide Scanner, Perkin Elmer, Waltham, Mass., United States of America). Lungs were also harvested, observed for the gross examination of tumor nodules, or sectioned and stained with H&E for quantification of metastasis area, or digested with collagenase type IV/elastase cocktail and cultured with 60 µM 6-thioguanine for 10 days. The colonies formed by clonogenic metastatic cancer cells were then fixed with methanol and stained with 0.1% crystal violet. For quantification, the crystal violet stained colonies were dissolved with 10% acetic acid and their absorbance at 590 nm was measured and normalized to the PBS control group.

Figure 42B:
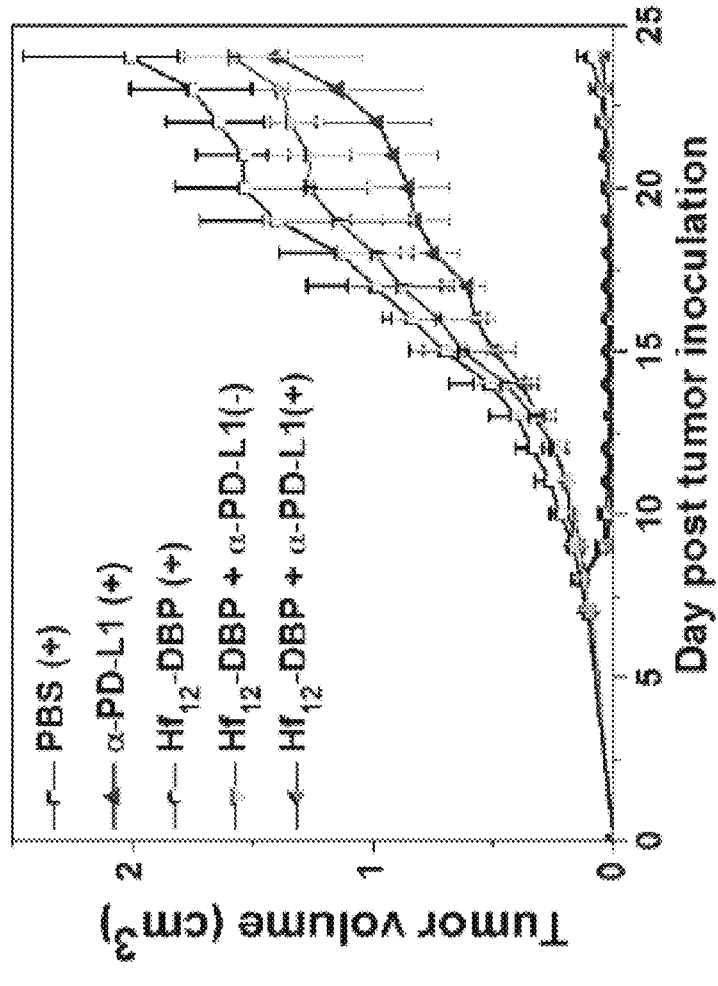
FIG. 42B is a graph showing the tumor growth curves of 4T1 orthotopic tumor-bearing mice treated with nano metal-organic frameworks (nMOFs) comprising hafnium twelve di(p-benzoato)porphyrin (Hf$_{12}$-DBP) with anti-PD-L1 antibodies and X-ray irradiation (leftward pointing triangles); Hf$_{12}$-DBP and anti-PD-L1 antibodies without X-ray irradiation (downward pointing triangles); Hf$_{12}$-DBP and X-ray irradiation (circles), anti-PD-L1 antibody and X-ray irradiation (upward pointing triangles); or phosphate buffered saline (PBS, squares) with X-rays irradiation. Treatment began at day 7 after tumor inoculation when the tumor reached a volume of 100-150 cubic millimeters (mm$^3$). X-ray irradiation was carried out on mice 12 hours after the intratumoral (i.t.) injection of PBS or nanoparticles on ten consecutive days at a dose of 1 gray (Gy)/fraction (225 peak kilovoltage (kVp), 13 milliampere (mA), 0.2-millimeter (mm) copper (Cu) filter). Antibody was given every three days at a dose of 75 micrograms (μg)/mouse. N=5.

As shown in FIG. 42B and Table 15, compared to the PBS control, $Hf_{12}$-DBP plus X-ray or anti-PD-L1 plus X-ray showed little effect on preventing lung metastasis, while the combination treatment significantly reduced tumor nodules. Only one or two tumor nodules were observed for the $Hf_{12}$-DBP plus anti-PD-L1 group upon X-ray irradiation.

To evaluate anti-metastatic effects, lungs were harvested, observed for the gross examination of tumor nodules. Compared to the PBS control, anti-PD-L1 with or without X-ray irradiation showed little effect on preventing lung metastasis, while the combination treatment significantly reduced number of metastatic tumor nodules.

Lungs were further sectioned and stained with H&E to quantify the proportion of the metastasis area to the whole lung. Combination treatment significantly decreased the percentage of metastasis in the lung to only 3%, indicating that the combination treatment was much more effective in preventing lung metastasis than anti-PD-L1 alone.

Lungs were also digested with collagenase type IV/elastase cocktail and cultured with 60 µM 6-thioguanine for 10 days. The colonies formed by clonogenic metastatic cancer cells were then fixed with methanol and stained with 0.1% crystal violet. For quantification, the crystal violet stained colonies were dissolved with 10% acetic acid and their absorbance at 590 nm was measured and normalized to the PBS control group. The results showed that the absorbance of the combination treatment group was only 10.0±2.8% of the PBS control group, which indicated that there were much less clonogenic metastatic cancer cells in the lungs treated with $Hf_{12}$-DBP-mediated RDT plus PD-L1 checkpoint blockade compared with PBS treated group. Taken together, the combination of $Hf_{12}$-DBP and PD-L1 antibody (with X-ray irradiations) not only effectively regressed treated tumors, but also significantly suppressed the metastasis of 4T1 tumors to the lungs. These results support the systemic antitumor immunity induced by $Hf_{12}$-DBP-mediated RT-RDT and immune checkpoint blockade.

TABLE 15

Anti-metastatic effect results of $Hf_{12}$-DBP-mediated RT-RDT plus PD-L1 antibody.

| | PBS (+) | $Hf_{12}$-DBP/ aPD-L1(−) | aPD-L1(+) | $Hf_{12}$-DBP/ aPD-L1(+) |
|---|---|---|---|---|
| Number of tumor nodules | 17 ± 4 | 22 ± 6 | 14 ± 3 | 3 ± 1 |
| % of lung metastatic area | 33.9 ± 13.4 | 30.0 ± 0.7 | 12.4 ± 1.6 | 3.2 ± 2.1 |
| absorption of crystal violet | 100.0 ± 11.18 | 74.3 ± 12.6 | 66.2 ± 7.5 | 10.0 ± 2.8 |

19.9 In Vivo Anticancer Efficacy-SCCVII Bilateral Model

The in vivo anticancer efficacy of $Hf_{12}$-DBP on SCCVII tumor bearing C3H mice was evaluated with the combination of immuno checkpoint blockade therapy. Bilateral model was established to assess both the local radiodynamic therapy and the systemic immunotherapy. 2 million cells and 1 million cells were respectively inoculated into right and left side subcutaneous tissue on day 0. When the right tumors reached 100-150 mm³ in volume, $Hf_{12}$-DBP particles with Hf amount of 0.2 µmol was intratumorally injected followed by daily X-ray irradiation at a dose of 1 Gy/fraction (225 kVp, 13 mA, 0.2 mm-Cu filter) for a total of 8 fractions on SCCVII bilateral model on consecutive days. See FIG. 43A. Anti-PD-L1, anti-CTLA-4, anti-PD-1 antibody was given every three days by intraperitoneal injection at a dose of 75 µg/mouse. All the mice were sacrificed on Day 22. Body weight of each group was monitored and no systemic toxicity was observed in any of the groups.

Anti-PD-1 alone did not significantly suppress either primary or distant tumors. See FIGS. 43B and 43C. $Hf_{12}$-DBP-mediated X-ray irradiation treatment effectively inhibited primary tumor growth but failed to inhibit the distant tumors. The combination of $Hf_{12}$-DBP-mediated RT-RDT and antibody (anti-PD-1, PD-L1 and CTLA-4) blockade induced significant inhibition of treated right primary tumors (92%, 95% and 88% reduction in tumor size compared to PBS control group without irradiation treatment, respectively) and effective control of the nonirradiated distant left tumors (92%, 92% and 85% reduction in tumor size compared to the PBS control group without irradiation, respectively).

19.10 In Vivo Anticancer Efficacy-CT26 Bilateral Model

The in vivo anticancer efficacy of $Hf_{12}$-DBP on CT26 tumor bearing mice was evaluated with the combination of immuno checkpoint blockade therapy. Bilateral model was established to assess both the local radiodynamic therapy and the systemic immunotherapy. 5 million cells and 2 million cells were respectively inoculated into right and left side subcutaneous tissue on day 0. When the right tumors reached 100-150 mm³ in volume, $Hf_{12}$-DBP particles with Hf amount of 0.2 µmol was intratumorally injected followed by daily X-ray irradiation at a dose of 1 Gy/fraction (225 kVp, 13 mA, 0.2 mm-Cu filter) for a total of 8 fractions on CT26 bilateral model on consecutive days. See FIG. 44A. Anti-PD-L1, anti-CTLA-4, anti-PD-1 antibody was given every three days by intraperitoneal injection at a dose of 75 µg/mouse. All the mice were sacrificed on Day 20. Body weight of each group was monitored and no systemic toxicity was observed in any of the groups.

As shown in FIGS. 44B and 44C, the combination of $Hf_{12}$-DBP-mediated RT-RDT and antibody (anti-PD-1, PD-L1 and CTLA-4) blockade induced significant inhibition of treated right primary tumors (99%, 99% and 94% reduction in tumor size compared to PD-L1 treated group, respectively) and effective control of the nonirradiated distant left tumors (88%, 97% and 86% reduction in tumor size compared to PD-L1 treated group, respectively).

19.11 Anticancer Efficacy of $Hf_2$-DBP with T Cell Depletion

Figure 45A:
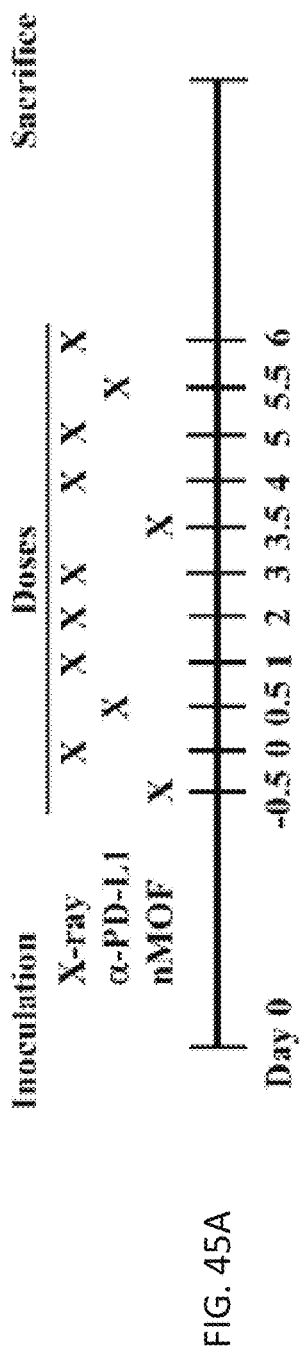
FIG. 45A is a schematic drawing showing the dosing schedule of an in vivo study of the efficacy of nano metal-organic frameworks (nMOFs), antibody, and X-ray irradiation on TUBO tumor bearing mice with T cell or B cell depletion.
Figure 45B:
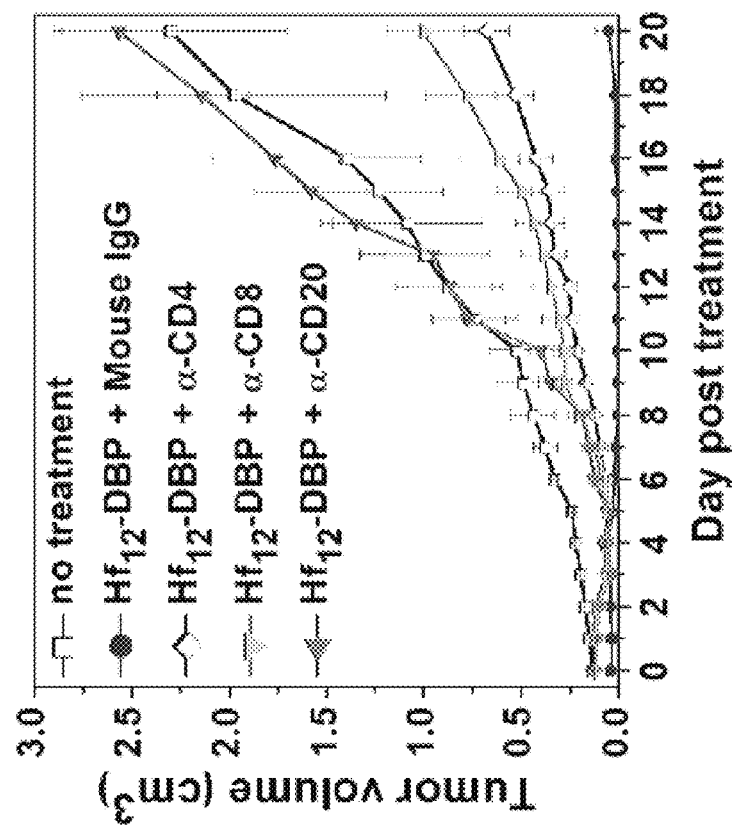
FIG. 45B is a graph showing the tumor growth curves of tumors in TUBO tumor-bearing BALB/c mice treated with 0.15 milligram nano metal-organic frameworks (nMOFs) comprising hafnium twelve/di(p-benzoato)porphyrin (Hf$_{12}$-DBP) and X-ray irradiation with T cell or B cell depletion. Data for mice treated with nMOFs and mouse IgG is shown in circles, data for mice treated with nMOFs and anti-CD4 antibodies is shown with diamonds, data for mice treated with nMOFs and anti-CD8 antibody is shown with downward pointing triangles, and data for mice treated with nMOFs and anti-CD20 antibodies is shown with leftward pointing triangles. Data from control mice that did not receive a treatment is shown with squares. Treatments began when the tumors reached 100-150 cubic millimeters (mm$^3$) in volume. The X-ray irradiation (0.5 gray (Gy)/fraction) was carried out on mice 12 hours post intratumoral injection of Hf$_{12}$-DBP on 6 consecutive days. N=3.

Because both .OH and $^1O_2$ have been shown to exhibit immunomodulatory properties, how immune cells mediate the therapeutic effects of the nMOF-enabled RT-RDT process was investigated. The anticancer efficacy of $Hf_{12}$-DBP was evaluated in the subcutaneous murine breast cancer TUBO model with depletions of CD4⁺ T cell, CD8⁺ T cell, or B cells. Mice receiving i.p. injections of anti-CD4, anti-CD8, anti-CD20, or mouse IgG antibodies were treated with $Hf_{12}$-DBP and X-ray irradiation. See FIG. 45A. Mouse IgG did not have any effect on tumor growth, but other antibody-treated groups all showed rapid growth progression after termination of X-ray treatment. See FIG. 45B. These results indicate that T cells and B cells play essential roles in the anticancer efficacy of our treatment and support the possibility of using nMOF-enabled RT-RDT to augment checkpoint blockade cancer immunotherapy.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A composition comprising a metal-organic framework (MOF) comprising:
   a) a photosensitizer; and
   b) a plurality of metal-containing secondary building units (SBUs) linked together via one or more bridging ligands, wherein the SBUs comprise hafnium (Hf) oxo clusters and wherein each of the one or more bridging ligands comprises an organic compound bound to two or three SBUs.

2. The composition of claim 1, wherein the Hf oxo clusters are $Hf_6$ oxo clusters.

3. The composition of claim 1, wherein the Hf oxo clusters are $Hf_{12}$ oxo clusters or a combination of $Hf_{12}$ and $Hf_6$ oxo clusters.

4. The composition of claim 1, wherein each of the one or more bridging ligands comprises at least two groups wherein each of said two groups is individually selected from the group consisting of a carboxylate, a nitrogen-containing group, a phenol, an acetylacetonate, a phosphonate, and a phosphate.

5. The composition of claim 1, wherein at least one of the one or more bridging ligands comprises the photosensitizer or a derivative of the photosensitizer.

6. The composition of claim 5, wherein at least one of the one or more bridging ligands comprises a porphyrin, a chlorin, a chlorophyll, a phthalocyanine, a ruthenium-bipyridine complex, or an iridium-bipyridine complex.

7. The composition of claim 6, wherein at least one of the one or more bridging ligands comprises a diphenyl-di(benzoate)porphyrin, a dibenzoato(bipyridine)ruthenium bis(bipyridine), or a dibenzoato-(bipyridine)ruthenium bis(phenylpyridine).

8. The composition of claim 1, wherein at least one of the one or more bridging ligands comprises 5, 15-di(p-benzoato)porphyrin (DBP) or a derivative and/or metal complex thereof; 5, 15-di(p-benzoato)chlorin (DBC) or a derivative and/or metal complex thereof; 5, 15-di(p-benzoato)bacteriochlorin (DBBC) or a derivative and/or metal complex thereof; a platinum or palladium complex of di(5'-benzoatosalycylidene)-1,2-cyclohexylidenediamine; or motexafin lutetium.

9. The composition of claim 1, further comprising a non-covalently bound chemotherapeutic agent and/or immunotherapeutic agent.

10. The composition of claim 9, wherein the MOF further comprises a non-covalently bound immunotherapeutic agent, wherein said immunotherapeutic agent is an IDO inhibitor (IDOi).

11. The composition of claim 10, wherein the IDOi is selected from the group consisting of ICBN24360, 1-methyl-D-tryptophan, and 1-methyl-L-tryptophan.

12. The composition of claim 1, further comprising a polyethylene glycol (PEG) moiety and/or one or more lipid moiety bound covalently or electrostatically.

13. A pharmaceutical formulation comprising a composition of claim 1 and a pharmaceutically acceptable carrier.

14. A method for treating a cancer in a patient, the method comprising:
   administering to a patient the composition of claim 1; and
   exposing at least a portion of the patient to ionizing irradiation energy.

15. A method for treating a disease in a patient, wherein the disease is selected from a head and neck cancer, breast cancer, prostate cancer, a glioblastoma, a gynecological tumor, a brain tumor, colorectal cancer, and pancreatic cancer; the method comprising:
   administering to a patient the composition of claim 1; and
   exposing at least a portion of the patient to ionizing irradiation energy.

16. A method for treating a metastatic cancer in a patient, the method comprising:
   administering to a patient the composition of claim 1; and
   exposing at least a portion of the patient to ionizing irradiation energy.

17. A method for treating a disease in a patient, wherein the disease is selected from a head and neck cancer, breast cancer, prostate cancer, a glioblastoma, a gynecological tumor, a brain tumor, colorectal cancer, pancreatic cancer, and a metastatic cancer, the method comprising:
   administering to a patient the composition of claim 1; and
   exposing at least a portion of the patient to ionizing irradiation energy;
   wherein the method further comprises administering to the patient an immunotherapy agent.

18. The method of claim 17, wherein the immunotherapy agent is selected from the group consisting of a PD-1/PD-L1 antibody, an IDO inhibitor, CTLA-4 antibody, a OX40 antibody, a TIM3 antibody, a LAG3 antibody, an siRNA targeting PD-1/PD-L1, an siRNA targeting IDO and an siRNA targeting CCR7.

* * * * *